(12) United States Patent
Yang et al.

(10) Patent No.: US 11,878,968 B2
(45) Date of Patent: Jan. 23, 2024

(54) ARYL COMPOUNDS AND PHARMACEUTICAL COMPOSITIONS THAT MODULATE IKZF2

(71) Applicant: Plexium, Inc., San Diego, CA (US)

(72) Inventors: Pengyu Yang, San Diego, CA (US); Simon Bailey, San Diego, CA (US)

(73) Assignee: Plexium, Inc., San Diego, CA (US)

( * ) Notice: Subject to any disclaimer, the term of this patent is extended or adjusted under 35 U.S.C. 154(b) by 0 days.

(21) Appl. No.: 18/052,462

(22) Filed: Nov. 3, 2022

(65) Prior Publication Data

US 2023/0265071 A1   Aug. 24, 2023

Related U.S. Application Data

(63) Continuation of application No. 17/860,922, filed on Jul. 8, 2022, now abandoned.

(60) Provisional application No. 63/314,992, filed on Feb. 28, 2022, provisional application No. 63/220,323, filed on Jul. 9, 2021.

(51) Int. Cl.
*C07D 401/14* (2006.01)
*A61P 35/00* (2006.01)

(52) U.S. Cl.
CPC ................. *C07D 401/14* (2013.01)

(58) Field of Classification Search
CPC ............... C07D 401/14; A61P 35/00
See application file for complete search history.

(56) References Cited

U.S. PATENT DOCUMENTS

| | | |
|---|---|---|
| 5,559,127 A | 9/1996 | Hartman et al. |
| 6,593,322 B1 | 7/2003 | Bhagwat et al. |
| 2003/0203922 A1 | 10/2003 | Patel et al. |
| 2003/0203946 A1 | 10/2003 | Behrens et al. |
| 2004/0116710 A1 | 6/2004 | Wallace et al. |
| 2005/0075358 A1 | 4/2005 | Carboni et al. |
| 2006/0247263 A1 | 11/2006 | Siegmund |
| 2008/0267879 A1 | 10/2008 | Elmaleh et al. |
| 2010/0316607 A1 | 12/2010 | Or et al. |
| 2011/0190343 A1 | 8/2011 | Gochin et al. |
| 2013/0112948 A1 | 5/2013 | Jung et al. |
| 2013/0313536 A1 | 11/2013 | Nishimura et al. |
| 2014/0027744 A1 | 1/2014 | Yoshida et al. |
| 2015/0148375 A1 | 5/2015 | Yue et al. |
| 2015/0168415 A1 | 6/2015 | Yang |
| 2016/0243077 A1 | 8/2016 | Brown et al. |
| 2017/0012214 A1 | 1/2017 | Pyo et al. |
| 2017/0352817 A1 | 12/2017 | Nakano et al. |
| 2018/0099940 A1 | 4/2018 | Crew et al. |
| 2018/0215731 A1 | 8/2018 | Crew et al. |
| 2019/0062310 A1 | 2/2019 | Wang et al. |
| 2019/0081253 A1 | 3/2019 | Xia et al. |
| 2019/0248744 A1 | 8/2019 | Wang et al. |
| 2020/0157078 A1 | 5/2020 | Fan et al. |

FOREIGN PATENT DOCUMENTS

| | | |
|---|---|---|
| AU | 2012204508 A1 | 4/2013 |
| CA | 2524027 A1 | 12/2004 |
| CN | 107827809 A | 3/2018 |
| CN | 107973742 A | 5/2018 |
| CN | 108003089 A | 5/2018 |
| CN | 108689942 A | 10/2018 |
| CN | 109553608 A | 4/2019 |
| CN | 110092804 A | 8/2019 |
| CN | 110885332 A | 3/2020 |
| CN | 112010858 A | 12/2020 |
| CN | 112047932 A | 12/2020 |
| CN | 112125885 A | 12/2020 |
| CN | 112430216 A | 3/2021 |
| CN | 112552293 A | 3/2021 |
| CN | 113013346 A | 6/2021 |
| DE | 10238002 A1 | 3/2004 |
| EP | 0516588 A1 | 12/1992 |
| EP | 1726589 A2 | 11/2006 |
| EP | 2371828 A1 | 10/2011 |
| GB | 2396154 A | 6/2004 |

(Continued)

OTHER PUBLICATIONS

International Search Report and Written Opinion, dated Oct. 20, 2022, regarding International Application No. PCT/US2022/036511, 13 pages.

(Continued)

*Primary Examiner* — Samira J Jean-Louis

(74) *Attorney, Agent, or Firm* — Sheppard Mullin Richter & Hampton LLP

(57) ABSTRACT

Disclosed are compounds and salts thereof that bind to and modulate cereblon activity. In some embodiments, the binding and modulation of cereblon results in the degradation of IKAROS family zinc finger proteins (e.g., IKZF2). The compounds are of formula I:

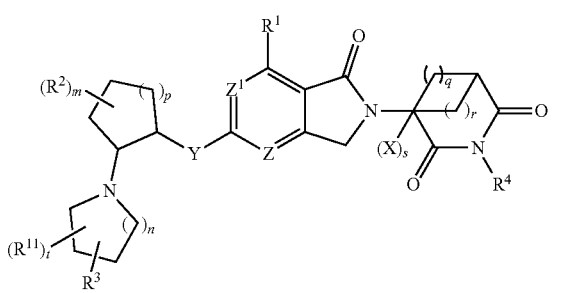

40 Claims, No Drawings

Specification includes a Sequence Listing.

(56) References Cited

FOREIGN PATENT DOCUMENTS

| | | |
|---|---|---|
| JP | S 62050751 A | 3/1987 |
| JP | H 11335283 A | 12/1999 |
| JP | 2005053058 A | 3/2005 |
| JP | 2007022937 A | 2/2007 |
| JP | 2012123292 A | 6/2012 |
| JP | 2013084945 A | 5/2013 |
| JP | 2019034904 A | 3/2019 |
| KR | 20090007075 A | 1/2009 |
| KR | 20100007143 A | 1/2010 |
| KR | 20120079616 A | 7/2012 |
| KR | 20140111214 A | 9/2014 |
| KR | 20140141337 A | 12/2014 |
| KR | 20180064861 A | 6/2018 |
| KR | 20200084172 A | 7/2020 |
| WO | WO 1993008799 A1 | 5/1993 |
| WO | WO 1994008962 A1 | 4/1994 |
| WO | WO 1998000412 A1 | 1/1998 |
| WO | WO 2000076969 A1 | 12/2000 |
| WO | WO 2001057020 A1 | 8/2001 |
| WO | WO 2001058871 A1 | 8/2001 |
| WO | WO 2001077075 A2 | 10/2001 |
| WO | WO 2002000612 A1 | 1/2002 |
| WO | WO 2002028850 A1 | 4/2002 |
| WO | WO 2002040445 A1 | 5/2002 |
| WO | WO 2002060426 A2 | 8/2002 |
| WO | WO 2002068406 A1 | 9/2002 |
| WO | WO 2002072549 A1 | 9/2002 |
| WO | WO 2003048140 A1 | 6/2003 |
| WO | WO 2003074046 A1 | 9/2003 |
| WO | WO 2003077914 A1 | 9/2003 |
| WO | WO 2003091258 A1 | 11/2003 |
| WO | WO 2004002984 A2 | 1/2004 |
| WO | WO 2004039318 A2 | 5/2004 |
| WO | WO 2004041277 A1 | 5/2004 |
| WO | WO 2004063147 A1 | 7/2004 |
| WO | WO 2004074253 A1 | 9/2004 |
| WO | WO 2004096210 A1 | 11/2004 |
| WO | WO 2004098494 A2 | 11/2004 |
| WO | WO 2004113330 A1 | 12/2004 |
| WO | WO 2005021510 A2 | 3/2005 |
| WO | WO 2005051300 A2 | 6/2005 |
| WO | WO 2005063738 A1 | 7/2005 |
| WO | WO 2005074375 A2 | 8/2005 |
| WO | WO 2005082089 A2 | 9/2005 |
| WO | WO 2005086754 A2 | 9/2005 |
| WO | WO 2006047237 A2 | 5/2006 |
| WO | WO 2006049304 A1 | 5/2006 |
| WO | WO 2006061193 A1 | 6/2006 |
| WO | WO 2006091496 A2 | 8/2006 |
| WO | WO 2006099256 A2 | 9/2006 |
| WO | WO 2007007910 A1 | 1/2007 |
| WO | WO 2007016485 A2 | 2/2007 |
| WO | WO 2007099423 A1 | 9/2007 |
| WO | WO 2007117262 A2 | 10/2007 |
| WO | WO 2007140222 A2 | 12/2007 |
| WO | WO 2008008020 A1 | 1/2008 |
| WO | WO 2008029168 A2 | 3/2008 |
| WO | WO 2008048991 A2 | 4/2008 |
| WO | WO 2008130669 A1 | 10/2008 |
| WO | WO 2009029622 A2 | 3/2009 |
| WO | WO 2009112445 A1 | 9/2009 |
| WO | WO 2009127321 A1 | 10/2009 |
| WO | WO 2009142732 A2 | 11/2009 |
| WO | WO 2010075376 A2 | 7/2010 |
| WO | WO 2010120935 A1 | 10/2010 |
| WO | WO 2010138791 A1 | 12/2010 |
| WO | WO 2010148006 A1 | 12/2010 |
| WO | WO 2011017561 A1 | 2/2011 |
| WO | WO 2011116356 A2 | 9/2011 |
| WO | WO 2011146401 A1 | 11/2011 |
| WO | WO 2012016133 A2 | 2/2012 |
| WO | WO 2012026766 A2 | 3/2012 |
| WO | WO 2012030990 A1 | 3/2012 |
| WO | WO 2012031004 A1 | 3/2012 |
| WO | WO 2012041987 A1 | 4/2012 |
| WO | WO 2012054535 A2 | 4/2012 |
| WO | WO 2012075381 A1 | 6/2012 |
| WO | WO 2012083061 A2 | 6/2012 |
| WO | WO 2012119949 A1 | 9/2012 |
| WO | WO 2012122891 A1 | 9/2012 |
| WO | WO 2012130829 A1 | 10/2012 |
| WO | WO 2012154777 A1 | 11/2012 |
| WO | WO 2012162580 A2 | 11/2012 |
| WO | WO 2012167053 A1 | 12/2012 |
| WO | WO 2013056079 A1 | 4/2013 |
| WO | WO 2013059278 A2 | 4/2013 |
| WO | WO 2013106409 A1 | 7/2013 |
| WO | WO 2013116823 A1 | 8/2013 |
| WO | WO 2013118855 A1 | 8/2013 |
| WO | WO 2013142817 A2 | 9/2013 |
| WO | WO 2013182519 A1 | 12/2013 |
| WO | WO 2013191866 A1 | 12/2013 |
| WO | WO 2014066318 A1 | 5/2014 |
| WO | WO 2014153001 A1 | 9/2014 |
| WO | WO 2014202763 A1 | 12/2014 |
| WO | WO 2015001726 A1 | 1/2015 |
| WO | WO 2015062486 A1 | 5/2015 |
| WO | WO 2015161016 A1 | 10/2015 |
| WO | WO 2015187850 A2 | 12/2015 |
| WO | WO 2015193506 A1 | 12/2015 |
| WO | WO 2016016421 A1 | 2/2016 |
| WO | WO 2016033445 A1 | 3/2016 |
| WO | WO 2016105518 A1 | 6/2016 |
| WO | WO 2016164487 A1 | 10/2016 |
| WO | WO 2016175624 A1 | 11/2016 |
| WO | WO 2017039318 A1 | 3/2017 |
| WO | WO 2017044858 A2 | 3/2017 |
| WO | WO 2017048197 A1 | 3/2017 |
| WO | WO 2017051319 A1 | 3/2017 |
| WO | WO 2017117449 A1 | 7/2017 |
| WO | WO 2017176957 A1 | 10/2017 |
| WO | WO 2017176958 A1 | 10/2017 |
| WO | WO 2018010142 A1 | 1/2018 |
| WO | WO 2018010637 A1 | 1/2018 |
| WO | WO 2018052945 A1 | 3/2018 |
| WO | WO 2018052949 A1 | 3/2018 |
| WO | WO 2018081108 A1 | 5/2018 |
| WO | WO 2018119441 A1 | 6/2018 |
| WO | WO 2018189679 A1 | 10/2018 |
| WO | WO 2018191146 A1 | 10/2018 |
| WO | WO 2018208985 A2 | 11/2018 |
| WO | WO 2019001572 A1 | 1/2019 |
| WO | WO 2019023651 A2 | 1/2019 |
| WO | WO 2019032671 A1 | 2/2019 |
| WO | WO 2019038717 A1 | 2/2019 |
| WO | WO 2019124345 A1 | 6/2019 |
| WO | WO 2019164932 A1 | 8/2019 |
| WO | WO 2019164953 A1 | 8/2019 |
| WO | WO 2019190101 A1 | 10/2019 |
| WO | WO 2019193541 A1 | 10/2019 |
| WO | WO 2019199816 A1 | 10/2019 |
| WO | WO 2019222349 A1 | 11/2019 |
| WO | WO 2020012334 A1 | 1/2020 |
| WO | WO 2020012337 A1 | 1/2020 |
| WO | WO 2020014599 A1 | 1/2020 |
| WO | WO 2020017552 A1 | 1/2020 |
| WO | WO 2020023782 A1 | 1/2020 |
| WO | WO 2020041405 A1 | 2/2020 |
| WO | WO 2020041406 A1 | 2/2020 |
| WO | WO 2020198435 A1 | 3/2020 |
| WO | WO 2020081450 A1 | 4/2020 |
| WO | WO 2020081695 A1 | 4/2020 |
| WO | WO 2020117759 A1 | 6/2020 |
| WO | WO 2020118036 A1 | 6/2020 |
| WO | WO 2020128972 A1 | 6/2020 |
| WO | WO 2020140959 A1 | 7/2020 |
| WO | WO 2020162725 A1 | 8/2020 |
| WO | WO 2020165833 A1 | 8/2020 |
| WO | WO 2020165834 A1 | 8/2020 |
| WO | WO 2020176424 A1 | 9/2020 |
| WO | WO 2020225398 A1 | 11/2020 |
| WO | WO 2020228649 A1 | 11/2020 |
| WO | WO 2020252041 A1 | 12/2020 |

(56) References Cited

FOREIGN PATENT DOCUMENTS

| WO | WO 2020253860 A1 | 12/2020 |
|---|---|---|
| WO | WO 2021011913 A1 | 1/2021 |
| WO | WO 2021016388 A1 | 1/2021 |
| WO | WO 2021051034 A1 | 3/2021 |
| WO | WO 2021055756 A1 | 3/2021 |
| WO | WO 2021066873 A1 | 4/2021 |
| WO | WO 2021078227 A1 | 4/2021 |
| WO | WO 2021096238 A1 | 5/2021 |
| WO | WO 2021101919 A1 | 5/2021 |
| WO | WO 2021126973 A1 | 6/2021 |
| WO | WO 2021126974 A1 | 6/2021 |
| WO | WO 2021129653 A1 | 7/2021 |
| WO | WO 2021142450 A1 | 7/2021 |
| WO | WO 2021170078 A1 | 9/2021 |
| WO | WO 2021194320 A1 | 9/2021 |
| WO | WO 2021194914 A1 | 9/2021 |
| WO | WO 2021205391 A1 | 10/2021 |
| WO | WO 2021236885 A1 | 11/2021 |
| WO | WO 2021260528 A1 | 12/2021 |
| WO | WO 2022029573 A1 | 2/2022 |
| WO | WO 2022081976 A1 | 4/2022 |

OTHER PUBLICATIONS

Hsieh et al., "Convergent Synthesis of Polyimide Dendrimers from an ABB' Intermediate," Advanced Materials Research, Jul. 2013, vol. 76, pp. 438-442.
Wang et al., "Acute pharmacological degradation of Helios destabilizes regulatory T cells," Nature Chemical Biology, Jun. 2021, vol. 17, pp. 711-717.

SEQUENCE LISTING

```
Sequence total quantity: 7
SEQ ID NO: 1          moltype = DNA  length = 3075
FEATURE               Location/Qualifiers
source                1..3075
                      mol_type = other DNA
                      organism = synthetic construct
SEQUENCE: 1
atggatgctg atgagggtca agacatgtcc caagtttcag ggaaggaaag cccccctgta  60
agcgatactc cagatgaggg cgatgagccc atgccgatcc ccgaggacct ctccaccacc  120
tcgggaggac agcaaagctc caagagtgac agagtcgtgg ccagtaatgt taaagtagag  180
actcagagtg atgaagagaa tgggcgtgcc tgtgaaatga atggggaaga atgtgcggag  240
gatttacgaa tgcttgatgc ctcggagag aaaatgaatg gctcccacag ggaccaaggc  300
agctcggctt tgtcgggagt tggaggcatt cgacttccta acggaaaact aaagtgtgat  360
atctgtggga tcatttgcat cgggcccaat gtgctcatgg ttcacaaaag aagccacact  420
ggagaacggc ccttccagtg caatcagtgc ggggcctcat tcacccagaa gggcaacctg  480
ctccggcaca tcaagctgca ttccggggag aagcccttca aatgccacct ctgcaactac  540
gcctgccgcc ggagggacgc cctcactggc cacctgagga cgcactccgt tggtaaacct  600
cacaaatgtg gatattgtgg ccgaagctat aaacagcgaa gctctttaga ggaacataaa  660
gagcgctgcc acaactactt ggaaagcatg ggccttccgg gcacactgta cccagtcatt  720
aaagaagaaa ctaatcacag tgaaatggca gaagacctgt gcaagatagg atcagagaga  780
```

```
tctctcgtgc tggacagact agcaagtaac gtcgccaaac gtaagagctc tatgcctcag   840
aaatttcttg gggacaaggg cctgtccgac acgccctacg acagcagcgc cagctacgag   900
aaggagaacg aaatgatgaa gtcccacgtg atggaccaag ccatcaacaa cgccatcaac   960
tacctggggg ccgagtccct gcgcccgctg gtgcagacgc ccccgggcgg ttccgaggtg  1020
gtcccggtca tcagcccgat gtaccagctg cacaagccgc tcgcggaggg caccccgcgc  1080
tccaaccact cggccaggga cagcgccgtg gagaacctgc tgctgctctc caaggccaag  1140
ttggtgccct cggagcgcga ggcgtccccg agcaacagct gccaagactc cacggacacc  1200
gagagcaaca acgaggagca gcgcagcggt ctcatctacc tgaccaacca catcgccccg  1260
cacgcgcgca acgggctgtc gctcaaggag gagcaccgcg cctacgacct gctgcgcgcg  1320
gcctccgaga actcgcagga cgcgctccgc gtggtcagca ccagcgggga gcagatgaag  1380
gtgtacaagt gcgaacactg ccgggtgctc ttcctggatc acgtcatgta caccatccac  1440
atgggctgcc acggcttccg tgatcctttt gagtgcaaca tgtgcggcta ccacagccag  1500
gaccggtacg agttctcgtc gcacataacg cgaggggagc accgcttcca catgagcggt  1560
ggaggcggtt caggtggcgg aggaagcggg ggaggtgaca gtatggtgtc taaaggagaa  1620
gaagataata tggcttctct gcctgctaca cacgaactgc atattttcgg atctattaat  1680
ggcgtggatt tcgatatggt gggacaggga acaggaaacc ctaacgatgg atacgaagaa  1740
ctgaatctga agtctaccaa aggagatctg caattctctc cttggatcct ggtccctcac  1800
attggaatatg gattccatca atatctgcct taccctgacg gatgtctcc tttccaagct  1860
gctatggtcg atggctctgg atatcaggtc cacagaacaa tgcaatttga agatggcgcc  1920
tctctgacag tgaattacag atatacatac gaaggctctc atattaaagg cgaagcccaa  1980
gtgaaggca caggctttcc tgccgacggc cctgtgatga ccaactctct gaccgctgcc  2040
gattggtgca gatctaagaa gacctaccct aatgataaaa ccattatctc taccttcaaa  2100
tggtcttaca caacaggcaa tggcaagaga tacagatcta ccgccagaac cacctatacc  2160
tttgctaagc ctatggctgc caattacctg aaaaatcagc ctatgtatgt gttcagaaaa  2220
accgaactga aacactctaa aaccgaactg aatttcaaag aatggcaaaa ggcttttaca  2280
gatgtgatgg gaatggatga actgtacaag ggaagcggac tacaaatttt tagtcttctt  2340
aaacaagccg gtgacgtgga ggaaatccc ggcccaatgg tgagcaaggg cgaggccgtg  2400
atcaaggagt tcatgcgctt caaggtgcac atggagggca gcatgaacgg ccacgagttc  2460
gagatcgagg gcgagggcga gggccgcccc tacgagggca cccagaccgc caagctgaag  2520
gtgaccaagg gcggccccct gcccttctct tgggacatcc tgagccccca gttcatgtac  2580
ggcagccgcg ccttcaccaa gcaccccgcc gacatccccg actactacaa gcagagcttc  2640
cccgagggct tcaagtggga gcgcgtgatg aacttcgagg acggcggcgc cgtgaccgtg  2700
acccaggaca ccagcctgga ggacggcacc ctgatctaca aggtgaagct gcgcggcacc  2760
aacttccccc ccgacggccc cgtgatgcag aagaagacca tgggctggga ggccagcacc  2820
gagcgcctgt accccgagga cggcgtgctg aagggcctga tcaagatggc cctgcgcctg  2880
aaggacggcg gcagataccct ggccgacttc aagaccacct acaaggccaa gaagcccgtg  2940
cagatgcccg gcgcctacaa cgtggaccgc aagctggaca tcaccagcca caacgaggac  3000
tacaccgtgg tggagcagta cgagcgcagc gagggccgcc acagcaccgg cggcatggac  3060
gagctgtaca agtga                                                  3075
```

```
SEQ ID NO: 2           moltype = DNA   length = 3102
FEATURE                Location/Qualifiers
source                 1..3102
                       mol_type = other DNA
                       organism = synthetic construct
SEQUENCE: 2
atggaaacag aggctattga tggctatata acgtgtgaca atgagctttc acccgaaagg    60
gagcactcca atatggcaat tgacctcacc tcaagcacac ccaatggaca gcatgcctca   120
ccaagtcaca tgacaagcac aaattcagta aagctagaaa tgcagagtga tgaagagtgt   180
gacaggaaac ccctgagccg tgaagatgag atcaggggcc atgatgaggg tagcagccta   240
gaagaacccc taattgagag cagcgaggtg gctgacaaca ggaaagtcca ggagcttcaa   300
ggcgagggag gaatccggct tccgaatggt aaactgaaat gtgacgtctg tggcatggtt   360
tgcattgggc ccaatgtgct tatggtacat aaaaaggagtc acactggtga acgcccttc   420
cactgtaacc agtgtggagc ttcttttact cagaagggca accttctgag acacataaag   480
ttacactctg gagagaagcc gttcaaatgt ccttttctgta gctacgcctg tagaagaagg   540
gacgccctca caggacacct caggaccaat tctgtgggta aacctcacaa gtgcaactac   600
tgtgacgaa gctacaagca gcgcagttca ctggaggagc acaaggaacg ctgccacaac   660
tatctccaga atgtcagcat ggaggctgct gggcaggtca tgagtcacca tgtacctcct   720
atggaagatt gtaaggaaca agagctatt atggacaaca atatttctct ggtgcctttt   780
gagagacctg ctgtcataga gaagctcacg gggaatatgg gaaaacgtaa aagctccact   840
ccacaaaagt ttgtggggga aaagctcatg cgattcagct acccagatat tcactttgat   900
atgaacttaa catatgagaa ggaggctgag ctgatgcagt ctcatatgat ggaccaagcc   960
atcaacaatg caatcaccta ccttggagct gaggcccttc accctctgat gcagcacccg  1020
ccaagcacaa tcgctgaagt ggccccagtt ataagctcag cttattctca ggtctatcat  1080
ccaaatagga tagaaagacc cattagcagg gaaactgctg atagtcatga aacaacatg  1140
gatgccccca tctctctcat cagaccaaag agtcgacccc aggaaagaga ggcctctccc  1200
agcaatagct gcctggattc cactgactca gaaagcagcc atgatgacca ccagtcctac  1260
caaggacacc ctgccttaaa tcccaagagg aaacaaagcc cagcttacta gaaggaggat  1320
gtcaaagctt tggatactac caaggctcct aagggctctc tgaaggacat ctacaaggtc  1380
ttcaatggag aaggagaaca gattagggcc ttcaagtgtg agcactgccg agtcctttc   1440
ctagaccatg tcatgtacac cattcacatg ggttgccatg gctaccggga cccactggaa  1500
tgcaacatct gtggctacag aagccaggac cgttatgagt tttcatcaca cattgttcga  1560
ggggagcaca cattccacct cgacggtgga ggcggttcag gtggcggagg aagcggggga  1620
ggtggaagta tggtgtctaa aggagaagaa gataatatgg cttctctgcc tgctacacac  1680
gaactgcata ttttcggatc tattaatggc gtgatttcg atatggtggg acagggaaca  1740
ggaaaccccta acgatggata cgaagaactg aatctgaagt ctaccaaagg agatctgcaa  1800
ttctctcctt ggatcctggt ccctcacatt ggatatggat ccatcaata tctgccttac  1860
cctgacggaa tgtctccttt ccaagctgct atggtcgatg gctctggata tcaggtccac  1920
agaacaatgc aatttgaaga tggcgcctct ctgacagtga attacagata tacatacgaa  1980
```

-continued

```
ggctctcata ttaaaggcga agcccaagtg aaaggcacag gctttcctgc cgacggccct 2040
gtgatgacca actctctgac cgctgccgat tggtgcagat ctaagaagac ctaccctaat 2100
gataaaacca ttatctctac cttcaaatgg tcttacacaa caggcaatgg caagagatac 2160
agatctaccg ccagaaccac ctataccttt gctaagccta tggctgccaa ttacctgaaa 2220
aatcagccta tgtatgtgtt cagaaaaacc gaactgaaaa cctctaaaac cgaactgaat 2280
ttcaaagaat ggcaaaaggc tttcacagat gtgatgggaa tggatgaact gtacaagga 2340
agcggagcta caaattttag tcttcttaaa caagccggtg acgtggagga aaatcccggc 2400
ccaatggtga gcaagggcga ggccgtgatc aaggagttca tgcgcttcaa ggtgcacatg 2460
gagggcagca tgaacggcca cgagttcgag atcgagggcg agggcgaggg ccgcccctac 2520
gagggcaccc agaccgccaa gctgaaggtg accaaggcg ccccctgcc cttctcttgg 2580
gacatcctga gccccagtt catgtacggc agccgcgcct tcaccaagca cccgccgac 2640
atccccgact actacaagca gagcttcccc gagggcttca gtgggagcg cgtgatgaac 2700
ttcgaggacg gcggcgccgt gaccgtgacc caggacaccg cctggagga cggcaccctg 2760
atctacaagg tgaagctgcg cggcaccaac ttcccccccg acggccccgt gatgcagaag 2820
aagaccatgg gctgggaggc cagcaccgag cgcctgtacc ccgaggacgg cgtgctgaag 2880
ggcgacatca gatggccct cgcctgaag gacggcggca gatacctggc cgacttcaag 2940
accacctaca aggccaagaa gcccgtgcag atgcccggcg cctacaacgt ggaccgcaag 3000
ctggacatca ccagccacaa cgaggactac accgtggtgg agcagtacga gcgcagcgag 3060
ggccgccaca gcaccggcgg catggacgag ctgtacaagt ga 3102
```

```
SEQ ID NO: 3         moltype = DNA   length = 3051
FEATURE              Location/Qualifiers
source               1..3051
                     mol_type = other DNA
                     organism = synthetic construct
SEQUENCE: 3
atggaagata tacaaacaaa tgcggaactg aaaagcactc aggagcagtc tgtgcccgca 60
gaaagtgcag cggttttgaa tgactacagt ttaaccaaat ctcatgaaat ggaaaatgtg 120
gacagtggag aaggcccagc caatgaagat gaagacatag gagatgattc aatgaaagtg 180
aaagatgaat acagtgaaag agatgagaat gttttaaagt cagaacccat gggaaatgca 240
gaagagcctg aaatcccctta cagctattca agagaatata tgaatatga aacattaag 300
ttggagagac atgttgtctc attcgatagt agcaggccaa ccagtggaaa gatgaactgc 360
gatgtgtgtg gattatcctg catcagcttc aatgtcttaa tggttcataa gcgaagccat 420
actggtgaac gcccattcca gtgtaatcag tgtgggcat cttttactca gaaaggtaac 480
ctcctccgcc acattaaact gcacacaggg gaaaaacctt ttaagtgtca cctctgcaac 540
tatgcatgcc aaagaagaga tgcgctcacg gggcatctta ggacacattc tgtggagaaa 600
ccctacaaat gtgagttttg tggaaggagt tacaagcaga aagttccct tgaggagcac 660
aaggagcgct gccgtacatt tcttcagagc actgacccag ggacactgc aagtgcggag 720
gcaagacaca tcaaagcaga gatgggaagt gaaagagctc tcgtactgga cagattagca 780
agcaatgtgg caaaacgaaa agctcaatg cctcagaaat tcattggtga gaagcgccac 840
tgctttgatg tcaactataa ttcaagttac atgtatgaga aagagagtga gctcatacag 900
acccgcatga tggaccaagc catcaataac gccatcagct atcttggcgc gaagccctg 960
cgccccttgg tccagacacc gcctgctccc acctcggaga tggttccagt tatcagcagc 1020
atgtatccca tagccctcac ccgggctgag atgtcaaacg tgcccctca agagctgaa 1080
aagaaaagca tccaccttcc agagaagagc gtgccttctg agagaggcct ctctcccaac 1140
aatagtgacc acgaactcca ggactggaca aagaacgcca aatcacatc 1200
tatcagcaaa atcacatggt cctgtctcgg gccgcaatg gatgccact tctgaagag 1260
gttcccgct cttcgaact cctcaagccc ccgcccatct gcccaagaga ctccgtcaaa 1320
gtgatcaaca aggaaggga ggtgatggat gtgtatcggt gtgaccactg ccgcgtcctc 1380
ttcctggact atgtgatgtt cacgattcac atgggctgcc acggcttcg tgacccttc 1440
gagtgtaaca tgtgtggata tcgaagccat gatcggtatg agttctcgtc tcacatagcc 1500
agaggagaac acagagccct gctgaagctc gacggtggag gcggttcagg tggcggagga 1560
agcggggagg tgaagtat ggtgtctaaa ggagaagaag ataatatggc ttctctgcct 1620
gctacacacg aactgcatat tttcggatct attaatggcg tggattcga tatggtgga 1680
cagggaacag gaaaccctaa cgatggatac gaagaactga atctgaagtc taccaaagga 1740
gatctgcaat tctctccttg gatcctggtc cctcaatttg gatatggctt ccatcaatat 1800
ctgccttacc ctgacggaat gtctcctttc caagctgcta tggtcgatgg gtctggatat 1860
caggtccaca gaacaatgca atttgaagat ggcgcctctc tgacagtgaa ttacagatat 1920
acatacgaag gctctcatat taaaggcgaa gcccaagtga aggcacagg ctttcctgcc 1980
gacggccctg tgatgaccaa ctctctgacc gctgccgatt ggtgcagatc taagaagacc 2040
taccctaatg ataaaaccat tatctctacc ttcaaatgtc cttacacaac aggcaatgc 2100
aagagataca gatctaccgc cagaaccacc tataccttg ctaagcctat ggctgccaat 2160
tacctgaaaa atcagcctat gtatgtgttc agaaaaccg aactgaaaca ctctaaaacc 2220
gaactgaatt tcaagaatg gcaaaaggct ttcacagatg tgatgggaat ggatgaactg 2280
tacaaggga gcggagctac aaattttagt cttcttaaac aagccggtga cgtggaggaa 2340
aatcccggcc caatggtgag caagggcgag gccgtgatca aggagttcat gcgcttcaag 2400
gtgcacatgg agggcagcat gaacggccac gagttcgaga tcgagggcga gggcgagggg 2460
cgcccctacg agggcaccca gaccgccaag ctgaaggtga ccaagggcgg cccctgccc 2520
ttctcttggg acatcctgag ccccagttc atgtacggca gccgcgcctt caccaagcac 2580
cccgccgaca tccccgacta ctacaagcag agcttcccgg agggcttcaa gtgggagcgc 2640
gtgatgaact tcgaggacgg cggcgccgtg accgtgaccc aggacaccag cctggaggac 2700
ggcaccctga tctacaaggt gaagctgcgc ggcaccaact tcccccccga cggccccgtg 2760
atgcagaaga agaccatggg ctgggaggcc agcaccgagc gcctgtaccc cgaggacggc 2820
gtgctgaagg gcgacatcaa gatggcctc cgcctgaagg acggcggcag atacctggcc 2880
gacttcaaga ccacctacaa ggccaagaag cccgtgcaga tgcccggcgc ctacaacgtg 2940
gaccgcaagc tggacatcac cagccacaac gaggactaca ccgtggtgga gcagtacgag 3000
cgcagcgagg gccgccacag caccggcggc atggacgagc tgtacaagtg a 3051
```

```
SEQ ID NO: 4            moltype = DNA  length = 25
FEATURE                 Location/Qualifiers
source                  1..25
                        mol_type = other DNA
                        organism = synthetic construct
SEQUENCE: 4
tttctctgga accagtttca gaact                                            25

SEQ ID NO: 5            moltype = DNA  length = 141
FEATURE                 Location/Qualifiers
source                  1..141
                        mol_type = other DNA
                        organism = synthetic construct
SEQUENCE: 5
ttcctcacag tattgtgcag ggtcatcaag aaaatgctta gctaatcttc ttgaacagcc       60
gccagccgct cacgtccttc tctggaacca gtttcagaac ttttccaatt gcaatggtct     120
tacctagaaa tgaaatttta a                                               141

SEQ ID NO: 6            moltype = DNA  length = 24
FEATURE                 Location/Qualifiers
source                  1..24
                        mol_type = other DNA
                        organism = synthetic construct
SEQUENCE: 6
ggtttggcag taaagctagt taat                                             24

SEQ ID NO: 7            moltype = DNA  length = 21
FEATURE                 Location/Qualifiers
source                  1..21
                        mol_type = other DNA
                        organism = synthetic construct
SEQUENCE: 7
gtgaagtagg cttctgcagt c                                                21
```

ARYL COMPOUNDS AND PHARMACEUTICAL COMPOSITIONS THAT MODULATE IKZF2

CROSS-REFERENCE TO RELATED APPLICATIONS

This application is a continuation of U.S. patent application Ser. No. 17/860,922, filed on Jul. 8, 2022, which claims the benefit under 35 U.S.C. § 119(e) of United States Provisional Application Nos. 63/220,323, filed Jul. 9, 2021, and 63/314,992, filed Feb. 28, 2022, which are hereby incorporated by reference in their entirety.

REFERENCE TO AN ELECTRONIC SEQUENCE LISTING

The contents of the electronic sequence listing (78AW-334651-US2.xml; Size: 16,578 bytes; and Date of Creation: May 12, 2023) is herein incorporated by reference in its entirety.

FIELD

This disclosure provides for compounds and salts thereof that bind to cereblon, thereby modulating cereblon activity. In some embodiments, certain compounds described herein bind to cereblon, resulting in a reduction of cellular IKAROS Family Zinc Finger (IKZF) protein levels. In some embodiments, certain compounds described herein bind to cereblon, but do not result in a reduction of cellular IKZF protein levels. In some embodiments, compounds disclosed herein bind to cereblon, thereby initiating degradation of IKZF proteins (e.g., IKZF2). Also disclosed are pharmaceutical compositions comprising the compounds, or a salt (e.g., a pharmaceutically acceptable salt) thereof, and methods of using such compounds and/or their salts in the treatment of various IKZF2-mediated diseases or disorders.

STATE OF THE ART

IKAROS Family Zinc Finger 2 (IKZF2) (also known as Helios) is one of the five members of the Ikaros family of transcription factors found in mammals. IKZF2 is a critical regulator of T cell activity and function. Genetic deletion of Helios resulted in an enhanced anti-tumor immune response (Kim et al., Science 350:334-339 (2015)). Notably, Helios is highly expressed in regulatory T cells (Tregs) (Elkord et al., Expert Opin. Biol. Ther. 12:1423-1425 (2012)), a subpopulation of T cells that restricts the activity of effector T cells. Selective deletion of Helios in regulatory T cells resulted in both loss of suppressive activity and acquisition of effector T cell functions (Najagawa et al., Proc. Natl. Acad. Sci. USA 113:6248-6253 (2016); Yates et al., Proc. Natl. Acad. Sci. USA 115:2162-2167 (2018)). Therefore, Helios is a critical factor in restricting T cell effector function in Tregs.

Helios expression has also been reported to be upregulated in "exhausted" T cells, in the settings of both chronic viral infections (Crawford et al., Immunity 40:289-302 (2014), Doering et al., Immunity 371130-1144 (2012); Scott-Browne et al., Immunity 45:1327-1340 (2016)) and tumors (Martinez et al., Immunity 42:265-278 (2015); Mognol et al., Proc. Natl. Acad. Sci. USA 114:E2776-E2785 (2017); Pereira et al., J. Leukoc. Biol. 102:601-615 (2017); Singer et al., Cell 166:1500-1511 (2016); Schietinger et al., Immunity 45:389-401 (2016)), as well as in dysfunctional chimeric antigen receptor (CAR) T cells (Long et al., Nat. Med. 21:581-590 (2015)) 16). Overexpression or aberrant expression of Helios and various splice isoforms have been reported in several hematological malignancies, including T cell leukemias and lymphomas (Nakase at al., Exp. Hematol. 30:313-317 (2002); Tabayashi et al., Cancer Sci. 98:182-188 (2007); Asanuma et al., Cancer Sci. 104:1097-1106 (2013)). Moreover, knockdown of Helios in a model of mixed lineage leukemia (MLL)-driven myeloid leukemia potently suppressed proliferation and increased cell death (Park et al., J. Clin. Invest. 125:1286-1298 (2015); Park et al., Cell Stem Cell 24:153-165 (2019)).

Currently, anti-CTLA4 antibodies are used in the clinic to target Tregs in tumors. However, targeting CTLA4 often causes systemic activation of T-effector cells, resulting in excessive toxicity and limiting therapeutic utility. Up to 75% of patients treated with a combination of anti-PD1 and anti-CTLA4 have reported grade 3 or higher adverse events (National Cancer Institute, Division of Cancer Treatment & diagnosis, Common Terminology for Adverse Events (CTCAE), https://ctep.cancer.gov/protocolDevelopment/electronic_applications/ctc.htm).

There is a need for therapies that can target Tregs in tumors without causing systemic activation of T-effector cells. Accordingly, an IKZF2-specific modulator or degrader would have the potential to focus an enhanced immune response to areas within or near tumors providing a potentially more tolerable and less toxic therapy for the treatment of diseases mediated by IKZF2.

SUMMARY

Disclosed are compounds that bind to cereblon, thereby modulating cereblon activity. In some embodiments, certain compounds described herein bind to cereblon, resulting in a reduction of cellular IKAROS Family Zinc Finger (IKZF) protein levels. In some embodiments, certain compounds described herein bind to cereblon, but do not result in a reduction of cellular IKZF protein levels. In some embodiments, certain compounds disclosed herein bind to cereblon, thereby initiating degradation of IKZF proteins (e.g., IKZF2). Also disclosed are pharmaceutical compositions comprising the compounds, or a salt (e.g., a pharmaceutically acceptable salt) thereof, and methods of using such compounds and/or their salts in the treatment of various IKZF2-mediated diseases or disorders, including e.g., cancers.

In one embodiment, the disclosed compounds that bind to and modulate cereblon, and, in some instances, degrade IKZF2, are represented by formula I:

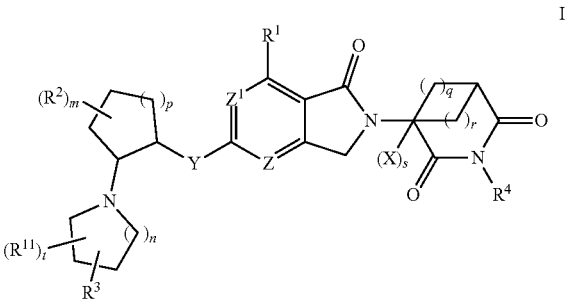

or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, n, p, q, r, s, and t of formula I are as defined in the detailed description and throughout the specification.

In one embodiment, the disclosed compounds that bind to and modulate cereblon, and, in some instances, degrade IKZF2, are represented by formula II:

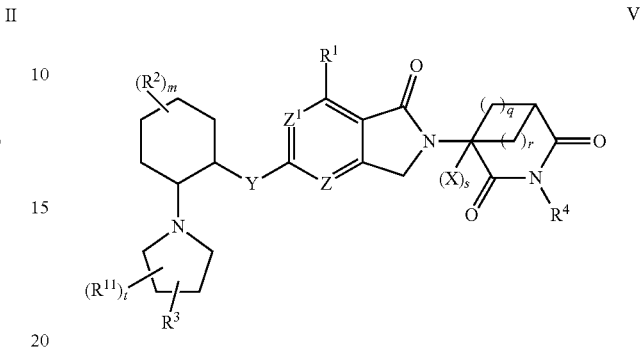

II or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, n, p, s, and t of formula II are as defined in the detailed description and throughout the specification.

In one embodiment, the disclosed compounds that bind to and modulate cereblon, and, in some instances, degrade IKZF2 are represented by formula III:

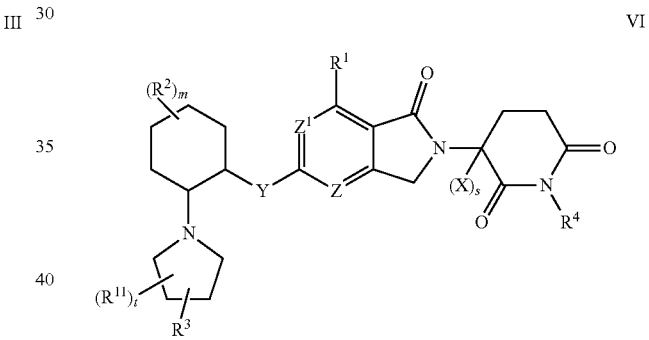

III or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, q, r, s, and t of formula III are as defined in the detailed description and throughout the specification.

In one embodiment, the disclosed compounds that bind to and modulate cereblon, and, in some instances, degrade IKZF2, are represented by formula IV:

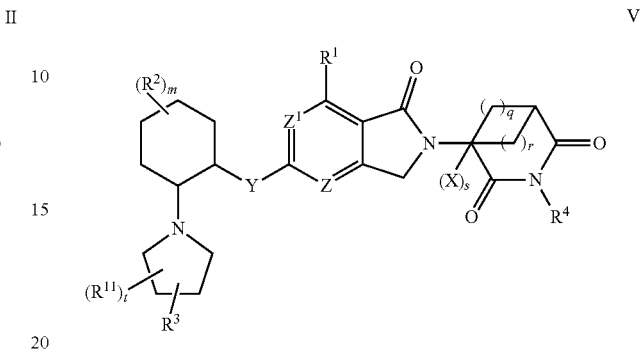

IV or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, s, and t of formula IV are as defined in the detailed description and throughout the specification.

In some embodiments, the disclosed compounds that bind to and modulate cereblon, and, in some instances, degrade IKZF2, are represented by formula V:

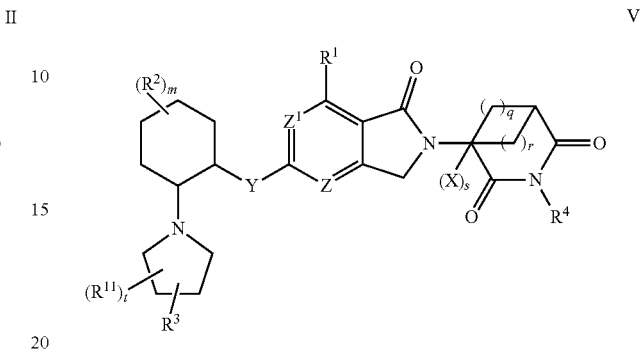

V or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, q, r, s, and t of formula V are as defined in the detailed description and throughout the specification.

In some embodiments, the disclosed compounds that bind to and modulate cereblon, and, in some instances, degrade IKZF2, are represented by formula VI:

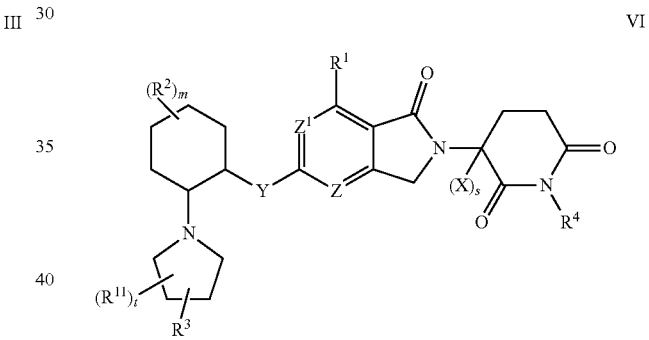

VI or a pharmaceutically acceptable salt, solvate, stereoisomer, and/or tautomer thereof, wherein $R^1$, $R^2$, $R^3$, $R^4$, $R^{11}$, X, Y, Z, $Z^1$, m, s, and t of formula VI are as defined in the detailed description and throughout the specification.

In one embodiment, provided is a compound of formula I or a sub-formulae thereof, which selectively modulates IKZF (e.g., over translation termination factor GSPT1 (G1 to S phase transition 1 protein)). In one embodiment, provided is a compound of formula I or a sub-formulae thereof, which selectively modulates IKZF2 over GSPT1.

In one embodiment, provided is a composition comprising a compound of formula I or any sub-formulae thereof, or a pharmaceutically acceptable salt, solvate, stereoisomer, or tautomer of a compound of formula I or any sub-formulae thereof. "Compound of formula I and sub-formulae thereof" refers to compounds of formula I, II or subformula thereof, III, IV, V, and VI as defined herein.

In one embodiment, this disclosure provides for a method for modulating cereblon, which method comprises contacting cereblon with an effective amount of a compound of formula I, II or subformula thereof, III, IV, V, or VI, or a pharmaceutically acceptable salt, solvate, stereoisomer, or tautomer thereof under conditions wherein cereblon is modulated.

In one embodiment, this disclosure provides for a method for degrading IKZF2, which method comprises contacting IKZF2 with an effective amount of a compound of formula I, II or subformula thereof, III, IV, V, or VI, or a pharmaceutically acceptable salt, solvate, stereoisomer, or tautomer thereof under conditions wherein IKZF2 is degraded.

In one embodiment, there is provided a method to degrade IKZF2 in a subject, which method comprises administering to said subject an effective amount of a compound of formula I, II or subformula thereof, III, IV, V, or VI, or a pharmaceutically acceptable salt, solvate, stereoisomer, or tautomer thereof, or administering to said subject a pharmaceutical composition comprising a pharmaceutically acceptable excipient and an effective amount of a compound of formula I, II or subformula thereof, III, IV, V, or VI, or a pharmaceutically acceptable salt, solvate, stereoisomer, or tautomer thereof.

Further provided is a method to treat cancer in a subject in need thereof, which method comprises selecting a subject whose cancer is mediated at least in part by IKZF2 and administering to said subject an effective amount of a compound of formula I, II or subformula thereof, III, IV, V, or VI, or a pharmaceutically acceptable salt, solvate, stereoisomer, and/or tautomer thereof, or administering to said subject a pharmaceutical composition comprising a pharmaceutically acceptable excipient and an effective amount of a compound of formula I, II or subformula thereof, III, IV, V, or VI, or a pharmaceutically acceptable salt, solvate, stereoisomer, or tautomer thereof.

DETAILED DESCRIPTION

This disclosure provides for compounds, pharmaceutical compositions comprising such compounds, and methods of using such compounds and compositions to treat diseases, disorders, or conditions mediated, at least in part, by IKZF2 transcription factors. However, prior to providing a detailed description of the disclosure, the following terms will first be defined. If not defined, terms used herein have their generally accepted scientific meaning.

Definitions

The terminology used herein is for the purpose of describing particular embodiments only and is not intended to be limiting of the disclosure. As used herein, the singular forms "a", "an" and "the" are intended to include the plural forms as well, unless the context clearly indicates otherwise.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line or a dashed line drawn through a line in a structure indicates a specified point of attachment of a group. Unless chemically or structurally required, no directionality or stereochemistry is indicated or implied by the order in which a chemical group is written or named.

The prefix "C$_{u-v}$" indicates that the following group has from u to v carbon atoms. For example, "C$_{1-6}$ alkyl" indicates that the alkyl group has from 1 to 6 carbon atoms.

The term "about" when used before a numerical designation, e.g., temperature, time, amount, concentration, and such other, including a range, indicates approximations which may vary by (+) or (−) 10%, 5%, 1%, or any subrange or subvalue there between. In one embodiment, the term "about" when used with regard to a dose amount means that the dose may vary by +/−10%.

"Comprising" or "comprises" is intended to mean that the compositions and methods include the recited elements, but not excluding others.

"Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed disclosure.

"Consisting of" shall mean excluding more than trace elements of other ingredients and substantial method steps. Embodiments defined by each of these transition terms are within the scope of this disclosure.

"Alkyl" refers to an unbranched or branched saturated hydrocarbon chain. As used herein, alkyl has 1 to 20 carbon atoms (i.e., C$_{1-20}$ alkyl), 1 to 12 carbon atoms (i.e., C$_{1-12}$ alkyl), 1 to 8 carbon atoms (i.e., C$_{1-8}$ alkyl), 1 to 6 carbon atoms (i.e., C$_{1-6}$ alkyl) or 1 to 4 carbon atoms (i.e., C$_{1-4}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e., —(CH$_2$)$_3$CH$_3$), sec-butyl (i.e., —CH(CH$_3$)CH$_2$CH$_3$), isobutyl (i.e., —CH$_2$CH(CH$_3$)$_2$), and tert-butyl (i.e., —C(CH$_3$)$_3$); and "propyl" includes n-propyl (i.e., —(CH$_2$)$_2$CH$_3$) and isopropyl (i.e., —CH(CH$_3$)$_2$).

Certain commonly used alternative chemical names may be used. For example, a divalent group such as a divalent "alkyl" group, a divalent "aryl" group, a divalent heteroaryl group, etc., may also be referred to as an "alkylene" group or an "alkylenyl" group (for example, methylenyl, ethylenyl, and propylenyl), an "arylene" group or an "arylenyl" group (for example, phenylenyl or napthylenyl, or quinolinyl for heteroarylene), respectively. Also, unless indicated explicitly otherwise, where combinations of groups are referred to herein as one moiety, e.g., arylalkyl or aralkyl, the last mentioned group contains the atom by which the moiety is attached to the rest of the molecule.

"Alkenyl" refers to an alkyl group containing at least one (e.g., 1-3, or 1) carbon-carbon double bond and having from 2 to 20 carbon atoms (i.e., C$_{2-20}$ alkenyl), 2 to 12 carbon atoms (i.e., C$_{2-12}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one (e.g., 1-3, or 1) carbon-carbon triple bond and having from 2 to 20 carbon atoms (i.e., C$_{2-20}$ alkynyl), 2 to 12 carbon atoms (i.e., C$_{2-12}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkoxy" refers to the group "alkyl-O—". Examples of alkoxy groups include, e.g., methoxy, ethoxy, n-propoxy, iso-propoxy, n-butoxy, tert-butoxy, sec-butoxy, n-pentoxy, n-hexoxy, and 1,2-dimethylbutoxy.

"Alkylthio" refers to the group "alkyl-S—". "Alkylsulfinyl" refers to the group "alkyl-S(O)—". "Alkylsulfonyl" refers to the group "alkyl-S(O)$_2$—". "Alkylsulfonylalkyl" refers to -alkyl-S(O)$_2$-alkyl.

"Acyl" refers to a group —C(O)R$^y$, wherein R$^y$ is hydrogen, alkyl, alkenyl, alkynyl, cycloalkyl, heterocyclyl, aryl, heteroalkyl, or heteroaryl; each of which may be unsubstituted or substituted, as defined herein. Examples of acyl include, e.g., formyl, acetyl, cyclohexylcarbonyl, cyclohexylmethyl-carbonyl, and benzoyl.

"Amido" refers to both a "C-amido" group which refers to the group —C(O)NR$^y$R$^z$ and an "N-amido" group which refers to the group —NR$^y$C(O)R$^z$, wherein R$^y$ and R$^z$ are independently hydrogen, alkyl, alkenyl, alkynyl, cycloalkyl, heterocyclyl, aryl, heteroalkyl, or heteroaryl; each of which may be unsubstituted or substituted, as defined herein, or R$^y$ and R$^z$ are taken together to form a cycloalkyl or heterocyclyl; each of which may be unsubstituted or substituted, as defined herein.

"Amino" refers to the group —NR$^y$R$^z$ wherein R$^y$ and R$^z$ are independently hydrogen, alkyl, alkenyl, alkynyl, cycloalkyl, heterocyclyl, aryl, heteroalkyl, or heteroaryl; each of which may be unsubstituted or substituted, as defined herein.

"Amidino" refers to —C(NR$^y$)(NR$^z$$_2$), wherein R$^y$ and R$^z$ are independently hydrogen, alkyl, alkenyl, alkynyl, cycloalkyl, heterocyclyl, aryl, heteroalkyl, or heteroaryl; each of which may be unsubstituted or substituted, as defined herein.

"Aryl" refers to an aromatic carbocyclic group having a single ring (e.g., monocyclic) or multiple rings (e.g., bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include, e.g., phenyl, naphthyl, fluorenyl, and anthryl. Aryl, however, does not encompass or overlap in any way with heteroaryl defined below. If one or more aryl groups are fused with a heteroaryl, the resulting ring system is heteroaryl regardless of point of attachment. If one or more aryl groups are fused with a heterocyclyl, the resulting ring system is heterocyclyl regardless of point of attachment. If one or more aryl groups are fused with a cycloalkyl, the resulting ring system is cycloalkyl regardless of point of attachment.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently hydrogen, alkyl, alkenyl, alkynyl, cycloalkyl, heterocyclyl, aryl, heteroalkyl, or heteroaryl; each of which may be unsubstituted or substituted, as defined herein.

"Carboxyl ester" or "ester" refer to both —OC(O)R$^x$ and —C(O)OR$^x$, wherein R$^x$ is alkyl, alkenyl, alkynyl, cycloalkyl, heterocyclyl, aryl, heteroalkyl, or heteroaryl; each of which may be unsubstituted or substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e., the cyclic group having at least one double bond) and carbocyclic fused ring systems having at least one sp$^3$ carbon atom (i.e., at least one non-aromatic ring). As used herein, cycloalkyl has from 3 to 20 ring carbon atoms (i.e., C$_{3-20}$ cycloalkyl), 3 to 14 ring carbon atoms (i.e., C$_{3-4}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Monocyclic groups include, for example, cyclopropyl, cyclobutyl, cyclopentyl, cyclohexyl, cycloheptyl, and cyclooctyl. Polycyclic groups include, for example, bicyclo[2.2.1]heptanyl, bicyclo[2.2.2]octanyl, adamantyl, norbornyl, decalinyl, 7,7-dimethyl-bicyclo[2.2.1]heptanyl, and the like. Further, the term cycloalkyl is intended to encompass any non-aromatic ring which may be fused to an aryl ring, regardless of the attachment to the remainder of the molecule. Still further, cycloalkyl also includes "spirocycloalkyl" when there are two positions for substitution on the same carbon atom, for example spiro[2.5]octanyl, spiro[4.5]decanyl, or spiro[5.5]undecanyl.

"Imino" refers to a group —C(NR$^y$)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be unsubstituted or substituted, as defined herein.

"Imido" refers to a group —C(O)NR$^y$C(O)R$^z$, wherein R$^y$ and R$^z$ are each independently hydrogen, alkyl, alkenyl, alkynyl, cycloalkyl, heterocyclyl, aryl, heteroalkyl, or heteroaryl; each of which may be unsubstituted or substituted, as defined herein.

"Halogen" or "halo" refers to atoms occupying group VIIA of the periodic table, such as fluoro, chloro, bromo, or iodo.

"Haloalkyl" refers to an unbranched or branched alkyl group as defined above, wherein one or more (e.g., 1 to 6 or 1 to 3) hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Haloalkoxy" refers to an alkoxy group as defined above, wherein one or more (e.g., 1 to 6 or 1 to 3) hydrogen atoms are replaced by a halogen.

"Hydroxyalkyl" refers to an alkyl group as defined above, wherein one or more (e.g., 1 to 6 or 1 to 3) hydrogen atoms are replaced by a hydroxy group.

"Heteroalkyl" refers to an alkyl group in which one or more of the carbon atoms (and any associated hydrogen atoms), excluding any terminal carbon atom(s), are each independently replaced with the same or different heteroatomic group, provided the point of attachment to the remainder of the molecule is through a carbon atom. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR$^y$—, —O—, —S—, —S(O)—, —S(O)$_2$—, and the like, wherein R$^y$ is hydrogen, alkyl, alkenyl, alkynyl, cycloalkyl, heterocyclyl, aryl, heteroalkyl, or heteroaryl; each of which may be unsubstituted or substituted, as defined herein. Examples of heteroalkyl groups include, e.g., ethers (e.g., —CH$_2$OCH$_3$, —CH(CH$_3$)OCH$_3$, —CH$_2$CH$_2$OCH$_3$, —CH$_2$CH$_2$OCH$_2$CH$_2$OCH$_3$, etc.), thioethers (e.g., —CH$_2$SCH$_3$, —CH(CH$_3$)SCH$_3$, —CH$_2$CH$_2$SCH$_3$, —CH$_2$CH$_2$SCH$_2$CH$_2$SCH$_3$, etc.), sulfones (e.g., —CH$_2$S(O)$_2$CH$_3$, —CH(CH$_3$)S(O)$_2$CH$_3$, —CH$_2$CH$_2$S(O)$_2$CH$_3$, —CH$_2$CH$_2$S(O)$_2$CH$_2$CH$_2$OCH$_3$, etc.), and amines (e.g., —CH$_2$NR$^y$CH$_3$, —CH(CH$_3$)NR$^y$CH$_3$, —CH$_2$CH$_2$NR$^y$CH$_3$, —CH$_2$CH$_2$NR$^y$CH$_2$CH$_2$NR$^y$CH$_3$, etc., where R$^y$ is hydrogen, alkyl, alkenyl, alkynyl, cycloalkyl, heterocyclyl, aryl, heteroalkyl, or heteroaryl; each of which may be unsubstituted or substituted, as defined herein). As used herein, heteroalkyl includes 2 to 10 carbon atoms, 2 to 8 carbon atoms, or 2 to 4 carbon atoms; and 1 to 3 heteroatoms, 1 to 2 heteroatoms, or 1 heteroatom.

"Heteroaryl" refers to an aromatic group having a single ring, multiple rings or multiple fused rings, with one or more ring heteroatoms independently selected from nitrogen, oxygen, and sulfur. As used herein, heteroaryl includes 1 to 20 ring carbon atoms (i.e., C$_{1-20}$ heteroaryl), 3 to 12 ring carbon atoms (i.e., C$_{3-12}$ heteroaryl), or 3 to 8 carbon ring atoms (i.e., C$_{3-8}$ heteroaryl), and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. In certain instances, heteroaryl includes 5-10 membered ring systems, 5-7 membered ring systems, or 5-6 membered ring systems, each independently having 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include, e.g., acridinyl, benzimidazolyl, benzothiazolyl, benzindolyl, benzofuranyl, benzothiazolyl, benzothiadiazolyl, benzonaphthofuranyl, benzoxazolyl, benzothienyl (benzothiophenyl), benzotriazolyl, benzo[4,6]imidazo[1,2-a]pyridyl, carbazolyl, cinnolinyl, dibenzofuranyl, dibenzothiophenyl, furanyl, isothiazolyl, imidazolyl, indazolyl, indolyl, indazolyl, isoindolyl, isoquinolyl, isoxazolyl, naphthyridinyl, oxadiazolyl, oxazolyl, 1-oxidopyridinyl, 1-oxidopyrimidinyl, 1-oxidopyrazinyl, 1-oxidopyridazinyl, phenazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, and triazinyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl"—used interchangeably with "heterocycloalkyl"—refers to a saturated or partially unsaturated cyclic alkyl group, with one or more ring heteroatoms independently selected from nitrogen, oxygen, and sulfur. The term "heterocyclyl" includes heterocycloalkenyl groups (i.e., the heterocyclyl group having at least one double bond), bridged-heterocyclyl groups, fused-heterocyclyl groups, and spiro-heterocyclyl groups. A heterocyclyl may be a single ring or multiple rings wherein the multiple rings may be fused, bridged, or spiro, and may comprise one or more (e.g., 1 to 3) oxo (=O) or N-oxide (—O—) moieties. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to a cycloalkyl, an aryl, or heteroaryl ring, regardless of the attachment to the remainder of the molecule. As used herein, heterocyclyl has 2 to 20 ring carbon atoms (i.e., C$_{2-20}$ heterocyclyl), 2 to 12 ring carbon atoms (i.e., C$_{2-12}$ heterocyclyl), 2 to 10 ring carbon atoms (i.e., C$_{2-10}$ heterocyclyl), 2 to 8 ring carbon atoms (i.e., C$_{2-8}$ heterocyclyl), 3 to 12 ring carbon atoms (i.e., C$_{3-12}$ heterocyclyl), 3 to 8 ring carbon atoms (i.e., C$_{3-8}$ heterocyclyl), or 3 to 6 ring carbon atoms (i.e., C$_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur, or oxygen. Examples of heterocyclyl groups include, e.g., azetidinyl, azepinyl, benzodioxolyl, benzo[b][1,4]dioxepinyl, 1,4-benzodioxanyl, benzopyranyl, benzodioxinyl, benzopyranonyl, benzofuranonyl, dioxolanyl, dihydropyranyl, hydropyranyl, thienyl[1,3]dithianyl, decahydroisoquinolyl, furanonyl, imidazolinyl, imidazolidinyl, indolinyl, indolizinyl, isoindolinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, oxiranyl, oxetanyl, phenothiazinyl, phenoxazinyl, piperidinyl, piperazinyl, 4-piperidonyl, pyrrolidinyl, pyrazolidinyl, quinuclidinyl, thiazolidinyl, tetrahydrofuryl, tetrahydropyranyl, trithianyl, tetrahydroquinolinyl, thiophenyl (i.e., thienyl), thiomorpholinyl, thiamorpholinyl, 1-oxo-thiomorpholinyl, and 1,1-dioxo-thiomorpholinyl. The term "heterocyclyl" also includes "spiroheterocyclyl" when there are two positions for substitution on the same carbon atom. Examples of the spiro-heterocyclyl rings include, e.g., bicyclic and tricyclic ring systems, such as oxabicyclo[2.2.2]octanyl, 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 4,5,6,7-tetrahydrothieno[2,3-c]pyridinyl, indolinyl, and isoindolinyl, where the heterocyclyl can be bound via either ring of the fused system. In some embodiments, the heterocycloalkyl may be substituted with oxo group(s) on a heteroatom (e.g., S=O, S(=O)$_2$).

"Oxime" refers to the group —CR$^y$(=NOH) wherein R$^y$ is hydrogen, alkyl, alkenyl, alkynyl, cycloalkyl, heterocyclyl, aryl, heteroalkyl, or heteroaryl; each of which may be unsubstituted or substituted, as defined herein.

"Oxo" refers to the moiety =O.

"Sulfonyl" refers to the group —S(O)$_2$R$^y$, where R$^y$ is hydrogen, alkyl, alkenyl, alkynyl, cycloalkyl, heterocyclyl, aryl, heteroalkyl, or heteroaryl; each of which may be unsubstituted or substituted, as defined herein. Examples of sulfonyl are methylsulfonyl, ethylsulfonyl, phenylsulfonyl, and toluenesulfonyl.

"Sulfinyl" refers to the group —S(O)R$^y$, where R$^y$ is hydrogen, alkyl, alkenyl, alkynyl, cycloalkyl, heterocyclyl, aryl, heteroalkyl, or heteroaryl; each of which may be unsubstituted or substituted, as defined herein. Examples of sulfinyl are methylsulfinyl, ethylsulfinyl, phenylsulfinyl, and toluenesulfinyl.

"Sulfonamido" refers to the groups —SO$_2$NR$^y$R$^z$ and —NR$^y$SO$_2$R$^z$, where R$^y$ and R$^z$ are each independently hydrogen, alkyl, alkenyl, alkynyl, cycloalkyl, heterocyclyl, aryl, heteroalkyl, or heteroaryl; each of which may be unsubstituted or substituted, as defined herein.

The terms "optional" or "optionally" means that the subsequently described event or circumstance may or may not occur and that the description includes instances where said event or circumstance occurs and instances in which it does not. Also, the term "optionally substituted" refers to any one or more (e.g., 1 to 5 or 1 to 3) hydrogen atoms on the designated atom or group may or may not be replaced by a moiety other than hydrogen.

The term "substituted" used herein means any of the above groups (i.e., alkyl, alkenyl, alkynyl, alkylene, alkoxy, haloalkyl, haloalkoxy, cycloalkyl, aryl, heterocyclyl, heteroaryl, and/or heteroalkyl) wherein at least one (e.g., 1 to 5 or 1 to 3) hydrogen atom is replaced by a bond to a non-hydrogen atom such as, but not limited to alkyl, alkenyl, alkynyl, alkoxy, alkylthio, acyl, amido, amino, amidino, aryl, aralkyl, azido, carbamoyl, carboxyl, carboxyl ester, cyano, cycloalkyl, cycloalkylalkyl, guanadino, halo, haloalkyl, haloalkoxy, hydroxyalkyl, heteroalkyl, heteroaryl, heteroarylalkyl, heterocyclyl, heterocyclylalkyl, —NHNH$_2$, =NNH$_2$, imino, imido, hydroxy, oxo, oxime, nitro, sulfonyl, sulfinyl, alkylsulfonyl, alkylsulfinyl, thiocyanate, —S(O)OH, —S(O)$_2$OH, sulfonamido, thiol, thioxo, N-oxide, or —Si(R$^y$)$_3$, wherein each R$^y$ is independently hydrogen, alkyl, alkenyl, alkynyl, heteroalkyl, cycloalkyl, aryl, heteroaryl, or heterocyclyl.

In certain embodiments, "substituted" includes any of the above alkyl, alkenyl, alkynyl, cycloalkyl, heterocyclyl, aryl, or heteroaryl groups in which one or more (e.g., 1 to 5 or 1 to 3) hydrogen atoms are independently replaced with deuterium, halo, cyano, nitro, azido, oxo, alkyl, alkenyl, alkynyl, haloalkyl, cycloalkyl, heterocyclyl, aryl, heteroaryl, —NR$^g$R$^h$, —NR$^g$C(O)R$^h$, —NR$^g$C(O)NR$^g$R$^h$, —NR$^g$C(O)OR$^h$, —NR$^g$S(O)$_{1-2}$R$^h$, —C(O)R$^g$, —C(O)OR$^g$, —OC(O)OR$^g$, —OC(O)R$^g$, —C(O)NR$^g$R$^h$, —OC(O)NR$^g$R$^h$, —OR$^g$, —SR$^g$, —S(O)R$^g$, —S(O)$_2$R$^g$, —OS(O)$_{1-2}$R$^g$, —S(O)$_{1-2}$OR$^g$, —NR$^g$S(O)$_{1-2}$NR$^g$R$^h$, =NSO$_2$R$^g$, =NOR$^g$, —S(O)$_{1-2}$ NR$^g$R$^h$, —SF$_5$, —SCF$_3$, or —OCF$_3$. In certain embodiments, "substituted" also means any of the above groups in which one or more (e.g., 1 to 5 or 1 to 3) hydrogen atoms are replaced with —C(O)R$^g$, —C(O)OR$^g$, —C(O)NR$^g$R$^h$, —CH$_2$SO$_2$R$^g$, or —CH$_2$SO$_2$NR$^g$R$^h$. In the foregoing, R$^g$ and R$^h$ are the same or different and independently hydrogen, alkyl, alkenyl, alkynyl, alkoxy, thioalkyl, aryl, aralkyl, cycloalkyl, cycloalkylalkyl, haloalkyl, heterocyclyl, heterocyclylalkyl, heteroaryl, and/or heteroarylalkyl. In certain embodiments, "substituted" also means any of the above groups in which one or more (e.g., 1 to 5 or 1 to 3) hydrogen atoms are replaced by a bond to an amino, cyano, hydroxy, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, and/or heteroarylalkyl, or two of R$^g$ and R$^h$ are taken together with the atoms to which they are attached to form a heterocyclyl ring unsubstituted or substituted with oxo, halo, or alkyl unsubstituted or substituted with oxo, halo, amino, hydroxy, or alkoxy.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein.

In certain embodiments, as used herein, the phrase "one or more" refers to one to five. In certain embodiments, as used herein, the phrase "one or more" refers to one to three.

Any compound or structure given herein, is also intended to represent unlabeled forms as well as isotopically labeled forms of the compounds. These forms of compounds may also be referred to as "isotopically enriched analogs." Isotopically labeled compounds have structures depicted herein, except that one or more atoms are replaced by an atom having a selected atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. Various isotopically labeled compounds of the present disclosure, for example those into which radioactive isotopes such as $^3$H and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The term "isotopically enriched analogs" includes "deuterated analogs" of compounds described herein in which one or more hydrogens is/are replaced by deuterium, such as a hydrogen on a carbon atom. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to absorption, distribution, metabolism, and excretion (ADME). Substitution with heavier isotopes such as deuterium may afford certain therapeutic advantages resulting from greater metabolic stability, for example increased in vivo half-life, reduced dosage requirements, and/or an improvement in therapeutic index. An $^{18}$F, $^3$H, or $^{11}$C labeled compound may be useful for PET or SPECT or other imaging studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in a compound described herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino, and/or carboxyl groups, or groups similar thereto.

Provided are also or a pharmaceutically acceptable salt, isotopically enriched analog, deuterated analog, stereoisomer, mixture of stereoisomers, and prodrugs of the compounds described herein. "Pharmaceutically acceptable" or "physiologically acceptable" refer to compounds, salts, compositions, dosage forms, and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound and which are not biologically or otherwise undesirable. "Pharmaceutically acceptable salts" or "physiologically acceptable salts" include, for example, salts with inorganic acids, and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic or organic acids. Salts derived from inorganic acids include, e.g., hydrochloric acid, hydrobromic acid, sulfuric acid, nitric acid, phosphoric acid, and the like. Salts derived from organic acids include, e.g., acetic acid, propionic acid, gluconic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic or organic bases. Salts derived from inorganic bases include, by way of example only, sodium, potassium, lithium, aluminum, ammonium, calcium, and magnesium salts. Salts derived from organic bases include, but are not limited to, salts of primary, secondary, and tertiary amines, such as alkyl amines (i.e., $NH_2$(alkyl)), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN(substituted\ alkyl)_2$), tri(substituted alkyl) amines (i.e., $N(substituted\ alkyl)_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN(substituted\ alkenyl)_2$), tri(substituted alkenyl) amines (i.e., $N(substituted\ alkenyl)_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2$(aryl), $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Some of the compounds exist as tautomers. Tautomers are in equilibrium with one another. For example, amide containing compounds may exist in equilibrium with imidic acid tautomers. Regardless of which tautomer is shown and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and/or fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

A "stereoisomer" refers to a compound made up of the same atoms bonded by the same bonds but having different three-dimensional structures, which are not interchangeable. The present disclosure contemplates various stereoisomers, or mixtures thereof, and includes "enantiomers," which refers to two stereoisomers whose molecules are nonsuperimposeable mirror images of one another.

"Diastereomers" are stereoisomers that have at least two asymmetric atoms, but which are not mirror-images of each other.

Relative centers of the compounds as depicted herein are indicated graphically using the "thick bond" style (bold or parallel lines) and absolute stereochemistry is depicted using wedge bonds (bold or parallel lines).

"Prodrugs" means any compound which releases an active parent drug according to a structure described herein in vivo when such prodrug is administered to a mammalian subject. Prodrugs of a compound described herein are prepared by modifying functional groups present in the compound described herein in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds described herein wherein a hydroxy, amino, carboxyl, or sulfhydryl group in a compound described herein is bonded to any group that may be cleaved in vivo to regenerate the free hydroxy, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds described herein, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs," ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

Compounds

In some embodiments, provided herein is a compound which binds to and modulates cereblon, and, in some instances, degrades IKZF2, of formula I:

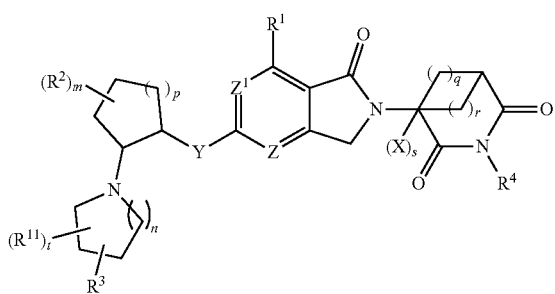

or a pharmaceutically acceptable salt, solvate, stereoisomer, and/or tautomer thereof,
wherein:
m, n, and p are independently zero, one, two, or three;
q is one, two, or three;
r is zero, one, or two;
s is zero when r is not zero and is one when r is zero;
t is zero or one;
X is hydrogen, deuterium, or fluoro;
Y is oxygen or NR where R is hydrogen or $C_1$-$C_4$ alkyl;
Z and $Z^1$ are each independently $CR^1$ or N;
each $R^1$ is independently selected from hydrogen, amino, ($C_1$-$C_4$ alkyl)amino unsubstituted or substituted with from one to three $R^5$ substituents, di-($C_1$-$C_4$ alkyl) amino unsubstituted or substituted with from one to three $R^5$ substituents on each alkyl group, cyano, halo, hydroxyl, $C_1$-$C_4$ alkyl unsubstituted or substituted with from one to three $R^5$ substituents, and $C_1$-$C_4$ alkoxy unsubstituted or substituted with from one to three $R^5$ substituents; or
when $Z^1$ is $CR^1$, then two adjacent $R^1$ together with the carbon atoms to which they are attached form a $C_3$-$C_7$ cycloalkyl, a $C_6$-$C_{10}$ aryl, a 4- to 7-membered heterocycloalkenyl having from one to three heteroatoms selected from oxygen, nitrogen, or sulfur, or a 5- to 6-membered heteroaryl having 1 to 3 heteroatoms selected from oxygen, nitrogen, and sulfur wherein each of said cycloalkyl, heterocycloalkenyl, aryl, and heteroaryl are independently substituted with one to three $R^6$ groups; each $R^2$ is independently selected from cyano, halo, hydroxyl, amino, $C_1$-$C_4$ alkylamino unsubstituted or substituted with from one to three $R^5$ substituents, di-($C_1$-$C_4$ alkyl)amino unsubstituted or substituted with from one to three $R^5$ substituents on each alkyl group, $C_1$-$C_4$ alkyl unsubstituted or substituted with from one to three $R^5$ substituents, and $C_1$-$C_4$ alkoxy unsubstituted or substituted with from one to three $R^5$ substituents;
$R^3$ is $C_6$-$C_{10}$ aryl unsubstituted or substituted with 1 to 3 $R^7$ substituents;
$R^4$ is selected from hydrogen and —$CH_2$—$OR^8$ where $R^8$ is C(O)—$R^9$ or —P(O)($OR^{10}$)$_2$, where $R^9$ is $C_1$-$C_4$ alkyl, or $C_1$-$C_4$ alkoxy, and where each $R^{10}$ is independently H or $C_1$-$C_4$ alkyl;
each $R^5$ is independently hydrogen, amino, ($C_1$-$C_4$ alkyl) amino, di-($C_1$-$C_4$ alkyl)amino, cyano, halo, hydroxyl, or $C_1$-$C_4$ alkoxy;
each $R^6$ is independently selected from amino, ($C_1$-$C_4$ alkyl)amino, di-($C_1$-$C_4$ alkyl)amino, cyano, halo, hydroxyl, and oxo;
each $R^7$ is independently selected from amino, $C_1$-$C_4$ alkyl unsubstituted or substituted with 1 to 3 halo, $C_1$-$C_4$ alkoxy unsubstituted or substituted with 1 to 3 halo, ($C_1$-$C_4$ alkyl)amino, di-($C_1$-$C_4$ alkyl)amino, cyano, halo, hydroxyl, nitro, oxo, $C_5$-$C_6$ heteroaryl having from 1 to 3 heteroatoms selected from O, NR, and/or S, 4- to 7-membered heterocycloalkyl having from 1 to 3 heteroatoms selected from oxygen, nitrogen, and/or sulfur, and —C(O)$CH_3$; and
$R^{11}$ is hydroxyl, halo, or cyano.

In some embodiments, provided herein is a compound which binds to and modulates cereblon, and, in some instances, degrades IKZF2, of formula I:

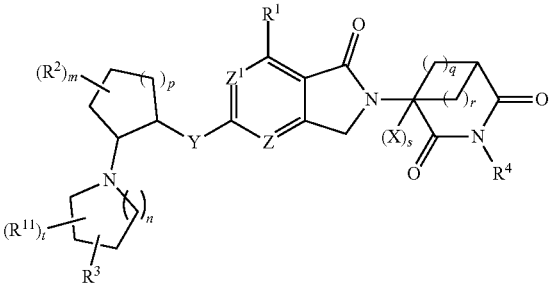

or a pharmaceutically acceptable salt, solvate, stereoisomer, and/or tautomer thereof wherein $R^1$, $R^2$, $R^3$, $R^4$, $R^{11}$, X, Y, Z, $Z^1$, m, n, p, q, r, s, and t are as defined herein.

In some embodiments, the compound which binds to and modulates cereblon, and, in some instances, degrades IKZF2, of formula I has the structure of formula II:

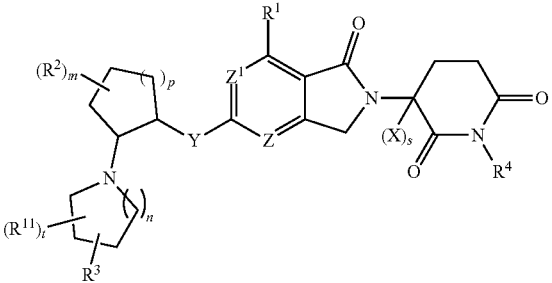

or a pharmaceutically acceptable salt, solvate, stereoisomer, and/or tautomer thereof wherein $R^1$, $R^2$, $R^3$, $R^4$, $R^{11}$, X, Y, Z, $Z^1$, m, n, p, s, and t are as defined herein.

In some embodiments, the compound which binds to and modulates cereblon, and, in some instances, degrades IKZF2, of formula I has the structure of formula II-1:

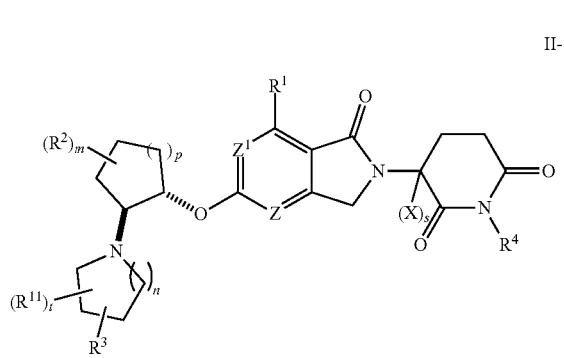

II-1 or a pharmaceutically acceptable salt, solvate, stereoisomer, and/or tautomer thereof wherein $R^1$, $R^2$, $R^3$, $R^4$, $R^{11}$, X, Y, Z, $Z^1$, m, n, p, s, and t are as defined herein.

In some embodiments, the compound which binds to and modulates cereblon, and, in some instances, degrades IKZF2, of formula I has the structure of formula II-2:

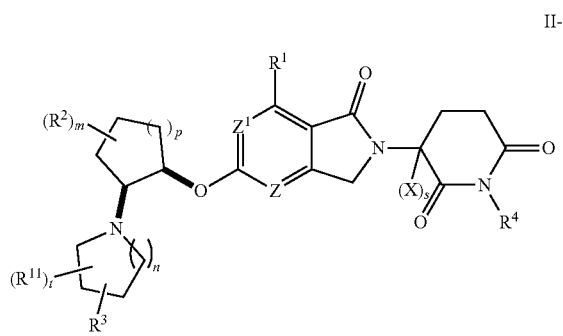

II-2 or a pharmaceutically acceptable salt, solvate, stereoisomer, and/or tautomer thereof wherein $R^1$, $R^2$, $R^3$, $R^4$, $R^{11}$, X, Y, Z, $Z^1$, m, n, p, s, and t are as defined herein.

In some embodiments, the compound which binds to and modulates cereblon, and, in some instances, degrades IKZF2, of formula I has the structure of formula II-A:

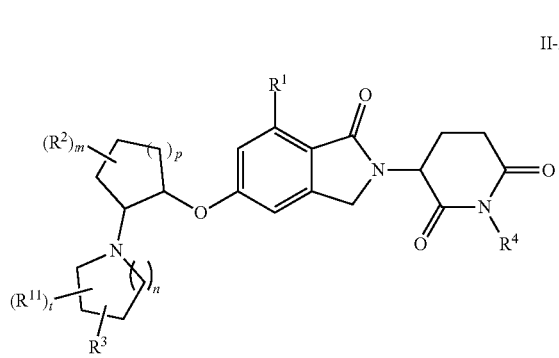

II-A or a pharmaceutically acceptable salt, solvate, stereoisomer, and/or tautomer thereof wherein $R^1$, $R^2$, $R^3$, $R^4$, $R^{11}$, m, n, p, and t are each independently as defined herein.

In some embodiments, the compound which binds to and modulates cereblon, and, in some instances, degrades IKZF2, of formula I has the structure of formula II-A1:

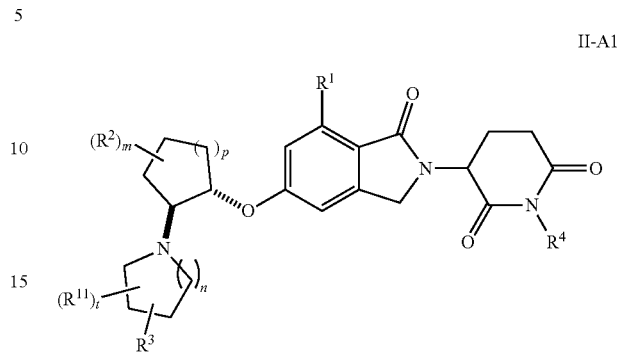

II-A1 or a pharmaceutically acceptable salt, solvate, stereoisomer, and/or tautomer thereof wherein $R^1$, $R^2$, $R^3$, $R^4$, $R^{11}$, m, n, p, and t are each independently as defined herein.

In some embodiments, the compound which binds to and modulates cereblon, and, in some instances, degrades IKZF2, of formula I has the structure of formula II-A2:

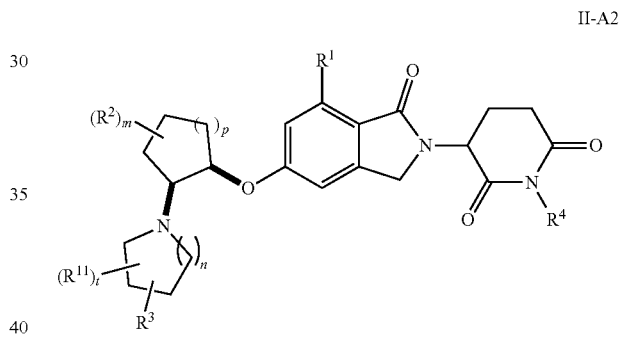

II-A2 or a pharmaceutically acceptable salt, solvate, stereoisomer, and/or tautomer thereof wherein $R^1$, $R^2$, $R^3$, $R^4$, $R^{11}$, m, n, p, and t are each independently as defined herein.

In some embodiments, the compound which binds to and modulates cereblon, and, in some instances, degrades IKZF2, of formula I has the structure of formula II-B:

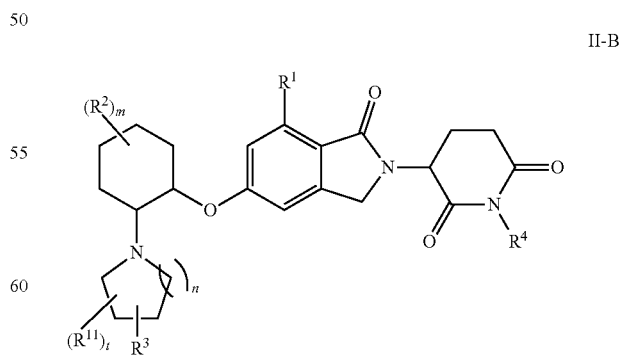

II-B or a pharmaceutically acceptable salt, solvate, stereoisomer, and/or tautomer thereof wherein $R^1$, $R^2$, $R^3$, $R^4$, $R^{11}$, m, n, and t are each independently as defined herein.

In some embodiments, the compound which binds to and modulates cereblon, and, in some instances, degrades IKZF2, of formula I has the structure of formula II-B1:

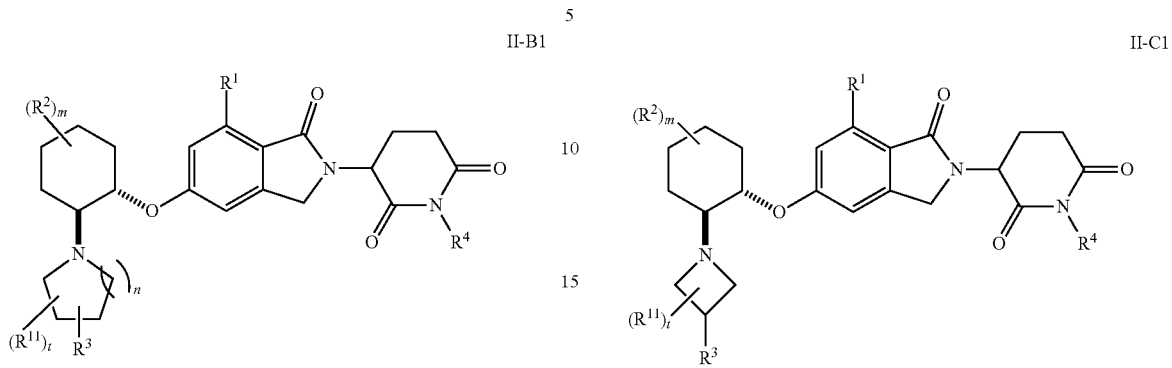

II-B1 or a pharmaceutically acceptable salt, solvate, stereoisomer, and/or tautomer thereof wherein $R^1$, $R^2$, $R^3$, $R^4$, $R^{11}$, m, n, and t are each independently as defined herein.

In some embodiments, the compound which binds to and modulates cereblon, and, in some instances, degrades IKZF2, of formula I has the structure of formula II-B2:

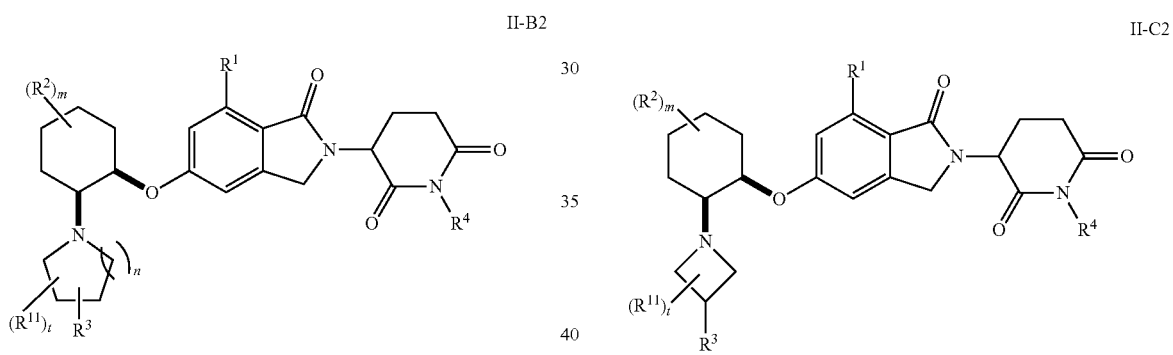

II-B2 or a pharmaceutically acceptable salt, solvate, stereoisomer, and/or tautomer thereof wherein $R^1$, $R^2$, $R^3$, $R^4$, $R^{11}$, m, n, and t are each independently as defined herein.

In some embodiments, the compound which binds to and modulates cereblon, and, in some instances, degrades IKZF2, of formula I has the structure of formula II-C:

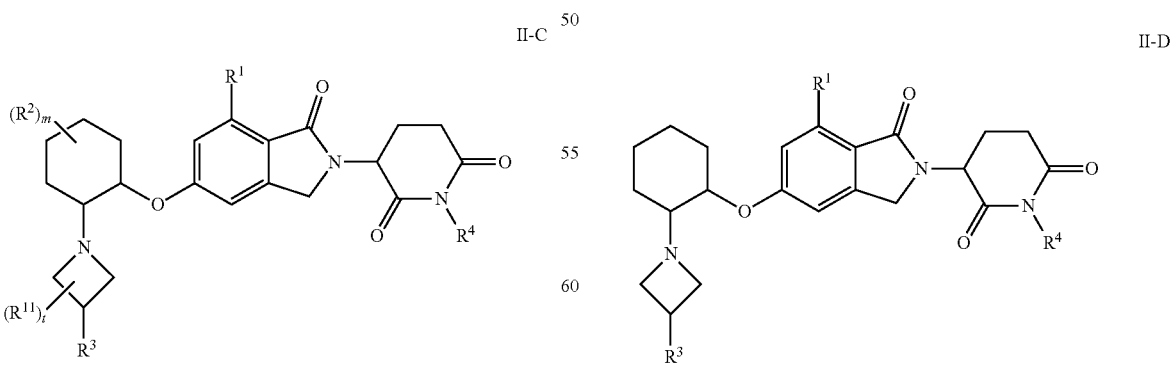

II-C or a pharmaceutically acceptable salt, solvate, stereoisomer, and/or tautomer thereof wherein $R^1$, $R^2$, $R^3$, $R^4$, $R^{11}$, m, and t are each independently as defined herein.

In some embodiments, the compound which binds to and modulates cereblon, and, in some instances, degrades IKZF2, of formula I has the structure of formula II-C1:

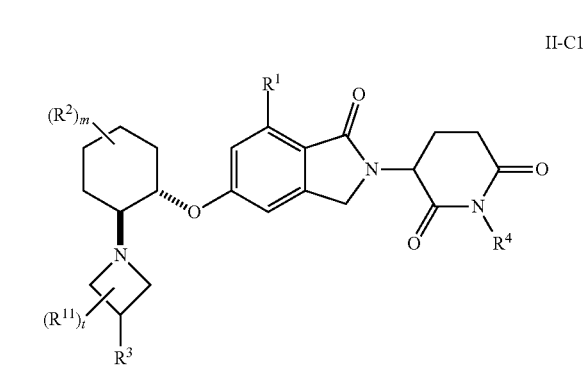

II-C1 or a pharmaceutically acceptable salt, solvate, stereoisomer, and/or tautomer thereof wherein $R^1$, $R^2$, $R^3$, $R^4$, $R^{11}$, m, and t are each independently as defined herein.

In some embodiments, the compound which binds to and modulates cereblon, and, in some instances, degrades IKZF2, of formula I has the structure of formula II-C2:

II-C2 or a pharmaceutically acceptable salt, solvate, stereoisomer, and/or tautomer thereof wherein $R^1$, $R^2$, $R^3$, $R^4$, $R^{11}$, m, and t are each independently as defined herein.

In some embodiments, the compound which binds to and modulates cereblon, and, in some instances, degrades IKZF2, of formula I has the structure of formula II-D:

II-D or a pharmaceutically acceptable salt, solvate, stereoisomer, and/or tautomer thereof wherein $R^1$, $R^3$, and $R^4$ are each independently as defined herein.

In some embodiments, the compound which binds to and modulates cereblon, and, in some instances, degrades IKZF2, of formula I has the structure of formula II-D1:

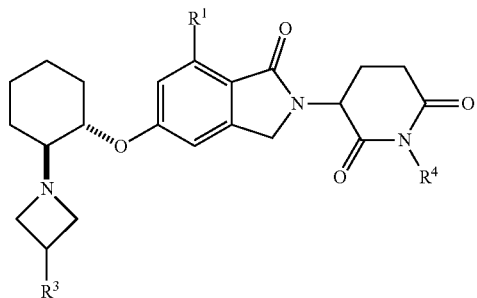

II-D1 or a pharmaceutically acceptable salt, solvate, stereoisomer, and/or tautomer thereof wherein $R^1$, $R^3$, and $R^4$ are each independently as defined herein.

In some embodiments, the compound which binds to and modulates cereblon, and, in some instances, degrades IKZF2, of formula I has the structure of formula II-D2:

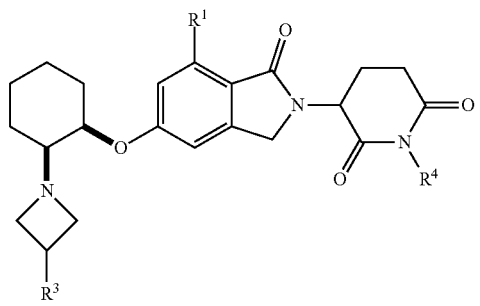

II-D2 or a pharmaceutically acceptable salt, solvate, stereoisomer, and/or tautomer thereof wherein $R^1$, $R^3$, and $R^4$ are each independently as defined herein.

In some embodiments, the compound which binds to and modulates cereblon, and, in some instances, degrades IKZF2, of formula I has the structure of formula II-E:

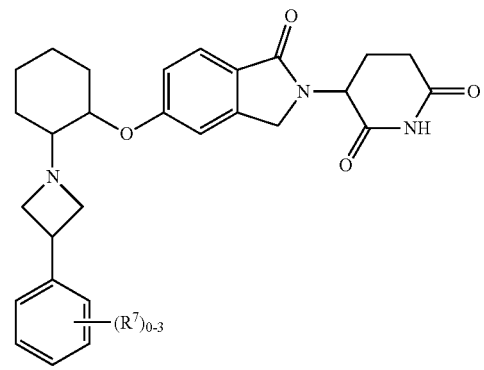

II-E or a pharmaceutically acceptable salt, solvate, stereoisomer, and/or tautomer thereof wherein $R^7$ is as defined herein.

In some embodiments, the compound which binds to and modulates cereblon, and, in some instances, degrades IKZF2, of formula I has the structure of formula II-E1:

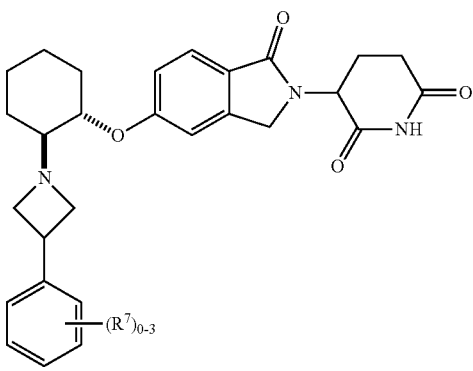

II-E1 or a pharmaceutically acceptable salt, solvate, stereoisomer, and/or tautomer thereof wherein $R^7$ is as defined herein.

In some embodiments, the compound which binds to and modulates cereblon, and, in some instances, degrades IKZF2, of formula I has the structure of formula II-E2:

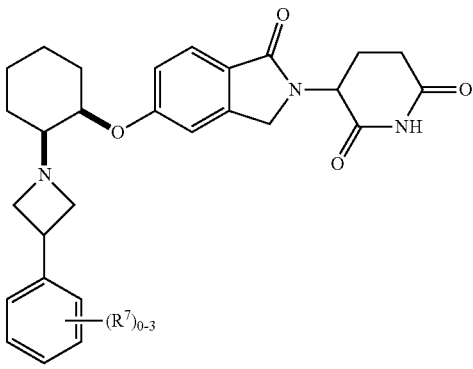

II-E2 or a pharmaceutically acceptable salt, solvate, stereoisomer, and/or tautomer thereof wherein $R^7$ is as defined herein.

In some embodiments, in a compound of formula I or formula II, or a pharmaceutically acceptable salt, solvate, stereoisomer, and/or tautomer thereof, X is hydrogen or deuterium. In some embodiments, X is hydrogen. In some embodiments, X is deuterium. In some embodiments, X is tritium.

In some embodiments, in a compound of formula I or formula II, or a pharmaceutically acceptable salt, solvate, stereoisomer, and/or tautomer thereof, X is fluoro.

In some embodiments, in a compound of formula I or formula II, or a pharmaceutically acceptable salt, solvate, stereoisomer, and/or tautomer thereof, p is 1. In some embodiments, in a compound of formula I or formula II, or a pharmaceutically acceptable salt, solvate, stereoisomer, and/or tautomer thereof, p is 2. In some embodiments, in a compound of formula I or formula II, or a pharmaceutically acceptable salt, solvate, stereoisomer, and/or tautomer thereof, p is 3.

In some embodiments, in a compound of formula I or formula II or any subformula thereof, or a pharmaceutically acceptable salt, solvate, stereoisomer, and/or tautomer thereof, n is 0. In some embodiments, in a compound of formula I or formula II, or a pharmaceutically acceptable salt, solvate, stereoisomer, and/or tautomer thereof, n is 1. In some embodiments, in a compound of formula I or formula II, or a pharmaceutically acceptable salt, solvate, stereoisomer, and/or tautomer thereof, n is 2. In some embodiments, in a compound of formula I or formula II, or a pharmaceutically acceptable salt, solvate, stereoisomer, and/or tautomer thereof, n is 3.

In some embodiments, in a compound of formula I or formula II or any subformula thereof, or a pharmaceutically acceptable salt, solvate, stereoisomer, and/or tautomer thereof, $R^4$ is hydrogen. In some embodiments, in a compound of formula I or formula II, or a pharmaceutically acceptable salt, solvate, stereoisomer, and/or tautomer thereof, $R^4$ is —$CH_2$—O—C(O)—$R^9$ or —$CH_2$—O—P(O)(OR$^1$)$_2$. In some embodiments, in a compound of formula I or formula II, or a pharmaceutically acceptable salt, solvate, stereoisomer, and/or tautomer thereof, $R^4$ is —$CH_2$—O—C(O)—$CH_3$, —$CH_2$—O—C(O)—$CH_2CH_3$, —$CH_2$—O—C(O)—$CH_2CH_2CH_3$, or —$CH_2$—O—C(O)—CH(CH$_3$)$_2$. In some embodiments, in a compound of formula I or formula II or any subformula thereof, or a pharmaceutically acceptable salt, solvate, stereoisomer, and/or tautomer thereof, $R^4$ is —$CH_2$—O—P(O)(OCH$_3$)$_2$, —$CH_2$—O—P(O)(OCH$_2$CH$_3$)$_2$, —$CH_2$—O—P(O)(OCH$_2$CH$_2$CH$_3$)$_2$, or —$CH_2$—O—P(O)(O(CH(CH$_3$)$_2$)$_2$.

In some embodiments, in a compound of formula I or formula II, or a pharmaceutically acceptable salt, solvate, stereoisomer, and/or tautomer thereof, Z and $Z^1$ are each C—$R^1$. In some of such embodiments, Z and $Z^1$ are each C—H. In some embodiments, in a compound of formula I or formula II, or a pharmaceutically acceptable salt, solvate, stereoisomer, and/or tautomer thereof, Z and $Z^1$ are each C—$R^1$, wherein one $R^1$ is a halo, such as bromo, fluoro, or chloro, and the other $R^1$ is hydrogen. In some embodiments, in a compound of formula I or formula II, or a pharmaceutically acceptable salt, solvate, stereoisomer, and/or tautomer thereof, Z and $Z^1$ are each N. In some embodiments, in a compound of formula I or formula II, or a pharmaceutically acceptable salt, solvate, stereoisomer, and/or tautomer thereof, one of Z or $Z^1$ is C—$R^1$ and the other of Z or $Z^1$ is N. In some of such embodiments, one of Z or $Z^1$ is C—H and the other of Z or $Z^1$ is N. In some embodiments, in a compound of formula I or formula II, or a pharmaceutically acceptable salt, solvate, stereoisomer, and/or tautomer thereof, $R^1$ is H. In some embodiments, in a compound of formula I or formula II, or a pharmaceutically acceptable salt, solvate, stereoisomer, and/or tautomer thereof, one $R^1$ is H, and the other $R^1$ is F. In some embodiments, in a compound of formula I or formula II, or a pharmaceutically acceptable salt, solvate, stereoisomer, and/or tautomer thereof, one $R^1$ is H, and the other $R^1$ is CL. In some embodiments, Z and $Z^1$ are each CH and $R^1$ is hydrogen.

In some embodiments, in a compound of formula I or formula II or any subformula thereof, or a pharmaceutically acceptable salt, solvate, stereoisomer, and/or tautomer thereof, m is zero. In some embodiments, in a compound of formula I or formula II, or a pharmaceutically acceptable salt, solvate, stereoisomer, and/or tautomer thereof, m is 1. In some embodiments, in a compound of formula I or formula II, or a pharmaceutically acceptable salt, solvate, stereoisomer, and/or tautomer thereof, m is 2.

In some embodiments, in a compound of formula I or formula II, or a pharmaceutically acceptable salt, solvate, stereoisomer, and/or tautomer thereof, q is 1, and r is 1. In some embodiments, in a compound of formula I or formula II, or a pharmaceutically acceptable salt, solvate, stereoisomer, and/or tautomer thereof, q is 1 and r is 0.

In some embodiments, a compound of formula I which binds to and modulates cereblon, and, in some instances, degrades IKZF2, has the structure of formula III:

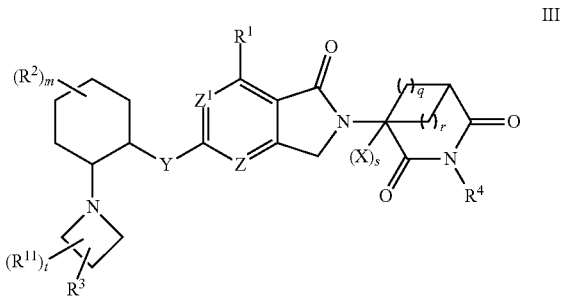

III or a pharmaceutically acceptable salt, solvate, stereoisomer, and/or tautomer thereof wherein $R^1$, $R^2$, $R^3$, $R^4$, $R^{11}$, X, Y, Z, $Z^1$, m, q, r, s, and t are as defined herein. In some embodiments of formula III, Y is O. In some embodiments of formula III, Y is NR. In some embodiments of formula III, Z and $Z^1$ are each C—H.

In some embodiments, a compound of formula III which binds to and modulates cereblon, and, in some instances, degrades IKZF2, has the structure of formula IV:

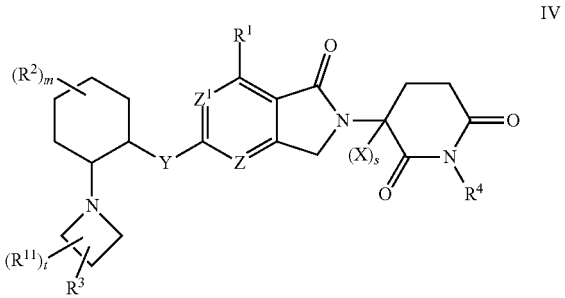

IV or a pharmaceutically acceptable salt, solvate, stereoisomer, and/or tautomer thereof wherein $R^1$, $R^2$, $R^3$, $R^4$, $R^{11}$, X, Y, Z, $Z^1$, m, s, and t are as defined herein. In some embodiments of formula IV, Y is O. In some embodiments of formula IV, Y is NR. In some embodiments of formula IV, Z and $Z^1$ are each C—H.

In some embodiments, a compound of formula I which binds to and modulates cereblon, and, in some instances, degrades IKZF2, has the structure of formula V:

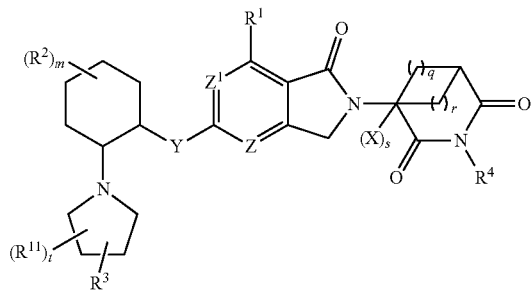

V or a pharmaceutically acceptable salt, solvate, stereoisomer, and/or tautomer thereof wherein $R^1$, $R^2$, $R^3$, $R^4$, $R^{11}$, X, Y, Z, $Z^1$, m, q, r, s, and t are as defined herein. In some embodiments of formula V, Y is O. In some embodiments of formula V, Y is NR. In some embodiments of formula V, Z and $Z^1$ are each C—H.

In some embodiments, a compound of formula V which binds to and modulates cereblon, and, in some instances, degrades IKZF2, has the structure of formula VI:

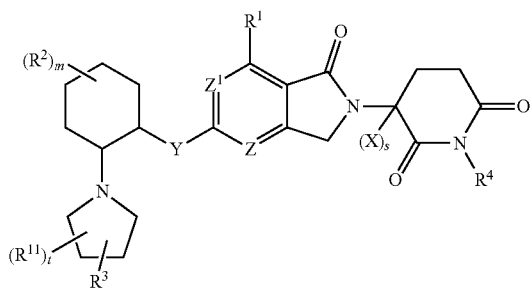

VI or a pharmaceutically acceptable salt, solvate, stereoisomer, and/or tautomer thereof wherein $R^1$, $R^2$, $R^3$, $R^4$, $R^{11}$, X, Y, Z, $Z^1$, m, s, and t are as defined herein. In some embodiments of formula VI, Y is O. In some embodiments of formula VI, Y is NR. In some embodiments of formula VI, Z and $Z^1$ are each C—H.

In some embodiments, for any compound of formula I or sub-formulae thereof, or a pharmaceutically acceptable salt, solvate, stereoisomer, and/or tautomer thereof,

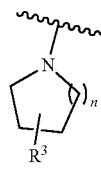

is selected from

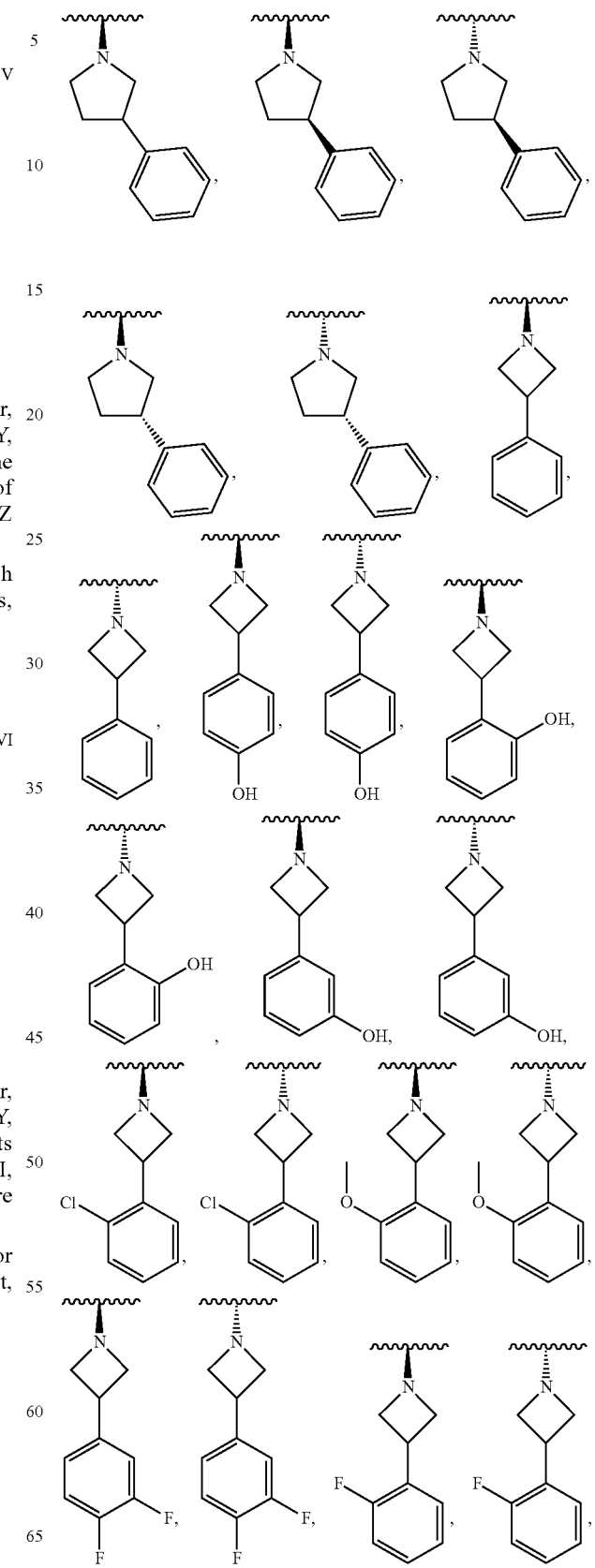

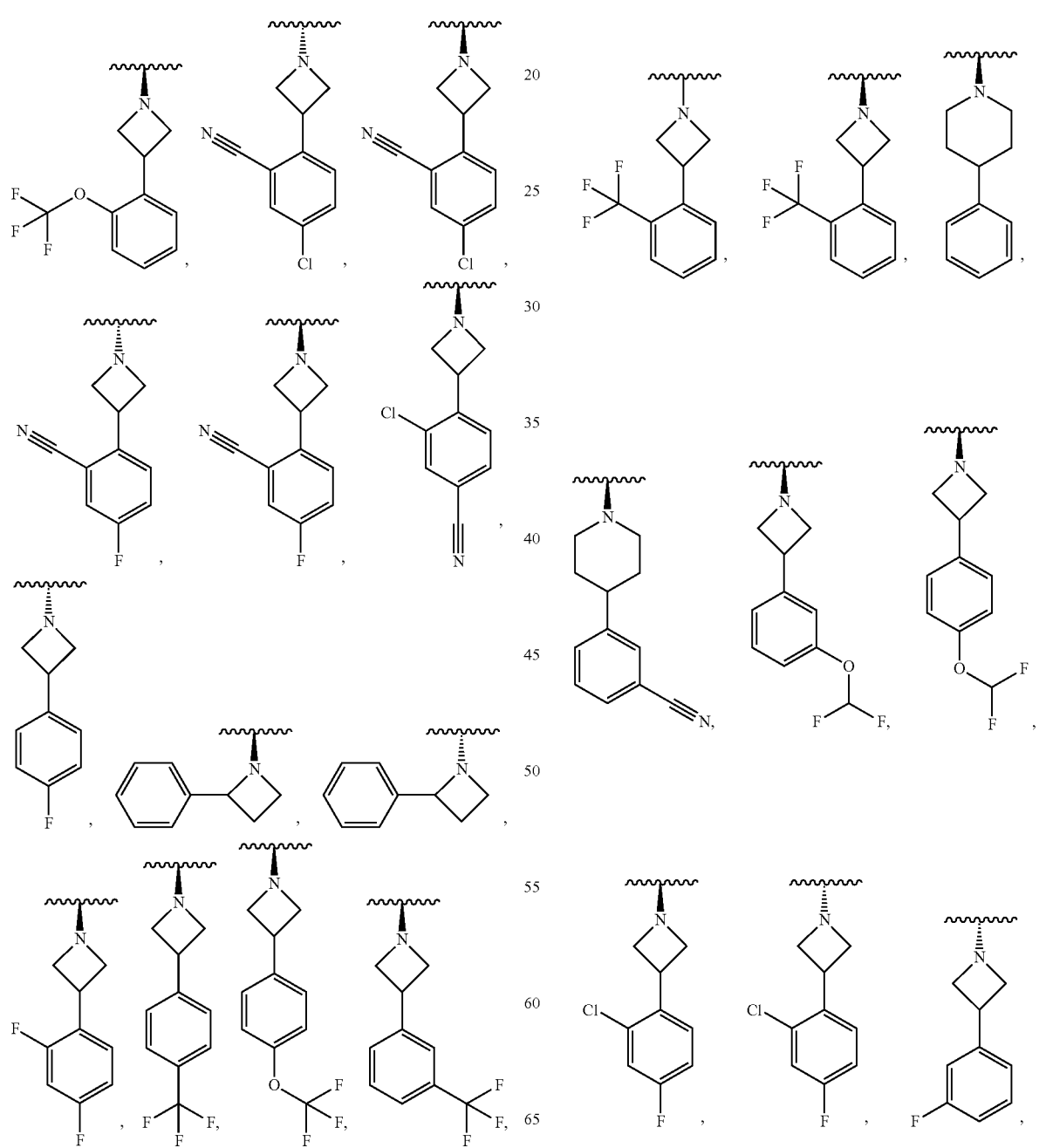

-continued

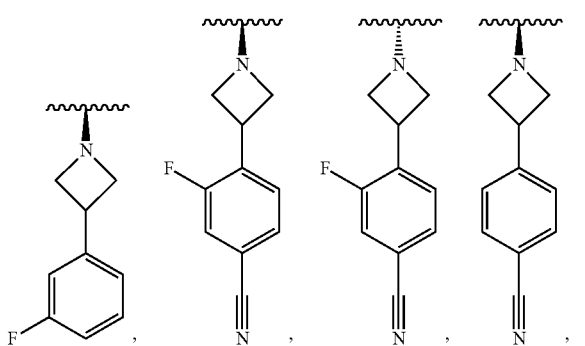

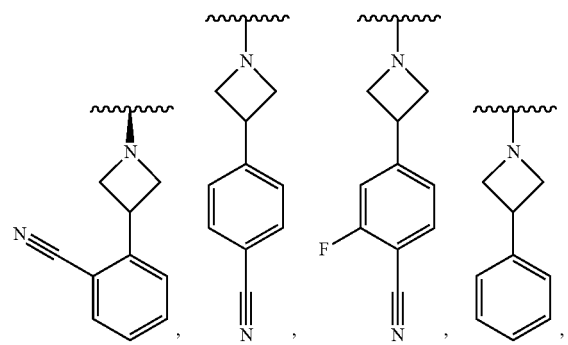

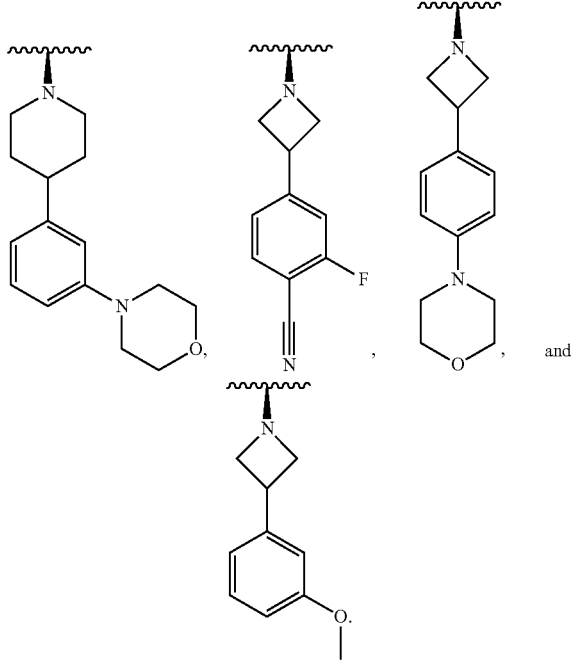

and

It is to be understood that the $R^3$ substituent can be located at any position on the heterocycloalkyl ring, other than the nitrogen.

In some embodiments, for any compound of formula I or sub-formulae thereof, or a pharmaceutically acceptable salt, solvate, stereoisomer, and/or tautomer thereof, where q is one, two, or three, and r is one or two, the moiety

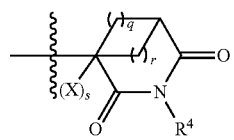

comprises a bridged ring system. In some of such embodiments, q is one, r is one, and s is zero, and the moiety

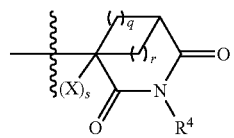

comprises a bridged ring system. In some embodiments, for any compound of formula I or sub-formulae thereof, or a pharmaceutically acceptable salt, solvate, stereoisomer, and/or tautomer thereof, where r is zero, the moiety

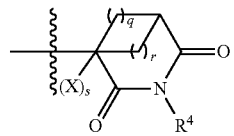

comprises a monocyclic ring and s is one.

In some embodiments, for any compound of formula I or sub-formulae thereof, or a pharmaceutically acceptable salt, solvate, stereoisomer, and/or tautomer thereof, Y is O. In some embodiments, for any compound of formula I or sub-formulae thereof, or a pharmaceutically acceptable salt, solvate, stereoisomer, and/or tautomer thereof, Y is NR. In some embodiments, for any compound of formula I or sub-formulae thereof, or a pharmaceutically acceptable salt, solvate, stereoisomer, and/or tautomer thereof, $R^2$ is halo, e.g., fluoro. In some embodiments, for any compound of formula I or sub-formulae thereof, or a pharmaceutically acceptable salt, solvate, stereoisomer, and/or tautomer thereof, $R^2$ is $C_1$-$C_4$ alkyl, e.g., methyl. In some embodiments, for any compound of formula I or sub-formulae thereof, or a pharmaceutically acceptable salt, solvate, stereoisomer, and/or tautomer thereof, t is zero. In some embodiments, for any compound of formula I or sub-formulae thereof, or a pharmaceutically acceptable salt, solvate, stereoisomer, and/or tautomer thereof, t is 1 and $R^{11}$ is hydroxyl.

In some embodiments, provided herein is a compound selected from Table 1, or a pharmaceutically acceptable salt, solvate, stereoisomer, and/or tautomer thereof.

TABLE 1

| # | Structure | Nomenclature |
|---|-----------|--------------|
| 1 | 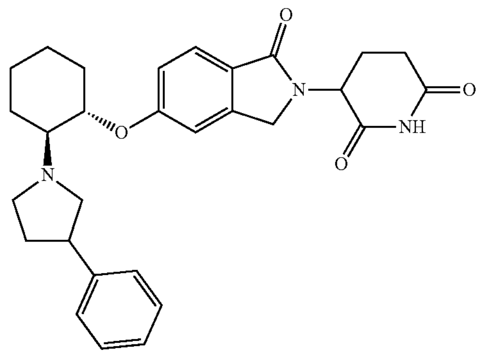 [SMILES: O=C1CCC(N2Cc3cc(O[C@H]4CCCC[C@@H]4N4CCC(c5ccccc5)C4)ccc3C2=O)C(=O)N1] | 3-(1-oxo-5-(((1S,2S)-2-(3-phenylpyrrolidin-1-yl)cyclohexyl)oxy)isoindolin-2-yl)piperidine-2,6-dione |
| 2 | 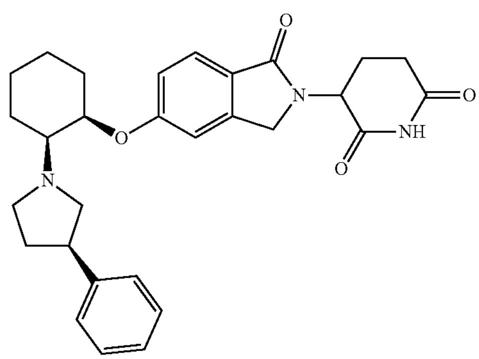 [SMILES: O=C1CCC(N2Cc3cc(O[C@@H]4CCCC[C@@H]4N4CC[C@H](c5ccccc5)C4)ccc3C2=O)C(=O)N1] | 3-(1-oxo-5-(((1R,2S)-2-((R)-3-phenylpyrrolidin-1-yl)cyclohexyl)oxy)isoindolin-2-yl)piperidine-2,6-dione |
| 3 | 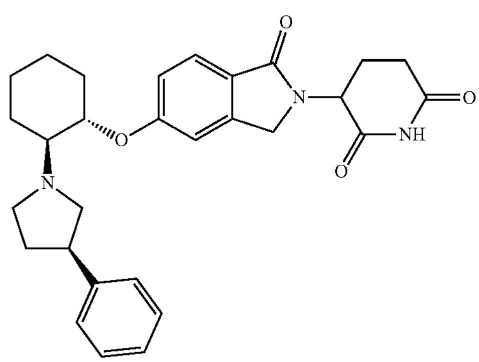 [SMILES: O=C1CCC(N2Cc3cc(O[C@H]4CCCC[C@@H]4N4CC[C@H](c5ccccc5)C4)ccc3C2=O)C(=O)N1] | 3-(1-oxo-5-(((1S,2S)-2-((R)-3-phenylpyrrolidin-1-yl)cyclohexyl)oxy)isoindolin-2-yl)piperidine-2,6-dione |
| 4 | 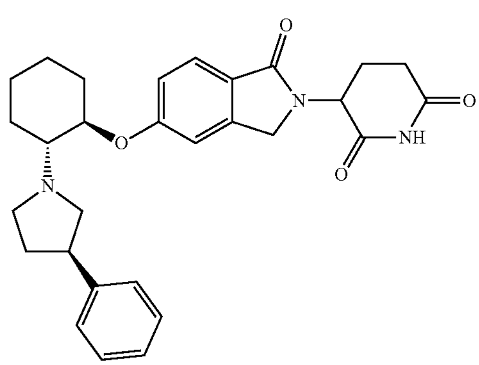 [SMILES: O=C1CCC(N2Cc3cc(O[C@@H]4CCCC[C@H]4N4CC[C@H](c5ccccc5)C4)ccc3C2=O)C(=O)N1] | 3-(1-oxo-5-(((1R,2R)-2-((R)-3-phenylpyrrolidin-1-yl)cyclohexyl)oxy)isoindolin-2-yl)piperidine-2,6-dione |

TABLE 1-continued

| # | Structure | Nomenclature |
|---|---|---|
| 5 | 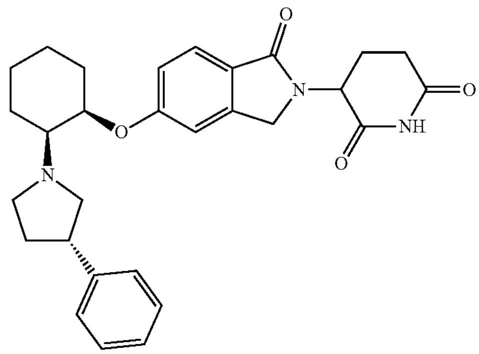 [SMILES: O=C1CCC(N2Cc3cc(O[C@@H]4CCCC[C@@H]4N4CC[C@@H](c5ccccc5)C4)ccc3C2=O)C(=O)N1] | 3-(1-oxo-5-(((1R,2S)-2-((S)-3-phenylpyrrolidin-1-yl)cyclohexyl)oxy)isoindolin-2-yl)piperidine-2,6-dione |
| 6 | 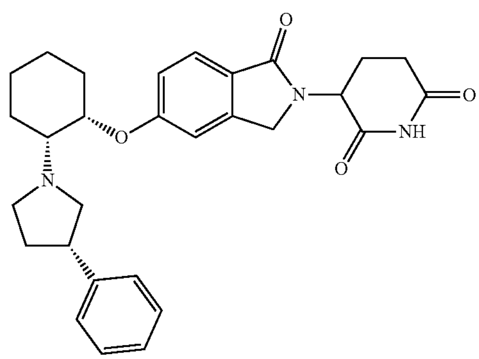 [SMILES: O=C1CCC(N2Cc3cc(O[C@H]4CCCC[C@H]4N4CC[C@@H](c5ccccc5)C4)ccc3C2=O)C(=O)N1] | 3-(1-oxo-5-(((1S,2R)-2-((S)-3-phenylpyrrolidin-1-yl)cyclohexyl)oxy)isoindolin-2-yl)piperidine-2,6-dione |
| 7 | 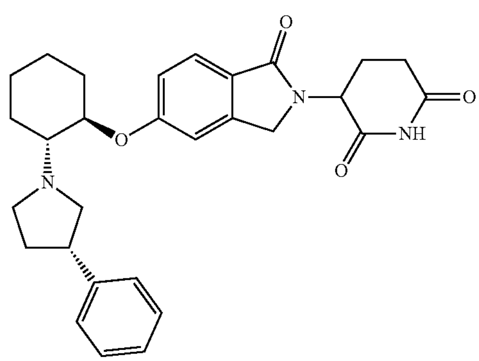 [SMILES: O=C1CCC(N2Cc3cc(O[C@@H]4CCCC[C@H]4N4CC[C@@H](c5ccccc5)C4)ccc3C2=O)C(=O)N1] | 3-(1-oxo-5-(((1R,2R)-2-((S)-3-phenylpyrrolidin-1-yl)cyclohexyl)oxy)isoindolin-2-yl)piperidine-2,6-dione |
| 8 | 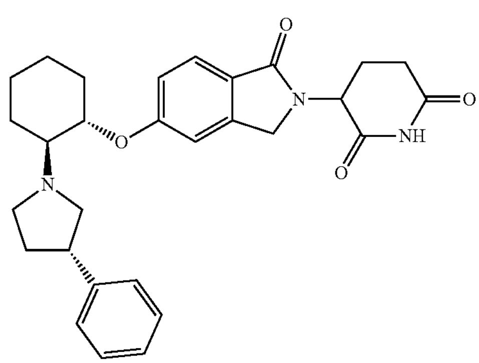 [SMILES: O=C1CCC(N2Cc3cc(O[C@H]4CCCC[C@@H]4N4CC[C@@H](c5ccccc5)C4)ccc3C2=O)C(=O)N1] | 3-(1-oxo-5-(((1S,2S)-2-((S)-3-phenylpyrrolidin-1-yl)cyclohexyl)oxy)isoindolin-2-yl)piperidine-2,6-dione |

TABLE 1-continued

| # | Structure | Nomenclature |
|---|---|---|
| 9 | 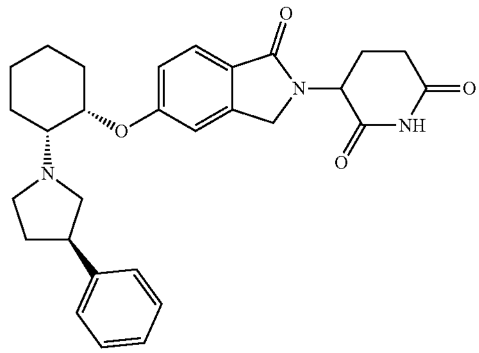 [SMILES: O=C1CCC(N2Cc3cc(O[C@H]4CCCC[C@H]4N4CC[C@H](c5ccccc5)C4)ccc3C2=O)C(=O)N1] | 3-(1-oxo-5-(((1S,2R)-2-((R)-3-phenylpyrrolidin-1-yl)cyclohexyl)oxy)isoindolin-2-yl)piperidine-2,6-dione |
| 10 | 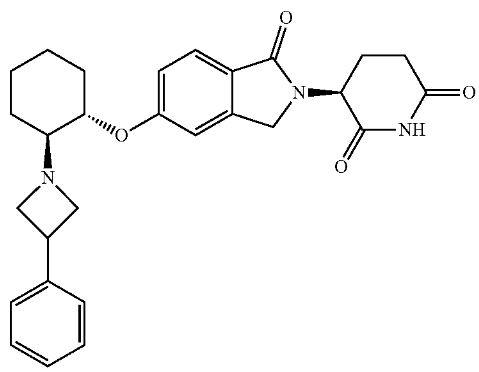 [SMILES: O=C1CC[C@H](N2Cc3cc(O[C@H]4CCCC[C@@H]4N4CC(c5ccccc5)C4)ccc3C2=O)C(=O)N1] | (S)-3-(1-oxo-5-(((1S,2S)-2-(3-phenylazetidin-1-yl)cyclohexyl)oxy)isoindolin-2-yl)piperidine-2,6-dione |
| 11 | 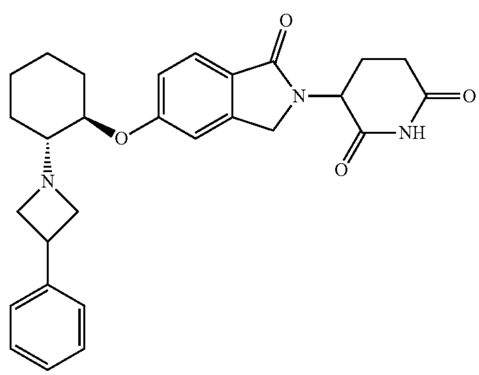 [SMILES: O=C1CCC(N2Cc3cc(O[C@@H]4CCCC[C@H]4N4CC(c5ccccc5)C4)ccc3C2=O)C(=O)N1] | 3-(1-oxo-5-(((1R,2R)-2-(3-phenylazetidin-1-yl)cyclohexyl)oxy)isoindolin-2-yl)piperidine-2,6-dione |
| 12 | 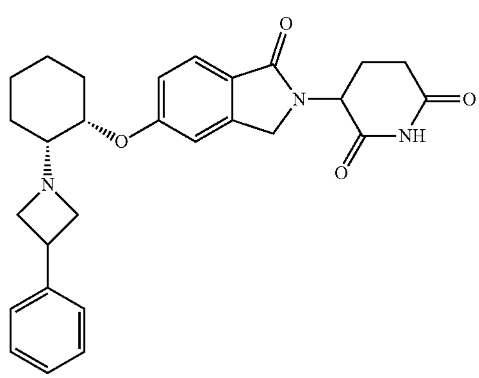 [SMILES: O=C1CCC(N2Cc3cc(O[C@H]4CCCC[C@H]4N4CC(c5ccccc5)C4)ccc3C2=O)C(=O)N1] | 3-(1-oxo-5-(((1S,2R)-2-(3-phenylazetidin-1-yl)cyclohexyl)oxy)isoindolin-2-yl)piperidine-2,6-dione |

TABLE 1-continued

| # | Structure | Nomenclature |
|---|---|---|
| 13 | 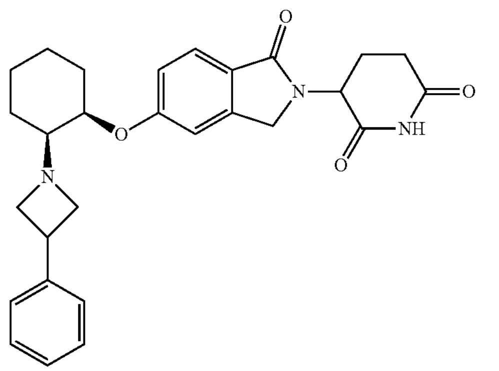 [SMILES: O=C1CCC(N2Cc3cc(O[C@@H]4CCCC[C@@H]4N4CC(c5ccccc5)C4)ccc3C2=O)C(=O)N1] | 3-(1-oxo-5-((((1R,2S)-2-(3-phenylazetidin-1-yl)cyclohexyl)oxy)isoindolin-2-yl)piperidine-2,6-dione |
| 14 | 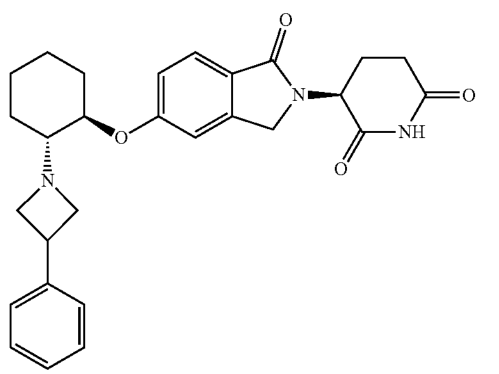 [SMILES: O=C1CC[C@H](N2Cc3cc(O[C@@H]4CCCC[C@H]4N4CC(c5ccccc5)C4)ccc3C2=O)C(=O)N1] | (S)-3-(1-oxo-5-((((1R,2R)-2-(3-phenylazetidin-1-yl)cyclohexyl)oxy)isoindolin-2-yl)piperidine-2,6-dione |
| 15 | 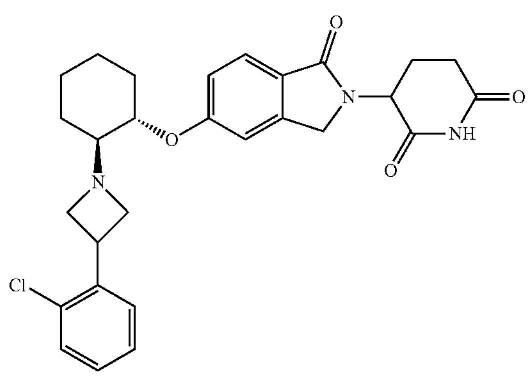 [SMILES: O=C1CCC(N2Cc3cc(O[C@H]4CCCC[C@@H]4N4CC(c5ccccc5Cl)C4)ccc3C2=O)C(=O)N1] | 3-(5-((((1S,2S)-2-(3-(2-chlorophenyl)azetidin-1-yl)cyclohexyl)oxy)-1-oxoisoindolin-2-yl)piperidine-2,6-dione |
| 16 | 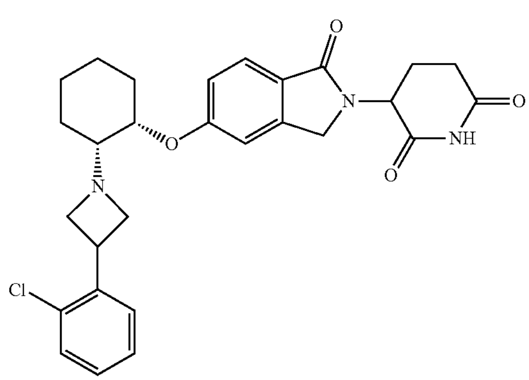 [SMILES: O=C1CCC(N2Cc3cc(O[C@H]4CCCC[C@H]4N4CC(c5ccccc5Cl)C4)ccc3C2=O)C(=O)N1] | 3-(5-((((1S,2R)-2-(3-(2-chlorophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 17 | 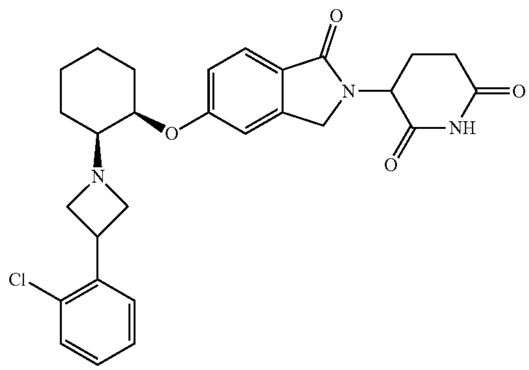 [SMILES: O=C1CCC(N2Cc3cc(O[C@@H]4CCCC[C@@H]4N4CC(c5ccccc5Cl)C4)ccc3C2=O)C(=O)N1] | 3-(5-(((1R,2S)-2-(3-(2-chlorophenyl)azetidin-1-yl)cyclohexyl)oxy)-1-oxoisoindolin-2-yl)piperidine-2,6-dione |
| 18 | 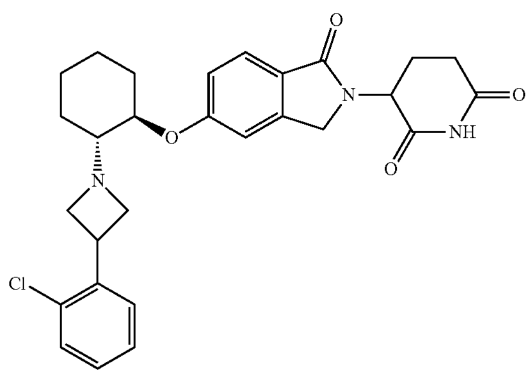 [SMILES: O=C1CCC(N2Cc3cc(O[C@@H]4CCCC[C@H]4N4CC(c5ccccc5Cl)C4)ccc3C2=O)C(=O)N1] | 3-(5-(((1R,2R)-2-(3-(2-chlorophenyl)azetidin-1-yl)cyclohexyl)oxy)-1-oxoisoindolin-2-yl)piperidine-2,6-dione |
| 19 | 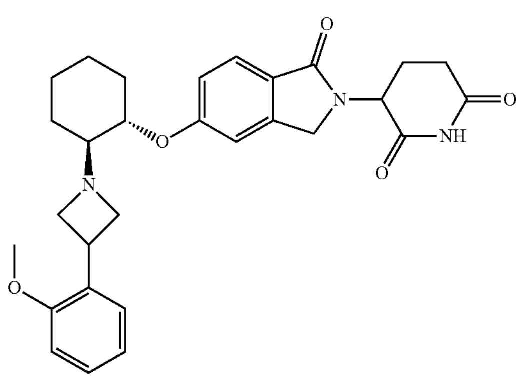 [SMILES: COc1ccccc1C1CN([C@H]2CCCC[C@@H]2Oc2ccc3c(c2)CN(C2CCC(=O)NC2=O)C3=O)C1] | 3-(5-(((1S,2S)-2-(3-(2-methoxyphenyl)azetidin-1-yl)cyclohexyl)oxy)-1-oxoisoindolin-2-yl)piperidine-2,6-dione |
| 20 | 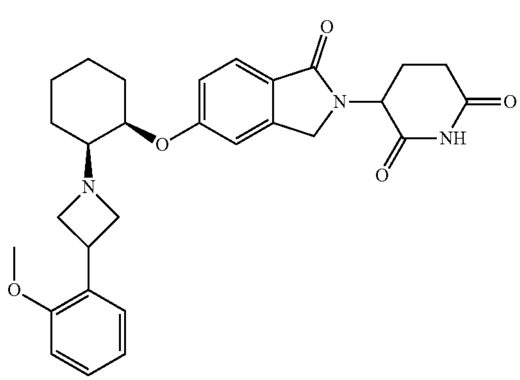 [SMILES: COc1ccccc1C1CN([C@H]2CCCC[C@H]2Oc2ccc3c(c2)CN(C2CCC(=O)NC2=O)C3=O)C1] | 3-(5-(((1R,2S)-2-(3-(2-methoxyphenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 21 | 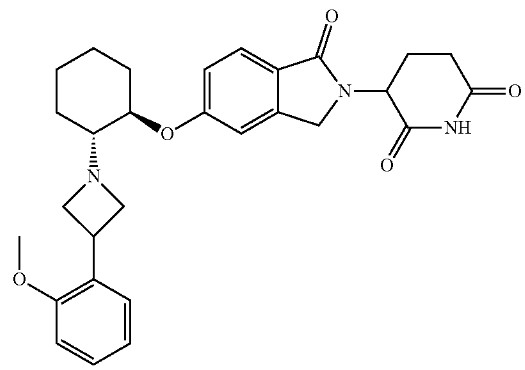 [SMILES: COc1ccccc1C1CN([C@@H]2CCCC[C@H]2Oc2ccc3c(c2)CN(C2CCC(=O)NC2=O)C3=O)C1] | 3-(5-((((1R,2R)-2-(3-(2-methoxyphenyl)azetidin-1-yl)cyclohexyl)oxy)-1-oxoisoindolin-2-yl)piperidine-2,6-dione |
| 22 | 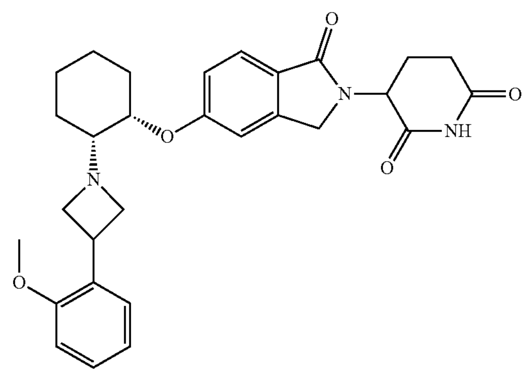 [SMILES: COc1ccccc1C1CN([C@@H]2CCCC[C@@H]2Oc2ccc3c(c2)CN(C2CCC(=O)NC2=O)C3=O)C1] | 3-(5-((((1S,2R)-2-(3-(2-methoxyphenyl)azetidin-1-yl)cyclohexyl)oxy)-1-oxoisoindolin-2-yl)piperidine-2,6-dione |
| 23 | 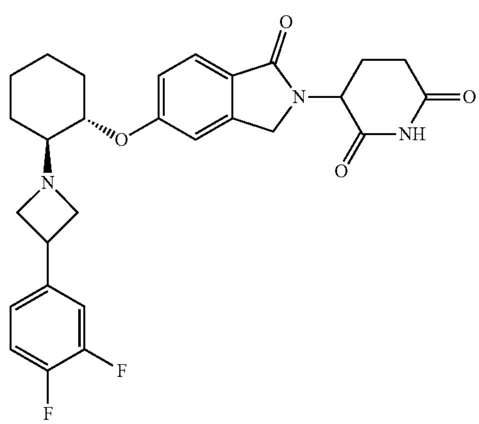 [SMILES: O=C1CCC(N2Cc3cc(O[C@H]4CCCC[C@@H]4N4CC(c5ccc(F)c(F)c5)C4)ccc3C2=O)C(=O)N1] | 3-(5-((((1S,2S)-2-(3-(3,4-difluorophenyl)azetidin-1-yl)cyclohexyl)oxy)-1-oxoisoindolin-2-yl)piperidine-2,6-dione |
| 24 | 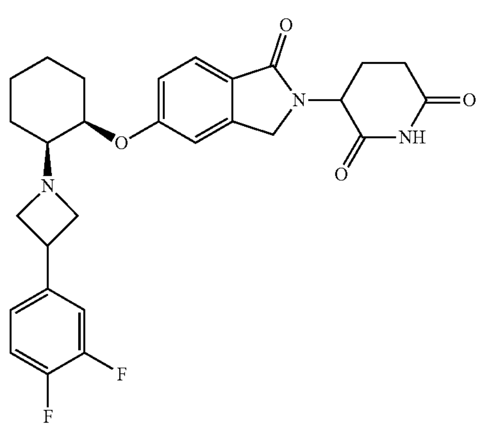 [SMILES: O=C1CCC(N2Cc3cc(O[C@@H]4CCCC[C@@H]4N4CC(c5ccc(F)c(F)c5)C4)ccc3C2=O)C(=O)N1] | 3-(5-((((1R,2S)-2-(3-(3,4-difluorophenyl)azetidin-1-yl)cyclohexyl)oxy)-1-oxoisoindolin-2-yl)piperidine-2,6-dione |

TABLE 1-continued

| # | Structure | Nomenclature |
|---|-----------|--------------|
| 25 | 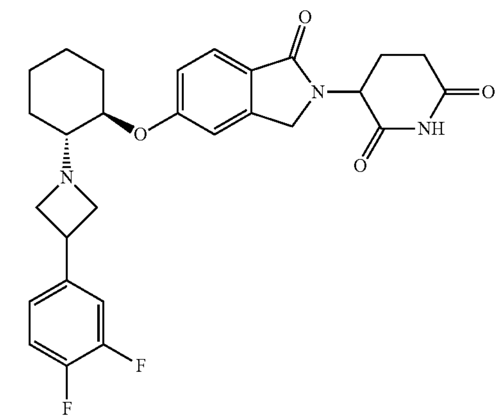 [SMILES: O=C1CCC(N2Cc3cc(O[C@@H]4CCCC[C@H]4N4CC(c5ccc(F)c(F)c5)C4)ccc3C2=O)C(=O)N1] | 3-(5-(((1R,2R)-2-(3-(3,4-difluorophenyl)azetidin-1-yl)cyclohexyl)oxy)-1-oxoisoindolin-2-yl)piperidine-2,6-dione |
| 26 | 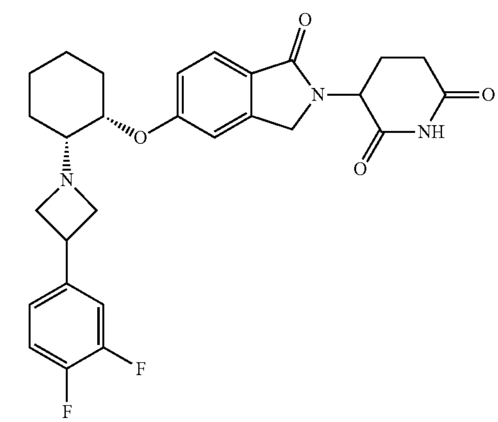 [SMILES: O=C1CCC(N2Cc3cc(O[C@H]4CCCC[C@H]4N4CC(c5ccc(F)c(F)c5)C4)ccc3C2=O)C(=O)N1] | 3-(5-(((1S,2R)-2-(3-(3,4-difluorophenyl)azetidin-1-yl)cyclohexyl)oxy)-1-oxoisoindolin-2-yl)piperidine-2,6-dione |
| 27 | 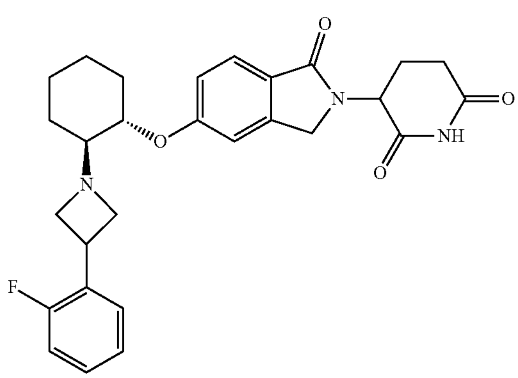 [SMILES: O=C1CCC(N2Cc3cc(O[C@H]4CCCC[C@@H]4N4CC(c5ccccc5F)C4)ccc3C2=O)C(=O)N1] | 3-(5-(((1S,2S)-2-(3-(2-fluorophenyl)azetidin-1-yl)cyclohexyl)oxy)-1-oxoisoindolin-2-yl)piperidine-2,6-dione |
| 28 | 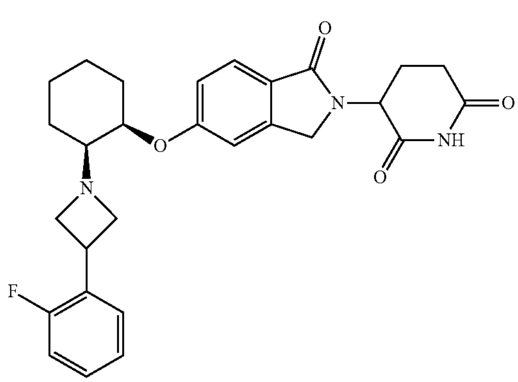 [SMILES: O=C1CCC(N2Cc3cc(O[C@@H]4CCCC[C@@H]4N4CC(c5ccccc5F)C4)ccc3C2=O)C(=O)N1] | 3-(5-(((1R,2S)-2-(3-(2-fluorophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 29 | 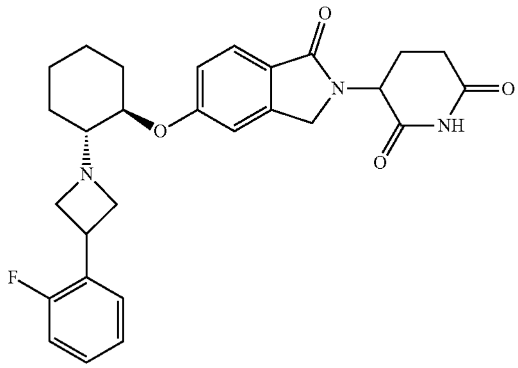 [SMILES: O=C1CCC(N2Cc3cc(O[C@@H]4CCCC[C@H]4N4CC(c5ccccc5F)C4)ccc3C2=O)C(=O)N1] | 3-(5-(((1R,2R)-2-(3-(2-fluorophenyl)azetidin-1-yl)cyclohexyl)oxy)-1-oxoisoindolin-2-yl)piperidine-2,6-dione |
| 30 | 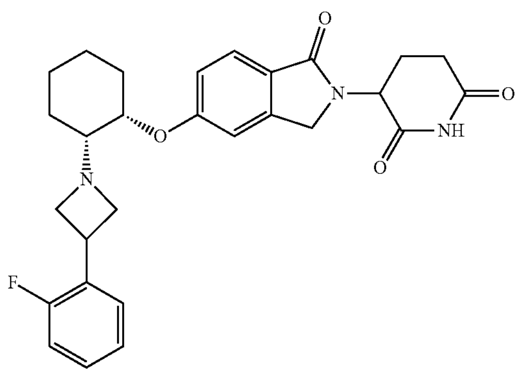 [SMILES: O=C1CCC(N2Cc3cc(O[C@H]4CCCC[C@H]4N4CC(c5ccccc5F)C4)ccc3C2=O)C(=O)N1] | 3-(5-(((1S,2R)-2-(3-(2-fluorophenyl)azetidin-1-yl)cyclohexyl)oxy)-1-oxoisoindolin-2-yl)piperidine-2,6-dione |
| 31 | 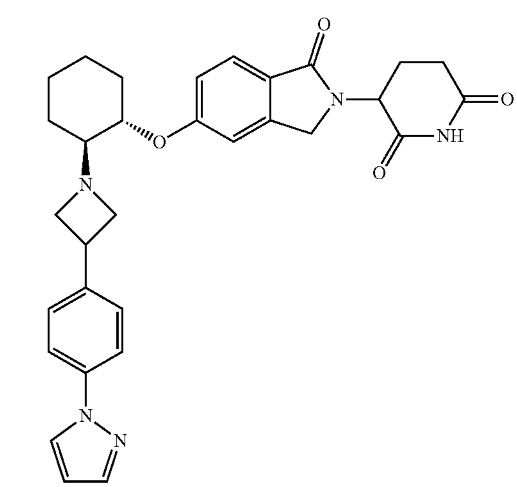 | 3-(5-(((1S,2S)-2-(3-(4-(1H-pyrazol-1-yl)phenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 32 | 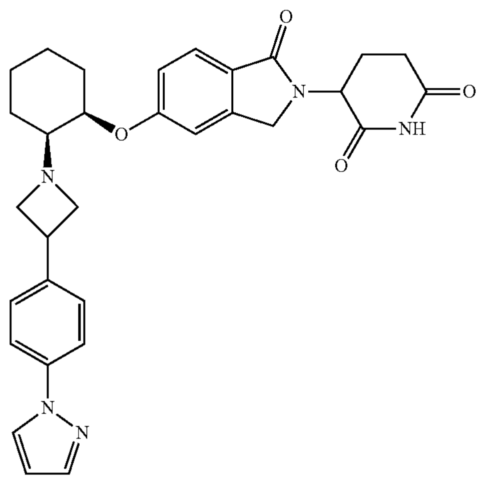 [SMILES: O=C1CCC(N2Cc3cc(O[C@@H]4CCCC[C@@H]4N4CC(c5ccc(-n6cccn6)cc5)C4)ccc3C2=O)C(=O)N1] | 3-(5-(((1R,2S)-2-(3-(4-(1H-pyrazol-1-yl)phenyl)azetidin-1-yl)cyclohexyl)oxy)-1-oxoisoindolin-2-yl)piperidine-2,6-dione |
| 33 | 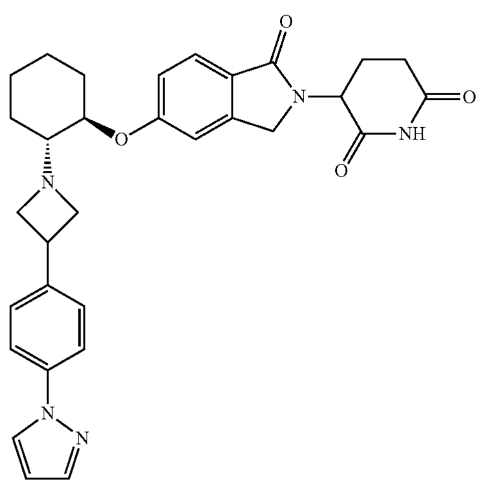 [SMILES: O=C1CCC(N2Cc3cc(O[C@@H]4CCCC[C@H]4N4CC(c5ccc(-n6cccn6)cc5)C4)ccc3C2=O)C(=O)N1] | 3-(5-((((1R,2R)-2-(3-(4-(1H-pyrazol-1-yl)phenyl)azetidin-1-yl)cyclohexyl)oxy)-1-oxoisoindolin-2-yl)piperidine-2,6-dione |
| 34 | 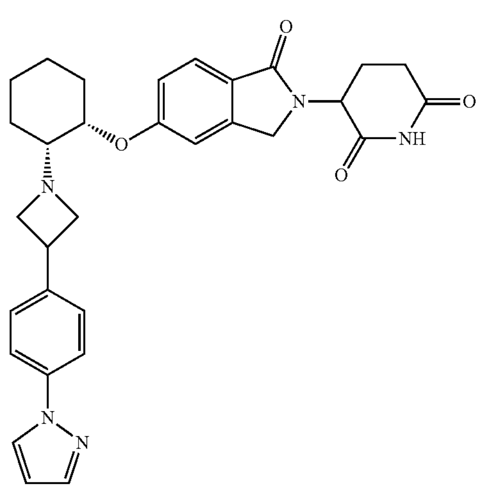 [SMILES: O=C1CCC(N2Cc3cc(O[C@H]4CCCC[C@H]4N4CC(c5ccc(-n6cccn6)cc5)C4)ccc3C2=O)C(=O)N1] | 3-(5-((((1S,2R)-2-(3-(4-(1H-pyrazol-1-yl)phenyl)azetidin-1-yl)cyclohexyl)oxy)-1-oxoisoindolin-2-yl)piperidine-2,6-dione |

TABLE 1-continued

| # | Structure | Nomenclature |
|---|-----------|--------------|
| 35 | 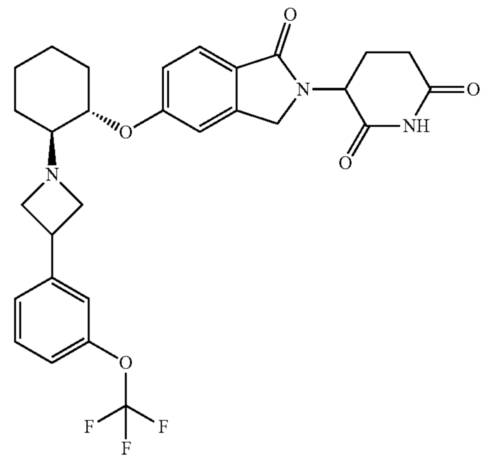 [SMILES: O=C1CCC(N2Cc3cc(O[C@H]4CCCC[C@@H]4N4CC(c5cccc(OC(F)(F)F)c5)C4)ccc3C2=O)C(=O)N1] | 3-(1-oxo-5-(((1S,2S)-2-(3-(3-(trifluoromethoxy)phenyl)azetidin-1-yl)cyclohexyl)oxy)isoindolin-2-yl)piperidine-2,6-dione |
| 36 | 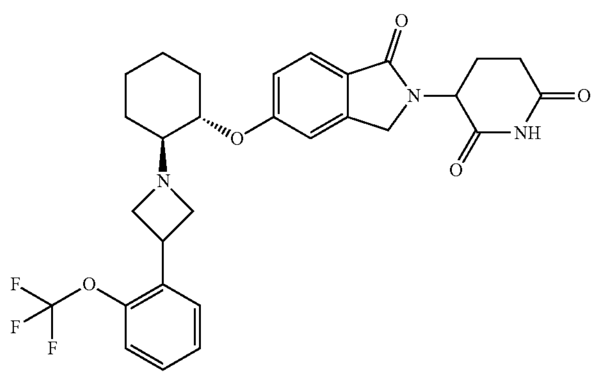 [SMILES: O=C1CCC(N2Cc3cc(O[C@H]4CCCC[C@@H]4N4CC(c5ccccc5OC(F)(F)F)C4)ccc3C2=O)C(=O)N1] | 3-(1-oxo-5-(((1S,2S)-2-(3-(2-(trifluoromethoxy)phenyl)azetidin-1-yl)cyclohexyl)oxy)isoindolin-2-yl)piperidine-2,6-dione |
| 37 | Diastereomer 1 | 5-chloro-2-(1-((1R,2S)-2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|---|---|
| 38 | 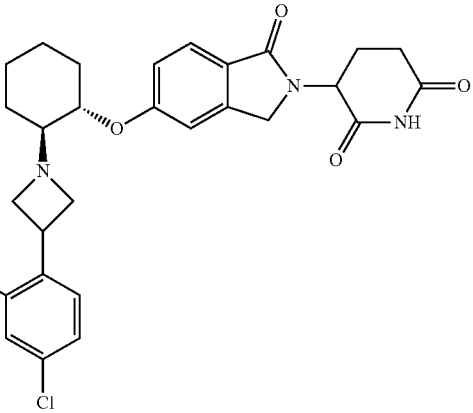<br>Diastereomer 2 | 5-chloro-2-(1-((1S,2S)-2-((2-(2,6-dioxopiperidin-3-yl)-1-oxoisoindolin-5-yl)oxy)cyclohexyl)azetidin-3-yl)benzonitrile |
| 39 | 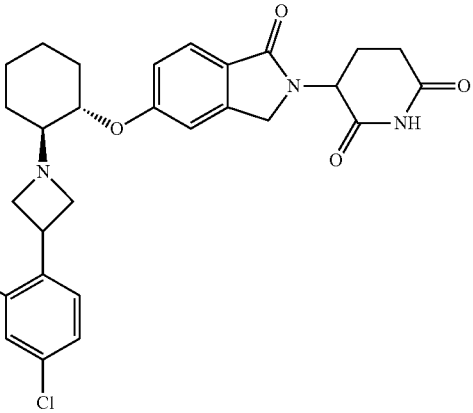<br>Diastereomer 3 | 5-chloro-2-(1-((1S,2S)-2-((2-(2,6-dioxopiperidin-3-yl)-1-oxoisoindolin-5-yl)oxy)cyclohexyl)azetidin-3-yl)benzonitrile |
| 40 | 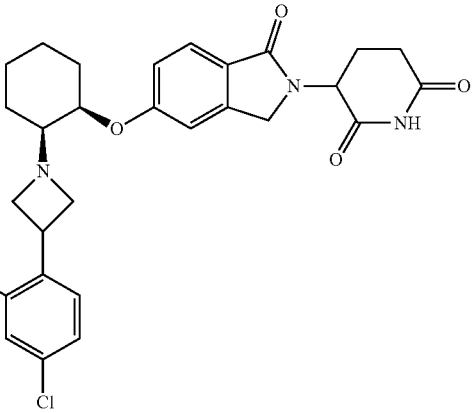<br>Diastereomer 4 | 5-chloro-2-(1-((1S,2R)-2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|-----------|--------------|
| 41 | Diastereomer 1 | 3-(4-chloro-1-oxo-5-((((1S,2S)-2-(3-phenylazetidin-1-yl)cyclohexyl)oxy)isoindolin-2-yl)piperidine-2,6-dione |
| 42 | Diastereomer 2 | 3-(4-chloro-1-oxo-5-((((1S,2S)-2-(3-phenylazetidin-1-yl)cyclohexyl)oxy)isoindolin-2-yl)piperidine-2,6-dione |
| 43 | Diastereomer 1 | 2-(1-((1R,2R)-2-((2-(2,6-dioxopiperidin-3-yl)-1-oxoisoindolin-5-yl)oxy)cyclohexyl)azetidin-3-yl)-5-fluorobenzonitrile |

TABLE 1-continued

| # | Structure | Nomenclature |
|---|---|---|
| 44 | Diastereomer 2 | 2-(1-((1S,2S)-2-((2-(2,6-dioxopiperidin-3-yl)-1-oxoisoindolin-5-yl)oxy)cyclohexyl)azetidin-3-yl)-5-fluorobenzonitrile |
| 45 | Diastereomer 3 | 2-(1-((1S,2S)-2-((2-(2,6-dioxopiperidin-3-yl)-1-oxoisoindolin-5-yl)oxy)cyclohexyl)azetidin-3-yl)-5-fluorobenzonitrile |
| 46 | Diastereomer 4 | 2-(1-((1S,2R)-2-((2-(2,6-dioxopiperidin-3-yl)-1-oxoisoindolin-5-yl)oxy)cyclohexyl)azetidin-3-yl)-5-fluorobenzonitrile |

TABLE 1-continued
| # | Structure | Nomenclature |
|---|---|---|
| 47 | 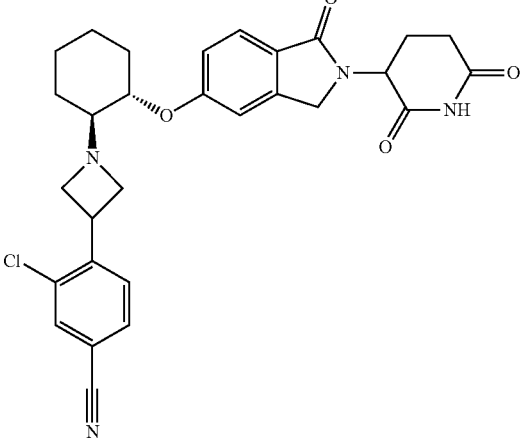Diastereomer 1 | 3-chloro-4-(1-((1S,2S)-2-((2-(2,6-dioxopiperidin-3-yl)-1-oxoisoindolin-5-yl)oxy)cyclohexyl)azetidin-3-yl)benzonitrile |
| 48 | 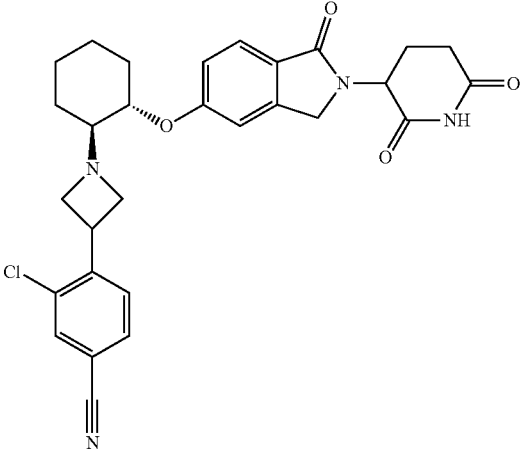Diastereomer 2 | 3-chloro-4-(1-((1S,2S)-2-((2-(2,6-dioxopiperidin-3-yl)-1-oxoisoindolin-5-yl)oxy)cyclohexyl)azetidin-3-yl)benzonitrile |
| 49 | 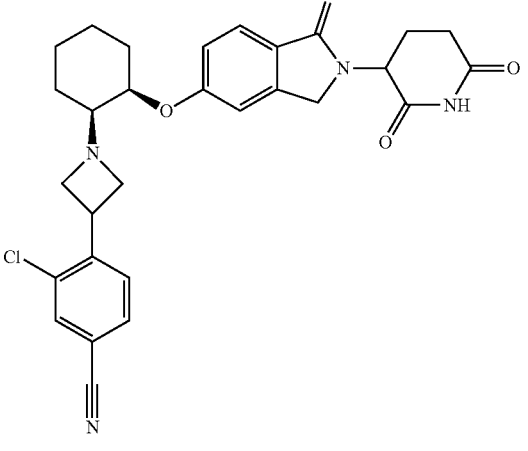Diastereomer 3 | 3-chloro-4-(1-((1S,2R)-2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|---|---|
| 50 | 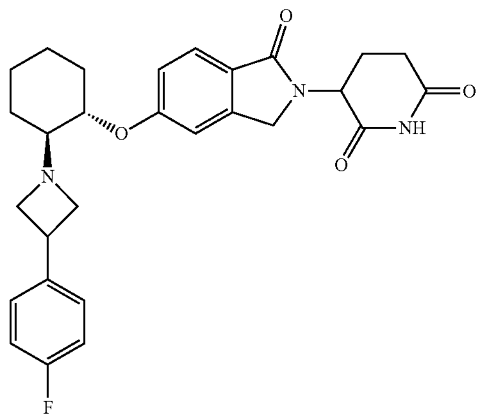 | 3-(5-(((1S,2S)-2-(3-(4-fluorophenyl)azetidin-1-yl)cyclohexyl)oxy)-1-oxoisoindolin-2-yl)piperidine-2,6-dione |
| | Diastereomer 1 | |
| 51 | 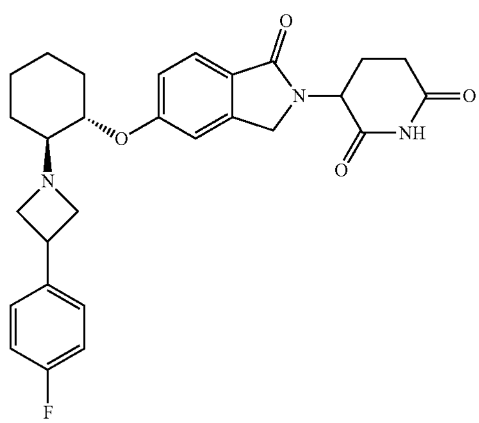 | 3-(5-(((1S,2S)-2-(3-(4-fluorophenyl)azetidin-1-yl)cyclohexyl)oxy)-1-oxoisoindolin-2-yl)piperidine-2,6-dione |
| | Diastereomer 2 | |
| 52 | 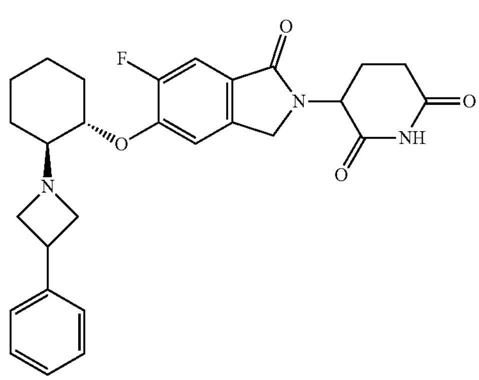 | 3-(6-fluoro-1-oxo-5-(((1S,2S)-2-(3-phenylazetidin-1-yl)cyclohexyl)oxy)isoindolin-2-yl)piperidine-2,6-dione |
| | Diastereomer 1 | |

TABLE 1-continued

| # | Structure | Nomenclature |
|---|---|---|
| 53 | Diastereomer 2 | 3-(6-fluoro-1-oxo-5-((((1S,2S)-2-(3-phenylazetidin-1-yl)cyclohexyl)oxy)isoindolin-2-yl)piperidine-2,6-dione |
| 54 | 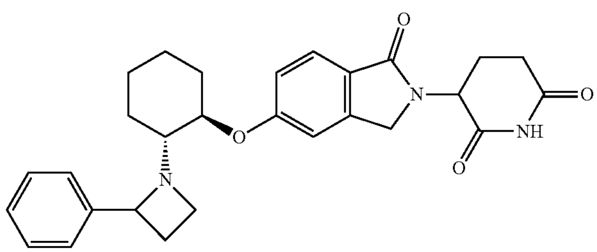 [SMILES: O=C1CCC(N2Cc3cc(O[C@@H]4CCCC[C@H]4N4CCC4c4ccccc4)ccc3C2=O)C(=O)N1] | 3-(1-oxo-5-((((1R,2R)-2-(2-phenylazetidin-1-yl)cyclohexyl)oxy)isoindolin-2-yl)piperidine-2,6-dione |
| 55 | 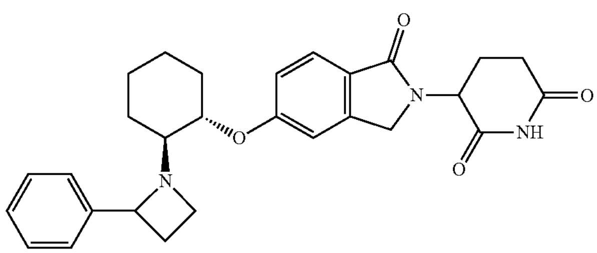 [SMILES: O=C1CCC(N2Cc3cc(O[C@H]4CCCC[C@@H]4N4CCC4c4ccccc4)ccc3C2=O)C(=O)N1] | 3-(1-oxo-5-((((1S,2S)-2-(2-phenylazetidin-1-yl)cyclohexyl)oxy)isoindolin-2-yl)piperidine-2,6-dione |
| 56 | 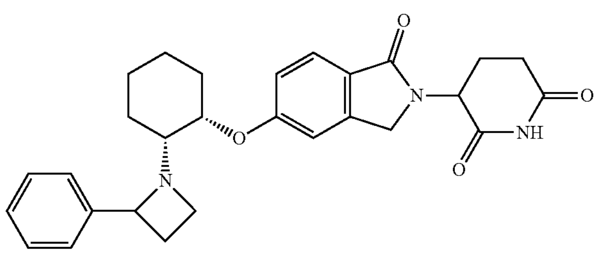 [SMILES: O=C1CCC(N2Cc3cc(O[C@H]4CCCC[C@H]4N4CCC4c4ccccc4)ccc3C2=O)C(=O)N1] | 3-(1-oxo-5-((((1S,2R)-2-(2-phenylazetidin-1-yl)cyclohexyl)oxy)isoindolin-2-yl)piperidine-2,6-dione |
| 57 | 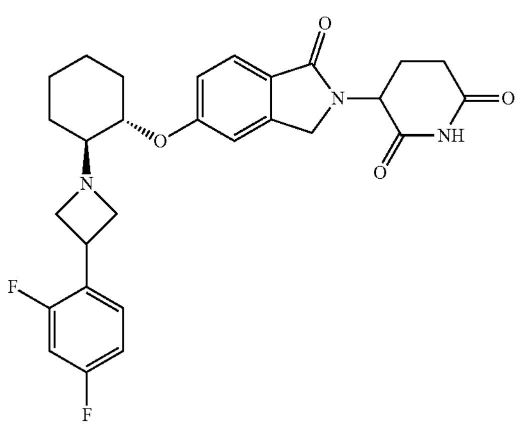 [SMILES: O=C1CCC(N2Cc3cc(O[C@H]4CCCC[C@@H]4N4CC(c5ccc(F)cc5F)C4)ccc3C2=O)C(=O)N1] | 3-(5-((((1S,2S)-2-(3-(2,4-difluorophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 58 | 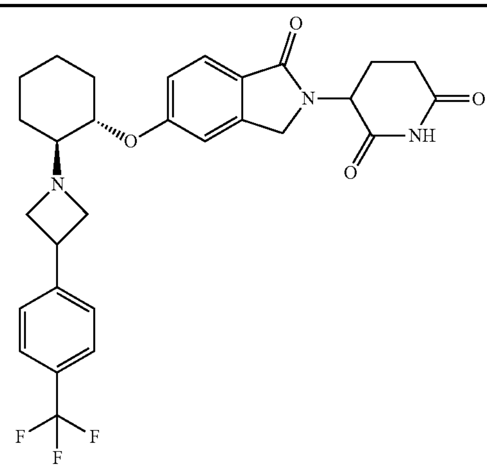 | 3-(1-oxo-5-((((1S,2S)-2-(3-(4-(trifluoromethyl)phenyl)azetidin-1-yl)cyclohexyl)oxy)isoindolin-2-yl)piperidine-2,6-dione |
| 59 | 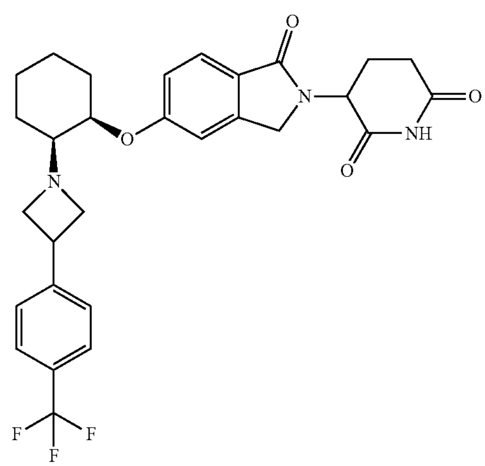 [SMILES: O=C1CCC(N2Cc3cc(O[C@@H]4CCCC[C@@H]4N4CC(c5ccc(C(F)(F)F)cc5)C4)ccc3C2=O)C(=O)N1] | 3-(1-oxo-5-((((1R,2S)-2-(3-(4-(trifluoromethyl)phenyl)azetidin-1-yl)cyclohexyl)oxy)isoindolin-2-yl)piperidine-2,6-dione |
| 60 | 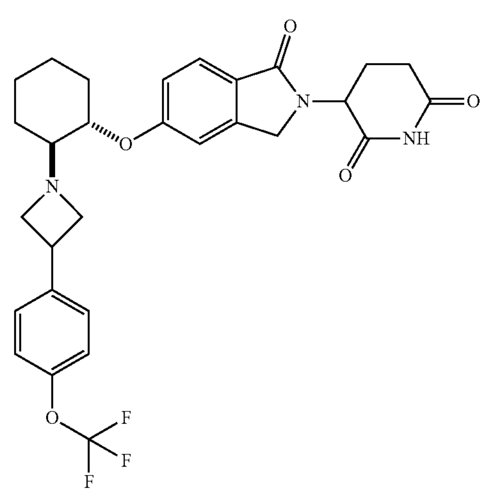 [SMILES: O=C1CCC(N2Cc3cc(O[C@H]4CCCC[C@@H]4N4CC(c5ccc(OC(F)(F)F)cc5)C4)ccc3C2=O)C(=O)N1] | Rac-3-(1-oxo-5-(((trans)-2-(3-(4-(trifluoromethoxy)phenyl)azetidin-1-yl)cyclohexyl)oxy)isoindolin-2-yl)piperidine-2,6-dione |

TABLE 1-continued

| # | Structure | Nomenclature |
|---|-----------|--------------|
| 61 | 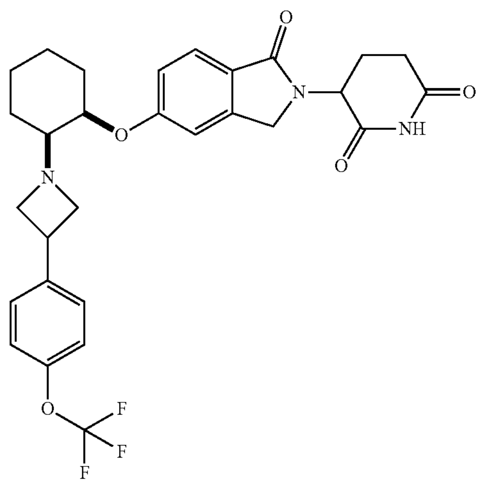 [SMILES: O=C1CCC(N2Cc3cc(O[C@@H]4CCCC[C@@H]4N4CC(c5ccc(OC(F)(F)F)cc5)C4)ccc3C2=O)C(=O)N1] | Rac-3-(1-oxo-5-(((cis)-2-(3-(4-(trifluoromethoxy)phenyl)azetidin-1-yl)cyclohexyl)oxy)isoindolin-2-yl)piperidine-2,6-dione |
| 62 | 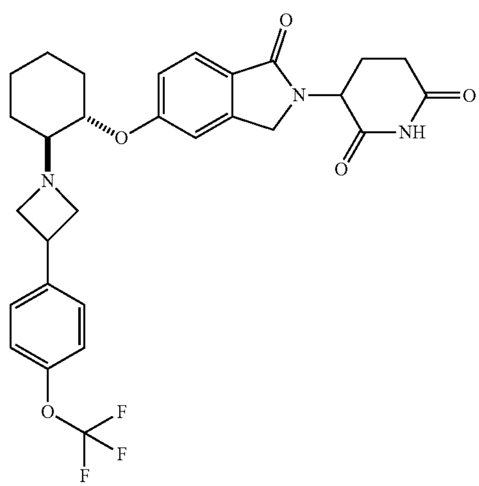 [SMILES: O=C1CCC(N2Cc3cc(O[C@H]4CCCC[C@@H]4N4CC(c5ccc(OC(F)(F)F)cc5)C4)ccc3C2=O)C(=O)N1] | Rac-3-(1-oxo-5-(((trans)-2-(3-(3-(trifluoromethyl)phenyl)azetidin-1-yl)cyclohexyl)oxy)isoindolin-2-yl)piperidine-2,6-dione |
| 63 | 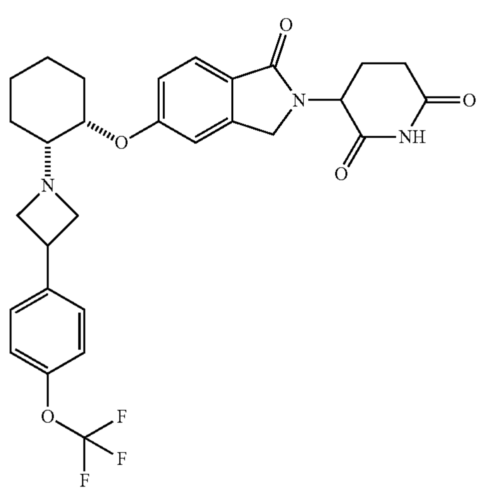 [SMILES: O=C1CCC(N2Cc3cc(O[C@H]4CCCC[C@H]4N4CC(c5ccc(OC(F)(F)F)cc5)C4)ccc3C2=O)C(=O)N1] | Rac-3-(1-oxo-5-(((cis)-2-(3-(3-(trifluoromethyl)phenyl)azetidin-1-yl)cyclohexyl)oxy)isoindolin-2-yl)piperidine-2,6-dione |

TABLE 1-continued

| # | Structure | Nomenclature |
|---|---|---|
| 64 | 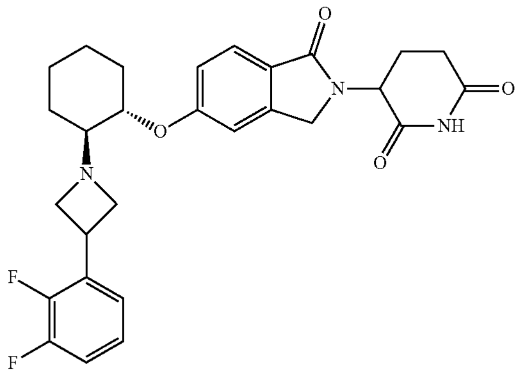 [SMILES: O=C1CCC(N2Cc3cc(O[C@H]4CCCC[C@@H]4N4CC(c5cccc(F)c5F)C4)ccc3C2=O)C(=O)N1] | 3-(5-(((1S,2S)-2-(3-(2,3-difluorophenyl)azetidin-1-yl)cyclohexyl)oxy)-1-oxoisoindolin-2-yl)piperidine-2,6-dione |
| 65 | Diastereomer 1 | 3-(4-fluoro-1-oxo-5-(((1S,2S)-2-(3-phenylazetidin-1-yl)cyclohexyl)oxy)isoindolin-2-yl)piperidine-2,6-dione |
| 66 | Diastereomer 2 | 3-(4-fluoro-1-oxo-5-(((1S,2S)-2-(3-phenylazetidin-1-yl)cyclohexyl)oxy)isoindolin-2-yl)piperidine-2,6-dione |

TABLE 1-continued

| # | Structure | Nomenclature |
|---|---|---|
| 67 | 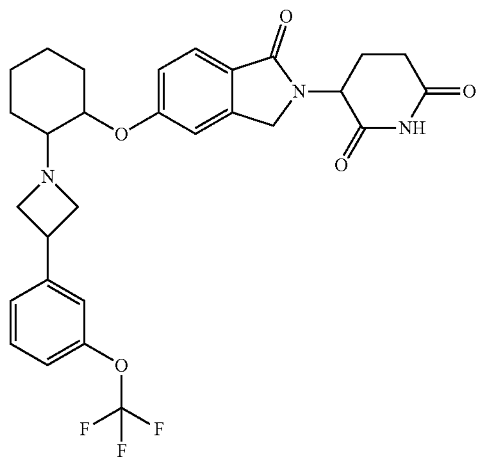 [SMILES: O=C1CCC(N2Cc3cc(OC4CCCCC4N4CC(c5cccc(OC(F)(F)F)c5)C4)ccc3C2=O)C(=O)N1] | 3-(1-oxo-5-((2-(3-(3-(trifluoromethoxy)phenyl)azetidin-1-yl)cyclohexyl)oxy)isoindolin-2-yl)piperidine-2,6-dione |
| 68 | 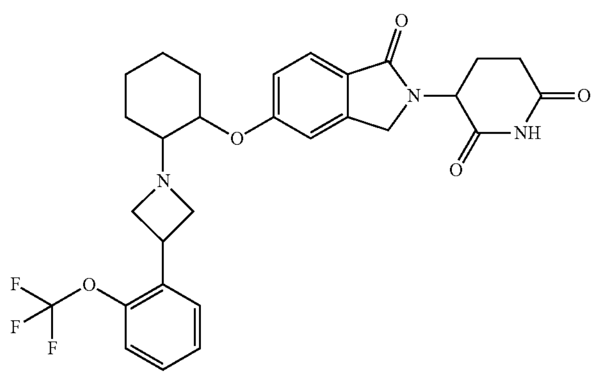 [SMILES: O=C1CCC(N2Cc3cc(OC4CCCCC4N4CC(c5ccccc5OC(F)(F)F)C4)ccc3C2=O)C(=O)N1] | 3-(1-oxo-5-((2-(3-(2-(trifluoromethoxy)phenyl)azetidin-1-yl)cyclohexyl)oxy)isoindolin-2-yl)piperidine-2,6-dione |
| 69 | 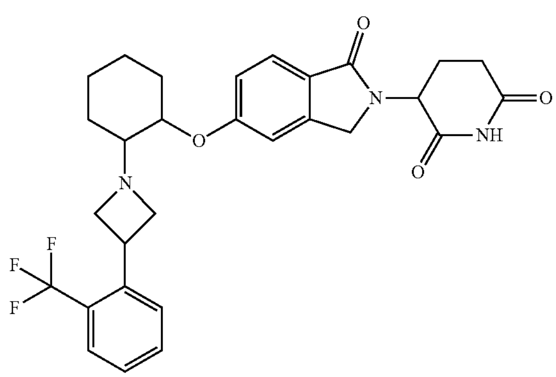 [SMILES: O=C1CCC(N2Cc3cc(OC4CCCCC4N4CC(c5ccccc5C(F)(F)F)C4)ccc3C2=O)C(=O)N1] | 3-(1-oxo-5-((2-(3-(2-(trifluoromethyl)phenyl)azetidin-1-yl)cyclohexyl)oxy)isoindolin-2-yl)piperidine-2,6-dione |
| 70 | 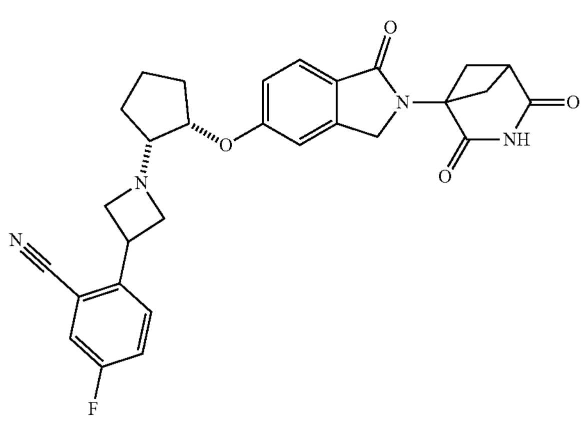 [SMILES: N#Cc1cc(F)ccc1C1CN([C@@H]2CCC[C@@H]2Oc2ccc3c(c2)CN(C24CC(C2)C(=O)NC4=O)C3=O)C1] | Rac-2-(1-((cis)-2-((2-(2,4-dioxo-3-azabicyclo[3.1.1]heptan-1-yl)-1-oxoisoindolin-5-yl)oxy)cyclopentyl)azetidin-3-yl)-5-fluorobenzonitrile |

TABLE 1-continued

| # | Structure | Nomenclature |
|---|---|---|
| 71 | 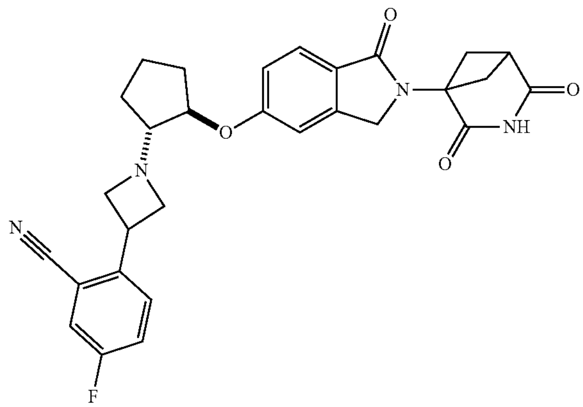 [SMILES: N#Cc1cc(F)ccc1C1CN([C@@H]2CCC[C@H]2Oc2ccc3c(c2)CN(C24CC(C2)C(=O)NC4=O)C3=O)C1] | Rac-2-(1-(((trans)-2-((2-(2,4-dioxo-3-azabicyclo[3.1.1]heptan-1-yl)-1-oxoisoindolin-5-yl)oxy)cyclopentyl)azetidin-3-yl)-5-fluorobenzonitrile |
| 72 | 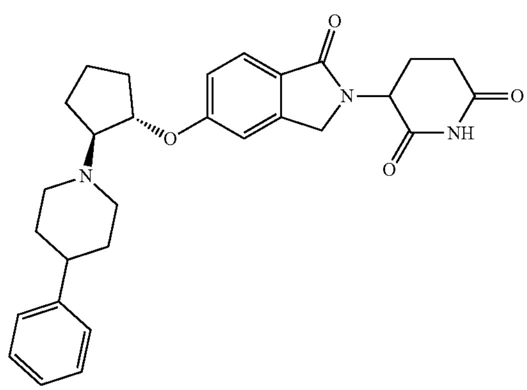 [SMILES: O=C1CCC(N2Cc3cc(O[C@H]4CCC[C@@H]4N4CCC(c5ccccc5)CC4)ccc3C2=O)C(=O)N1] | 3-(1-oxo-5-((((1S,2S)-2-(4-phenylpiperidin-1-yl)cyclopentyl)oxy)isoindolin-2-yl)piperidine-2,6-dione |
| 73 | 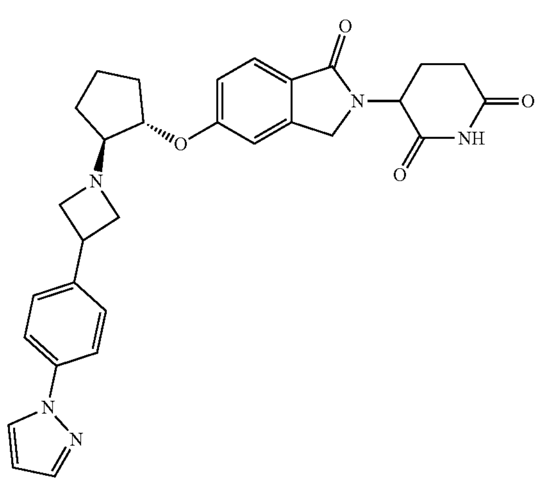 [SMILES: O=C1CCC(N2Cc3cc(O[C@H]4CCC[C@@H]4N4CC(c5ccc(-n6cccn6)cc5)C4)ccc3C2=O)C(=O)N1] | 3-(5-((((1S,2S)-2-(3-(4-(1H-pyrazol-1-yl)phenyl)azetidin-1-yl)cyclopentyl)oxy)-1-oxoisoindolin-2-yl)piperidine-2,6-dione |

TABLE 1-continued

| # | Structure | Nomenclature |
|---|---|---|
| 74 | 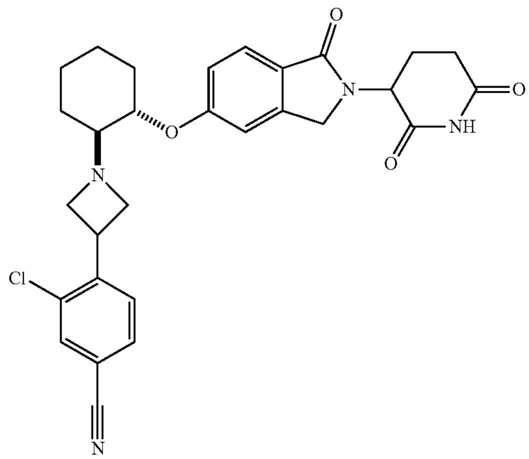 | Rac-3-chloro-4-(1-((trans)-2-((2-(2,6-dioxopiperidin-3-yl)-1-oxoisoindolin-5-yl)oxy)cyclohexyl)azetidin-3-yl)benzonitrile |
| 75 | 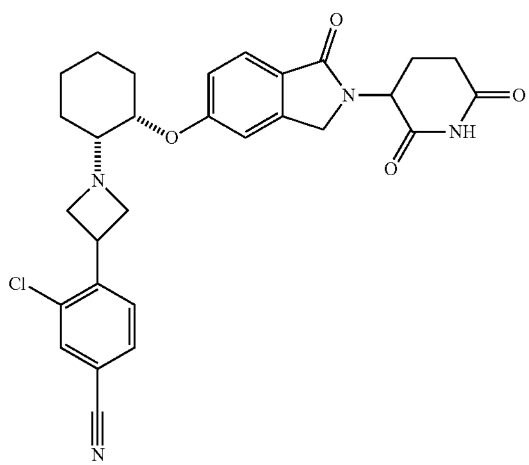 [SMILES: N#Cc1ccc(C2CN([C@@H]3CCCC[C@@H]3Oc3ccc4c(c3)CN(C3CCC(=O)NC3=O)C4=O)C2)c(Cl)c1] | Rac-3-chloro-4-(1-((cis)-2-((2-(2,6-dioxopiperidin-3-yl)-1-oxoisoindolin-5-yl)oxy)cyclohexyl)azetidin-3-yl)benzonitrile |
| 76 | 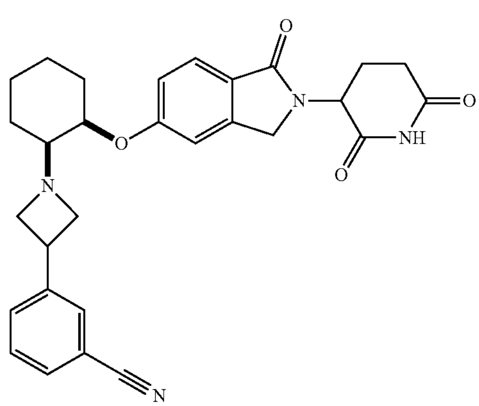 [SMILES: N#Cc1cccc(C2CN([C@H]3CCCC[C@H]3Oc3ccc4c(c3)CN(C3CCC(=O)NC3=O)C4=O)C2)c1] | Rac-3-(1-((cis)-2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|---|---|
| 77 | 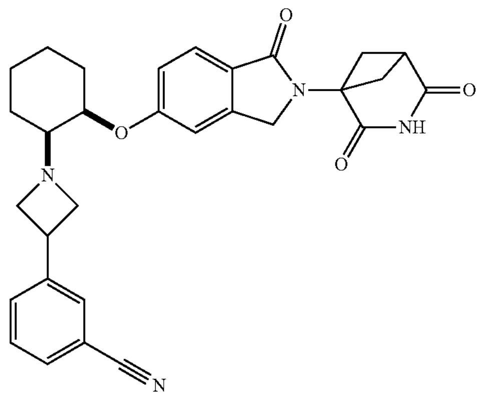 [SMILES: N#Cc1cccc(C2CN([C@H]3CCCC[C@H]3Oc3ccc4c(c3)CN(C35CC(C3)C(=O)NC5=O)C4=O)C2)c1] | Rac-3-(1-((cis)-2-((2-(2,4-dioxo-3-azabicyclo[3.1.1]heptan-1-yl)-1-oxoisoindolin-5-yl)oxy)cyclohexyl)azetidin-3-yl)benzonitrile |
| 78 | 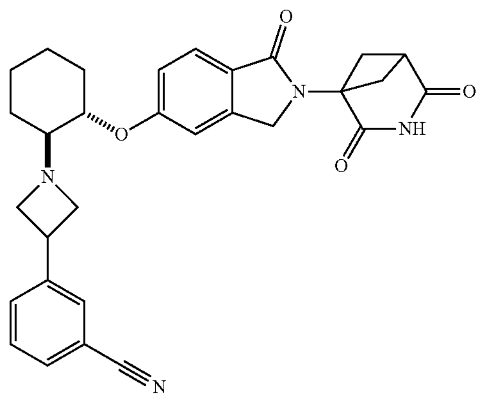 [SMILES: N#Cc1cccc(C2CN([C@H]3CCCC[C@@H]3Oc3ccc4c(c3)CN(C35CC(C3)C(=O)NC5=O)C4=O)C2)c1] | Rac-3-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile |
| 79 | 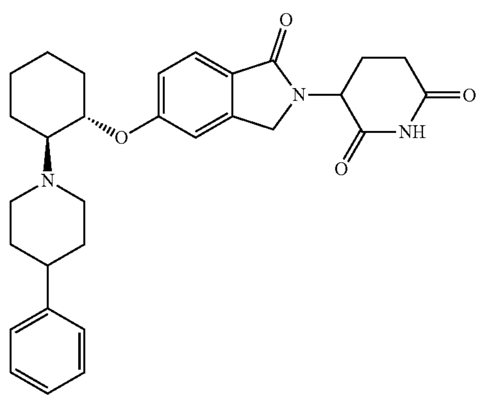 [SMILES: O=C1CCC(N2Cc3cc(O[C@H]4CCCC[C@@H]4N4CCC(c5ccccc5)CC4)ccc3C2=O)C(=O)N1] | 3-(1-oxo-5-(((1S,2S)-2-(4-phenylpiperidin-1-yl)cyclohexyl)oxy)isoindolin-2-yl)piperidine-2,6-dione |
| 80 | 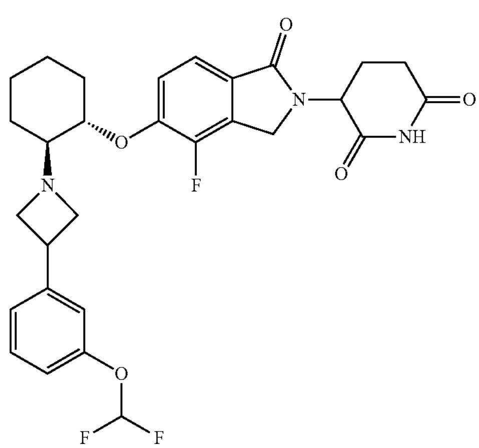 [SMILES: O=C1CCC(N2Cc3c(ccc(O[C@H]4CCCC[C@@H]4N4CC(c5cccc(OC(F)F)c5)C4)c3F)C2=O)C(=O)N1] | 3-(5-(((1S,2S)-2-(3-(3-(difluoromethoxy)phenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 81 | 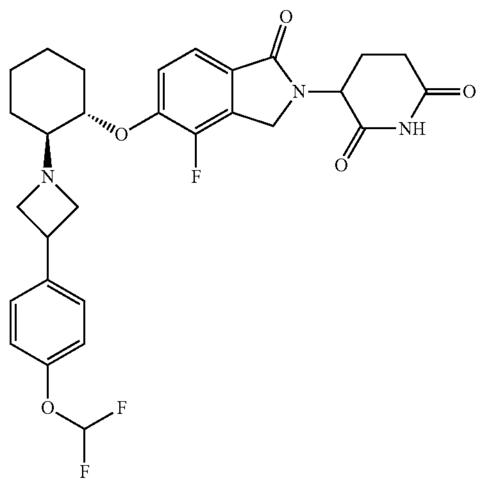 [SMILES: O=C1CCC(N2Cc3c(ccc(O[C@H]4CCCC[C@@H]4N4CC(c5ccc(OC(F)F)cc5)C4)c3F)C2=O)C(=O)N1] | 3-(5-(((1S,2S)-2-(3-(4-(difluoromethoxy)phenyl)azetidin-1-yl)cyclohexyl)oxy)-1-oxoisoindolin-2-yl)piperidine-2,6-dione |
| 82 | 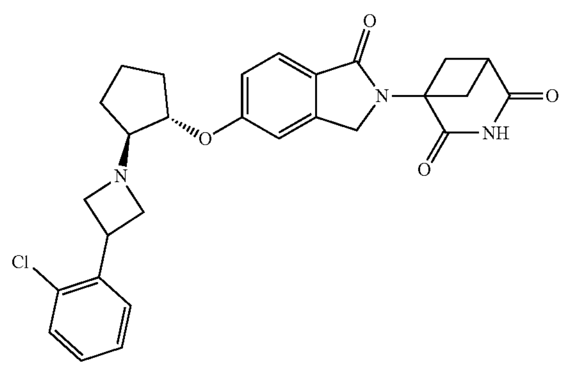 [SMILES: O=C1NC(=O)C2(N3Cc4cc(O[C@H]5CCC[C@@H]5N5CC(c6ccccc6Cl)C5)ccc4C3=O)CC1C2] | 1-(5-(((1S,2S)-2-(3-(2-chlorophenyl)azetidin-1-yl)cyclopentyl)oxy)-1-oxoisoindolin-2-yl)-3-azabicyclo[3.1.1]heptane-2,4-dione |
| 83 | 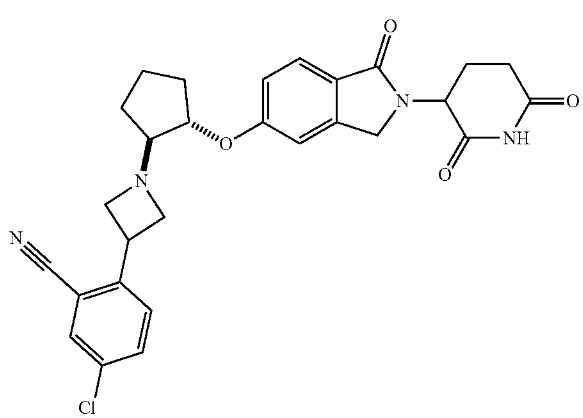 [SMILES: N#Cc1cc(Cl)ccc1C1CN([C@H]2CCC[C@@H]2Oc2ccc3c(c2)CN(C2CCC(=O)NC2=O)C3=O)C1] | Rac-5-chloro-2-(1-((trans)-2-((2-(2,6-dioxopiperidin-3-yl)-1-oxoisoindolin-5-yl)oxy)cyclopentyl)azetidin-3-yl)benzonitrile |

TABLE 1-continued

| # | Structure | Nomenclature |
|---|---|---|
| 84 | 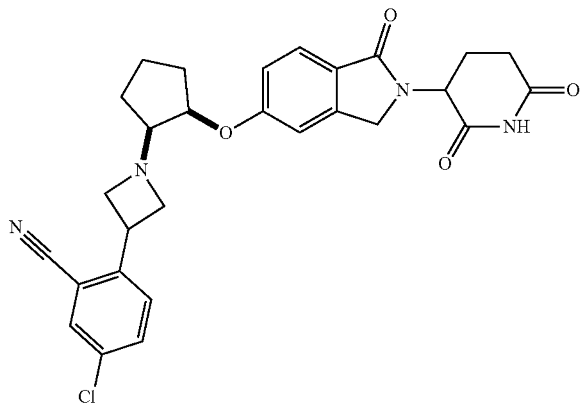 [SMILES: N#Cc1cc(Cl)ccc1C1CN([C@H]2CCC[C@H]2Oc2ccc3c(c2)CN(C2CCC(=O)NC2=O)C3=O)C1] | Rac-5-chloro-2-(1-((cis)-2-((2-(2,6-dioxopiperidin-3-yl)-1-oxoisoindolin-5-yl)oxy)cyclopentyl)azetidin-3-yl)benzonitrile |
| 85 | 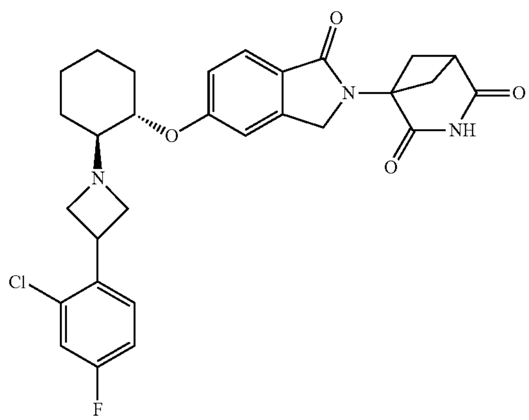 [SMILES: O=C1NC(=O)C2(N3Cc4cc(O[C@H]5CCCC[C@@H]5N5CC(c6ccc(F)cc6Cl)C5)ccc4C3=O)CC1C2] | 1-(5-((((1S,2S)-2-(3-(2-chloro-4-fluorophenyl)azetidin-1-yl)cyclohexyl)oxy)-1-oxoisoindolin-2-yl)-3-azabicyclo[3.1.1]heptane-2,4-dione |
| 86 | 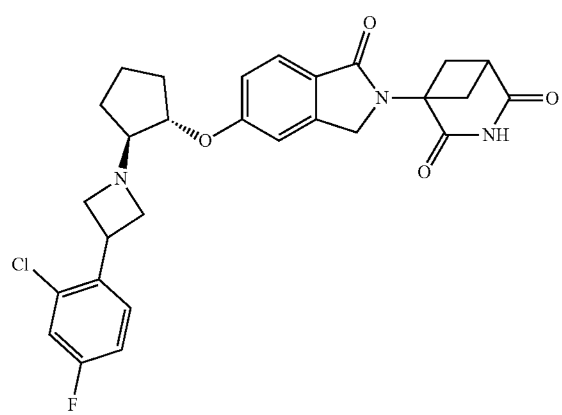 [SMILES: O=C1NC(=O)C2(N3Cc4cc(O[C@H]5CCC[C@@H]5N5CC(c6ccc(F)cc6Cl)C5)ccc4C3=O)CC1C2] | 1-(5-((((1S,2S)-2-(3-(2-chloro-4-fluorophenyl)azetidin-1-yl)cyclopentyl)oxy)-1-oxoisoindolin-2-yl)-3-azabicyclo[3.1.1]heptane-2,4-dione |
| 87 | 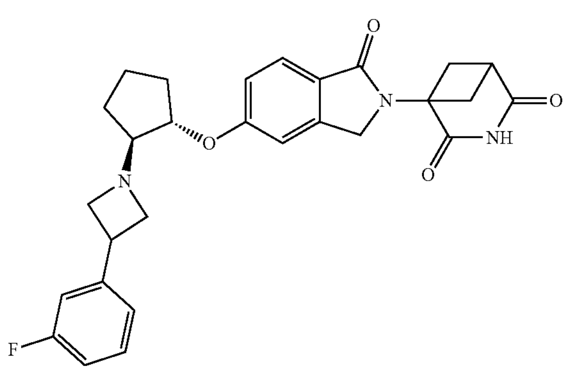 [SMILES: O=C1NC(=O)C2(N3Cc4cc(O[C@H]5CCC[C@@H]5N5CC(c6cccc(F)c6)C5)ccc4C3=O)CC1C2] | 1-(5-((((1S,2S)-2-(3-(3-fluorophenyl)azetidin-1-yl)cyclopentyl)oxy)-1-oxoisoindolin-2-yl)-3-azabicyclo[3.1.1]heptane-2,4-dione |

| # | Structure | Nomenclature |
|---|---|---|
| 88 | 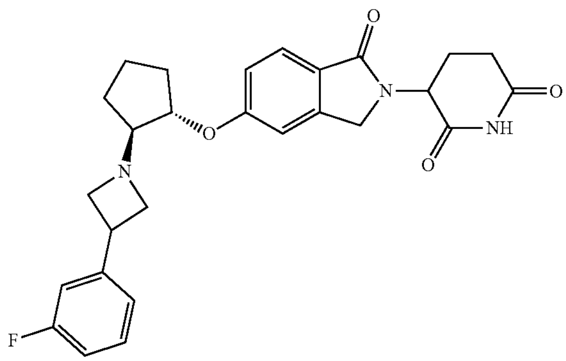 [SMILES: O=C1CCC(N2Cc3cc(O[C@H]4CCC[C@@H]4N4CC(c5cccc(F)c5)C4)ccc3C2=O)C(=O)N1] | 3-(5-(((1S,2S)-2-(3-(3-fluorophenyl)azetidin-1-yl)cyclopentyl)oxy)-1-oxoisoindolin-2-yl)piperidine-2,6-dione |
| 89 | 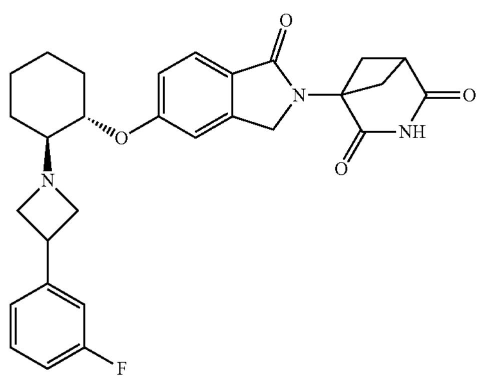 [SMILES: O=C1NC(=O)C2(N3Cc4cc(O[C@H]5CCCC[C@@H]5N5CC(c6cccc(F)c6)C5)ccc4C3=O)CC1C2] | 1-(5-(((1S,2S)-2-(3-(3-fluorophenyl)azetidin-1-yl)cyclohexyl)oxy)-1-oxoisoindolin-2-yl)-3-azabicyclo[3.1.1]heptane-2,4-dione |
| 90 | 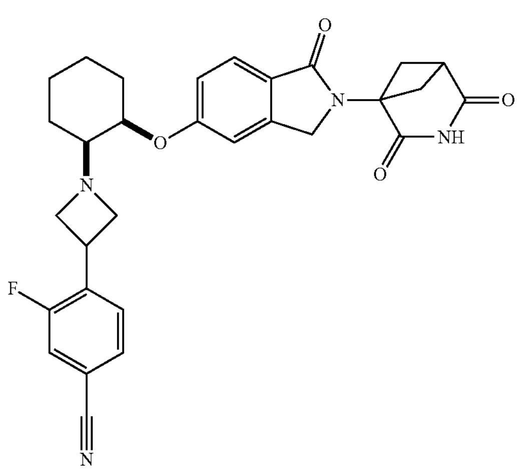 [SMILES: N#Cc1ccc(C2CN([C@H]3CCCC[C@H]3Oc3ccc4c(c3)CN(C35CC(C3)C(=O)NC5=O)C4=O)C2)c(F)c1] | Rac-4-(1-((cis)-2-((2-(2,4-dioxo-3-azabicyclo[3.1.1]heptan-1-yl)-1-oxoisoindolin-5-yl)oxy)cyclohexyl)azetidin-3-yl)-3-fluorobenzonitrile |

| # | Structure | Nomenclature |
|---|---|---|
| 91 | 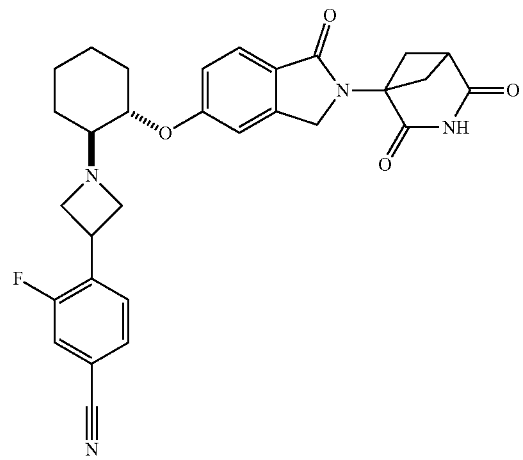 [SMILES: N#Cc1ccc(C2CN([C@H]3CCCC[C@@H]3Oc3ccc4c(c3)CN(C35CC(C3)C(=O)NC5=O)C4=O)C2)c(F)c1] | Rac-4-(1-((trans)-2-((2-(2,4-dioxo-3-azabicyclo[3.1.1]heptan-1-yl)-1-oxoisoindolin-5-yl)oxy)cyclohexyl)azetidin-3-yl)-3-fluorobenzonitrile |
| 92 | 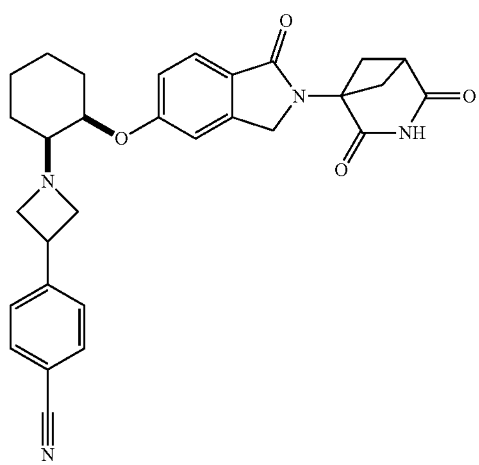 [SMILES: N#Cc1ccc(C2CN([C@H]3CCCC[C@H]3Oc3ccc4c(c3)CN(C35CC(C3)C(=O)NC5=O)C4=O)C2)cc1] | Rac-4-(1-((cis)-2-((2-(2,4-dioxo-3-azabicyclo[3.1.1]heptan-1-yl)-1-oxoisoindolin-5-yl)oxy)cyclohexyl)azetidin-3-yl)benzonitrile |
| 93 | 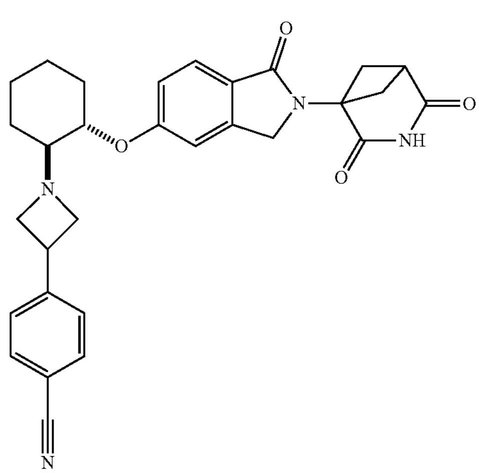 [SMILES: N#Cc1ccc(C2CN([C@H]3CCCC[C@@H]3Oc3ccc4c(c3)CN(C35CC(C3)C(=O)NC5=O)C4=O)C2)cc1] | Rac-4-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile |

TABLE 1-continued

| # | Structure | Nomenclature |
|---|---|---|
| 94 | 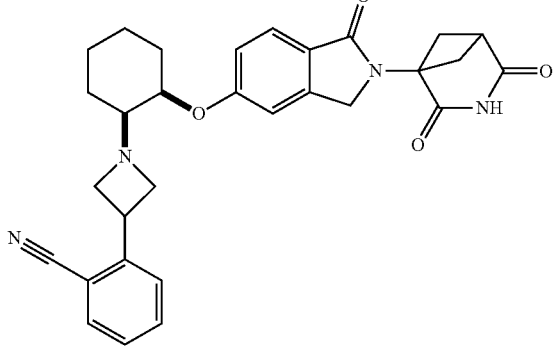 | Rac-2-(1-((cis)-2-((2-(2,4-dioxo-3-azabicyclo[3.1.1]heptan-1-yl)-1-oxoisoindolin-5-yl)oxy)cyclohexyl)azetidin-3-yl)benzonitrile |
| 95 | 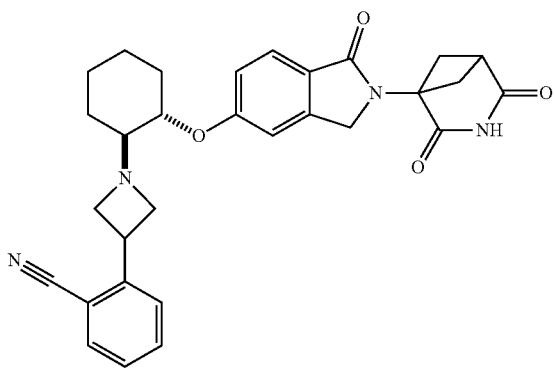 [SMILES: N#Cc1ccccc1C1CN([C@H]2CCCC[C@@H]2Oc2ccc3c(c2)CN(C24CC(C2)C(=O)NC4=O)C3=O)C1] | Rac-2-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile |
| 96 | 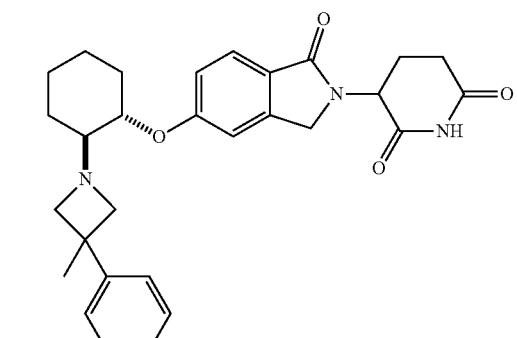 | Rac-3-(5-(((trans)-2-(3-hydroxy-3-phenylazetidin-1-yl)cyclohexyl)oxy)-1-oxoisoindolin-2-yl)piperidine-2,6-dione |
| 97 | 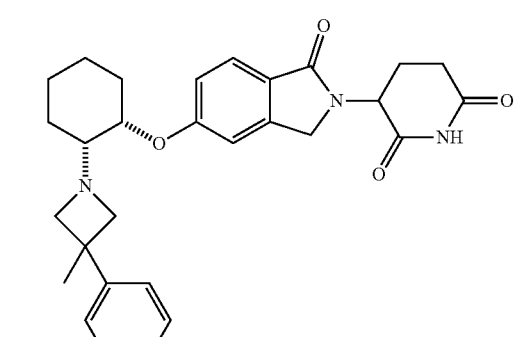 | Rac-3-(5-(((cis)-2-(3-hydroxy-3-phenylazetidin-1-yl)cyclohexyl)oxy)-1-oxoisoindolin-2-yl)piperidine-2,6-dione |

TABLE 1-continued

| # | Structure | Nomenclature |
|---|---|---|
| 98 | 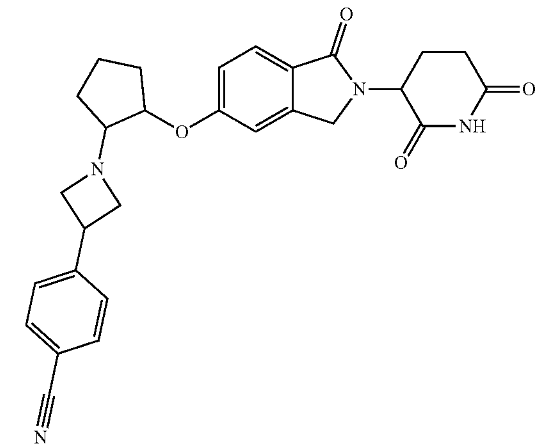 [SMILES: N#Cc1ccc(C2CN(C3CCCC3Oc3ccc4c(c3)CN(C3CCC(=O)NC3=O)C4=O)C2)cc1] | 4-(1-(2-((2-(2,6-dioxopiperidin-3-yl)-1-oxoisoindolin-5-yl)oxy)cyclopentyl)azetidin-3-yl)benzonitrile |
| 99 | 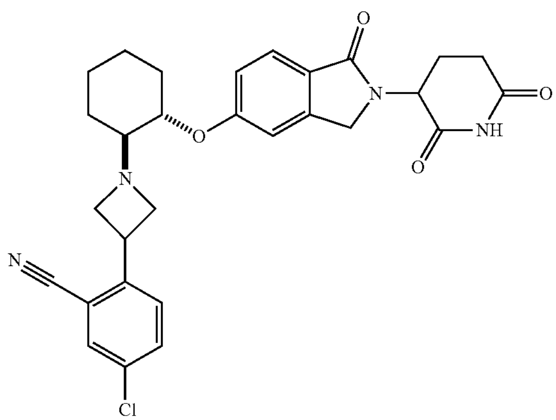 [SMILES: N#Cc1cc(Cl)ccc1C1CN([C@H]2CCCC[C@@H]2Oc2ccc3c(c2)CN(C2CCC(=O)NC2=O)C3=O)C1] | Rac-5-chloro-2-(1-((trans)-2-((2-(2,6-dioxopiperidin-3-yl)-1-oxoisoindolin-5-yl)oxy)cyclohexyl)azetidin-3-yl)benzonitrile |
| 100 | 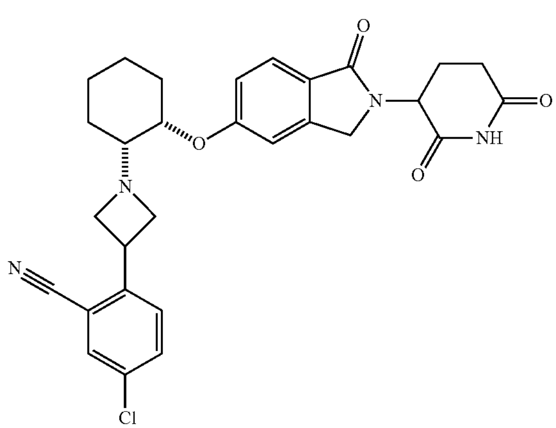 [SMILES: N#Cc1cc(Cl)ccc1C1CN([C@@H]2CCCC[C@@H]2Oc2ccc3c(c2)CN(C2CCC(=O)NC2=O)C3=O)C1] | Rac-5-chloro-2-(1-((cis)-2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|---|---|
| 101 | 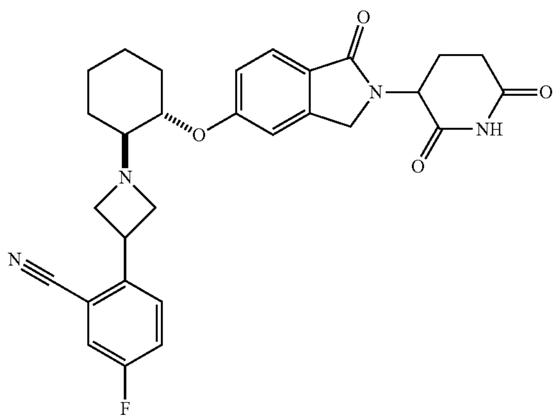 | Rac-2-(1-((trans)-2-((2-(2,6-dioxopiperidin-3-yl)-1-oxoisoindolin-5-yl)oxy)cyclohexyl)azetidin-3-yl)-5-fluorobenzonitrile |
| 102 | 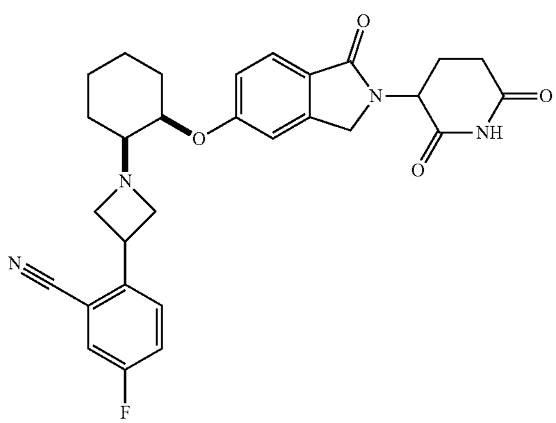 [SMILES: N#Cc1cc(F)ccc1C1CN([C@H]2CCCC[C@H]2Oc2ccc3c(c2)CN(C2CCC(=O)NC2=O)C3=O)C1] | Rac-2-(1-((cis)-2-((2-(2,6-dioxopiperidin-3-yl)-1-oxoisoindolin-5-yl)oxy)cyclohexyl)azetidin-3-yl)-5-fluorobenzonitrile |
| 103 | 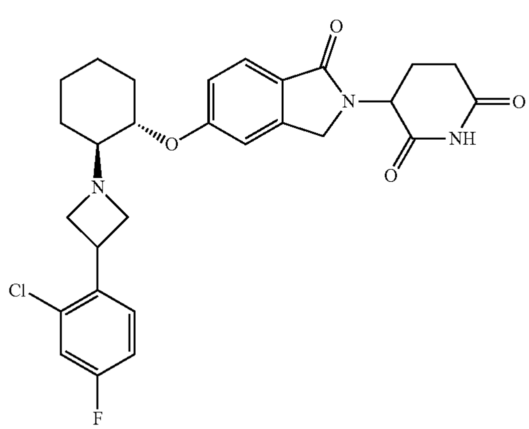 [SMILES: O=C1CCC(N2Cc3cc(O[C@H]4CCCC[C@@H]4N4CC(c5ccc(F)cc5Cl)C4)ccc3C2=O)C(=O)N1] | 3-(5-(((1S,2S)-2-(3-(2-chloro-4-fluorophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 104 | 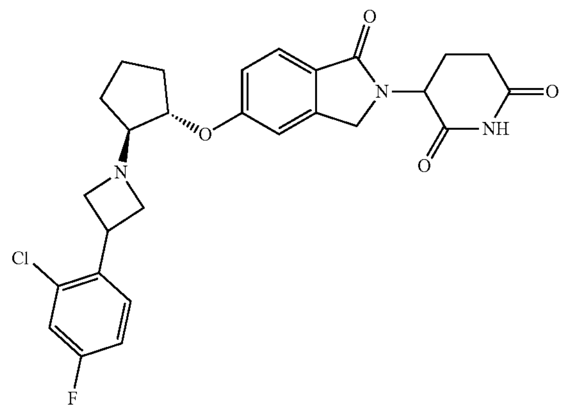 [SMILES: O=C1CCC(N2Cc3cc(O[C@H]4CCC[C@@H]4N4CC(c5ccc(F)cc5Cl)C4)ccc3C2=O)C(=O)N1] | 3-(5-(((1S,2S)-2-(3-(2-chloro-4-fluorophenyl)azetidin-1-yl)cyclopentyl)oxy)-1-oxoisoindolin-2-yl)piperidine-2,6-dione |
| 105 | 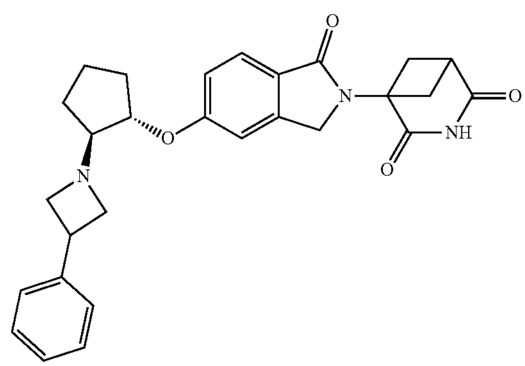 [SMILES: O=C1NC(=O)C2(N3Cc4cc(O[C@H]5CCC[C@@H]5N5CC(c6ccccc6)C5)ccc4C3=O)CC1C2] | 1-(1-oxo-5-(((1S,2S)-2-(3-phenylazetidin-1-yl)cyclopentyl)oxy)isoindolin-2-yl)-3-azabicyclo[3.1.1]heptane-2,4-dione |
| 106 | 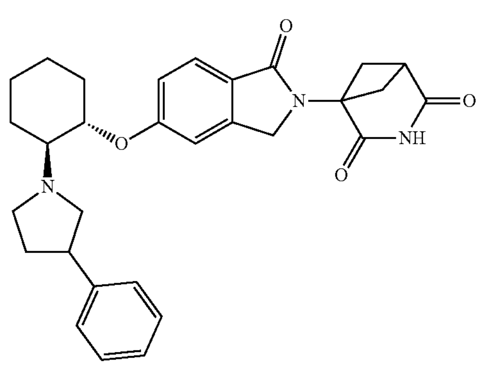 [SMILES: O=C1NC(=O)C2(N3Cc4cc(O[C@H]5CCCC[C@@H]5N5CCC(c6ccccc6)C5)ccc4C3=O)CC1C2] | 1-(1-oxo-5-(((1S,2S)-2-(3-phenylpyrrolidin-1-yl)cyclohexyl)oxy)isoindolin-2-yl)-3-azabicyclo[3.1.1]heptane-2,4-dione |
| 107 | 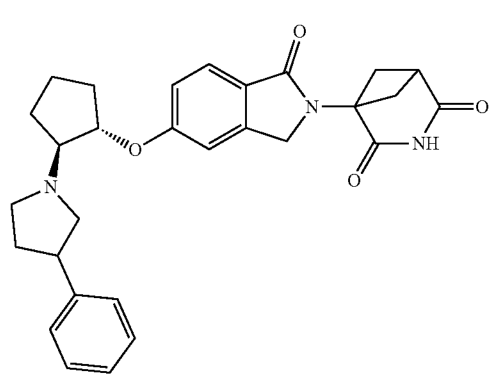 [SMILES: O=C1NC(=O)C2(N3Cc4cc(O[C@H]5CCC[C@@H]5N5CCC(c6ccccc6)C5)ccc4C3=O)CC1C2] | 1-(1-oxo-5-(((1S,2S)-2-(3-phenylpyrrolidin-1-yl)cyclopentyl)oxy)isoindolin-2-yl)-3-azabicyclo[3.1.1]heptane-2,4-dione |

TABLE 1-continued

| # | Structure | Nomenclature |
|---|---|---|
| 108 | 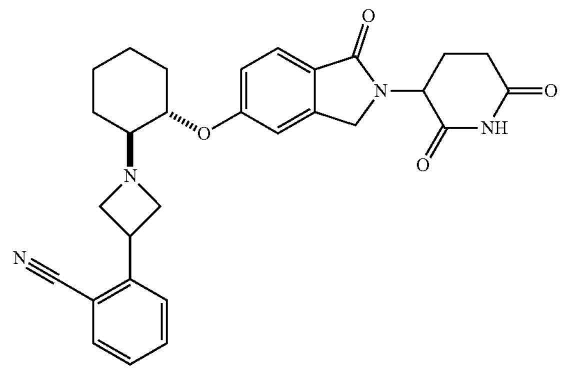 [SMILES: N#Cc1ccccc1C1CN([C@H]2CCCC[C@@H]2Oc2ccc3c(c2)CN(C2CCC(=O)NC2=O)C3=O)C1] | Rac-2-(1-((trans)-2-((2-(2,6-dioxopiperidin-3-yl)-1-oxoisoindolin-5-yl)oxy)cyclohexyl)azetidin-3-yl)benzonitrile |
| 109 | 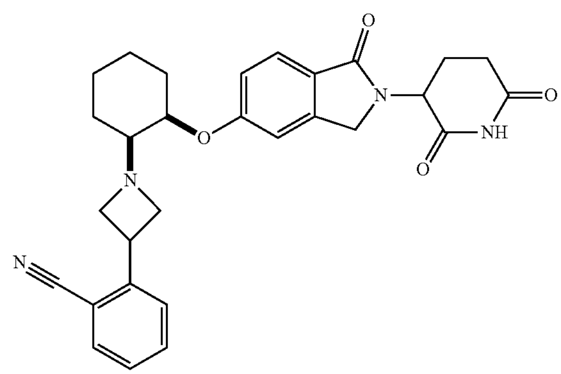 [SMILES: N#Cc1ccccc1C1CN([C@H]2CCCC[C@H]2Oc2ccc3c(c2)CN(C2CCC(=O)NC2=O)C3=O)C1] | Rac-2-(1-((cis)-2-((2-(2,6-dioxopiperidin-3-yl)-1-oxoisoindolin-5-yl)oxy)cyclohexyl)azetidin-3-yl)benzonitrile |
| 110 | 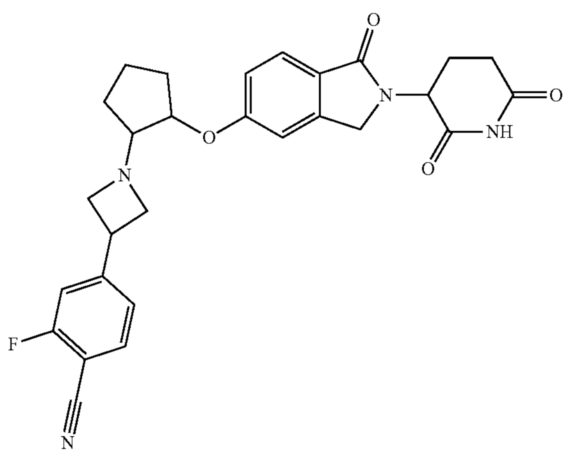 [SMILES: N#Cc1ccc(C2CN(C3CCCC3Oc3ccc4c(c3)CN(C3CCC(=O)NC3=O)C4=O)C2)cc1F] | 4-(1-(2-((2-(2,6-dioxopiperidin-3-yl)-1-oxoisoindolin-5-yl)oxy)cyclopentyl)azetidin-3-yl)-2-fluorobenzonitrile |
| 111 | 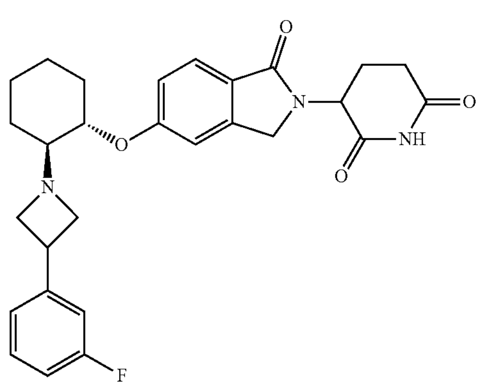 [SMILES: O=C1CCC(N2Cc3cc(O[C@H]4CCCC[C@@H]4N4CC(c5cccc(F)c5)C4)ccc3C2=O)C(=O)N1] | 3-(5-(((1S,2S)-2-(3-(3-fluorophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 112 | 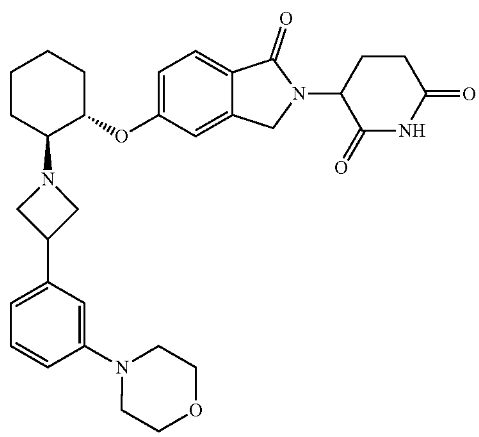 [SMILES: O=C1CCC(N2Cc3cc(O[C@H]4CCCC[C@@H]4N4CC(c5cccc(N6CCOCC6)c5)C4)ccc3C2=O)C(=O)N1] | 3-(5-(((1S,2S)-2-(3-(3-morpholinophenyl)azetidin-1-yl)cyclohexyl)oxy)-1-oxoisoindolin-2-yl)piperidine-2,6-dione |
| 113 | 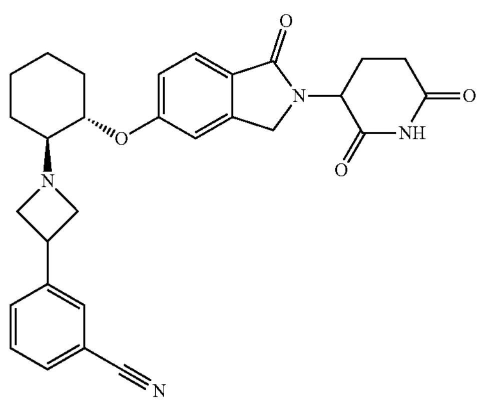 [SMILES: N#Cc1cccc(C2CN([C@H]3CCCC[C@@H]3Oc3ccc4c(c3)CN(C3CCC(=O)NC3=O)C4=O)C2)c1] | 3-(1-((1S,2S)-2-((2-(2,6-dioxopiperidin-3-yl)-1-oxoisoindolin-5-yl)oxy)cyclohexyl)azetidin-3-yl)benzonitrile |
| 114 | 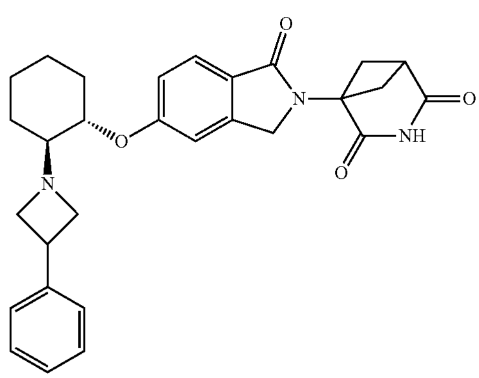 [SMILES: O=C1NC(=O)C2(N3Cc4cc(O[C@H]5CCCC[C@@H]5N5CC(c6ccccc6)C5)ccc4C3=O)CC1C2] | 1-(1-oxo-5-(((1S,2S)-2-(3-phenylazetidin-1-yl)cyclohexyl)oxy)isoindolin-2-yl)-3-azabicyclo[3.1.1]heptane-2,4-dione |

TABLE 1-continued
| # | Structure | Nomenclature |
|---|---|---|
| 115 | 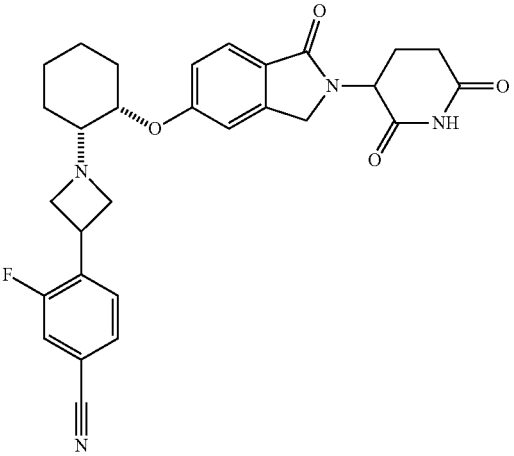 [SMILES: N#Cc1ccc(C2CN([C@@H]3CCCC[C@@H]3Oc3ccc4c(c3)CN(C3CCC(=O)NC3=O)C4=O)C2)c(F)c1] | Rac-4-(1-((cis)-2-((2-(2,6-dioxopiperidin-3-yl)-1-oxoisoindolin-5-yl)oxy)cyclohexyl)azetidin-3-yl)-3-fluorobenzonitrile |
| 116 | 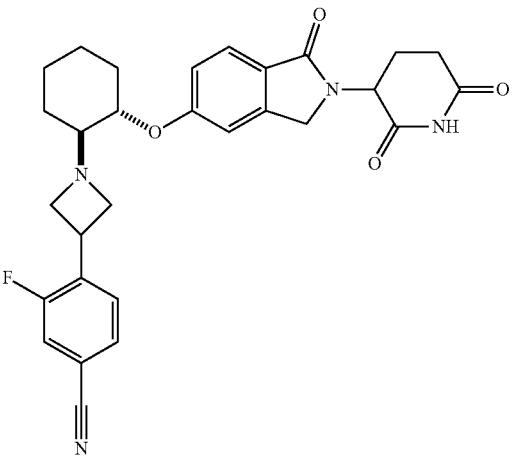 [SMILES: N#Cc1ccc(C2CN([C@H]3CCCC[C@@H]3Oc3ccc4c(c3)CN(C3CCC(=O)NC3=O)C4=O)C2)c(F)c1] | Rac-4-(1-((trans)-2-((2-(2,6-dioxopiperidin-3-yl)-1-oxoisoindolin-5-yl)oxy)cyclohexyl)azetidin-3-yl)-3-fluorobenzonitrile |
| 117 | 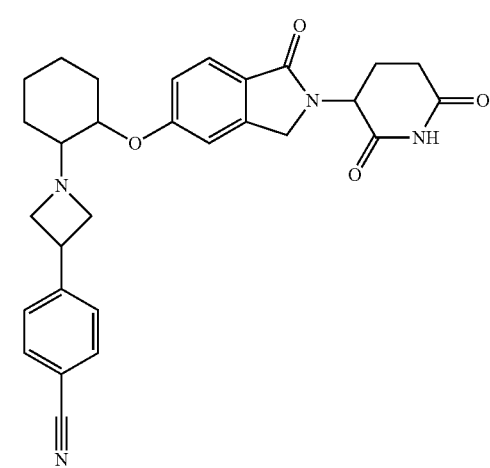 [SMILES: N#Cc1ccc(C2CN(C3CCCCC3Oc3ccc4c(c3)CN(C3CCC(=O)NC3=O)C4=O)C2)cc1] | 4-(1-(2-((2-(2,6-dioxopiperidin-3-yl)-1-oxoisoindolin-5-yl)oxy)cyclohexyl)azetidin-3-yl)benzonitrile |

TABLE 1-continued

| # | Structure | Nomenclature |
|---|-----------|--------------|
| 118 | 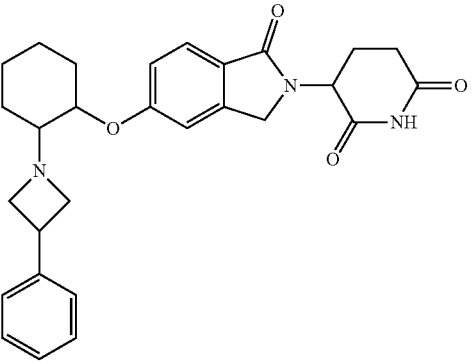 [SMILES: O=C1CCC(N2Cc3cc(OC4CCCCC4N4CC(c5ccccc5)C4)ccc3C2=O)C(=O)N1] | 3-(1-oxo-5-((2-(3-phenylazetidin-1-yl)cyclohexyl)oxy)isoindolin-2-yl)piperidine-2,6-dione |
| 119 | 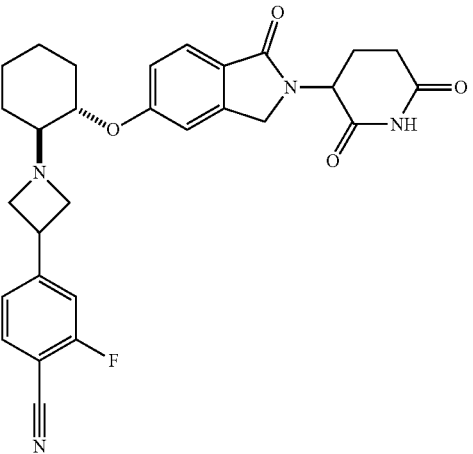 | Rac-4-(1-((trans)-2-((2-(2,6-dioxopiperidin-3-yl)-1-oxoisoindolin-5-yl)oxy)cyclohexyl)azetidin-3-yl)-2-fluorobenzonitrile |
| 120 | 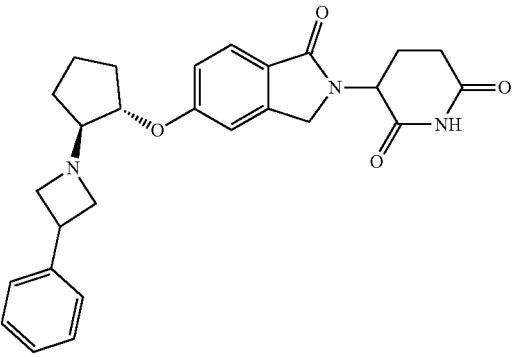 [SMILES: O=C1CCC(N2Cc3cc(O[C@H]4CCC[C@@H]4N4CC(c5ccccc5)C4)ccc3C2=O)C(=O)N1] | 3-(1-oxo-5-(((1S,2S)-2-(3-phenylazetidin-1-yl)cyclopentyl)oxy)isoindolin-2-yl)piperidine-2,6-dione |
| 121 | 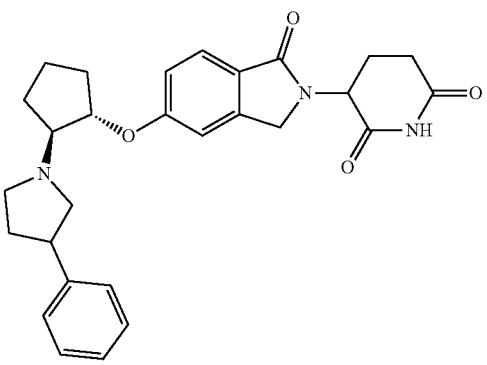 [SMILES: O=C1CCC(N2Cc3cc(O[C@H]4CCC[C@@H]4N4CCC(c5ccccc5)C4)ccc3C2=O)C(=O)N1] | 3-(1-oxo-5-(((1S,2S)-2-(3-phenylpyrrolidin-1-yl)cyclopentyl)oxy)isoindolin-2-yl)piperidine-2,6-dione |

TABLE 1-continued

| # | Structure | Nomenclature |
|---|---|---|
| 122 | 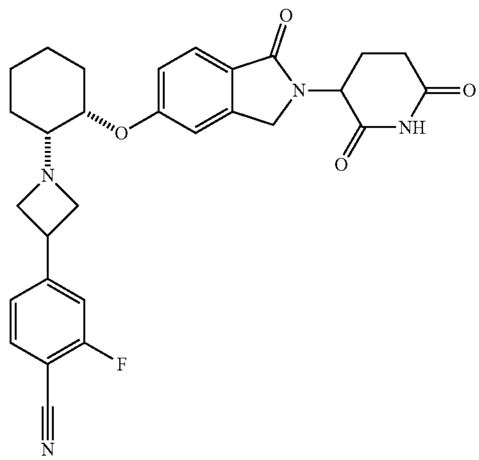 [SMILES: N#Cc1ccc(C2CN([C@@H]3CCCC[C@@H]3Oc3ccc4c(c3)CN(C3CCC(=O)NC3=O)C4=O)C2)cc1F] | Rac-4-(1-((cis)-2-((2-(2,6-dioxopiperidin-3-yl)-1-oxoisoindolin-5-yl)oxy)cyclohexyl)azetidin-3-yl)-2-fluorobenzonitrile |
| 123 | 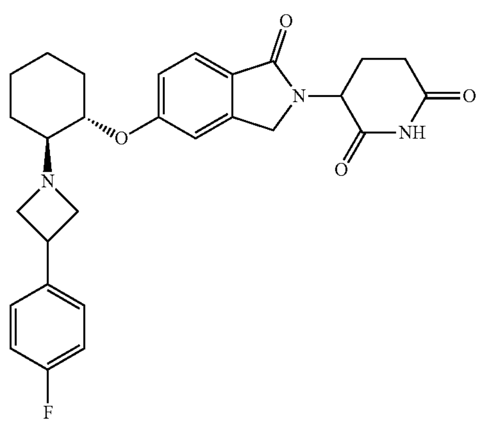 [SMILES: O=C1CCC(N2Cc3cc(O[C@H]4CCCC[C@@H]4N4CC(c5ccc(F)cc5)C4)ccc3C2=O)C(=O)N1] | 3-(5-(((1S,2S)-2-(3-(4-fluorophenyl)azetidin-1-yl)cyclohexyl)oxy)-1-oxoisoindolin-2-yl)piperidine-2,6-dione |
| 124 | 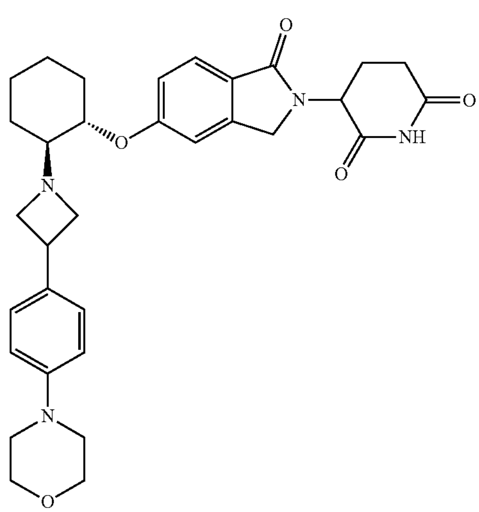 [SMILES: O=C1CCC(N2Cc3cc(O[C@H]4CCCC[C@@H]4N4CC(c5ccc(N6CCOCC6)cc5)C4)ccc3C2=O)C(=O)N1] | 3-(5-(((1S,2S)-2-(3-(4-morpholinophenyl)azetidin-1-yl)cyclohexyl)oxy)-1-oxoisoindolin-2-yl)piperidine-2,6-dione |

TABLE 1-continued

| # | Structure | Nomenclature |
|---|---|---|
| 125 | 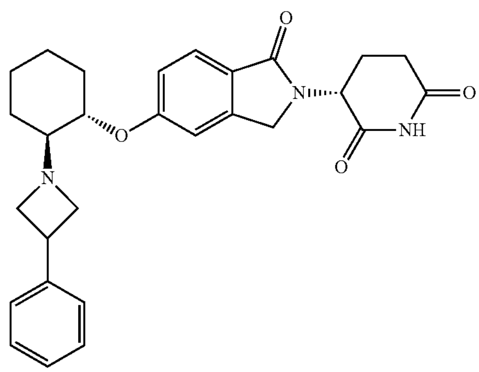 [SMILES: O=C1CC[C@@H](N2Cc3cc(O[C@H]4CCCC[C@@H]4N4CC(c5ccccc5)C4)ccc3C2=O)C(=O)N1] | (R)-3-(1-oxo-5-(((1S,2S)-2-(3-phenylazetidin-1-yl)cyclohexyl)oxy)isoindolin-2-yl)piperidine-2,6-dione |
| 126 | 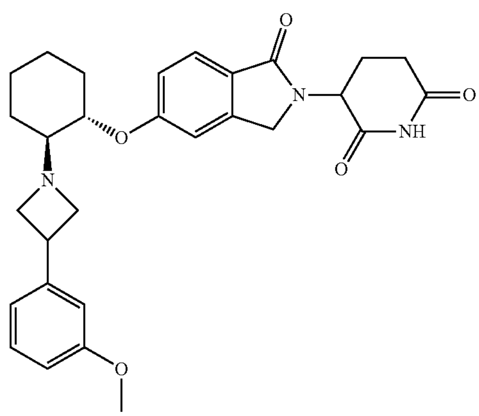 [SMILES: COc1cccc(C2CN([C@H]3CCCC[C@@H]3Oc3ccc4c(c3)CN(C3CCC(=O)NC3=O)C4=O)C2)c1] | 3-(5-(((1S,2S)-2-(3-(3-methoxyphenyl)azetidin-1-yl)cyclohexyl)oxy)-1-oxoisoindolin-2-yl)piperidine-2,6-dione |
| 127 | 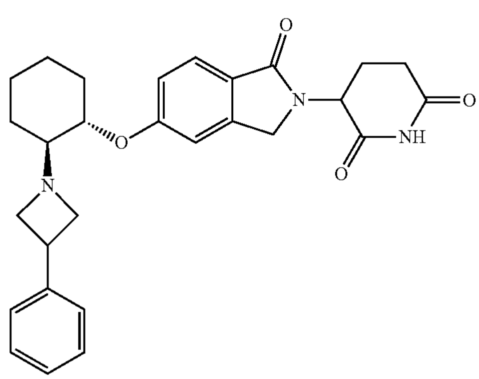 | 3-(1-oxo-5-(((1S,2S)-2-(3-phenylazetidin-1-yl)cyclohexyl)oxy)isoindolin-2-yl)piperidine-2,6-dione |
| 128 | 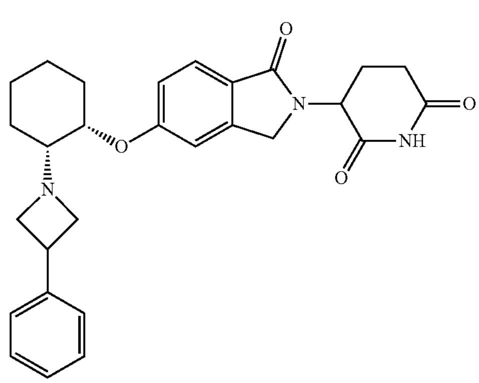 [SMILES: O=C1CCC(N2Cc3cc(O[C@H]4CCCC[C@H]4N4CC(c5ccccc5)C4)ccc3C2=O)C(=O)N1] | 3-(1-oxo-5-(((1S,2R)-2-(3-phenylazetidin-1-yl)cyclohexyl)oxy)isoindolin-2-yl)piperidine-2,6-dione |

TABLE 1-continued

| # | Structure | Nomenclature |
|---|---|---|
| 129 | 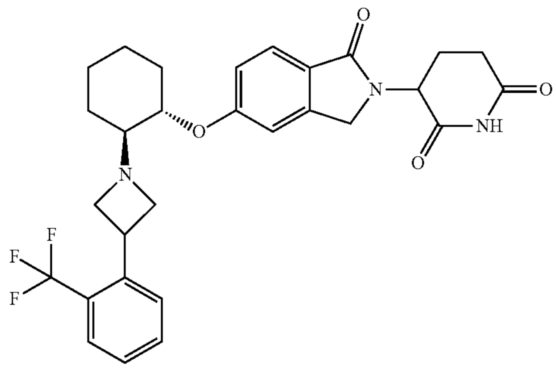 [SMILES: O=C1CCC(N2Cc3cc(O[C@H]4CCCC[C@@H]4N4CC(c5ccccc5C(F)(F)F)C4)ccc3C2=O)C(=O)N1] | 3-(1-oxo-5-((((1S,2S)-2-(3-(2-(trifluoromethyl)phenyl)azetidin-1-yl)cyclohexyl)oxy)isoindolin-2-yl)piperidine-2,6-dione |
| 130 | 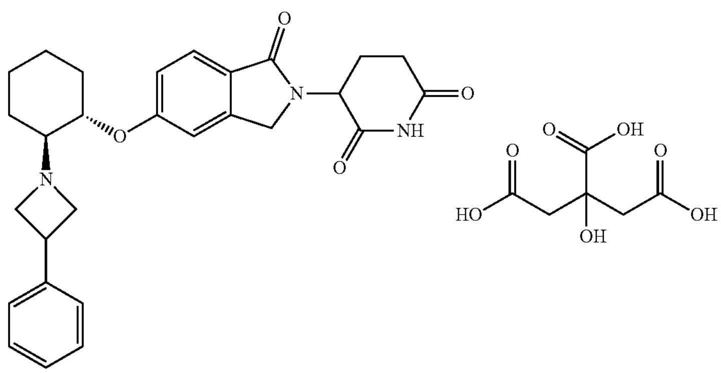 [SMILES: O=C1CCC(N2Cc3cc(O[C@H]4CCCC[C@@H]4N4CC(c5ccccc5)C4)ccc3C2=O)C(=O)N1 ; O=C(O)CC(O)(CC(=O)O)C(=O)O] | 3-(1-oxo-5-((((1S,2S)-2-(3-phenylazetidin-1-yl)cyclohexyl)oxy)isoindolin-2-yl)piperidine-2,6-dione 2-hydroxypropane-1,2,3-tricarboxylate |
| 131 | 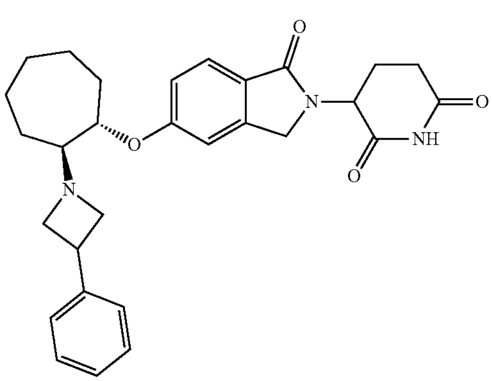 [SMILES: O=C1CCC(N2Cc3cc(O[C@H]4CCCCC[C@@H]4N4CC(c5ccccc5)C4)ccc3C2=O)C(=O)N1] | 3-(1-oxo-5-((((1S,2S)-2-(3-phenylazetidin-1-yl)cycloheptyl)oxy)isoindolin-2-yl)piperidine-2,6-dione |

TABLE 1-continued

| # | Structure | Nomenclature |
|---|---|---|
| 132 | 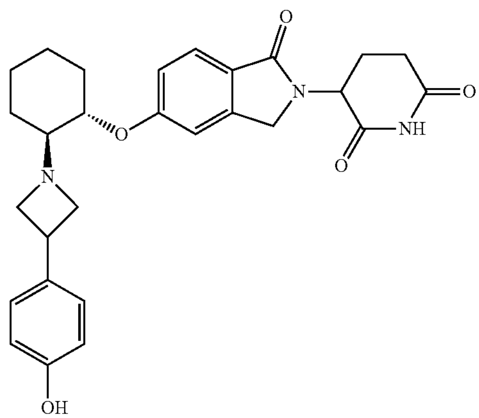 [SMILES: O=C1CCC(N2Cc3cc(O[C@H]4CCCC[C@@H]4N4CC(c5ccc(O)cc5)C4)ccc3C2=O)C(=O)N1] | 3-(5-(((1S,2S)-2-(3-(4-hydroxyphenyl)azetidin-1-yl)cyclohexyl)oxy)-1-oxoisoindolin-2-yl)piperidine-2,6-dione |
| 133 | 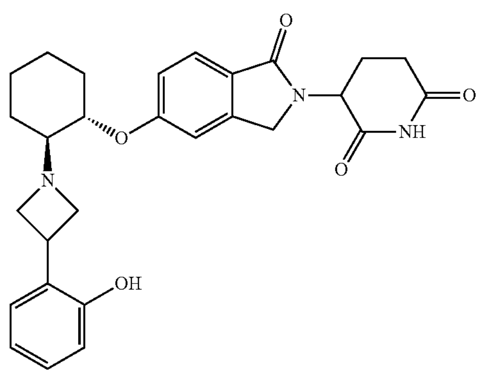 [SMILES: O=C1CCC(N2Cc3cc(O[C@H]4CCCC[C@@H]4N4CC(c5ccccc5O)C4)ccc3C2=O)C(=O)N1] | 3-(5-(((1S,2S)-2-(3-(2-hydroxyphenyl)azetidin-1-yl)cyclohexyl)oxy)-1-oxoisoindolin-2-1)piperidine-2,6-dione |
| 134 | 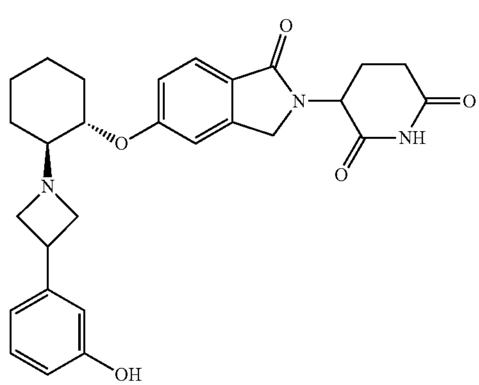 [SMILES: O=C1CCC(N2Cc3cc(O[C@H]4CCCC[C@@H]4N4CC(c5cccc(O)c5)C4)ccc3C2=O)C(=O)N1] | 3-(5-(((1S,2S)-2-(3-(3-hydroxyphenyl)azetidin-1-yl)cyclohexyl)oxy)-1-oxoisoindolin-2-yl)piperidine-2,6-dione |

In some embodiments, provided herein is a compound which binds cereblon selected from Table 1A, or a pharmaceutically acceptable salt, solvate, stereoisomer, and/or tautomer thereof.
TABLE 1A
| Structure |
|---|
| 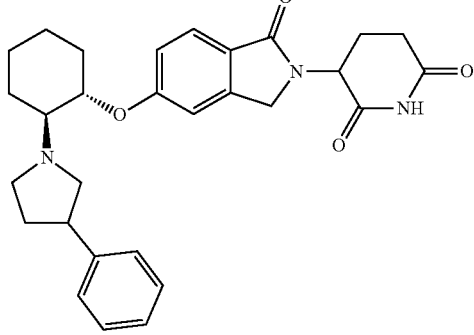 |
| 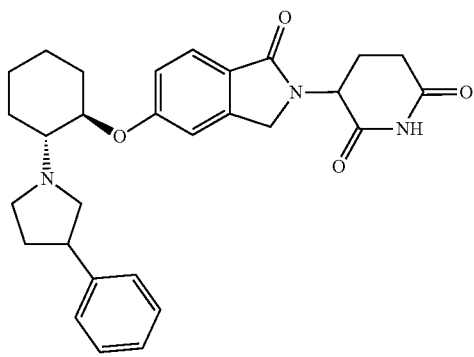 [SMILES: O=C1CCC(N2Cc3cc(O[C@@H]4CCCC[C@H]4N4CCC(c5ccccc5)C4)ccc3C2=O)C(=O)N1] |
| 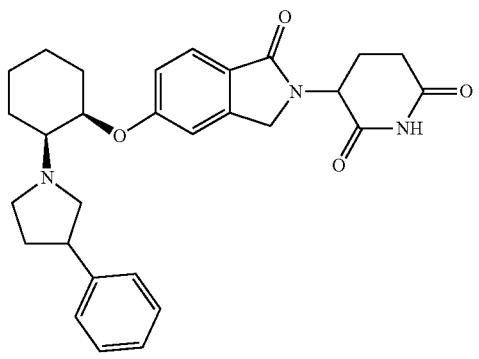 [SMILES: O=C1CCC(N2Cc3cc(O[C@@H]4CCCC[C@@H]4N4CCC(c5ccccc5)C4)ccc3C2=O)C(=O)N1] |
| 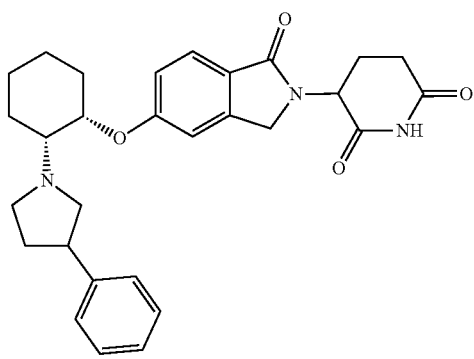 |
TABLE 1A-continued
| Structure |
|---|
|  |
|  |
|  |
|  |

TABLE 1A-continued
Structure
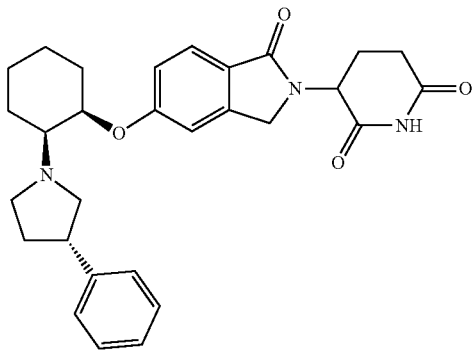 [SMILES: O=C1CCC(N2Cc3cc(O[C@@H]4CCCC[C@@H]4N4CC[C@@H](c5ccccc5)C4)ccc3C2=O)C(=O)N1]
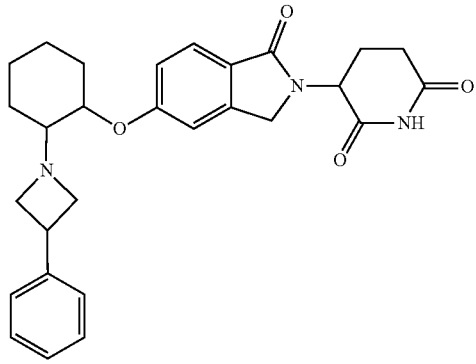
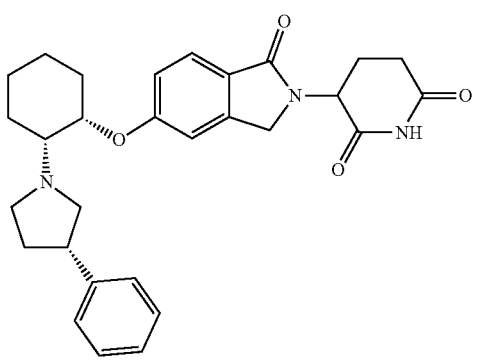 [SMILES: O=C1CCC(N2Cc3cc(O[C@H]4CCCC[C@H]4N4CC[C@@H](c5ccccc5)C4)ccc3C2=O)C(=O)N1]
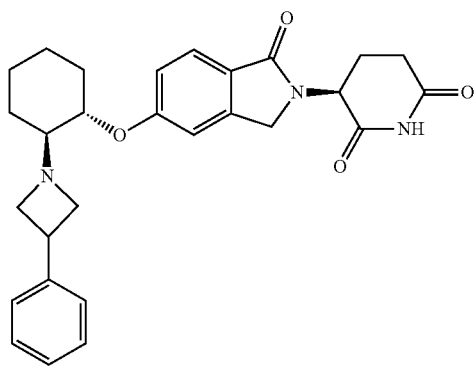
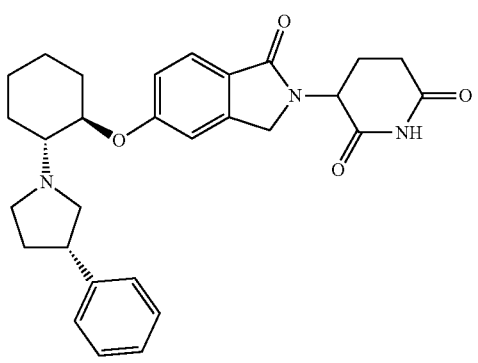 [SMILES: O=C1CCC(N2Cc3cc(O[C@@H]4CCCC[C@H]4N4CC[C@@H](c5ccccc5)C4)ccc3C2=O)C(=O)N1]
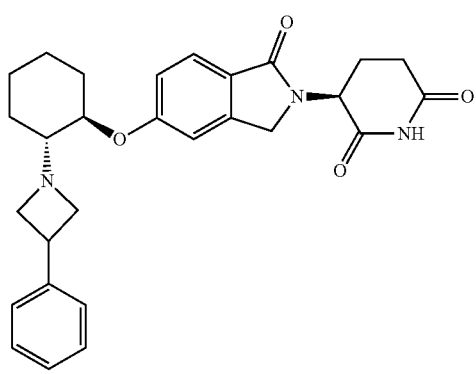
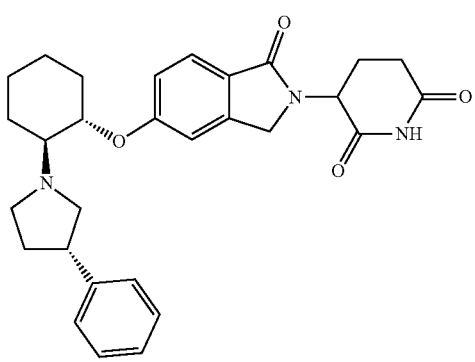 [SMILES: O=C1CCC(N2Cc3cc(O[C@H]4CCCC[C@@H]4N4CC[C@@H](c5ccccc5)C4)ccc3C2=O)C(=O)N1]
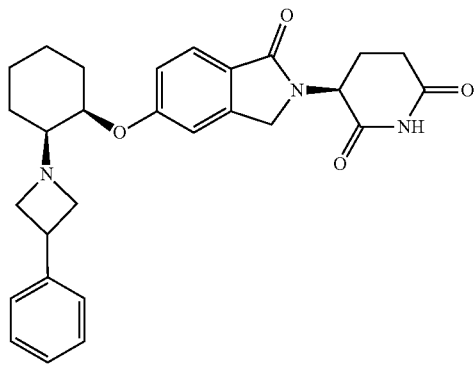 [SMILES: O=C1CC[C@H](N2Cc3cc(O[C@@H]4CCCC[C@@H]4N4CC(c5ccccc5)C4)ccc3C2=O)C(=O)N1]

TABLE 1A-continued

Structure

TABLE 1A-continued
| Structure |
|---|
|  |
| 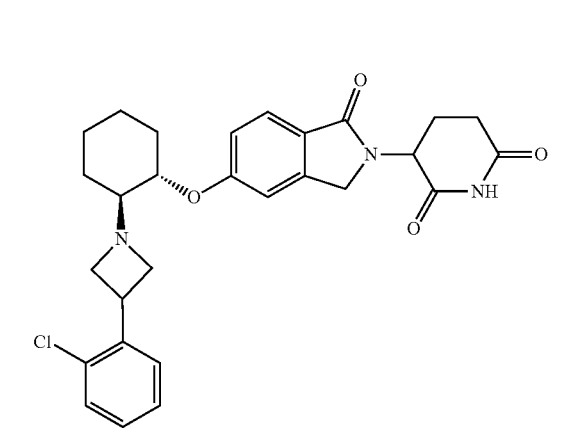 [SMILES: O=C1CCC(N2Cc3cc(O[C@H]4CCCC[C@@H]4N4CC(c5ccccc5Cl)C4)ccc3C2=O)C(=O)N1] |
| 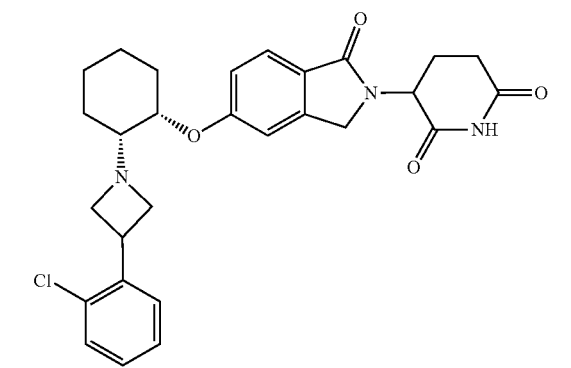 [SMILES: O=C1CCC(N2Cc3cc(O[C@H]4CCCC[C@H]4N4CC(c5ccccc5Cl)C4)ccc3C2=O)C(=O)N1] |
| 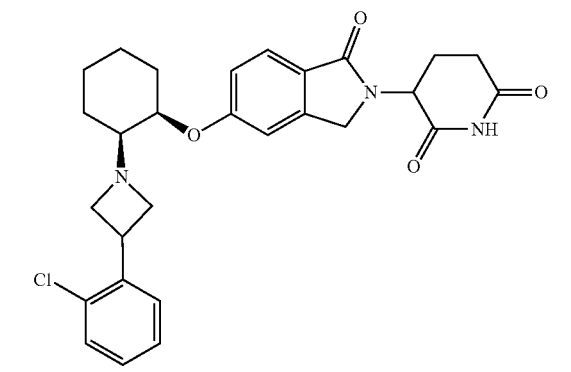 [SMILES: O=C1CCC(N2Cc3cc(O[C@@H]4CCCC[C@@H]4N4CC(c5ccccc5Cl)C4)ccc3C2=O)C(=O)N1] |
TABLE 1A-continued
| Structure |
|---|
| 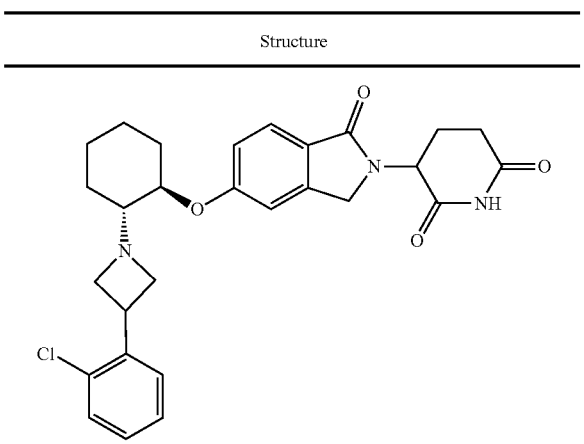 |
| 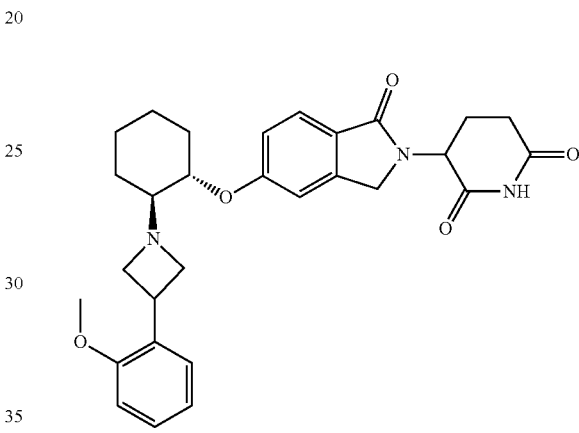 |
| 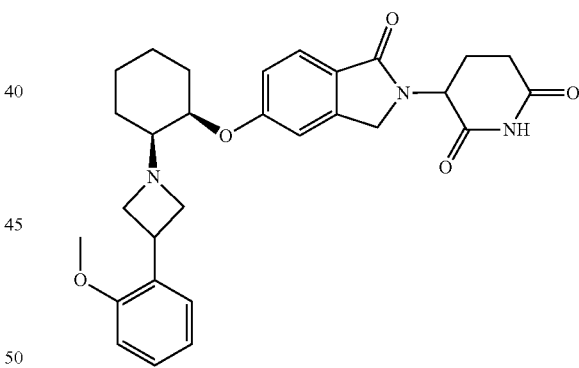 |
| 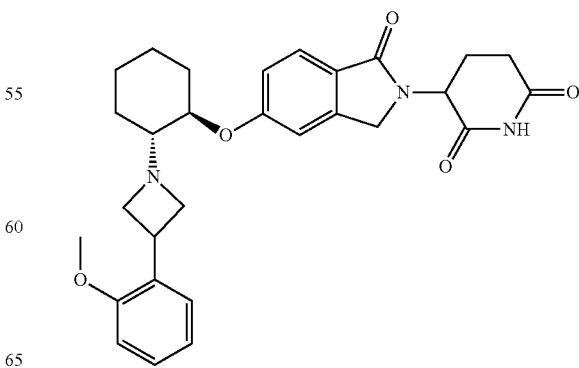 |

TABLE 1A-continued
Structure
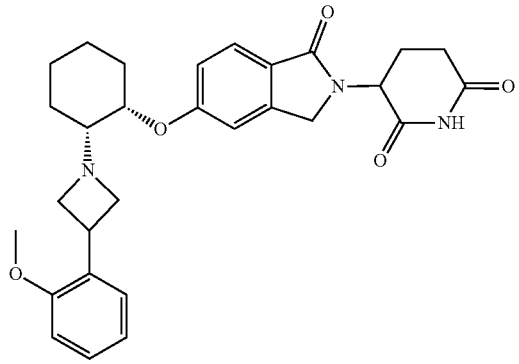
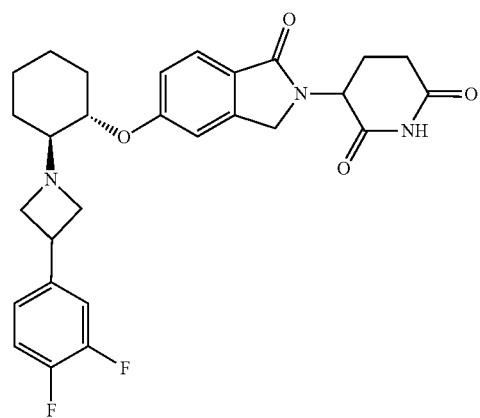 [SMILES: O=C1CCC(N2Cc3cc(O[C@H]4CCCC[C@@H]4N4CC(c5ccc(F)c(F)c5)C4)ccc3C2=O)C(=O)N1]
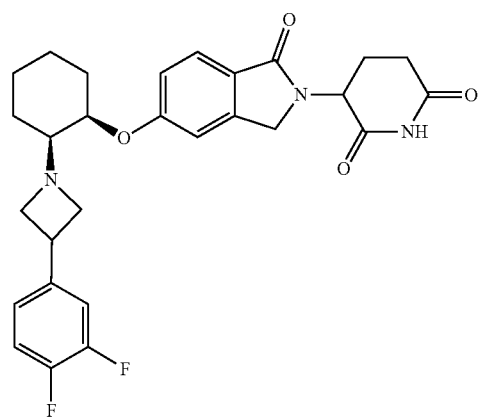 [SMILES: O=C1CCC(N2Cc3cc(O[C@@H]4CCCC[C@@H]4N4CC(c5ccc(F)c(F)c5)C4)ccc3C2=O)C(=O)N1]
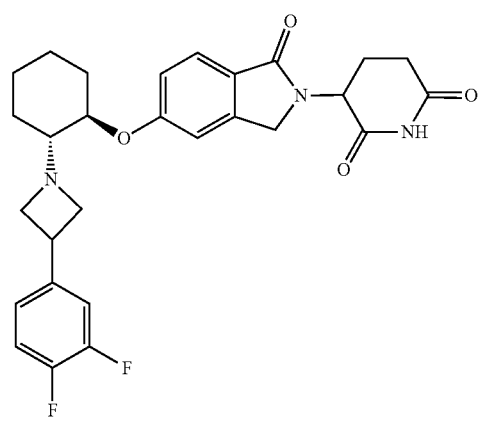 [SMILES: O=C1CCC(N2Cc3cc(O[C@@H]4CCCC[C@H]4N4CC(c5ccc(F)c(F)c5)C4)ccc3C2=O)C(=O)N1]
TABLE 1A-continued
Structure
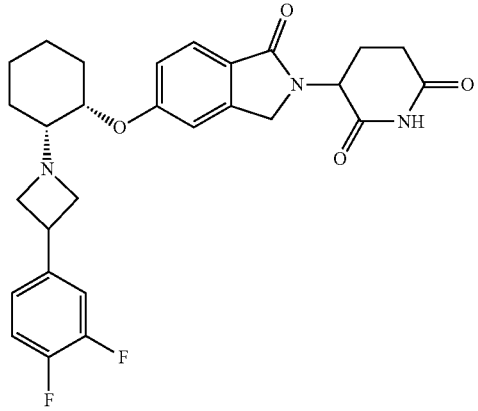 [SMILES: O=C1CCC(N2Cc3cc(O[C@H]4CCCC[C@H]4N4CC(c5ccc(F)c(F)c5)C4)ccc3C2=O)C(=O)N1]
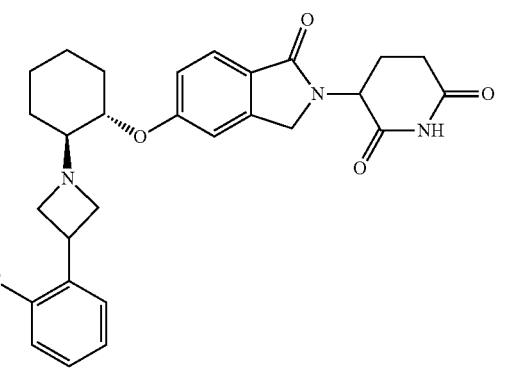
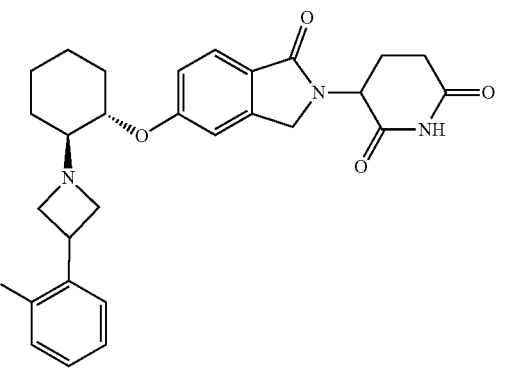

TABLE 1A-continued
Structure
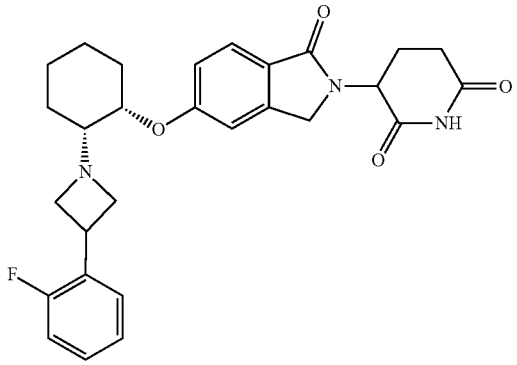
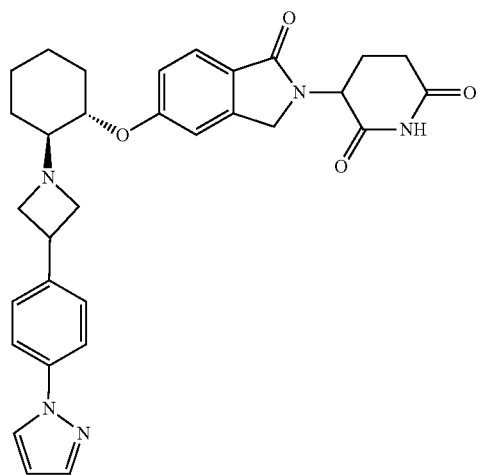 [SMILES: O=C1CCC(N2Cc3cc(O[C@H]4CCCC[C@@H]4N4CC(c5ccc(-n6cccn6)cc5)C4)ccc3C2=O)C(=O)N1]
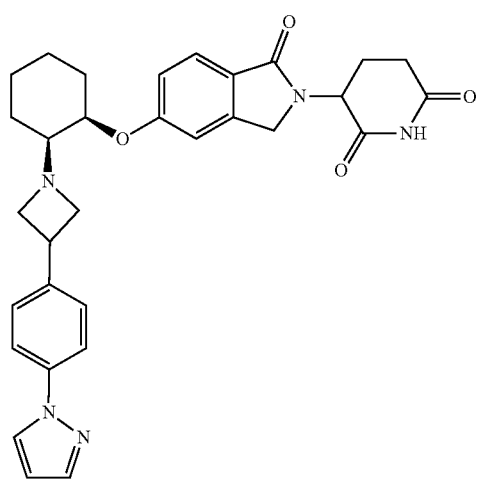 [SMILES: O=C1CCC(N2Cc3cc(O[C@@H]4CCCC[C@@H]4N4CC(c5ccc(-n6cccn6)cc5)C4)ccc3C2=O)C(=O)N1]
TABLE 1A-continued
Structure
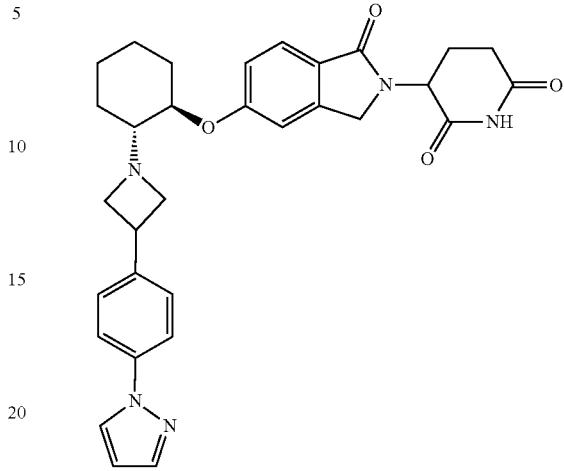
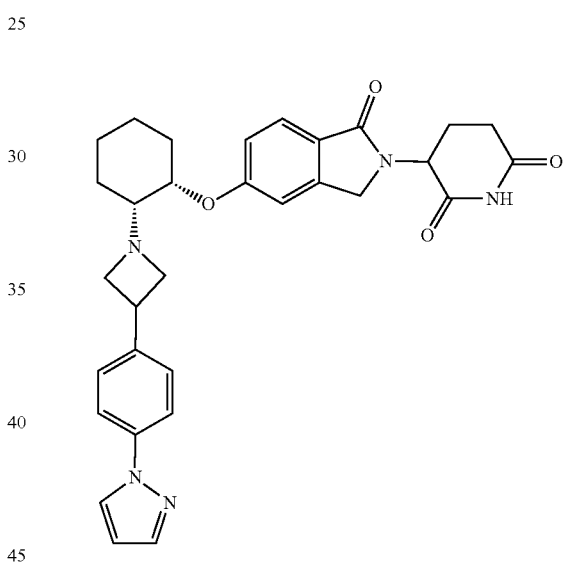
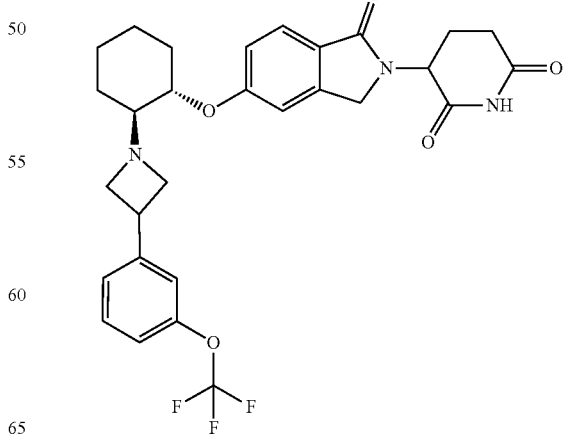

TABLE 1A-continued
| Structure |
|---|
| 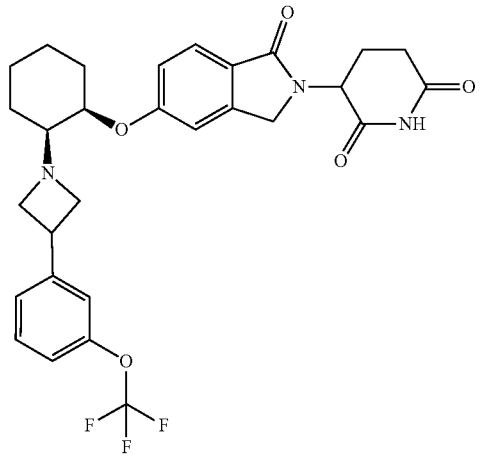 [SMILES: O=C1CCC(N2Cc3cc(O[C@@H]4CCCC[C@@H]4N4CC(c5cccc(OC(F)(F)F)c5)C4)ccc3C2=O)C(=O)N1] |
| 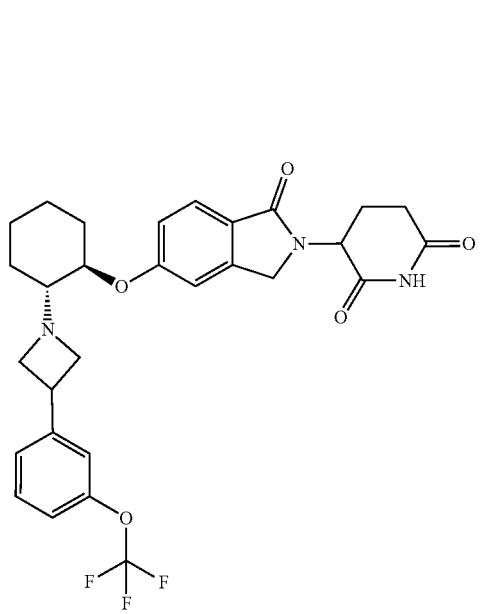 [SMILES: O=C1CCC(N2Cc3cc(O[C@@H]4CCCC[C@H]4N4CC(c5cccc(OC(F)(F)F)c5)C4)ccc3C2=O)C(=O)N1] |
|  |
TABLE 1A-continued
| Structure |
|---|
| 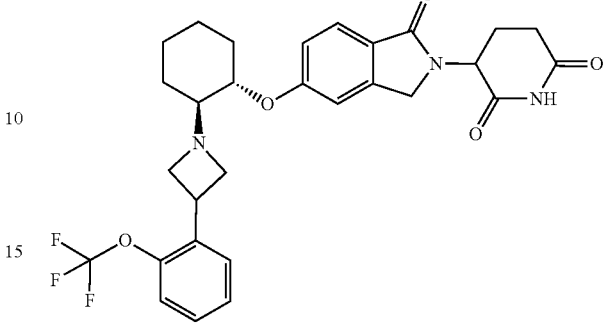 |
| 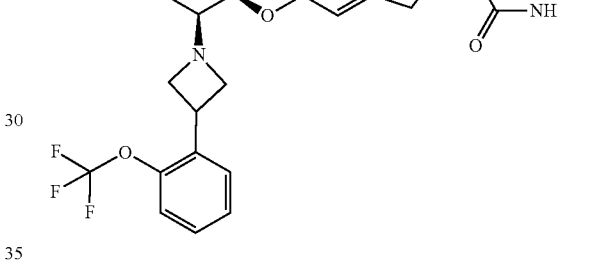 |
| 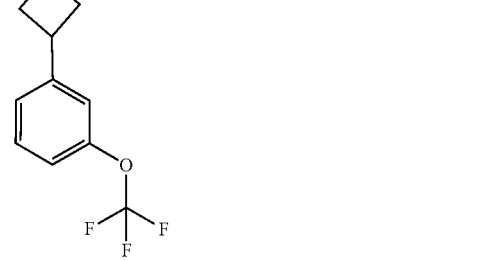 |
| 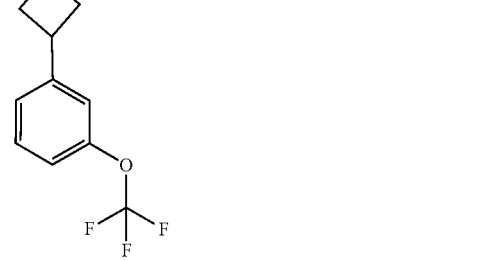 |

| 123 | 124 |
|---|---|
| TABLE 1A-continued | TABLE 1A-continued |
| Structure | Structure |//
| | |
|---|---|
|  | 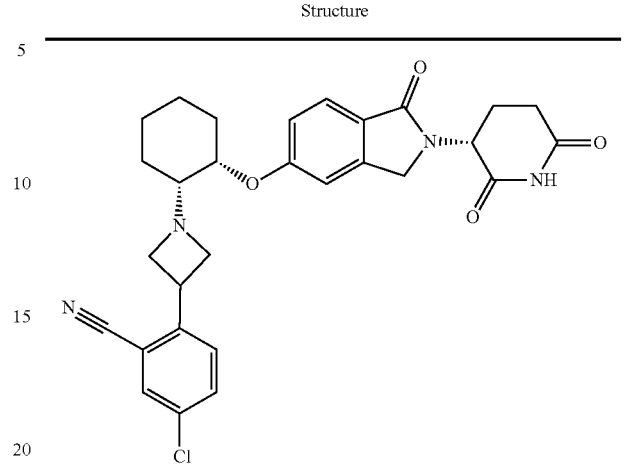 |
| 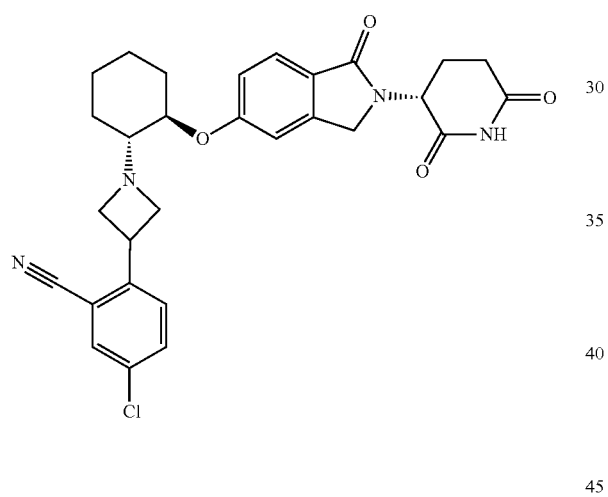 | 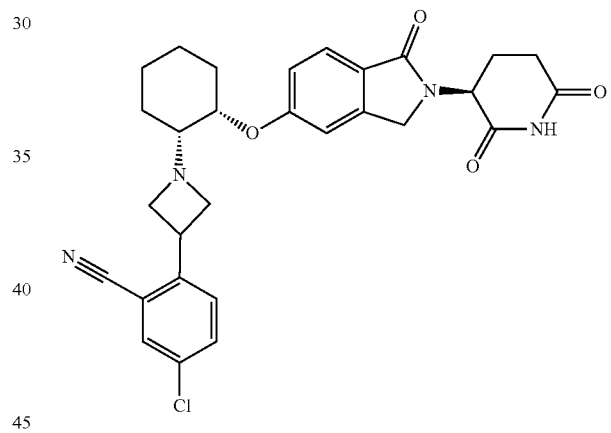 |
| 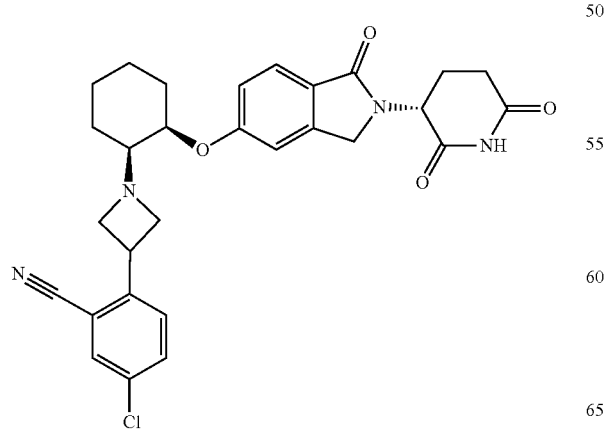 | 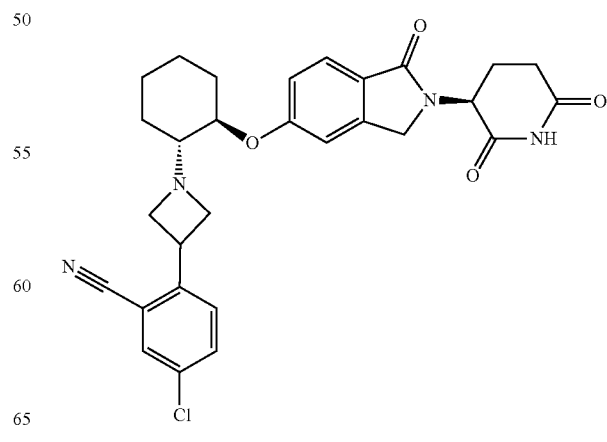 |

TABLE 1A-continued
Structure
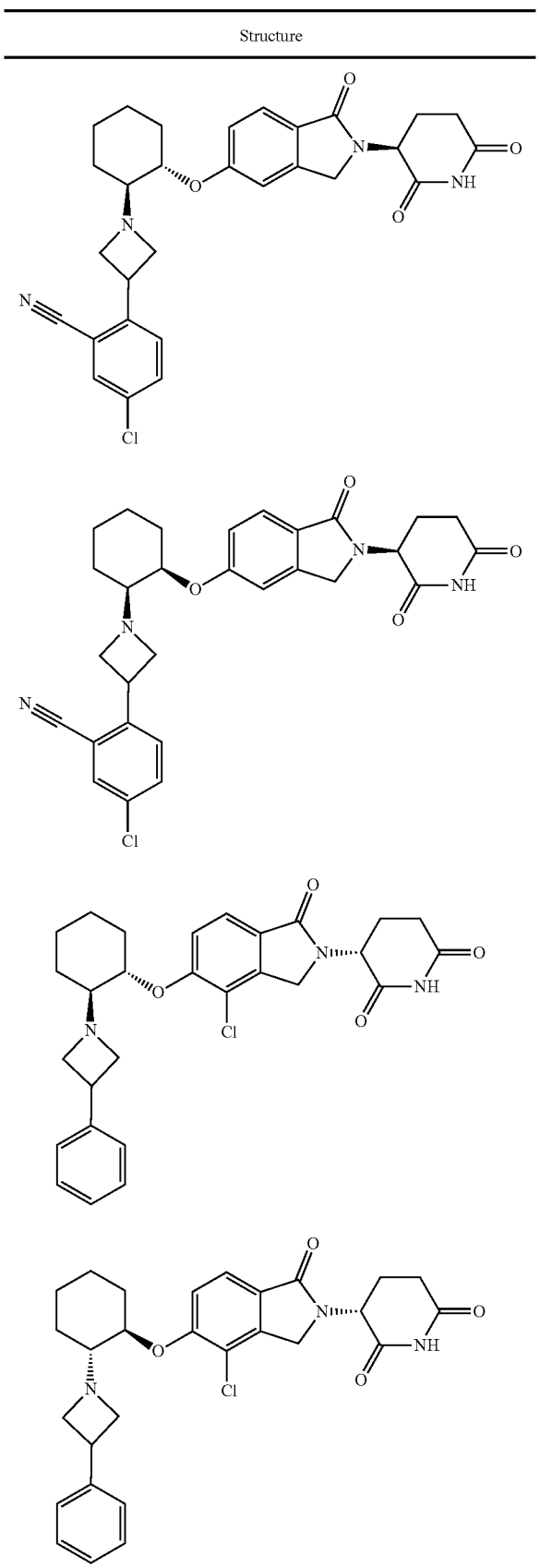
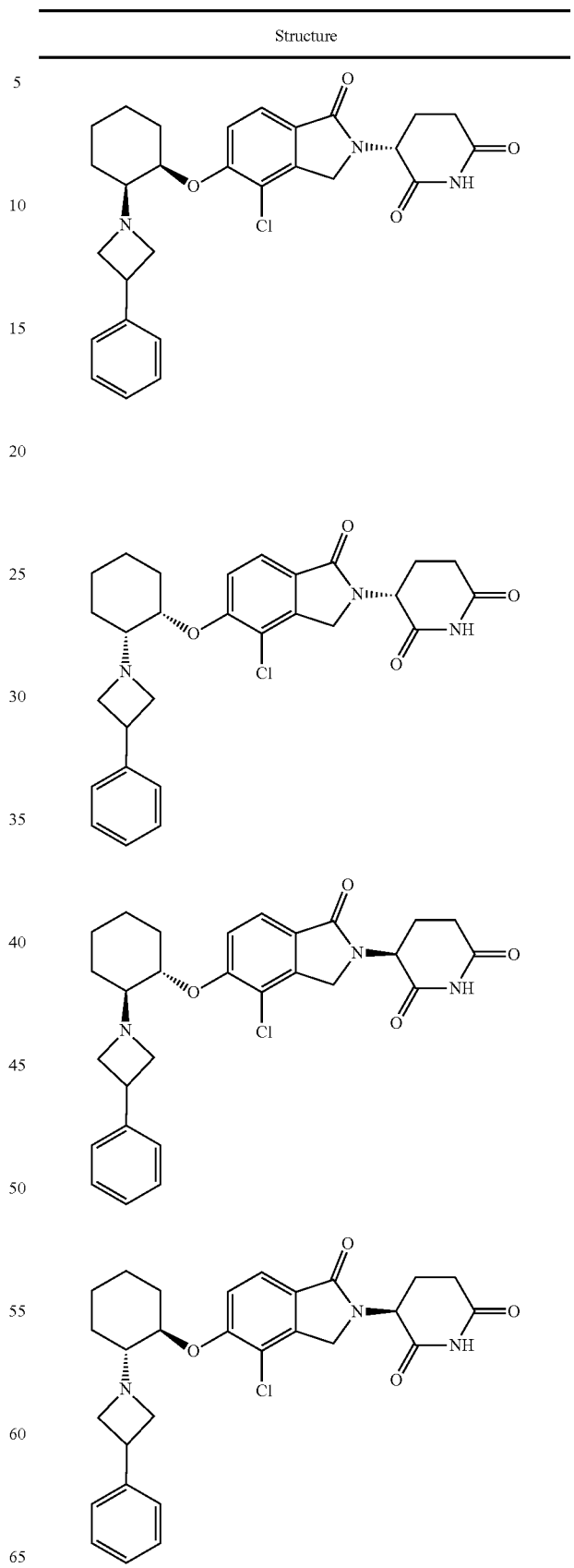

TABLE 1A-continued
Structure
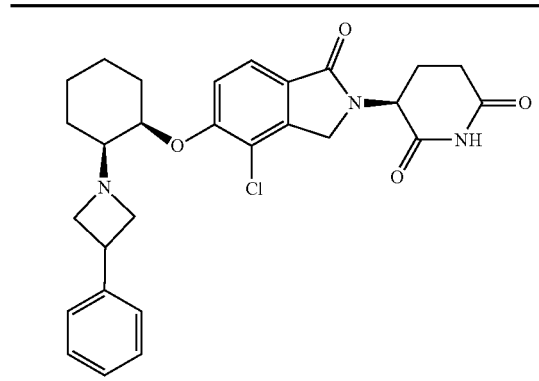
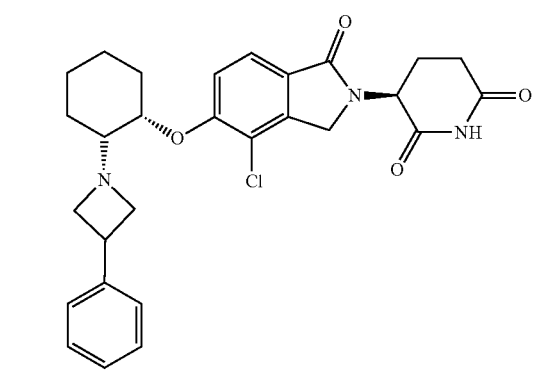
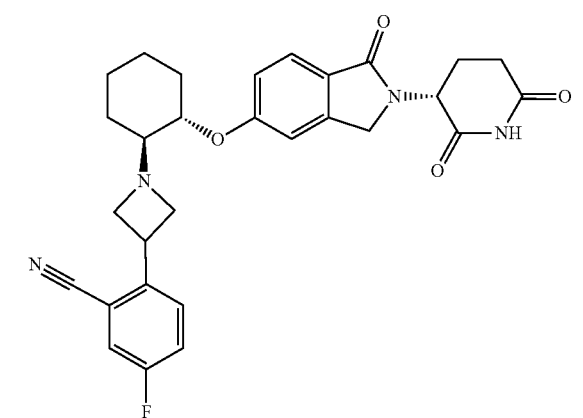 [SMILES: N#Cc1cc(F)ccc1C1CN([C@H]2CCCC[C@@H]2Oc2ccc3c(c2)CN([C@@H]2CCC(=O)NC2=O)C3=O)C1]
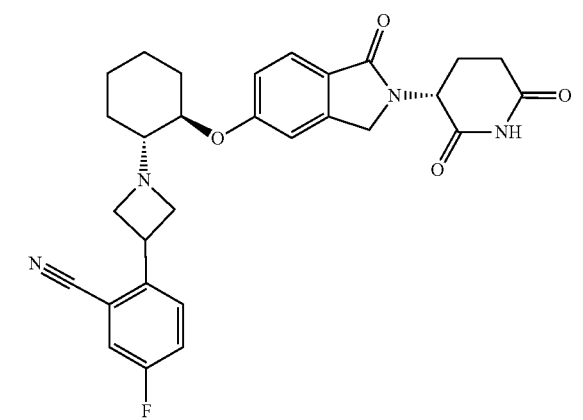 [SMILES: N#Cc1cc(F)ccc1C1CN([C@@H]2CCCC[C@H]2Oc2ccc3c(c2)CN([C@@H]2CCC(=O)NC2=O)C3=O)C1]
TABLE 1A-continued
Structure
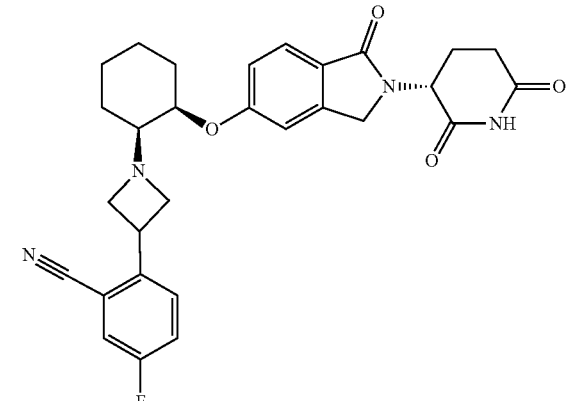
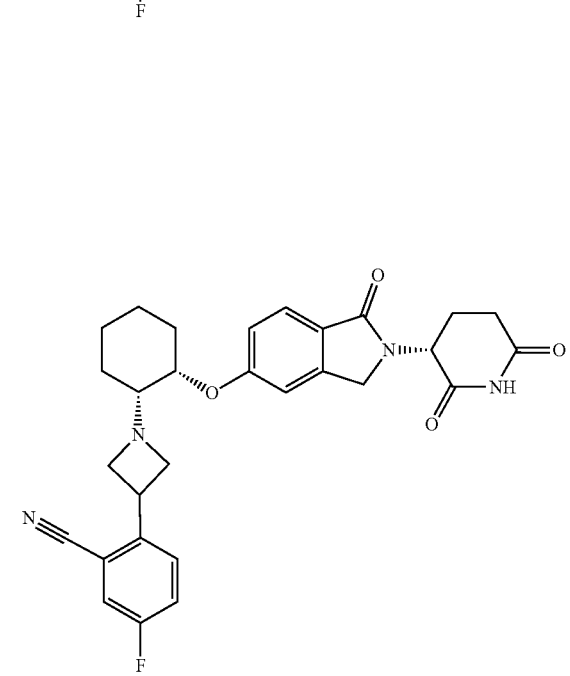
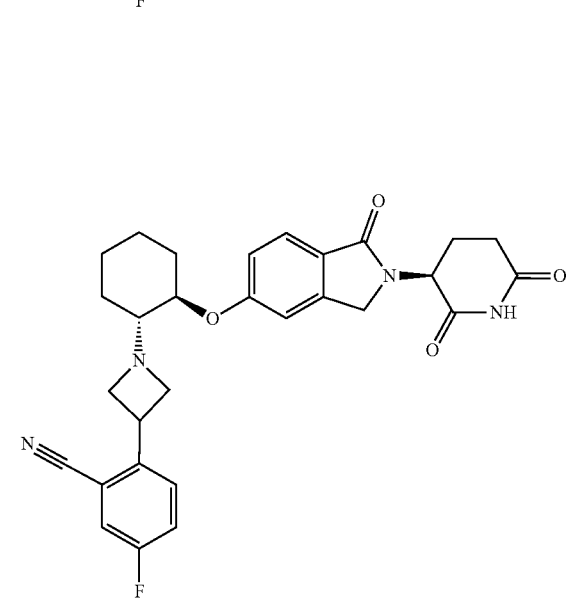

TABLE 1A-continued
| Structure |
|---|
| 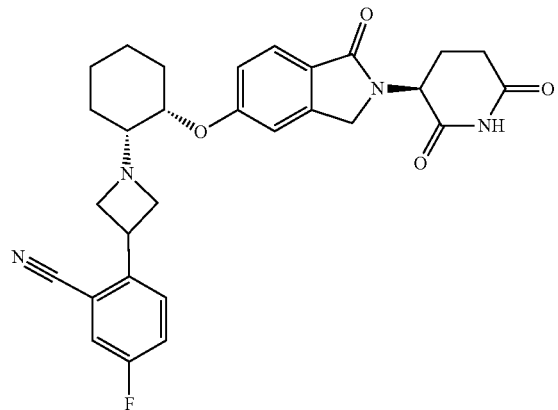 [SMILES: N#Cc1cc(F)ccc1C1CN([C@@H]2CCCC[C@@H]2Oc2ccc3c(c2)CN([C@H]2CCC(=O)NC2=O)C3=O)C1] |
| 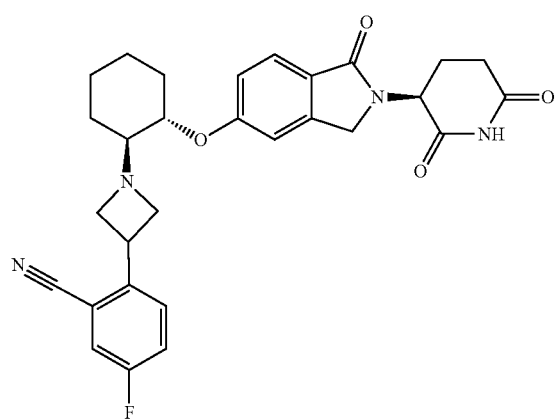 [SMILES: N#Cc1cc(F)ccc1C1CN([C@H]2CCCC[C@@H]2Oc2ccc3c(c2)CN([C@H]2CCC(=O)NC2=O)C3=O)C1] |
| 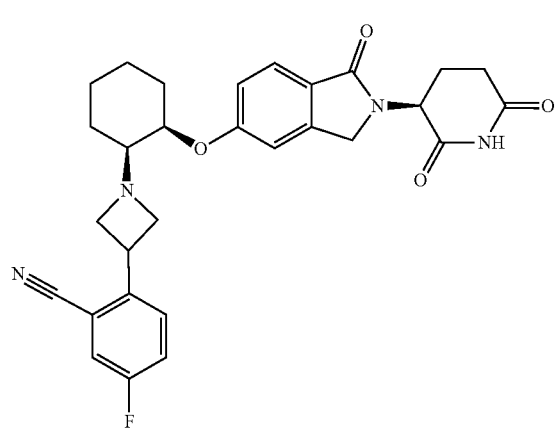 [SMILES: N#Cc1cc(F)ccc1C1CN([C@H]2CCCC[C@H]2Oc2ccc3c(c2)CN([C@H]2CCC(=O)NC2=O)C3=O)C1] |
| 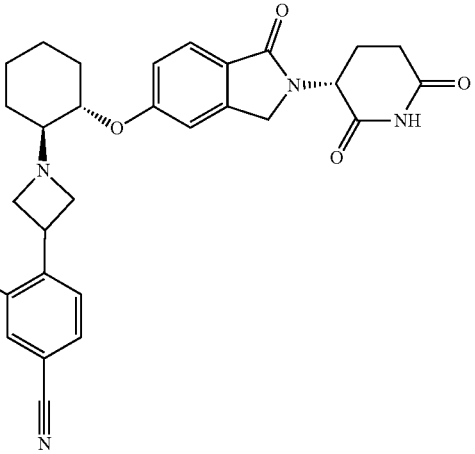 |
| 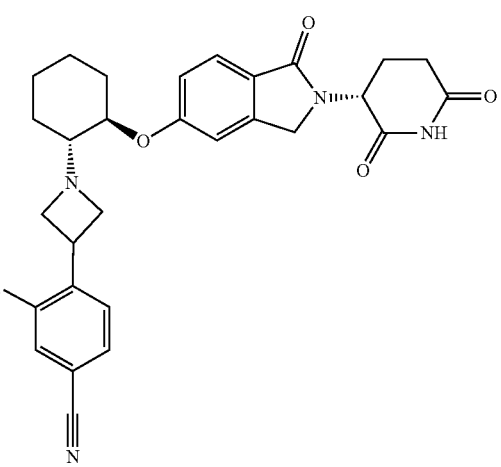 |

TABLE 1A-continued
| Structure |
|---|
| 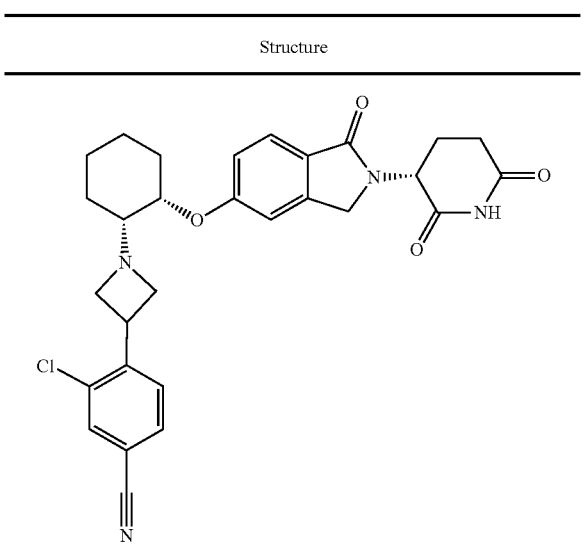 |
| 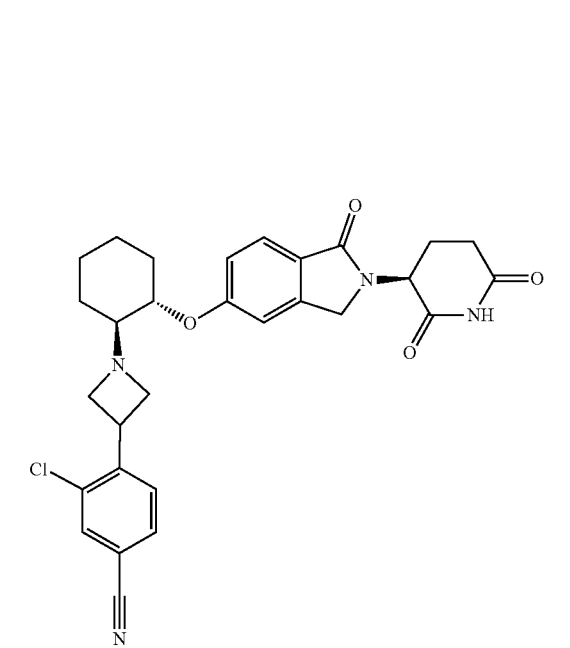 [SMILES: N#Cc1ccc(C2CN([C@H]3CCCC[C@@H]3Oc3ccc4c(c3)CN([C@H]3CCC(=O)NC3=O)C4=O)C2)c(Cl)c1] |
| 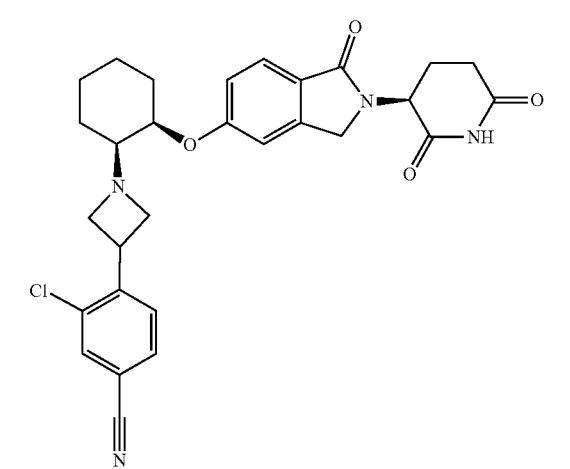 [SMILES: N#Cc1ccc(C2CN([C@H]3CCCC[C@H]3Oc3ccc4c(c3)CN([C@H]3CCC(=O)NC3=O)C4=O)C2)c(Cl)c1] |
TABLE 1A-continued
| Structure |
|---|
| 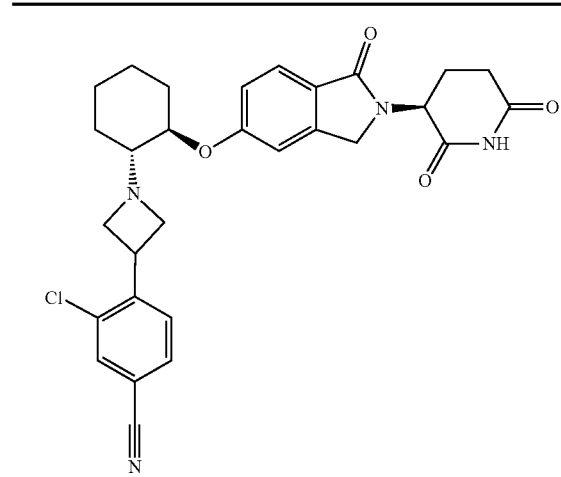 |
| 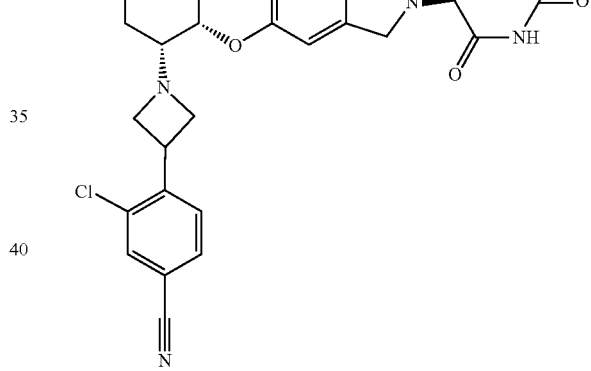 |
| 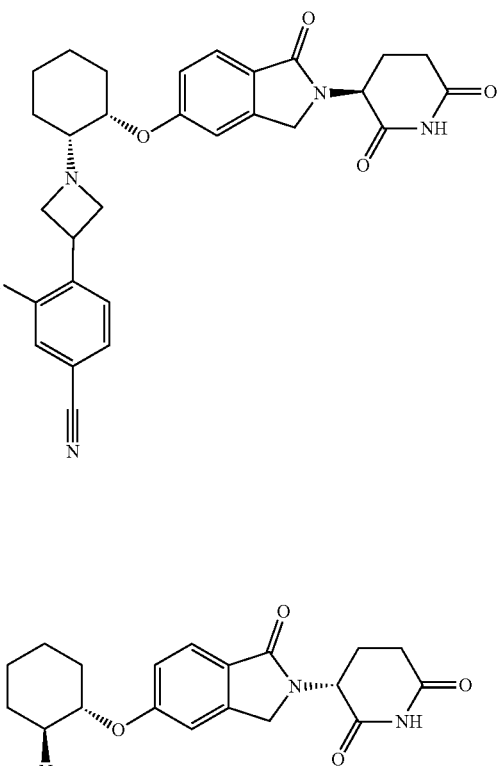 |

TABLE 1A-continued
Structure
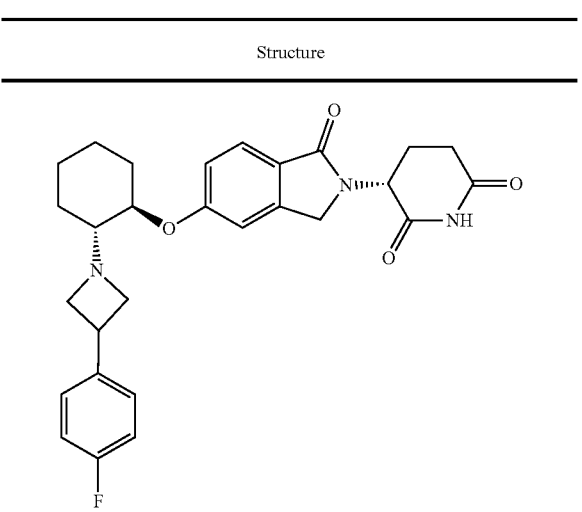
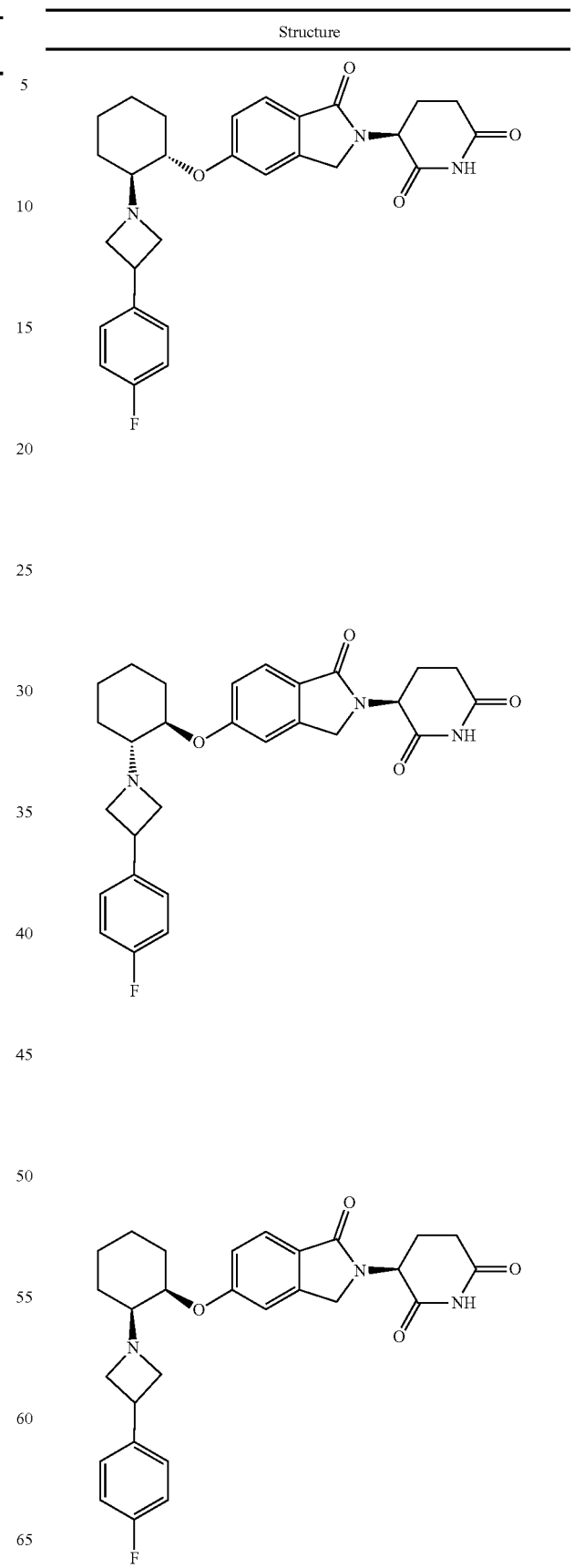

TABLE 1A-continued
Structure
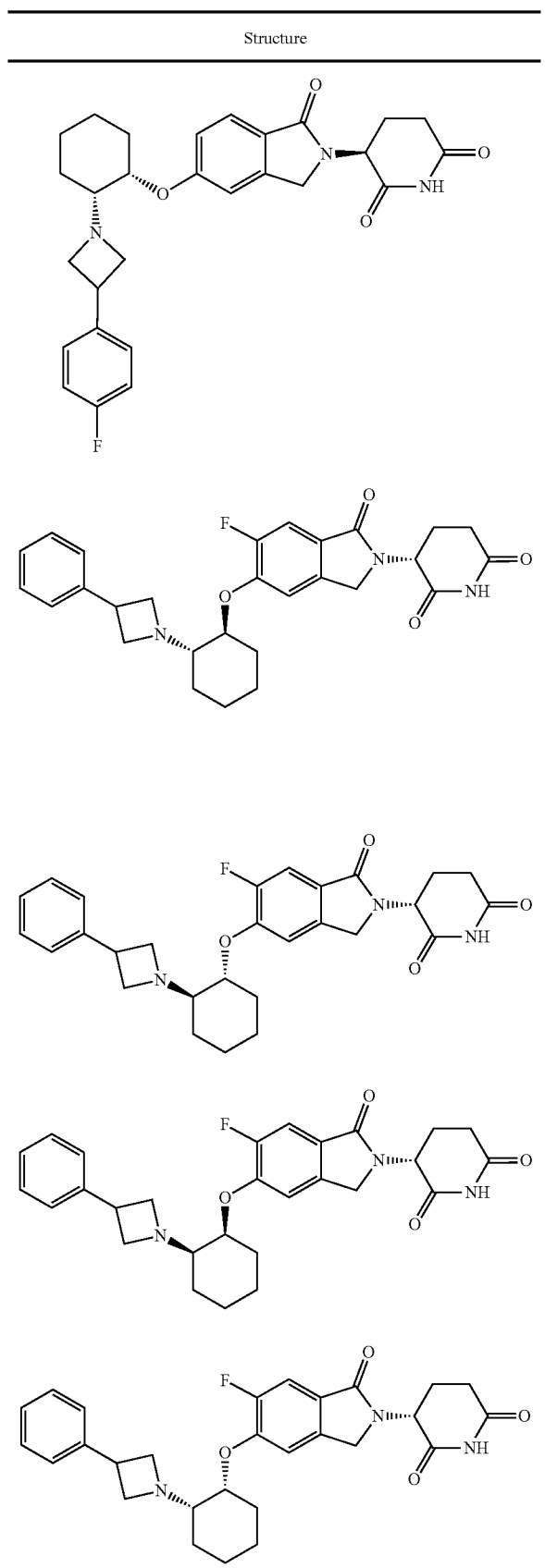
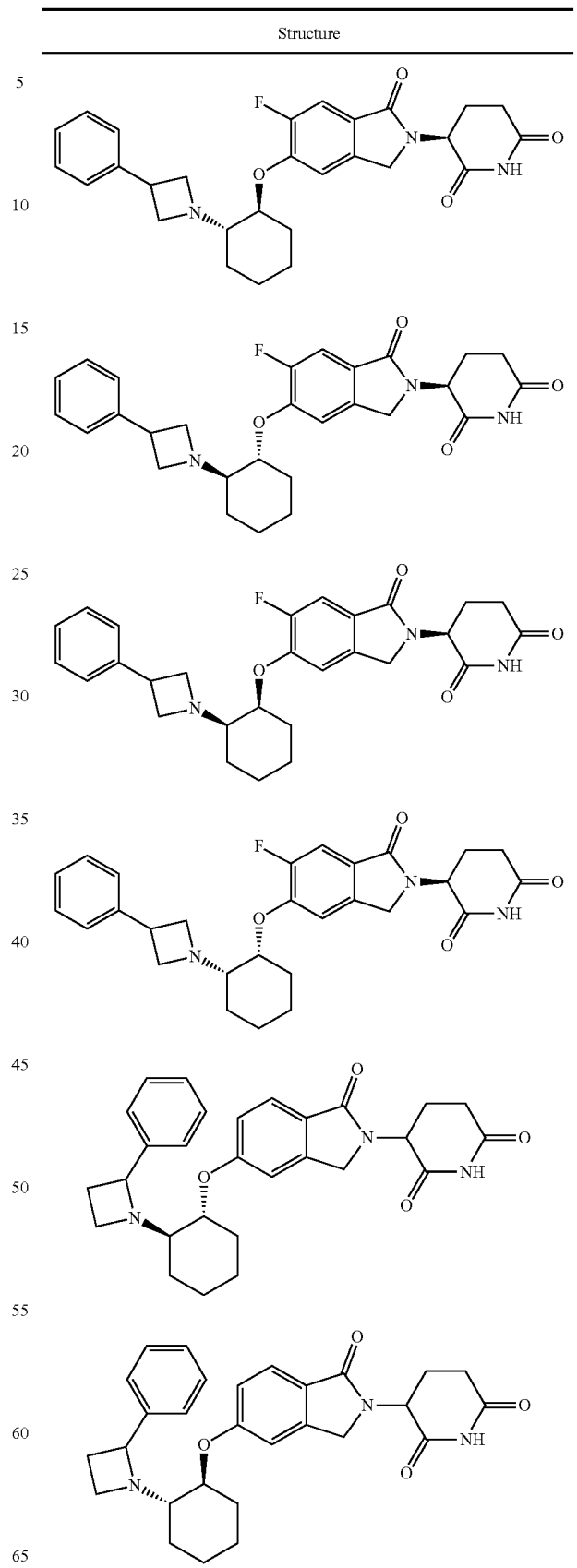

TABLE 1A-continued
Structure
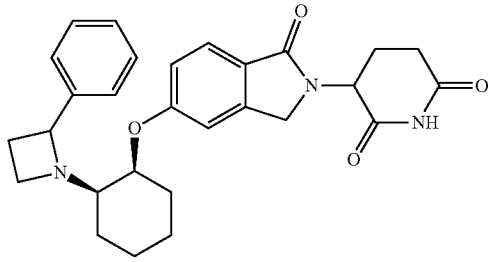 [SMILES: O=C1CCC(N2Cc3cc(O[C@H]4CCCC[C@H]4N4CCC4c4ccccc4)ccc3C2=O)C(=O)N1]
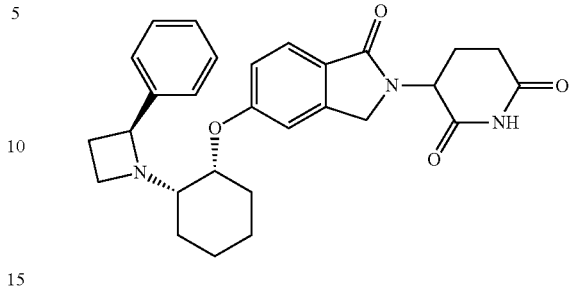
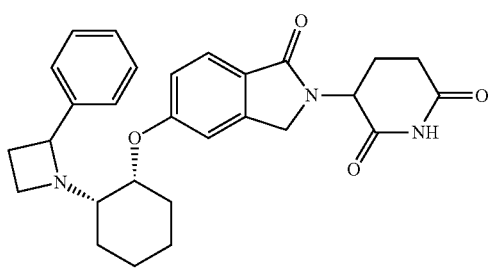 [SMILES: O=C1CCC(N2Cc3cc(O[C@@H]4CCCC[C@@H]4N4CCC4c4ccccc4)ccc3C2=O)C(=O)N1]
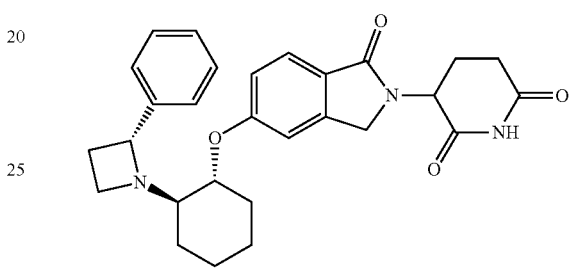
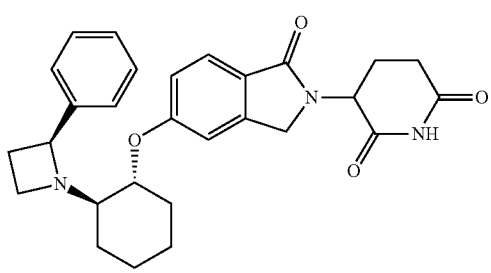 [SMILES: O=C1CCC(N2Cc3cc(O[C@@H]4CCCC[C@H]4N4CC[C@H]4c4ccccc4)ccc3C2=O)C(=O)N1]
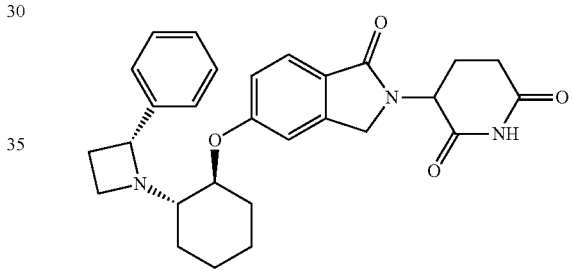
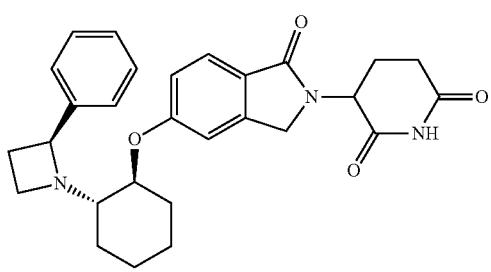 [SMILES: O=C1CCC(N2Cc3cc(O[C@H]4CCCC[C@@H]4N4CC[C@H]4c4ccccc4)ccc3C2=O)C(=O)N1]
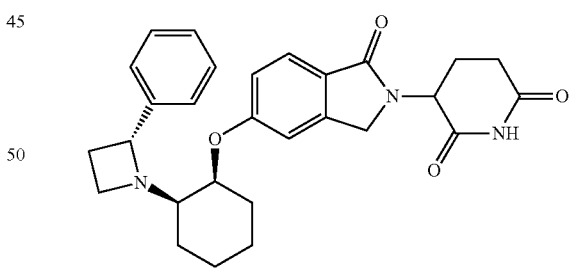
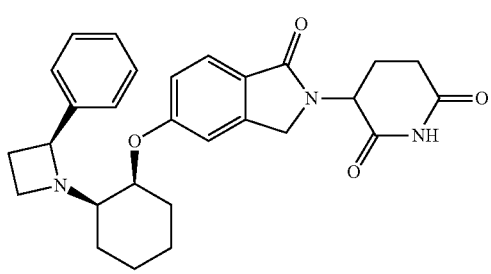 [SMILES: O=C1CCC(N2Cc3cc(O[C@H]4CCCC[C@H]4N4CC[C@H]4c4ccccc4)ccc3C2=O)C(=O)N1]
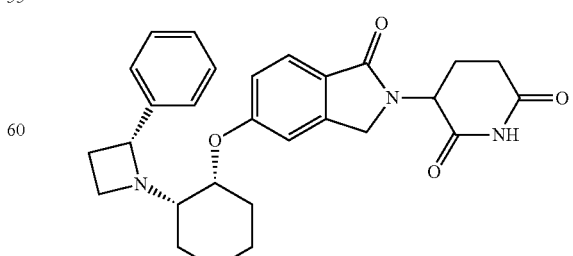

TABLE 1A-continued
Structure
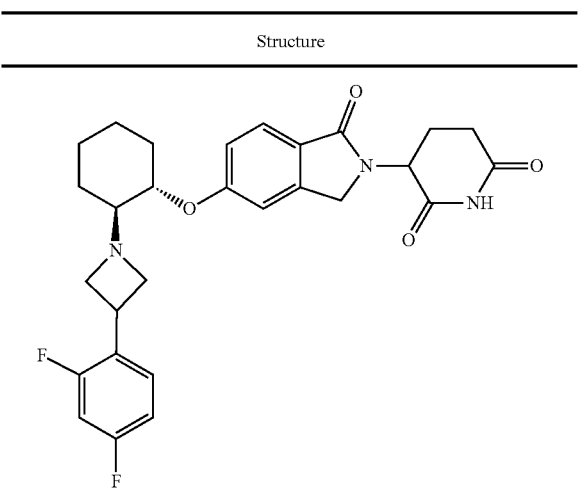
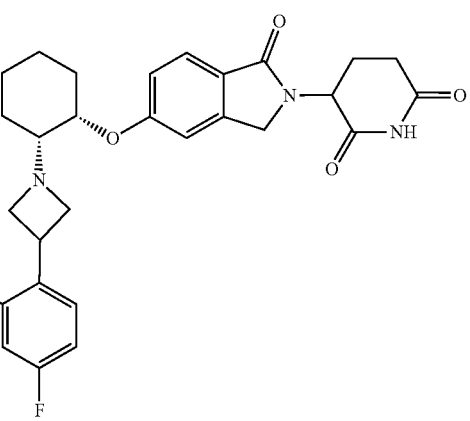
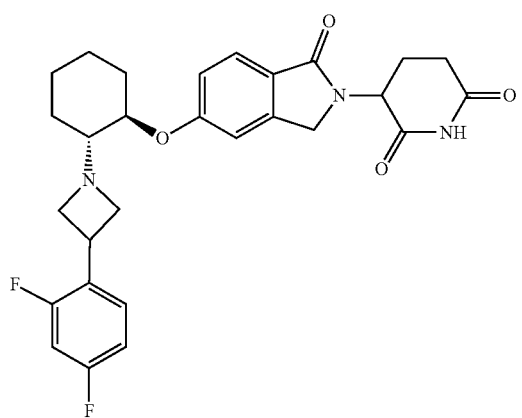
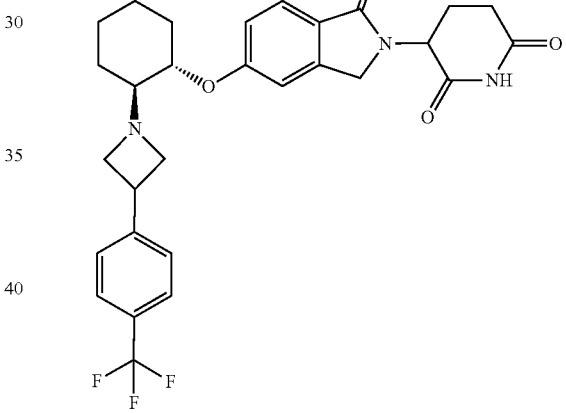
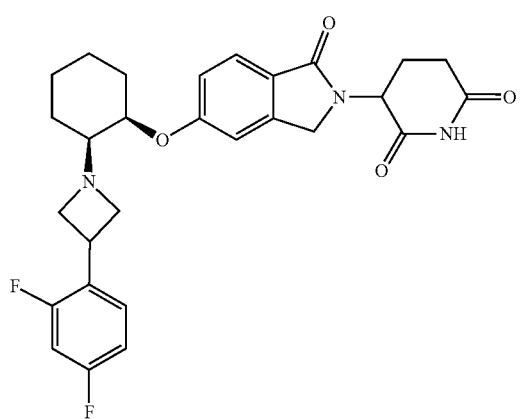
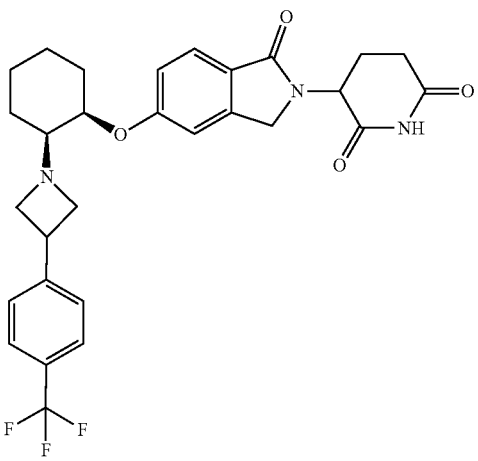

TABLE 1A-continued
| Structure |
|---|
| 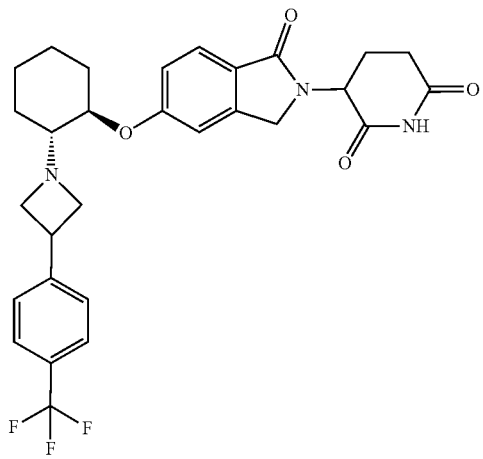 [SMILES: O=C1CCC(N2Cc3cc(O[C@@H]4CCCC[C@H]4N4CC(c5ccc(C(F)(F)F)cc5)C4)ccc3C2=O)C(=O)N1] |
| 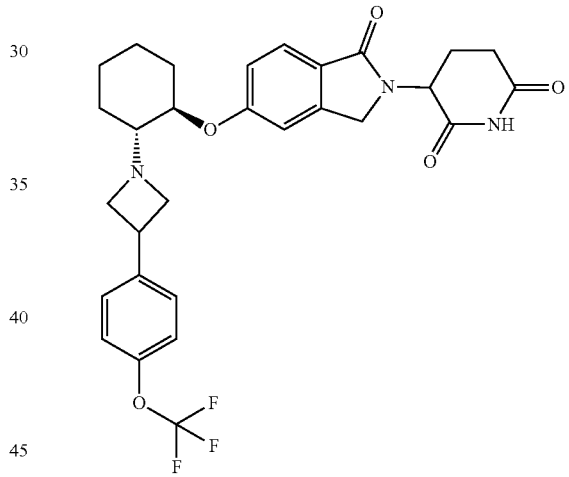 |
| 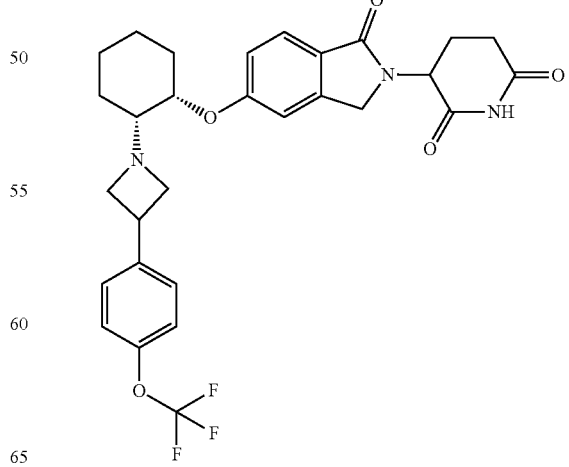 |
TABLE 1A-continued
| Structure |
|---|
| 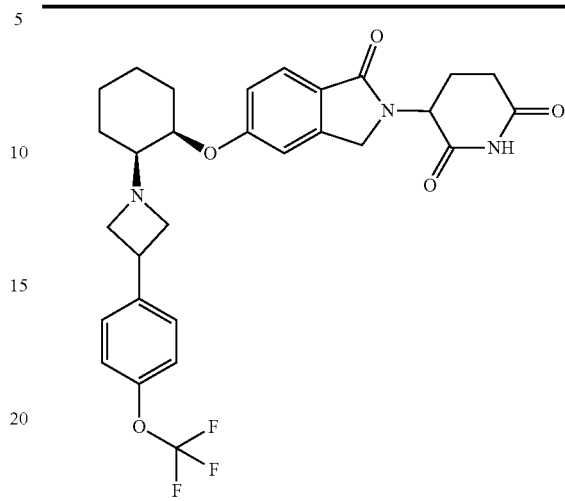 |

TABLE 1A-continued
Structure
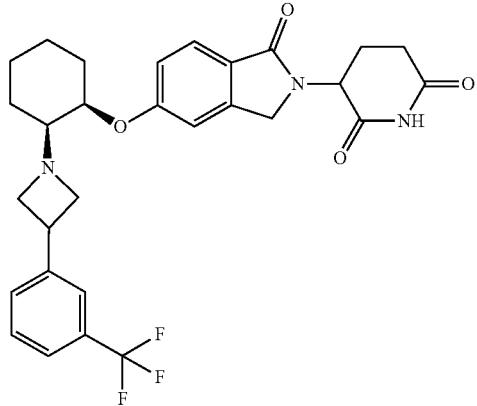 [SMILES: O=C1CCC(N2Cc3cc(O[C@@H]4CCCC[C@@H]4N4CC(c5cccc(C(F)(F)F)c5)C4)ccc3C2=O)C(=O)N1]
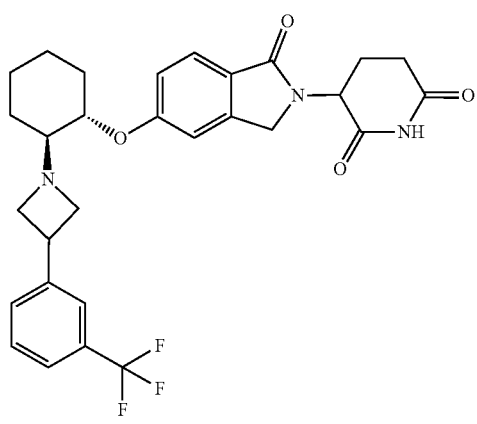 [SMILES: O=C1CCC(N2Cc3cc(O[C@H]4CCCC[C@@H]4N4CC(c5cccc(C(F)(F)F)c5)C4)ccc3C2=O)C(=O)N1]
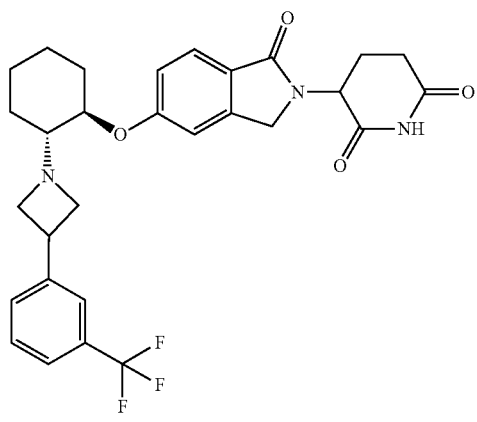 [SMILES: O=C1CCC(N2Cc3cc(O[C@@H]4CCCC[C@H]4N4CC(c5cccc(C(F)(F)F)c5)C4)ccc3C2=O)C(=O)N1]
TABLE 1A-continued
Structure
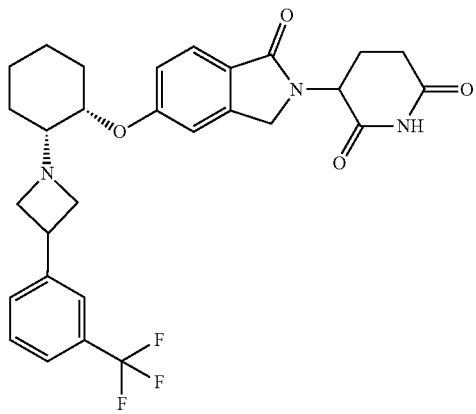 [SMILES: O=C1CCC(N2Cc3cc(O[C@H]4CCCC[C@H]4N4CC(c5cccc(C(F)(F)F)c5)C4)ccc3C2=O)C(=O)N1]
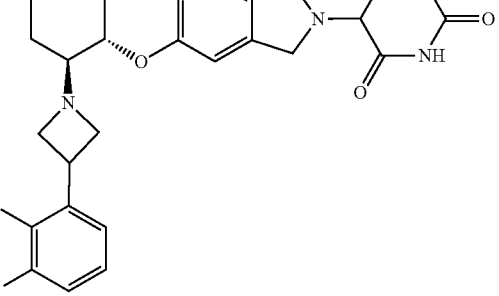
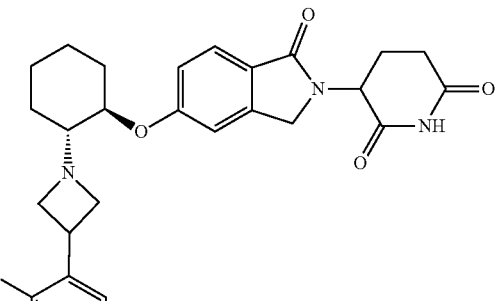
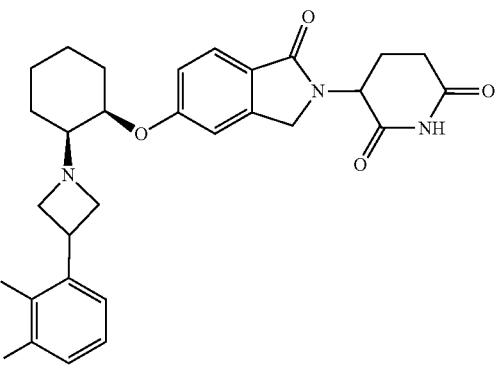

TABLE 1A-continued
| Structure |
|---|
| 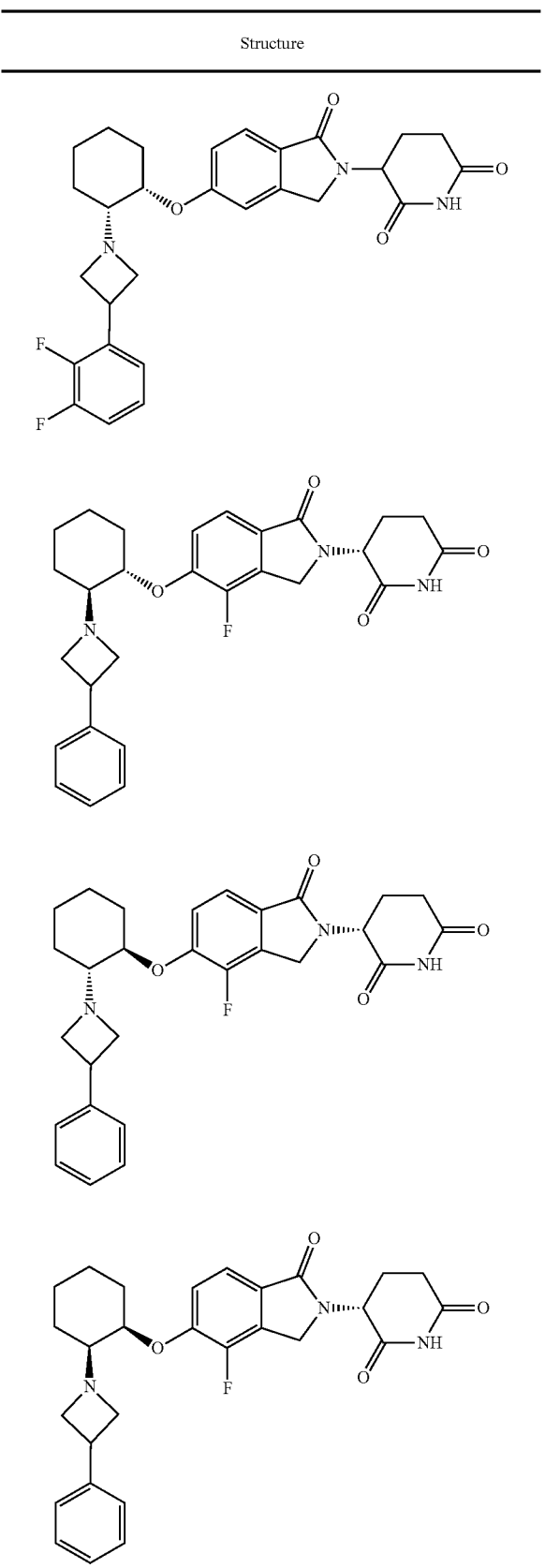 |
TABLE 1A-continued
| Structure |
|---|
| 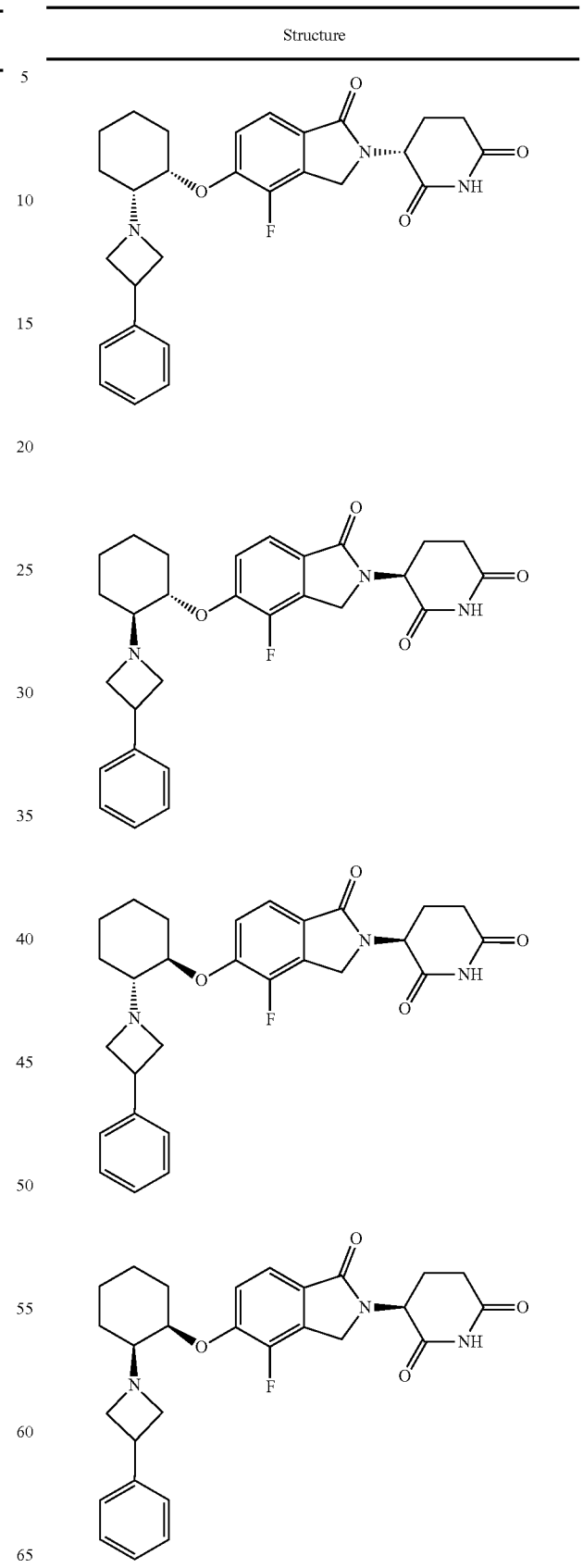 |

TABLE 1A-continued
Structure
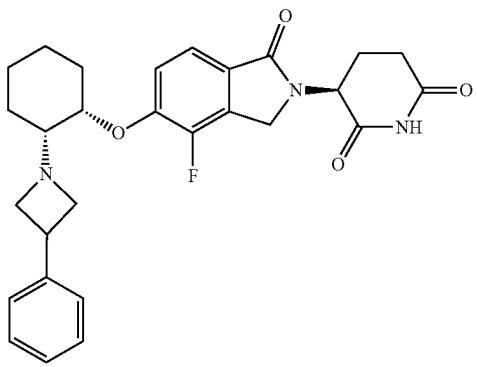 [SMILES: O=C1CC[C@H](N2Cc3c(ccc(O[C@H]4CCCC[C@H]4N4CC(c5ccccc5)C4)c3F)C2=O)C(=O)N1]
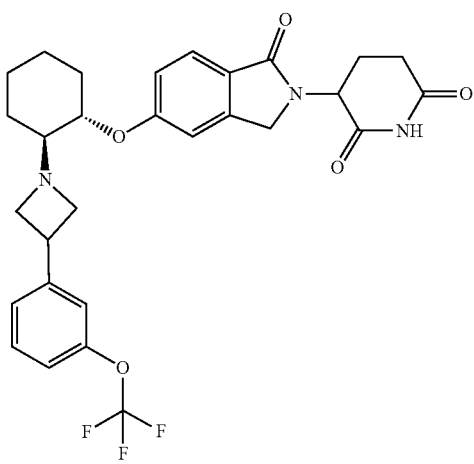
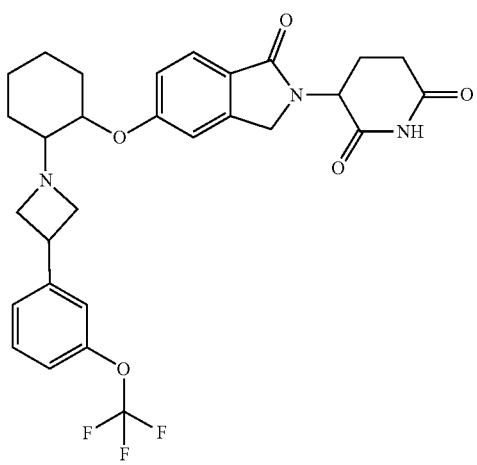 [SMILES: O=C1CCC(N2Cc3cc(OC4CCCCC4N4CC(c5cccc(OC(F)(F)F)c5)C4)ccc3C2=O)C(=O)N1]
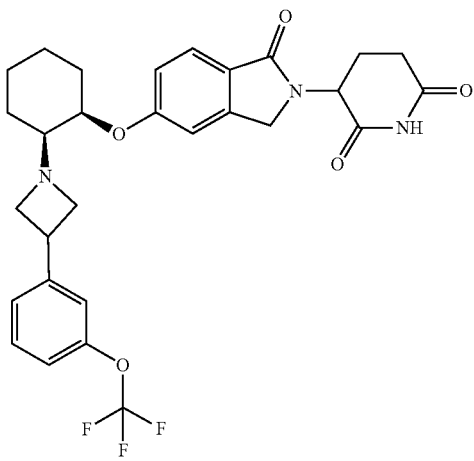
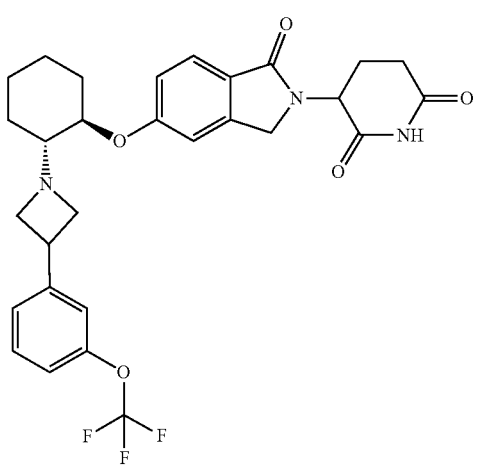 [SMILES: O=C1CCC(N2Cc3cc(O[C@@H]4CCCC[C@H]4N4CC(c5cccc(OC(F)(F)F)c5)C4)ccc3C2=O)C(=O)N1]
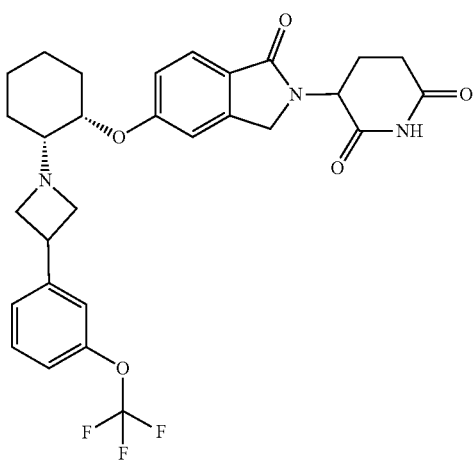 [SMILES: O=C1CCC(N2Cc3cc(O[C@H]4CCCC[C@H]4N4CC(c5cccc(OC(F)(F)F)c5)C4)ccc3C2=O)C(=O)N1]

149
TABLE 1A-continued
Structure
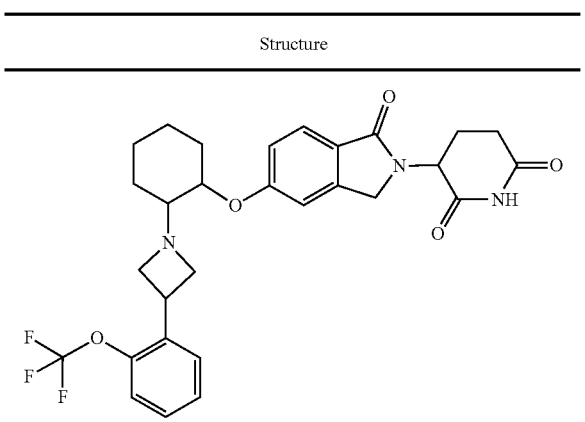
150
TABLE 1A-continued
Structure
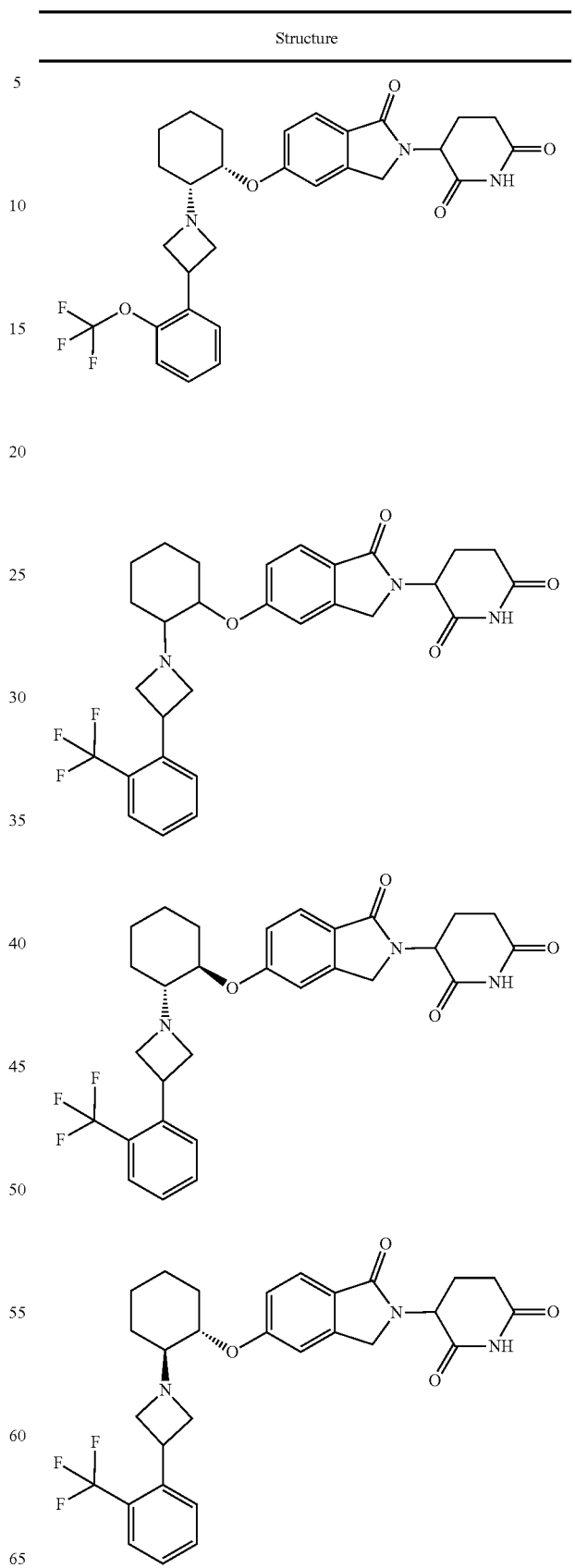

TABLE 1A-continued
Structure
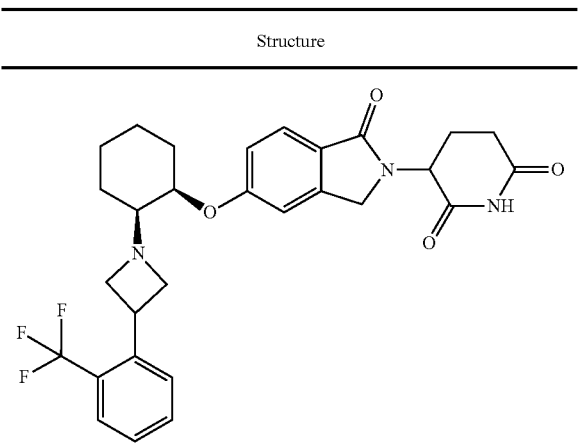
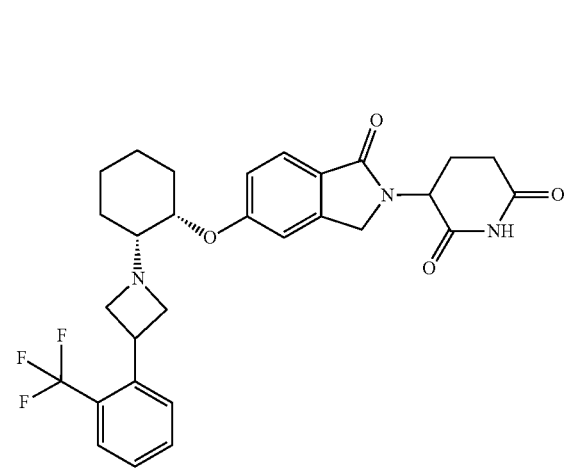 [SMILES: O=C1CCC(N2Cc3cc(O[C@H]4CCCC[C@H]4N4CC(c5ccccc5C(F)(F)F)C4)ccc3C2=O)C(=O)N1]
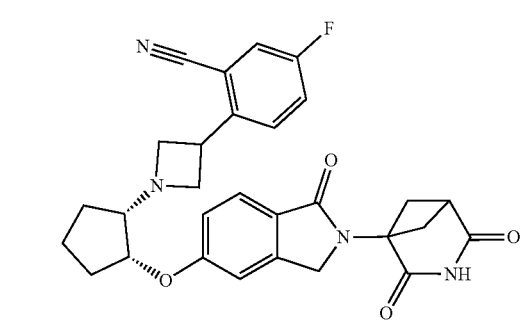 [SMILES: N#Cc1cc(F)ccc1C1CN([C@H]2CCC[C@H]2Oc2ccc3c(c2)CN(C24CC(C2)C(=O)NC4=O)C3=O)C1]
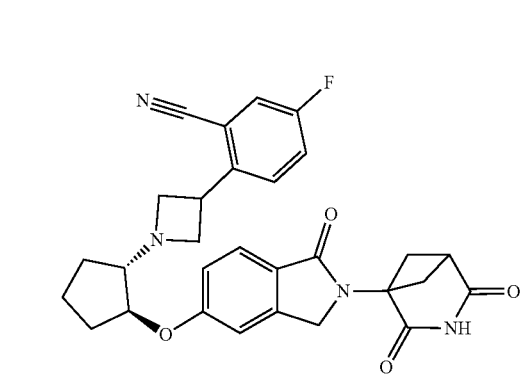 [SMILES: N#Cc1cc(F)ccc1C1CN([C@H]2CCC[C@@H]2Oc2ccc3c(c2)CN(C24CC(C2)C(=O)NC4=O)C3=O)C1]
TABLE 1A-continued
Structure
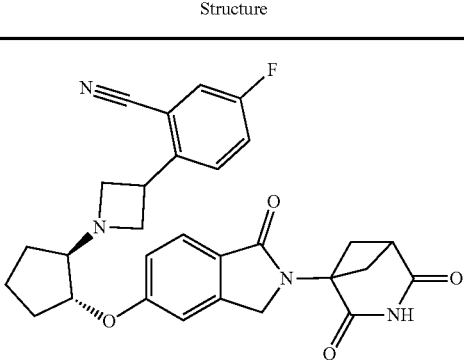
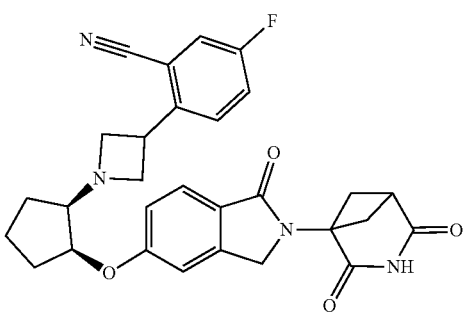 [SMILES: N#Cc1cc(F)ccc1C1CN([C@@H]2CCC[C@@H]2Oc2ccc3c(c2)CN(C24CC(C2)C(=O)NC4=O)C3=O)C1]
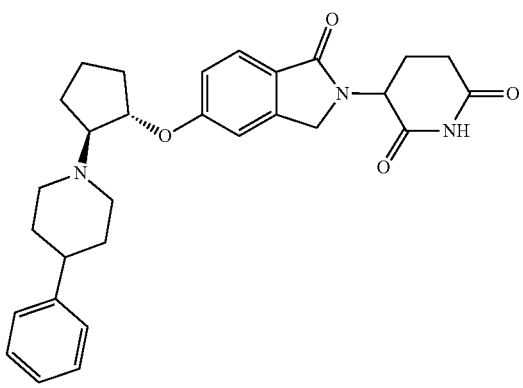 [SMILES: O=C1CCC(N2Cc3cc(O[C@H]4CCC[C@@H]4N4CCC(c5ccccc5)CC4)ccc3C2=O)C(=O)N1]
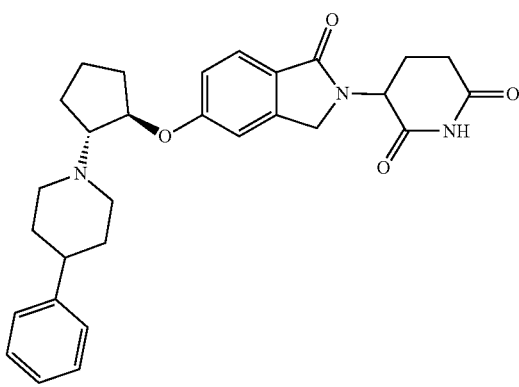 [SMILES: O=C1CCC(N2Cc3cc(O[C@@H]4CCC[C@H]4N4CCC(c5ccccc5)CC4)ccc3C2=O)C(=O)N1]

TABLE 1A-continued
| Structure |
|---|
| 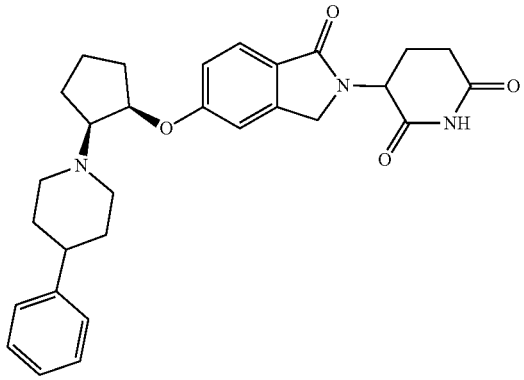 [SMILES: O=C1CCC(N2Cc3cc(O[C@@H]4CCC[C@@H]4N4CCC(c5ccccc5)CC4)ccc3C2=O)C(=O)N1] |
| 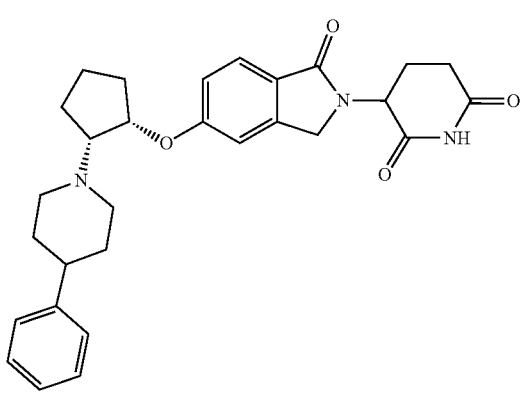 [SMILES: O=C1CCC(N2Cc3cc(O[C@H]4CCC[C@H]4N4CCC(c5ccccc5)CC4)ccc3C2=O)C(=O)N1] |
| 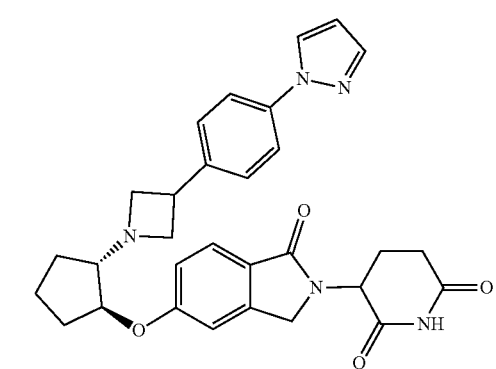 [SMILES: O=C1CCC(N2Cc3cc(O[C@H]4CCC[C@@H]4N4CC(c5ccc(-n6cccn6)cc5)C4)ccc3C2=O)C(=O)N1] |
| 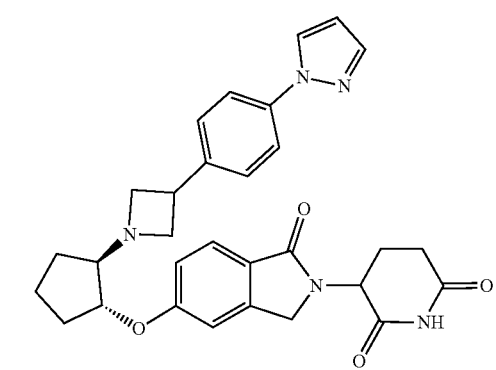 [SMILES: O=C1CCC(N2Cc3cc(O[C@@H]4CCC[C@H]4N4CC(c5ccc(-n6cccn6)cc5)C4)ccc3C2=O)C(=O)N1] |
TABLE 1A-continued
| Structure |
|---|
| 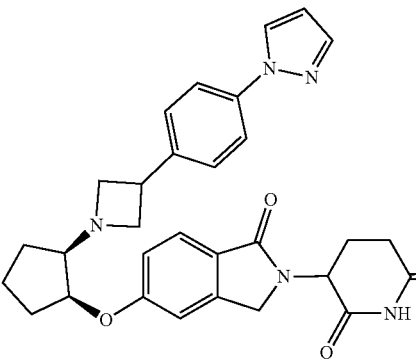 |
| 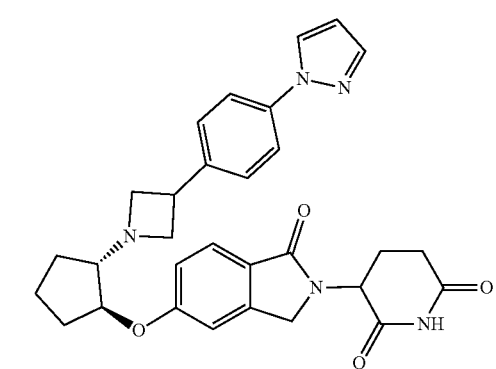 [SMILES: O=C1CCC(N2Cc3cc(O[C@H]4CCC[C@@H]4N4CC(c5ccc(-n6cccn6)cc5)C4)ccc3C2=O)C(=O)N1] |
| 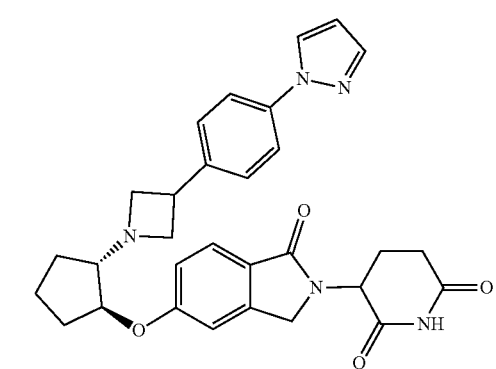 [SMILES: O=C1CCC(N2Cc3cc(O[C@H]4CCC[C@@H]4N4CC(c5ccc(-n6cccn6)cc5)C4)ccc3C2=O)C(=O)N1] |

TABLE 1A-continued
| Structure |
| --- |
| 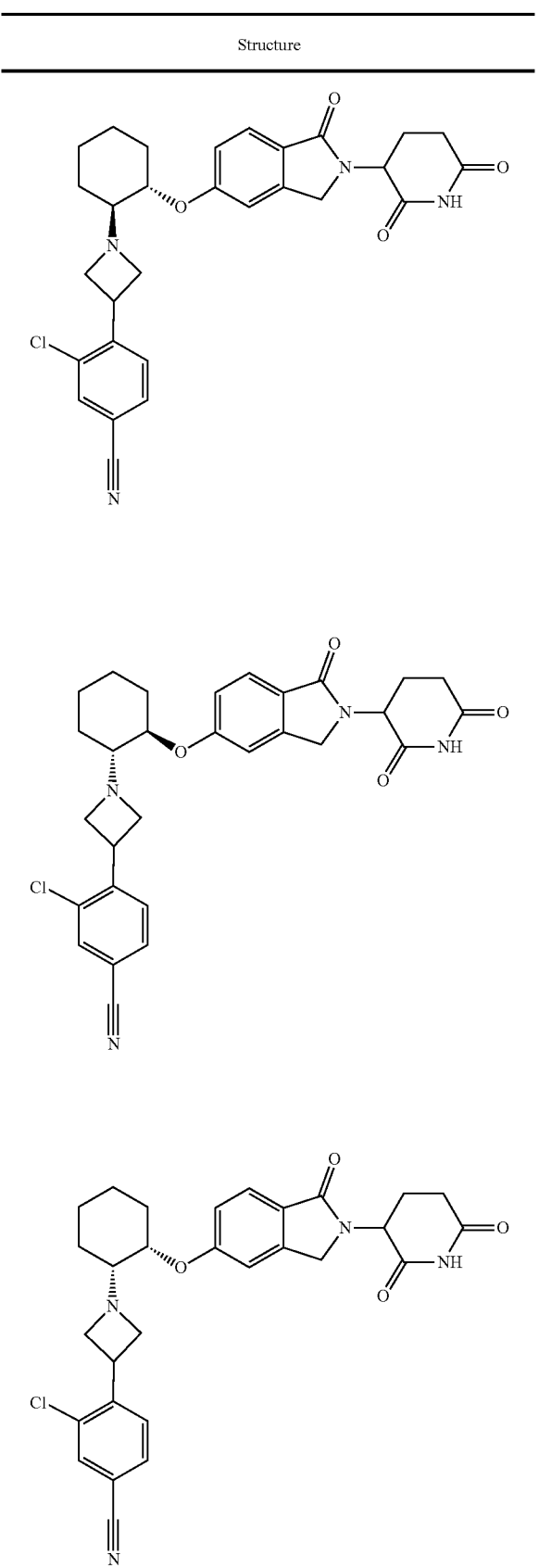 |
TABLE 1A-continued
| Structure |
| --- |
| 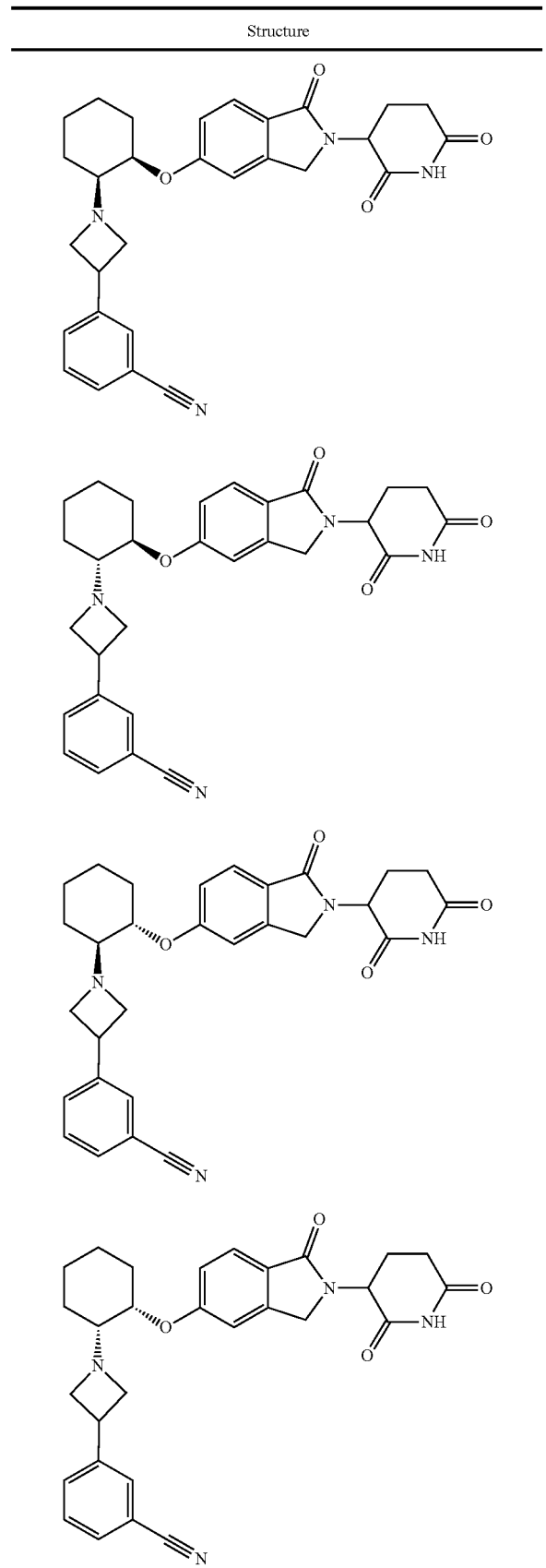 |

TABLE 1A-continued

| Structure |
|---|

| 159 | 160 |
|---|---|
| TABLE 1A-continued | TABLE 1A-continued |
| Structure | Structure |
| 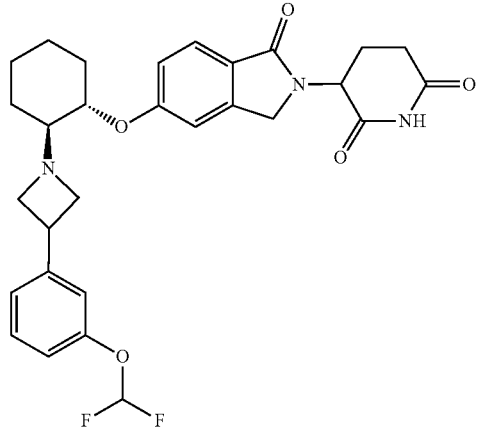 [SMILES: O=C1CCC(N2Cc3cc(O[C@H]4CCCC[C@@H]4N4CC(c5cccc(OC(F)F)c5)C4)ccc3C2=O)C(=O)N1] | 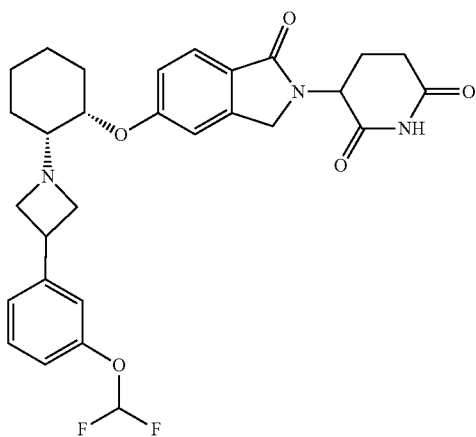 [SMILES: O=C1CCC(N2Cc3cc(O[C@H]4CCCC[C@H]4N4CC(c5cccc(OC(F)F)c5)C4)ccc3C2=O)C(=O)N1] |
| | 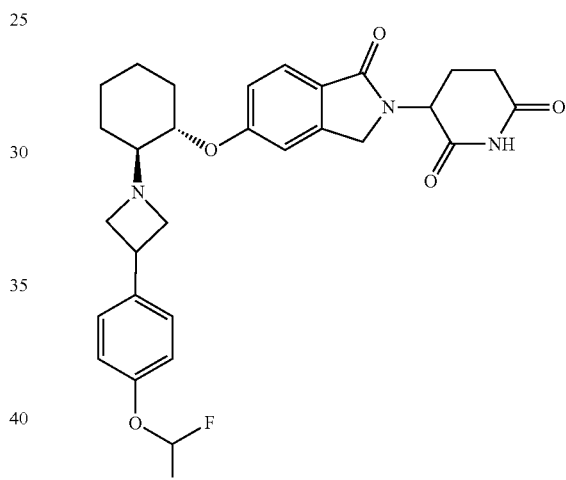 |
| | 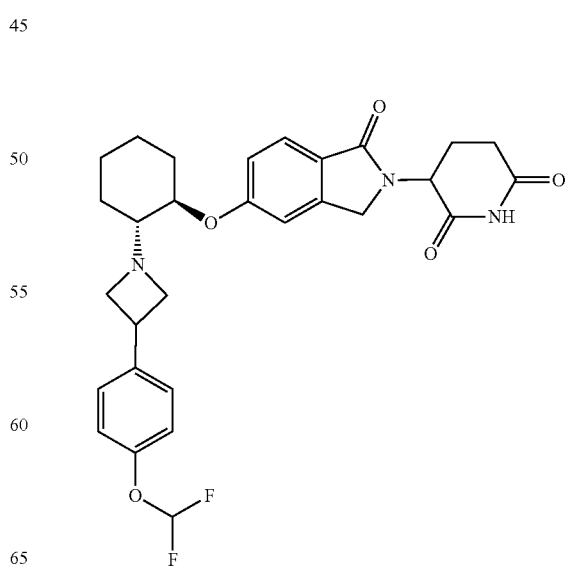 |

TABLE 1A-continued
| Structure |
|---|
| 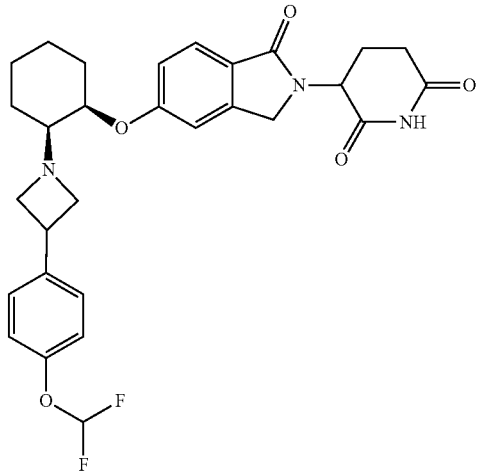 [SMILES: O=C1CCC(N2Cc3cc(O[C@@H]4CCCC[C@@H]4N4CC(c5ccc(OC(F)F)cc5)C4)ccc3C2=O)C(=O)N1] |
| 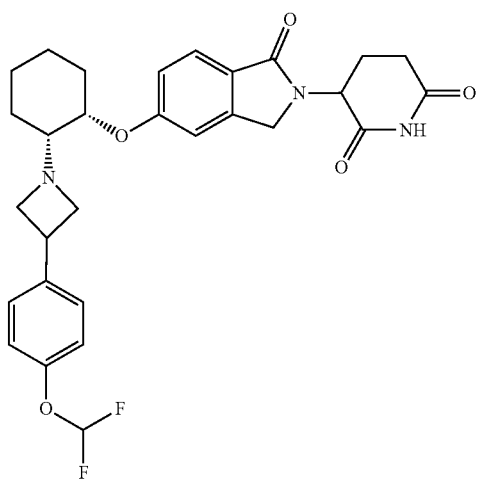 [SMILES: O=C1CCC(N2Cc3cc(O[C@H]4CCCC[C@H]4N4CC(c5ccc(OC(F)F)cc5)C4)ccc3C2=O)C(=O)N1] |
| 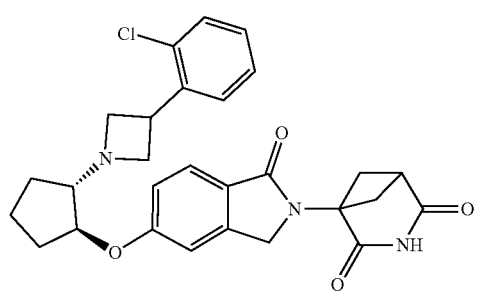 [SMILES: O=C1NC(=O)C2(N3Cc4cc(O[C@H]5CCC[C@@H]5N5CC(c6ccccc6Cl)C5)ccc4C3=O)CC1C2] |
| 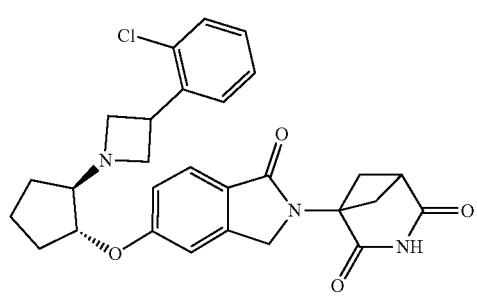 [SMILES: O=C1NC(=O)C2(N3Cc4cc(O[C@@H]5CCC[C@H]5N5CC(c6ccccc6Cl)C5)ccc4C3=O)CC1C2] |
TABLE 1A-continued
| Structure |
|---|
| 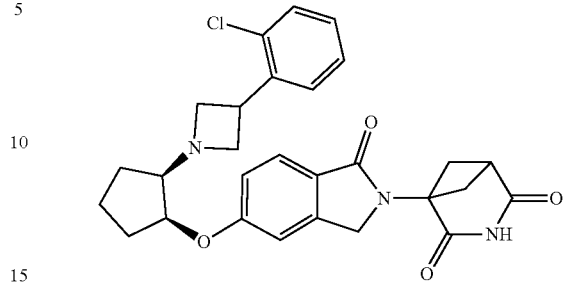 |
| 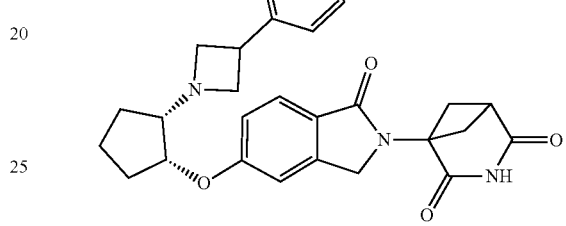 |
| 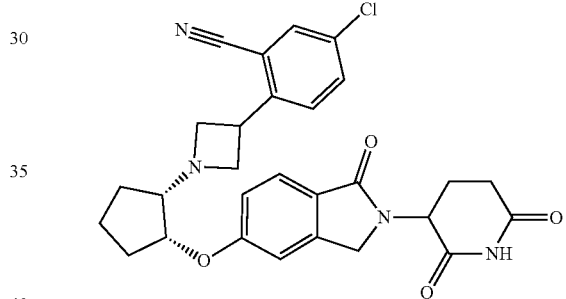 |
| 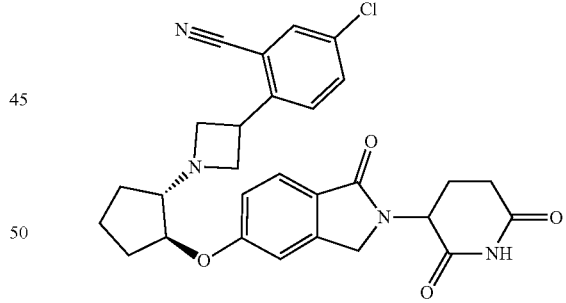 |
| 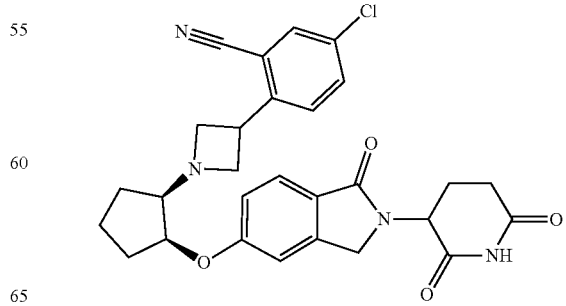 |

TABLE 1A-continued
Structure
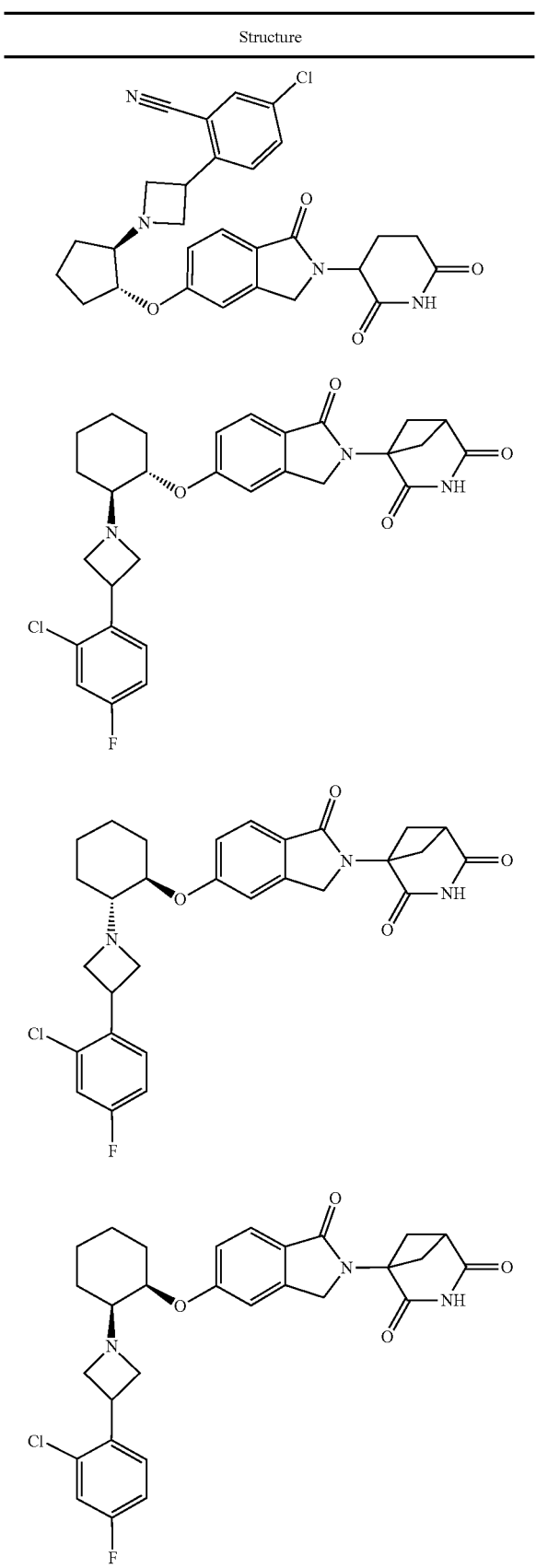
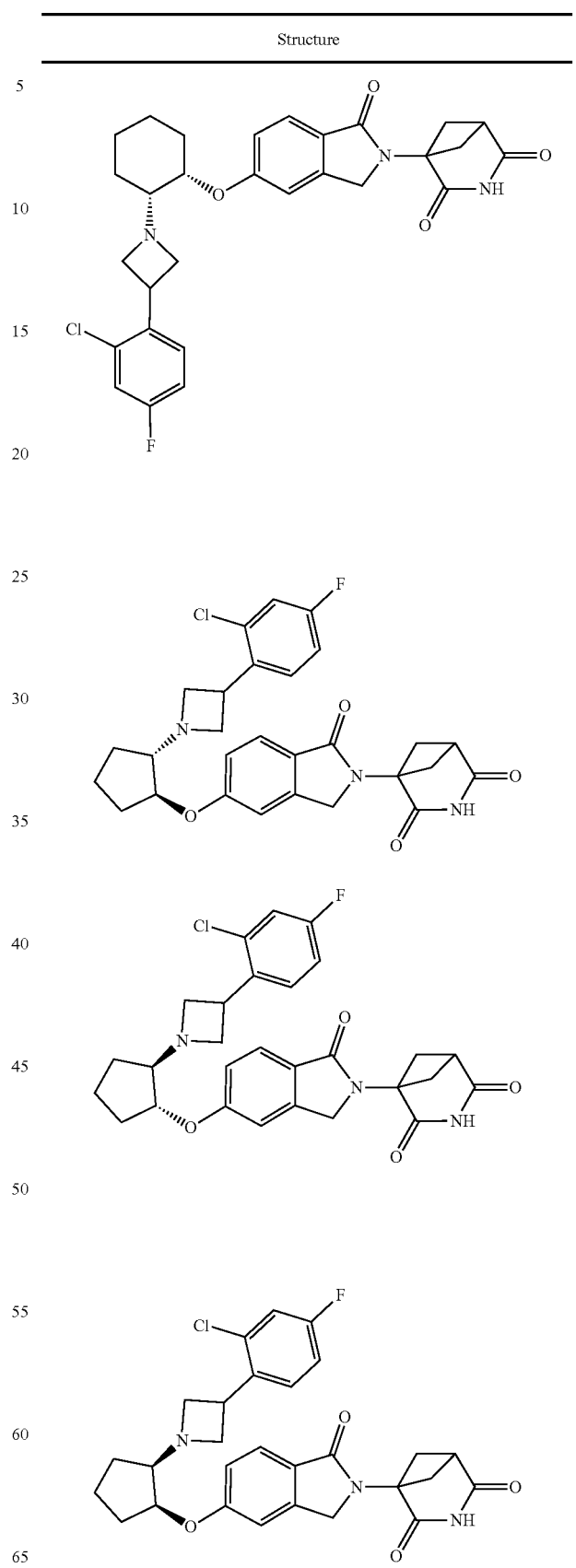

TABLE 1A-continued
Structure
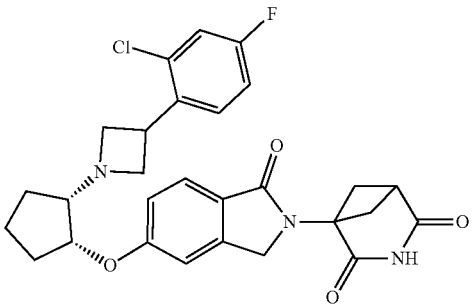 [SMILES: O=C1NC(=O)C2(N3Cc4cc(O[C@@H]5CCC[C@@H]5N5CC(c6ccc(F)cc6Cl)C5)ccc4C3=O)CC1C2]
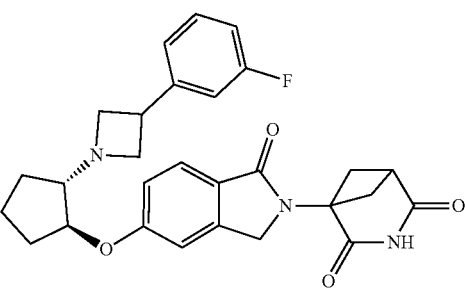 [SMILES: O=C1NC(=O)C2(N3Cc4cc(O[C@H]5CCC[C@@H]5N5CC(c6cccc(F)c6)C5)ccc4C3=O)CC1C2]
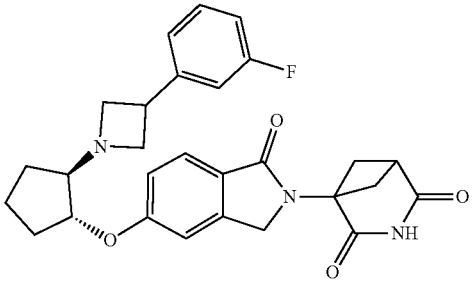 [SMILES: O=C1NC(=O)C2(N3Cc4cc(O[C@@H]5CCC[C@H]5N5CC(c6cccc(F)c6)C5)ccc4C3=O)CC1C2]
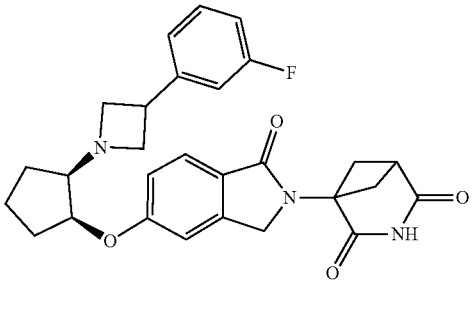 [SMILES: O=C1NC(=O)C2(N3Cc4cc(O[C@H]5CCC[C@H]5N5CC(c6cccc(F)c6)C5)ccc4C3=O)CC1C2]
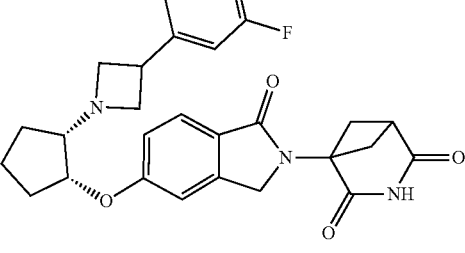
TABLE 1A-continued
Structure
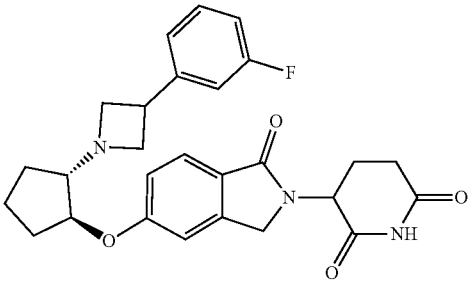 [SMILES: O=C1CCC(N2Cc3cc(O[C@H]4CCC[C@@H]4N4CC(c5cccc(F)c5)C4)ccc3C2=O)C(=O)N1]
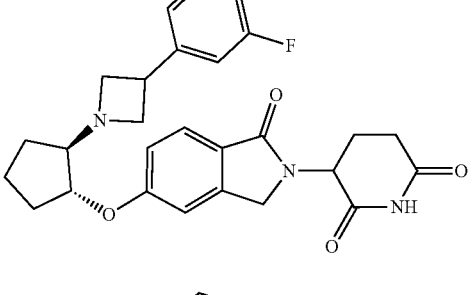
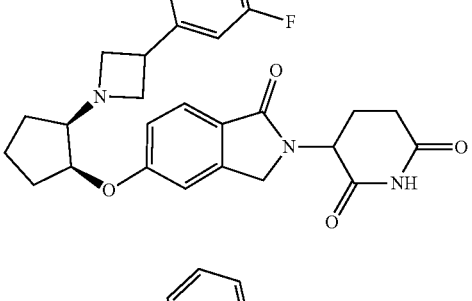
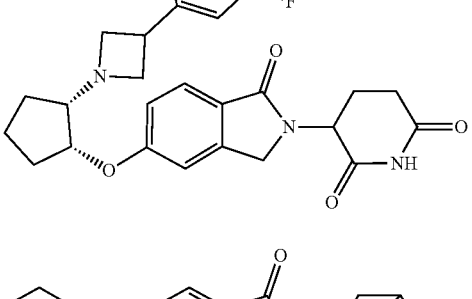
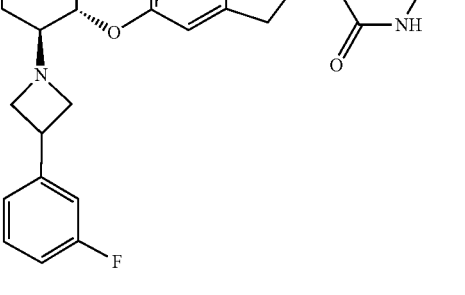

TABLE 1A-continued
Structure
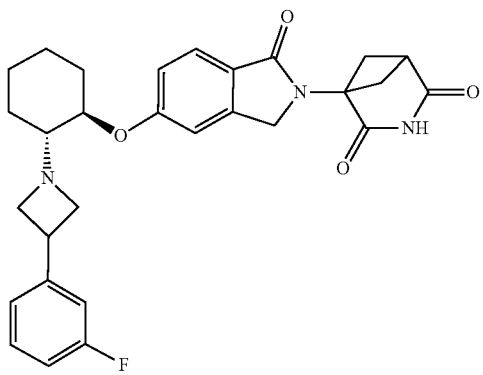 [SMILES: O=C1NC(=O)C2(N3Cc4cc(O[C@@H]5CCCC[C@H]5N5CC(c6cccc(F)c6)C5)ccc4C3=O)CC1C2]
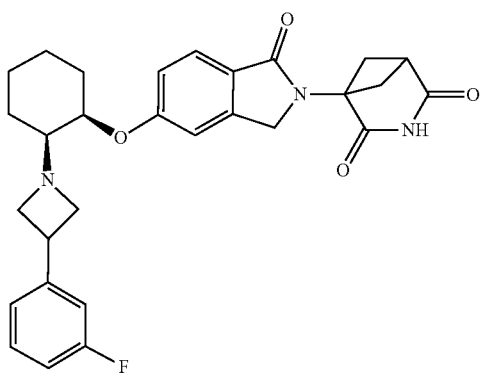 [SMILES: O=C1NC(=O)C2(N3Cc4cc(O[C@@H]5CCCC[C@@H]5N5CC(c6cccc(F)c6)C5)ccc4C3=O)CC1C2]
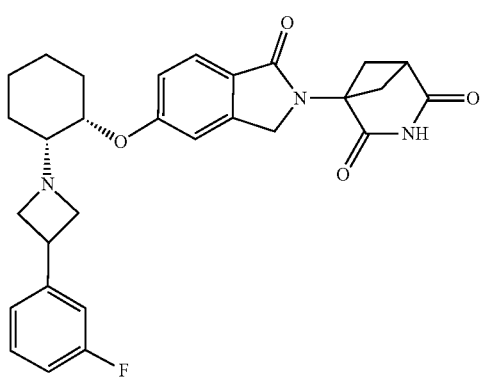 [SMILES: O=C1NC(=O)C2(N3Cc4cc(O[C@H]5CCCC[C@H]5N5CC(c6cccc(F)c6)C5)ccc4C3=O)CC1C2]
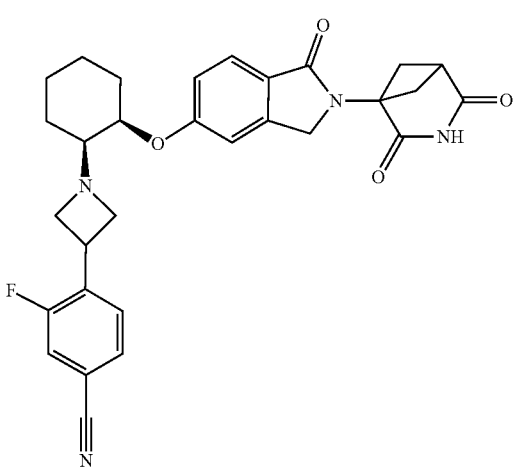 [SMILES: N#Cc1ccc(C2CN([C@H]3CCCC[C@H]3Oc3ccc4c(c3)CN(C35CC(C3)C(=O)NC5=O)C4=O)C2)c(F)c1]
TABLE 1A-continued
Structure
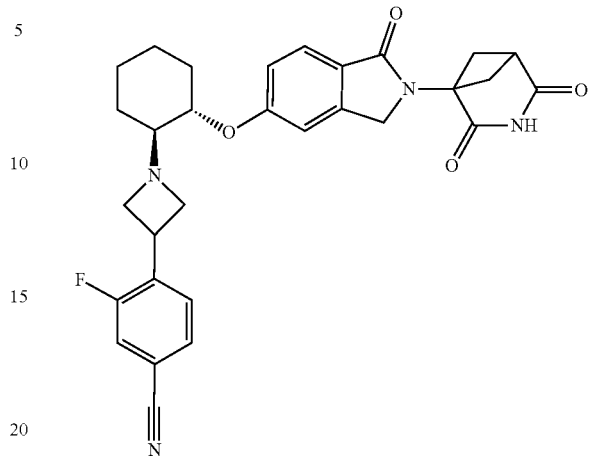
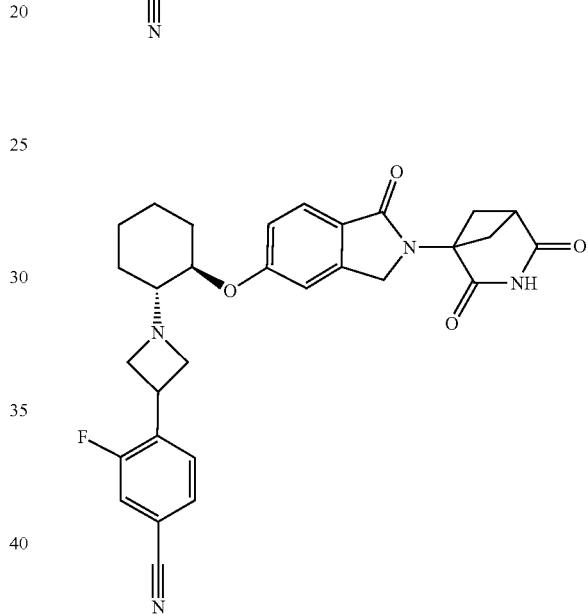
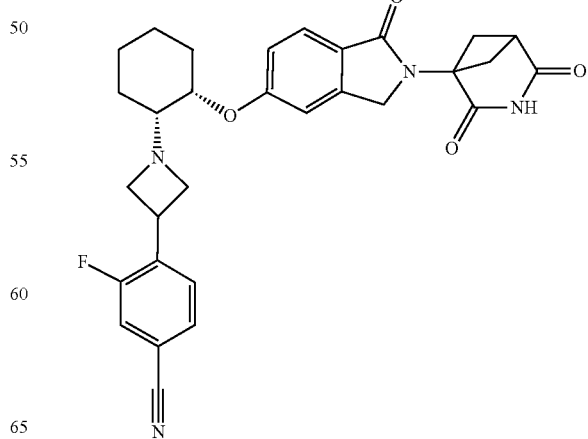

TABLE 1A-continued
Structure
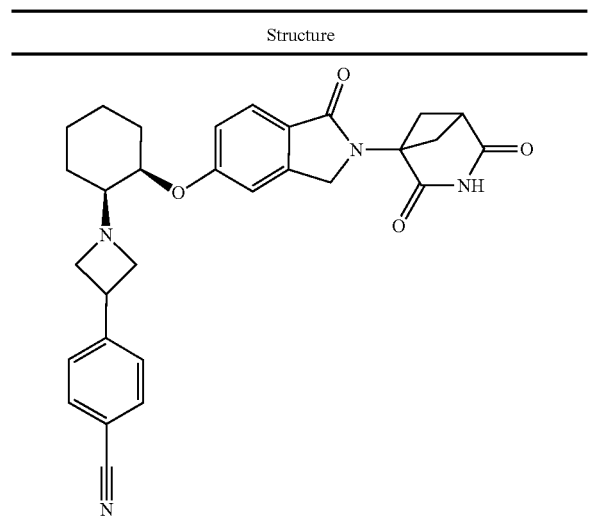
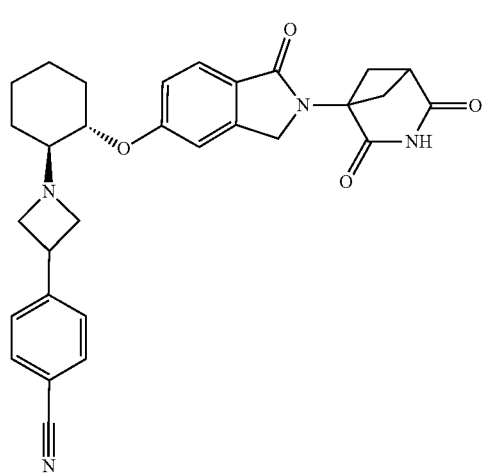 [SMILES: N#Cc1ccc(C2CN([C@H]3CCCC[C@@H]3Oc3ccc4c(c3)CN(C35CC(C3)C(=O)NC5=O)C4=O)C2)cc1]
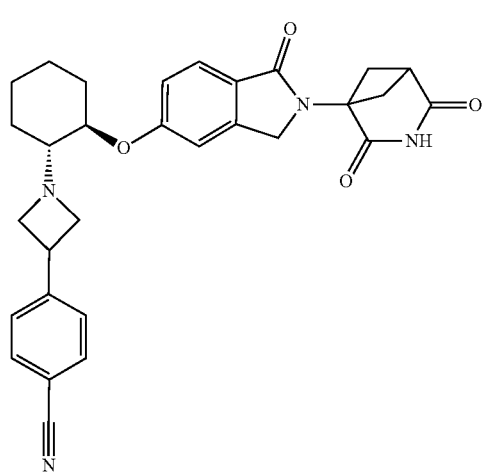 [SMILES: N#Cc1ccc(C2CN([C@@H]3CCCC[C@H]3Oc3ccc4c(c3)CN(C35CC(C3)C(=O)NC5=O)C4=O)C2)cc1]
TABLE 1A-continued
Structure
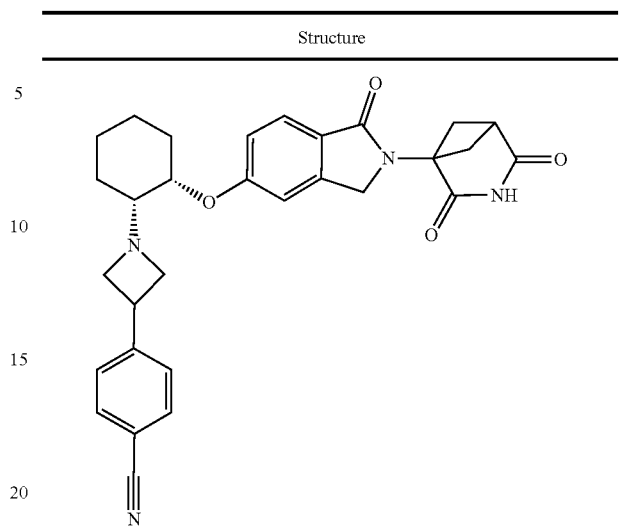
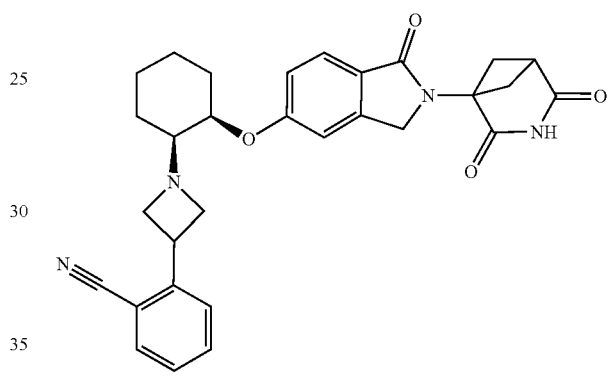
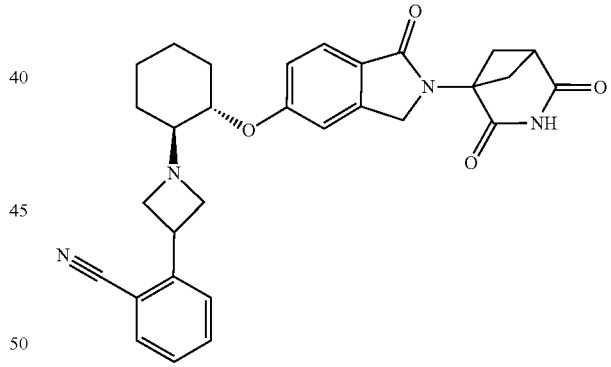
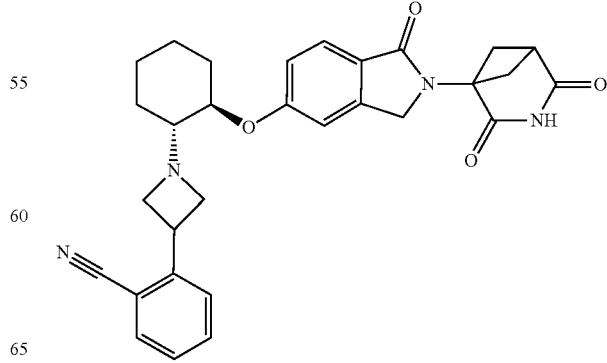

TABLE 1A-continued
Structure
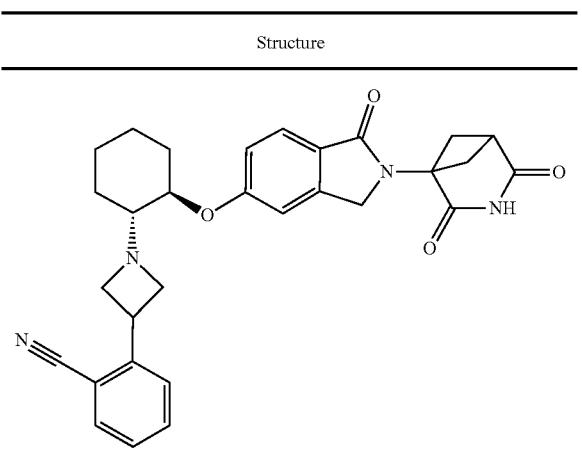
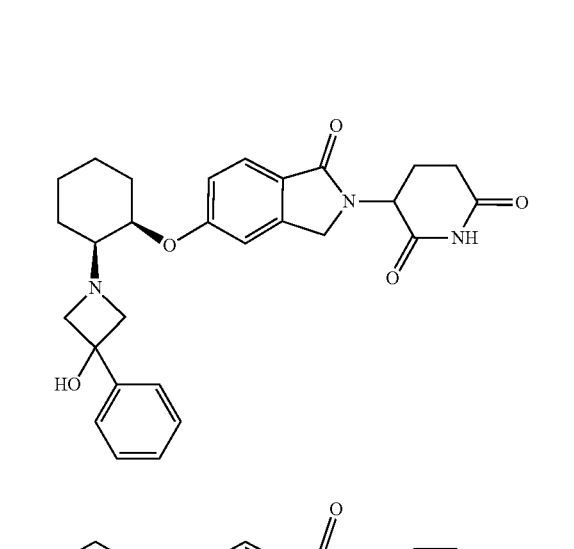
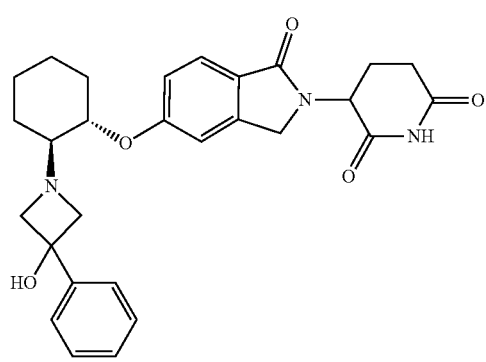 [SMILES: O=C1CCC(N2Cc3cc(O[C@H]4CCCC[C@@H]4N4CC(O)(c5ccccc5)C4)ccc3C2=O)C(=O)N1]
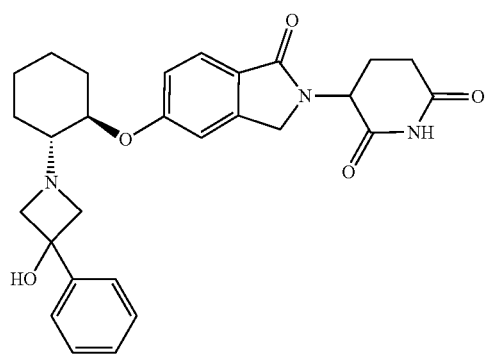 [SMILES: O=C1CCC(N2Cc3cc(O[C@@H]4CCCC[C@H]4N4CC(O)(c5ccccc5)C4)ccc3C2=O)C(=O)N1]
TABLE 1A-continued
Structure
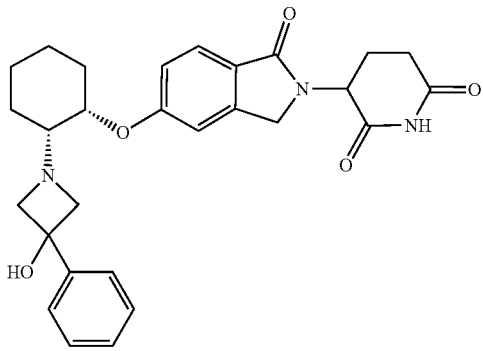 [SMILES: O=C1CCC(N2Cc3cc(O[C@H]4CCCC[C@H]4N4CC(O)(c5ccccc5)C4)ccc3C2=O)C(=O)N1]
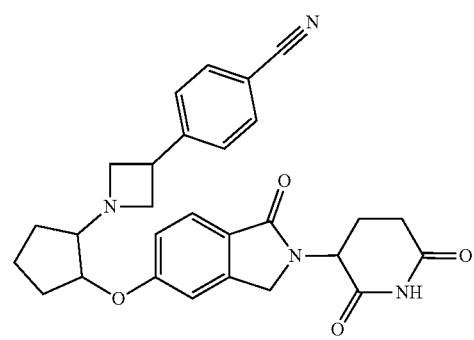 [SMILES: N#Cc1ccc(C2CN(C3CCCC3Oc3ccc4c(c3)CN(C3CCC(=O)NC3=O)C4=O)C2)cc1]
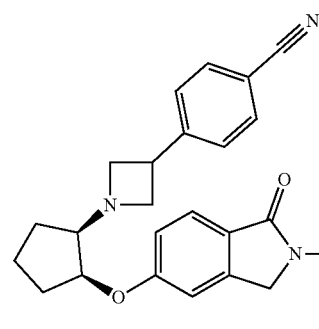
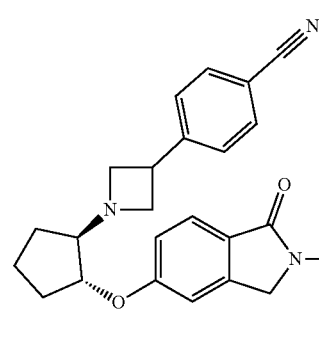

TABLE 1A-continued
Structure
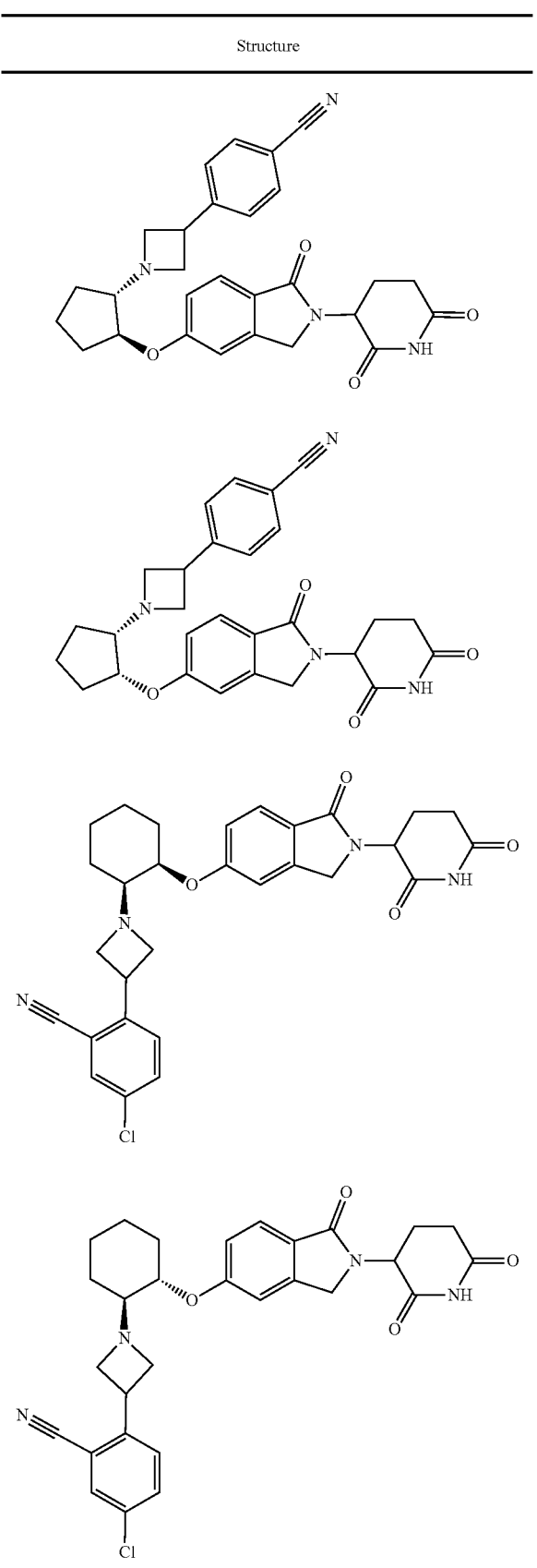
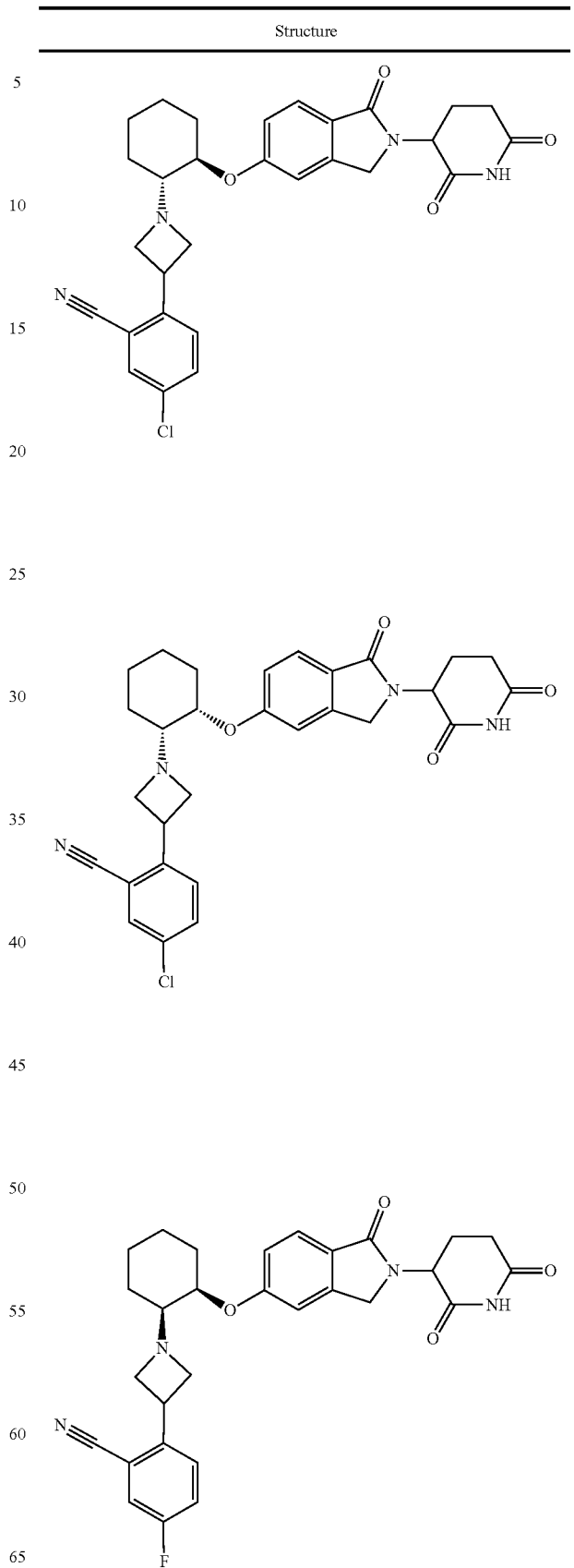

TABLE 1A-continued
Structure
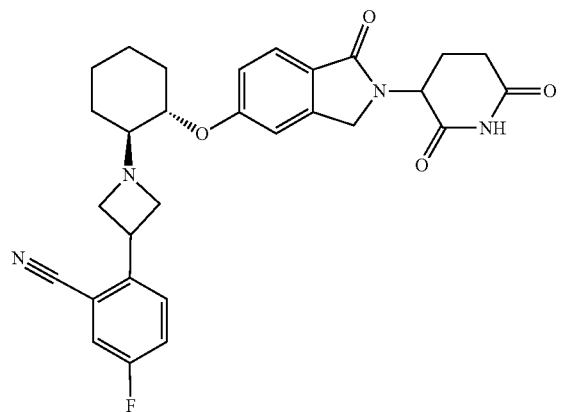 [SMILES: N#Cc1cc(F)ccc1C1CN([C@H]2CCCC[C@@H]2Oc2ccc3c(c2)CN(C2CCC(=O)NC2=O)C3=O)C1]
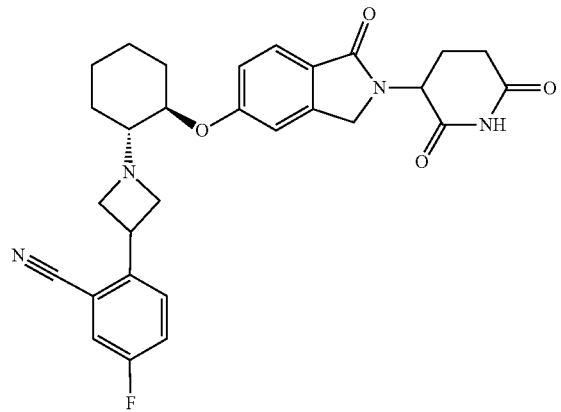
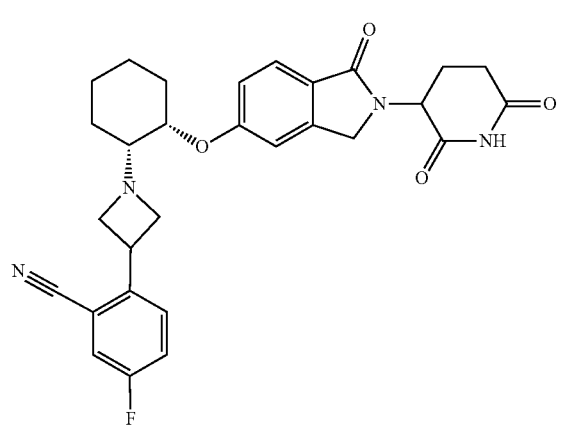 [SMILES: N#Cc1cc(F)ccc1C1CN([C@@H]2CCCC[C@@H]2Oc2ccc3c(c2)CN(C2CCC(=O)NC2=O)C3=O)C1]
TABLE 1A-continued
Structure
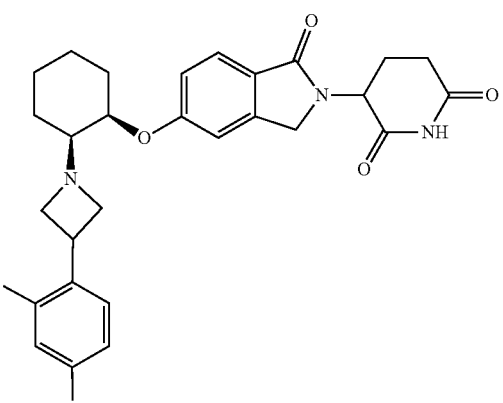
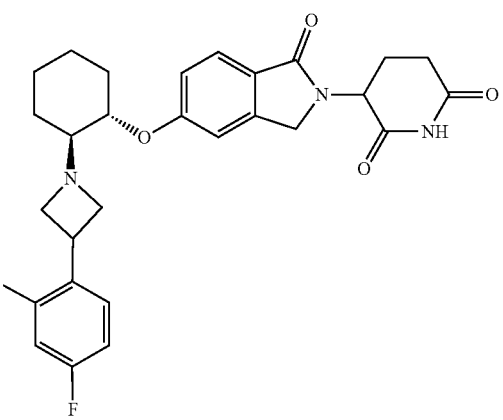

TABLE 1A-continued
Structure
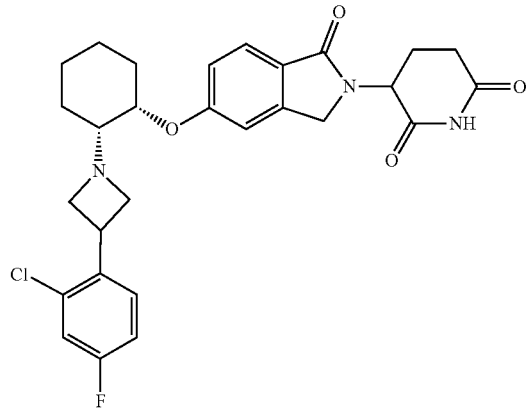 [SMILES: O=C1CCC(N2Cc3cc(O[C@H]4CCCC[C@H]4N4CC(c5ccc(F)cc5Cl)C4)ccc3C2=O)C(=O)N1]
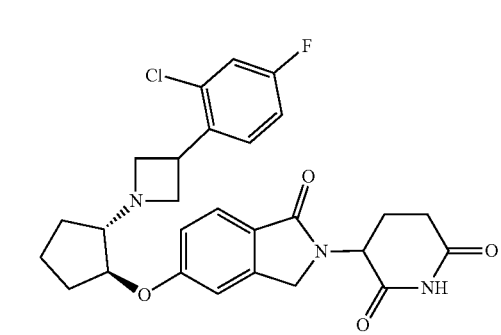 [SMILES: O=C1CCC(N2Cc3cc(O[C@H]4CCC[C@@H]4N4CC(c5ccc(F)cc5Cl)C4)ccc3C2=O)C(=O)N1]
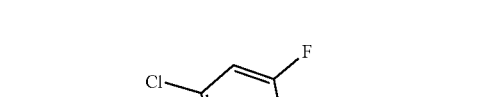
TABLE 1A-continued
Structure
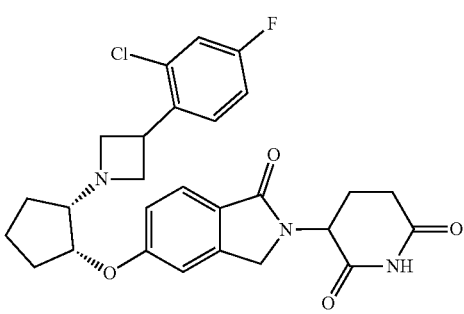 [SMILES: O=C1CCC(N2Cc3cc(O[C@@H]4CCC[C@@H]4N4CC(c5ccc(F)cc5Cl)C4)ccc3C2=O)C(=O)N1]
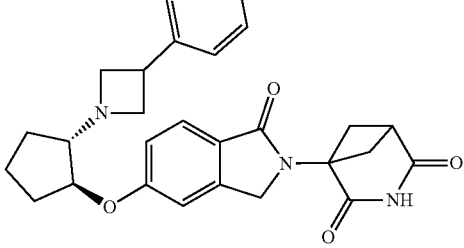
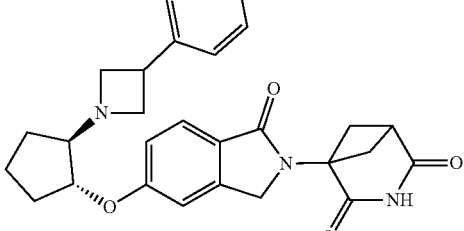
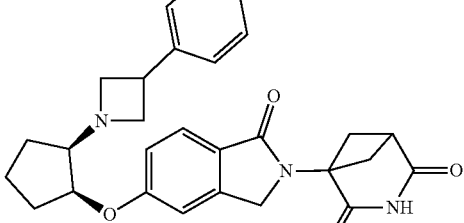
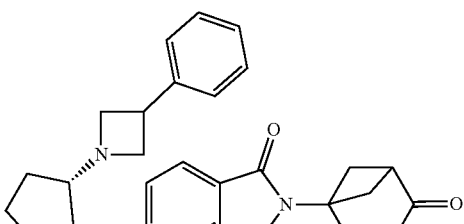

TABLE 1A-continued
Structure
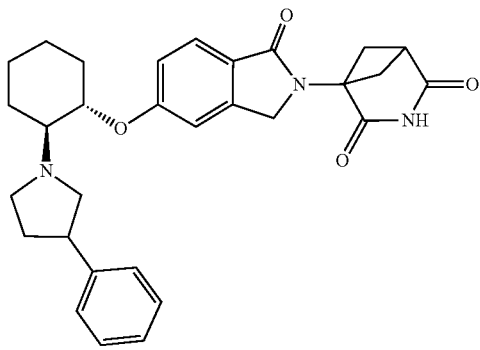 [SMILES: O=C1NC(=O)C2(N3Cc4cc(O[C@H]5CCCC[C@@H]5N5CCC(c6ccccc6)C5)ccc4C3=O)CC1C2]
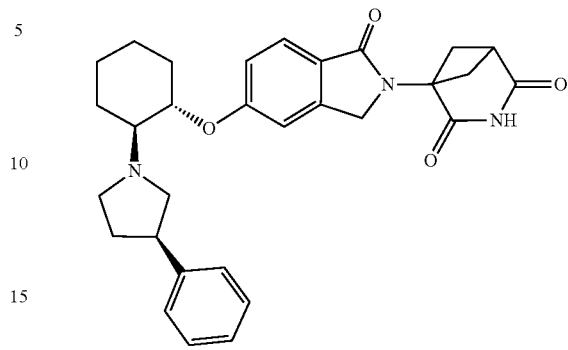
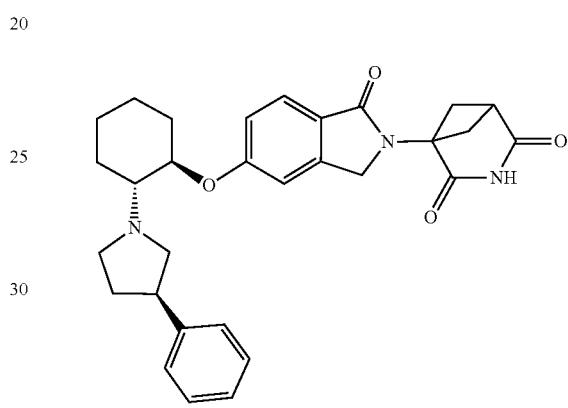
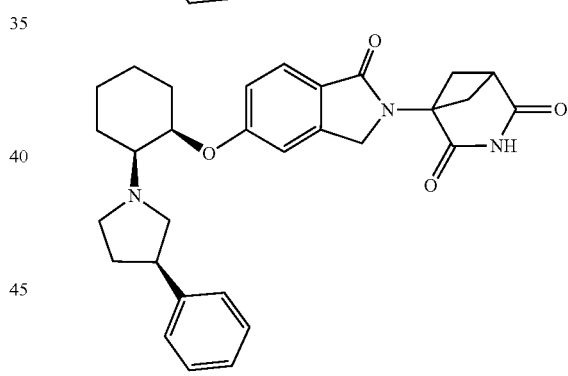
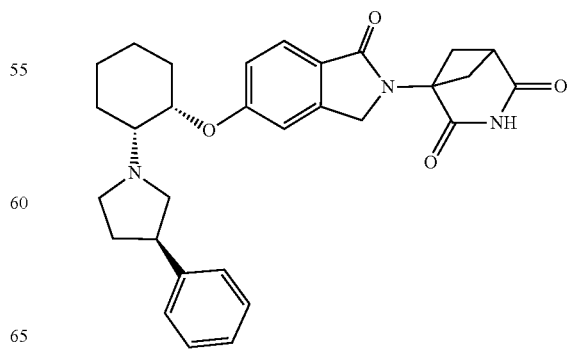

TABLE 1A-continued
Structure
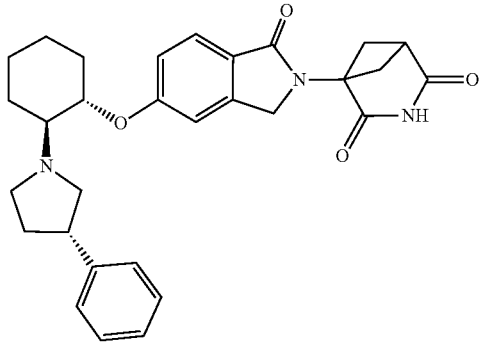 [SMILES: O=C1NC(=O)C2(N3Cc4cc(O[C@H]5CCCC[C@@H]5N5CC[C@@H](c6ccccc6)C5)ccc4C3=O)CC1C2]
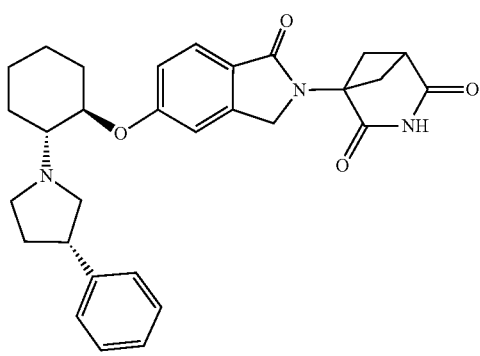 [SMILES: O=C1NC(=O)C2(N3Cc4cc(O[C@@H]5CCCC[C@H]5N5CC[C@@H](c6ccccc6)C5)ccc4C3=O)CC1C2]
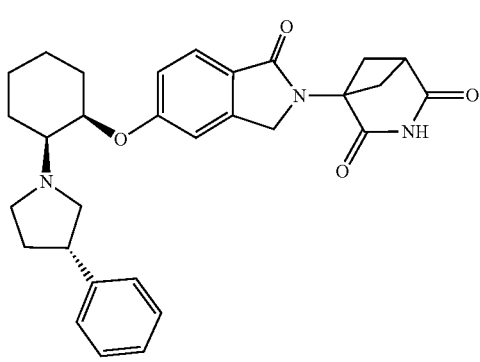 [SMILES: O=C1NC(=O)C2(N3Cc4cc(O[C@@H]5CCCC[C@@H]5N5CC[C@@H](c6ccccc6)C5)ccc4C3=O)CC1C2]
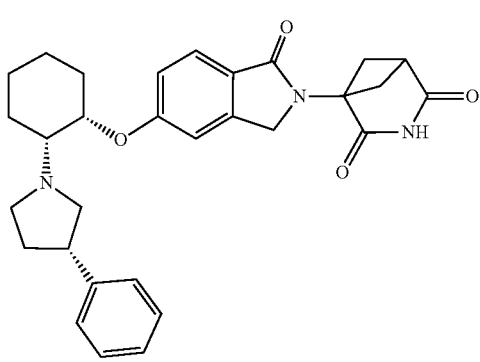 [SMILES: O=C1NC(=O)C2(N3Cc4cc(O[C@H]5CCCC[C@H]5N5CC[C@@H](c6ccccc6)C5)ccc4C3=O)CC1C2]
TABLE 1A-continued
Structure
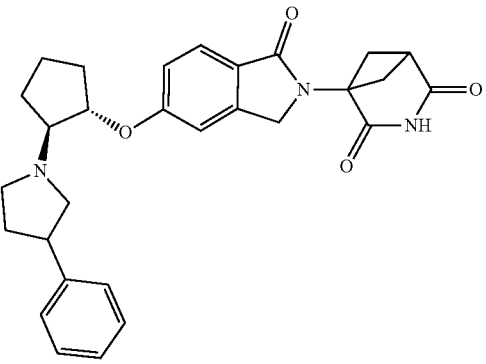 [SMILES: O=C1NC(=O)C2(N3Cc4cc(O[C@H]5CCC[C@@H]5N5CCC(c6ccccc6)C5)ccc4C3=O)CC1C2]
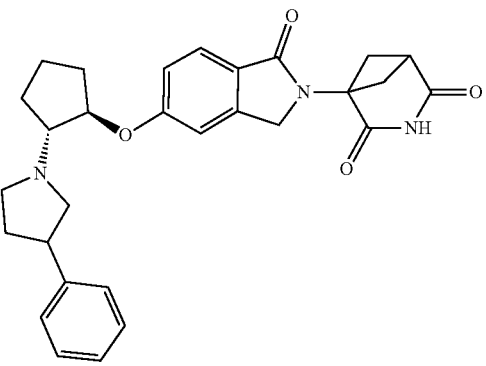 [SMILES: O=C1NC(=O)C2(N3Cc4cc(O[C@@H]5CCC[C@H]5N5CCC(c6ccccc6)C5)ccc4C3=O)CC1C2]
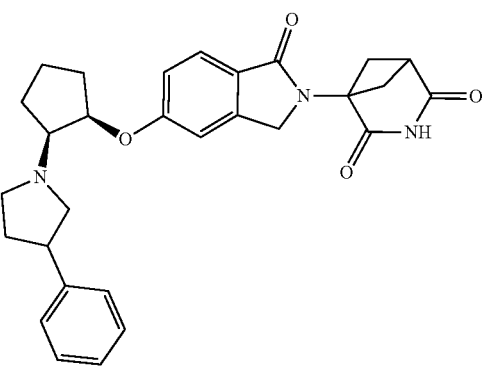 [SMILES: O=C1NC(=O)C2(N3Cc4cc(O[C@@H]5CCC[C@@H]5N5CCC(c6ccccc6)C5)ccc4C3=O)CC1C2]
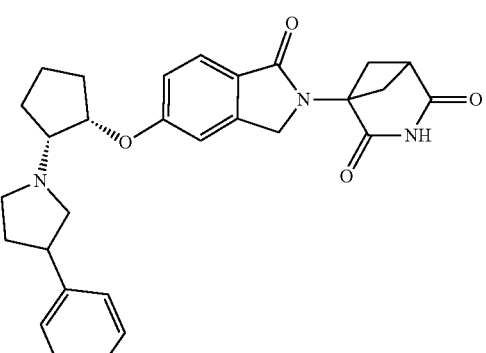

TABLE 1A-continued
| Structure |
|---|
| 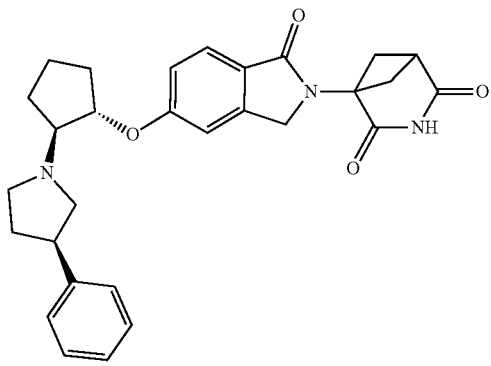 [SMILES: O=C1NC(=O)C2(N3Cc4cc(O[C@H]5CCC[C@@H]5N5CC[C@H](c6ccccc6)C5)ccc4C3=O)CC1C2] |
| 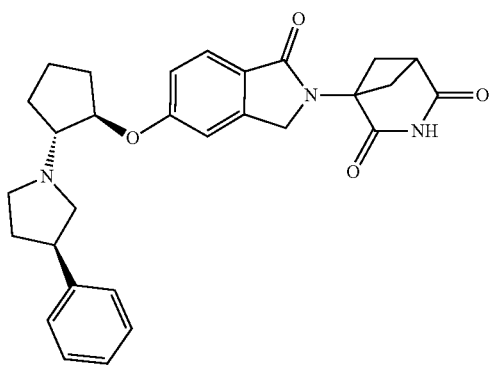 [SMILES: O=C1NC(=O)C2(N3Cc4cc(O[C@@H]5CCC[C@H]5N5CC[C@H](c6ccccc6)C5)ccc4C3=O)CC1C2] |
| 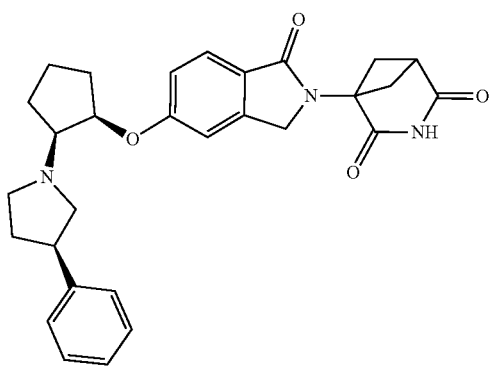 [SMILES: O=C1NC(=O)C2(N3Cc4cc(O[C@@H]5CCC[C@@H]5N5CC[C@H](c6ccccc6)C5)ccc4C3=O)CC1C2] |
| 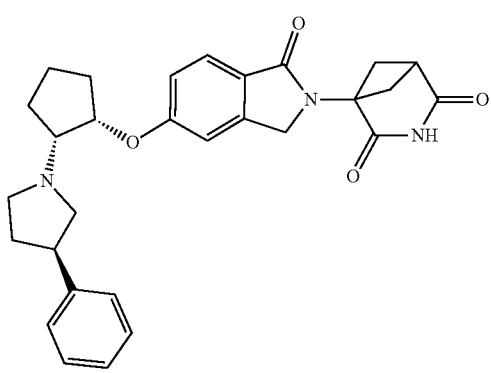 [SMILES: O=C1NC(=O)C2(N3Cc4cc(O[C@H]5CCC[C@H]5N5CC[C@H](c6ccccc6)C5)ccc4C3=O)CC1C2] |
TABLE 1A-continued
| Structure |
|---|
| 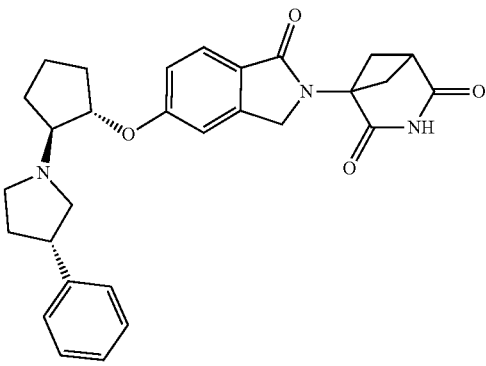 [SMILES: O=C1NC(=O)C2(N3Cc4cc(O[C@H]5CCC[C@@H]5N5CC[C@@H](c6ccccc6)C5)ccc4C3=O)CC1C2] |
| 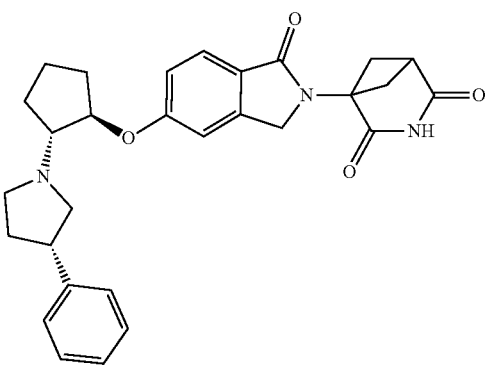 [SMILES: O=C1NC(=O)C2(N3Cc4cc(O[C@@H]5CCC[C@H]5N5CC[C@@H](c6ccccc6)C5)ccc4C3=O)CC1C2] |
| 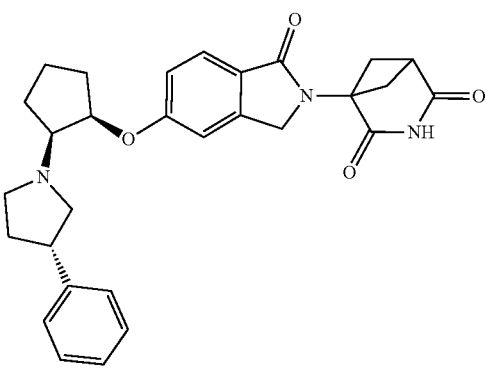 [SMILES: O=C1NC(=O)C2(N3Cc4cc(O[C@@H]5CCC[C@@H]5N5CC[C@@H](c6ccccc6)C5)ccc4C3=O)CC1C2] |
| 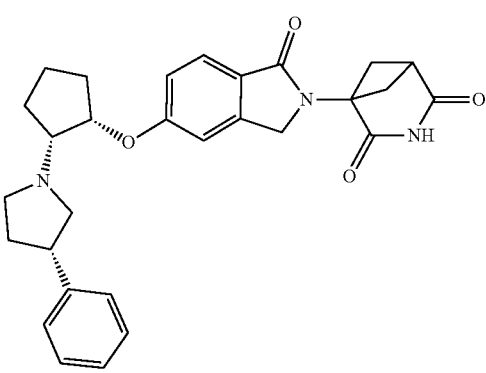 [SMILES: O=C1NC(=O)C2(N3Cc4cc(O[C@H]5CCC[C@H]5N5CC[C@@H](c6ccccc6)C5)ccc4C3=O)CC1C2] |

TABLE 1A-continued
Structure
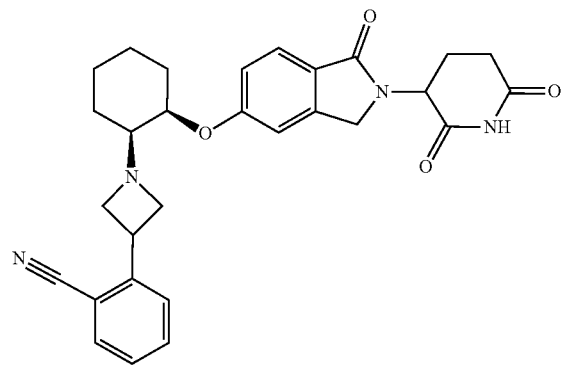 [SMILES: N#Cc1ccccc1C1CN([C@H]2CCCC[C@H]2Oc2ccc3c(c2)CN(C2CCC(=O)NC2=O)C3=O)C1]
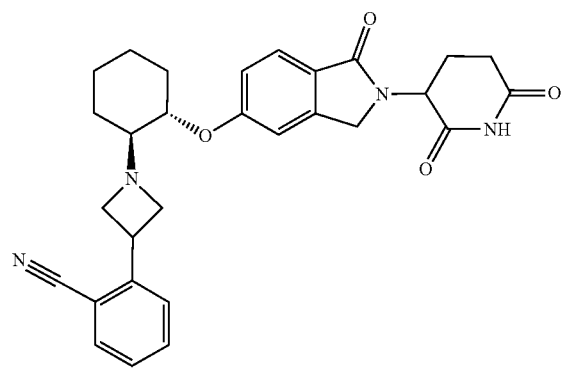 [SMILES: N#Cc1ccccc1C1CN([C@H]2CCCC[C@@H]2Oc2ccc3c(c2)CN(C2CCC(=O)NC2=O)C3=O)C1]
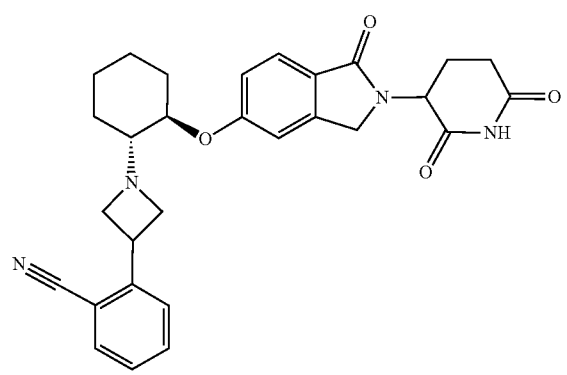 [SMILES: N#Cc1ccccc1C1CN([C@@H]2CCCC[C@H]2Oc2ccc3c(c2)CN(C2CCC(=O)NC2=O)C3=O)C1]
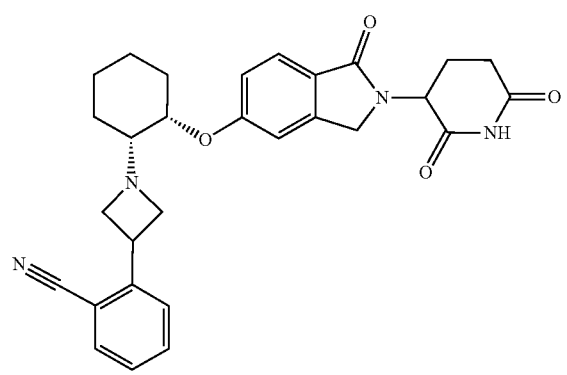 [SMILES: N#Cc1ccccc1C1CN([C@@H]2CCCC[C@@H]2Oc2ccc3c(c2)CN(C2CCC(=O)NC2=O)C3=O)C1]
TABLE 1A-continued
Structure
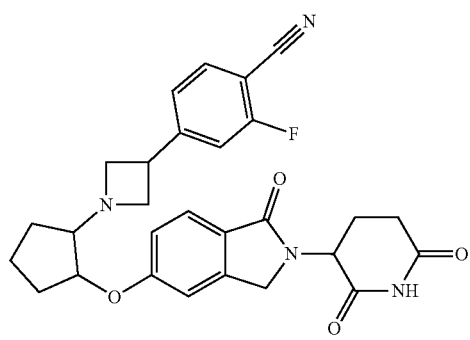 [SMILES: N#Cc1ccc(C2CN(C3CCCC3Oc3ccc4c(c3)CN(C3CCC(=O)NC3=O)C4=O)C2)cc1F]
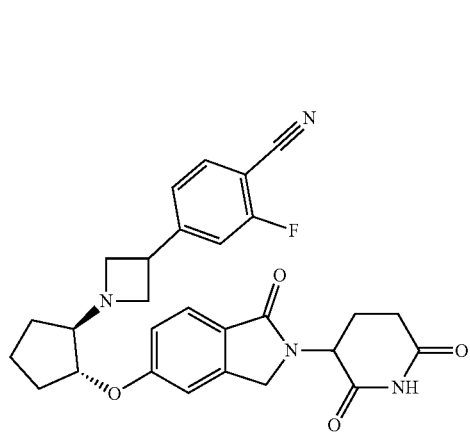 [SMILES: N#Cc1ccc(C2CN([C@@H]3CCC[C@H]3Oc3ccc4c(c3)CN(C3CCC(=O)NC3=O)C4=O)C2)cc1F]
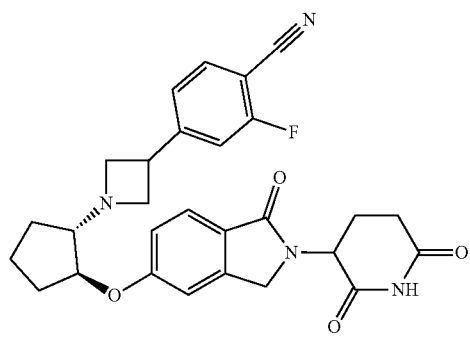 [SMILES: N#Cc1ccc(C2CN([C@H]3CCC[C@@H]3Oc3ccc4c(c3)CN(C3CCC(=O)NC3=O)C4=O)C2)cc1F]
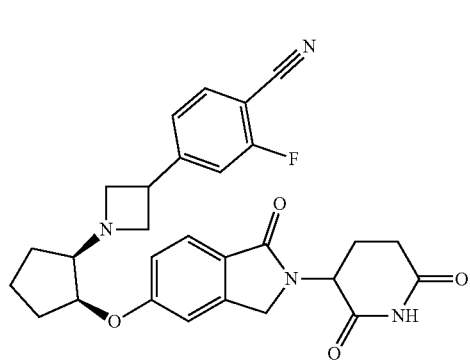 [SMILES: N#Cc1ccc(C2CN([C@@H]3CCC[C@@H]3Oc3ccc4c(c3)CN(C3CCC(=O)NC3=O)C4=O)C2)cc1F]

TABLE 1A-continued
Structure
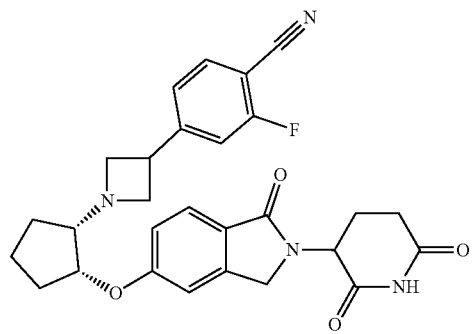 [SMILES: N#Cc1ccc(C2CN([C@H]3CCC[C@H]3Oc3ccc4c(c3)CN(C3CCC(=O)NC3=O)C4=O)C2)cc1F]
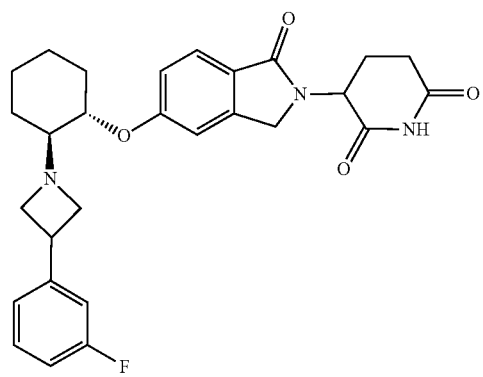 [SMILES: O=C1CCC(N2Cc3cc(O[C@H]4CCCC[C@@H]4N4CC(c5cccc(F)c5)C4)ccc3C2=O)C(=O)N1]
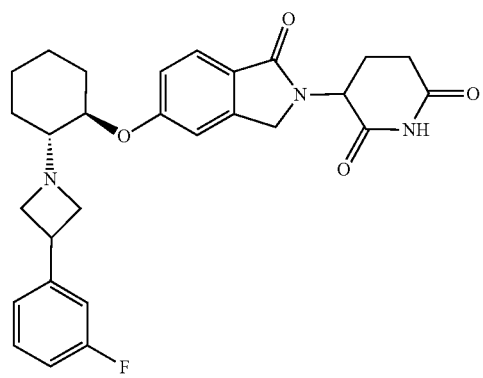 [SMILES: O=C1CCC(N2Cc3cc(O[C@@H]4CCCC[C@H]4N4CC(c5cccc(F)c5)C4)ccc3C2=O)C(=O)N1]
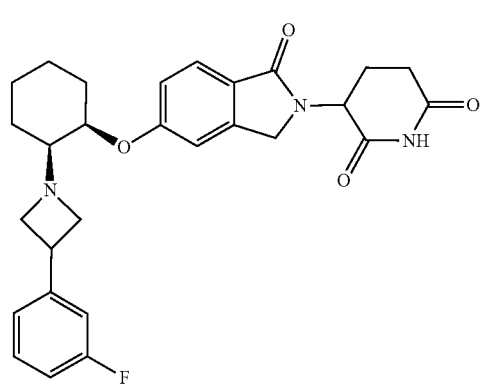 [SMILES: O=C1CCC(N2Cc3cc(O[C@@H]4CCCC[C@@H]4N4CC(c5cccc(F)c5)C4)ccc3C2=O)C(=O)N1]
TABLE 1A-continued
Structure
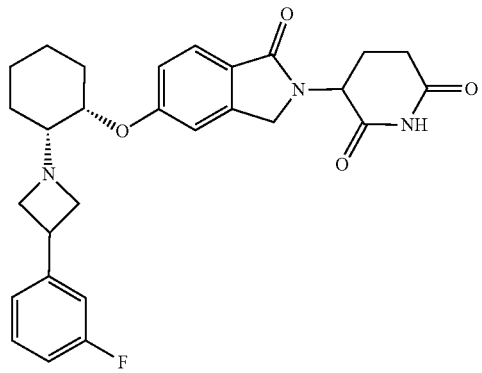 [SMILES: O=C1CCC(N2Cc3cc(O[C@H]4CCCC[C@H]4N4CC(c5cccc(F)c5)C4)ccc3C2=O)C(=O)N1]
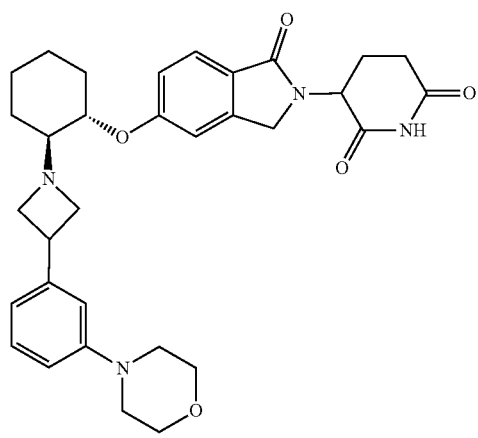 [SMILES: O=C1CCC(N2Cc3cc(O[C@H]4CCCC[C@@H]4N4CC(c5cccc(N6CCOCC6)c5)C4)ccc3C2=O)C(=O)N1]
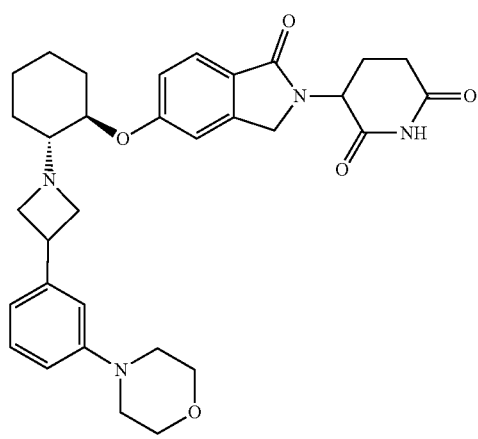 [SMILES: O=C1CCC(N2Cc3cc(O[C@@H]4CCCC[C@H]4N4CC(c5cccc(N6CCOCC6)c5)C4)ccc3C2=O)C(=O)N1]

TABLE 1A-continued

Structure

TABLE 1A-continued

Structure

TABLE 1A-continued
| Structure |
|---|
| 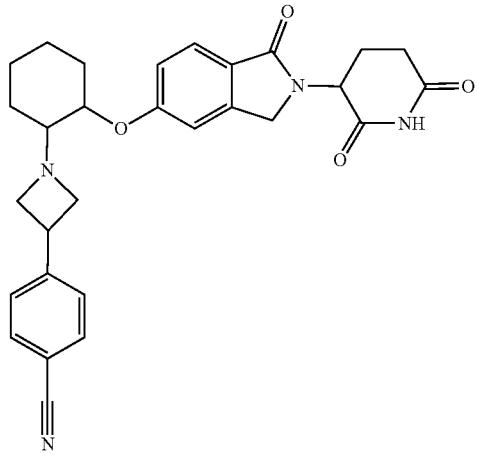 [SMILES: N#Cc1ccc(C2CN(C3CCCCC3Oc3ccc4c(c3)CN(C3CCC(=O)NC3=O)C4=O)C2)cc1] |
| 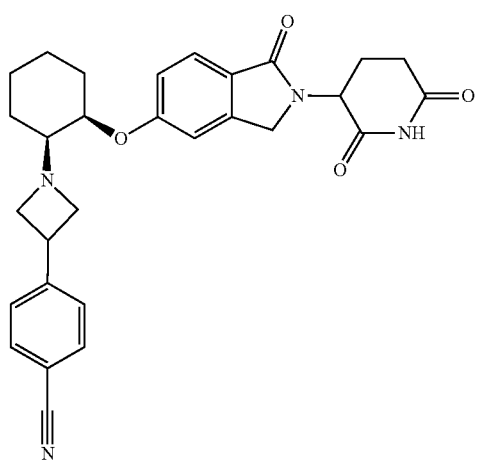 [SMILES: N#Cc1ccc(C2CN([C@H]3CCCC[C@H]3Oc3ccc4c(c3)CN(C3CCC(=O)NC3=O)C4=O)C2)cc1] |
| 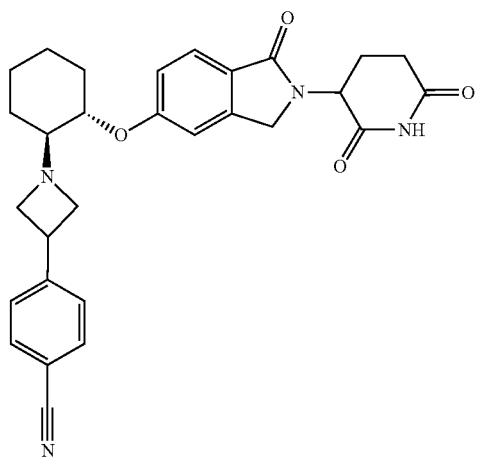 [SMILES: N#Cc1ccc(C2CN([C@H]3CCCC[C@@H]3Oc3ccc4c(c3)CN(C3CCC(=O)NC3=O)C4=O)C2)cc1] |
TABLE 1A-continued
| Structure |
|---|
| 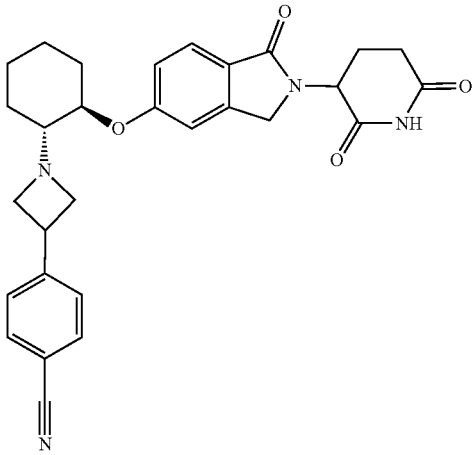 [SMILES: N#Cc1ccc(C2CN([C@@H]3CCCC[C@H]3Oc3ccc4c(c3)CN(C3CCC(=O)NC3=O)C4=O)C2)cc1] |
| 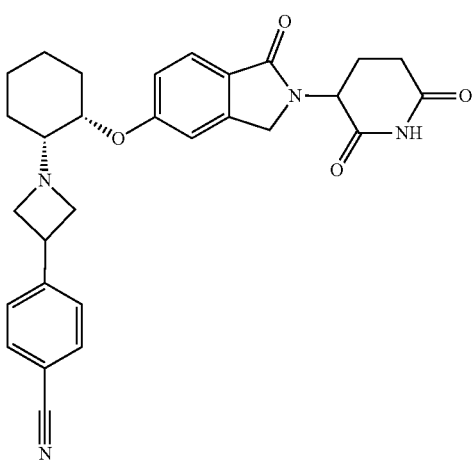 [SMILES: N#Cc1ccc(C2CN([C@@H]3CCCC[C@@H]3Oc3ccc4c(c3)CN(C3CCC(=O)NC3=O)C4=O)C2)cc1] |
| 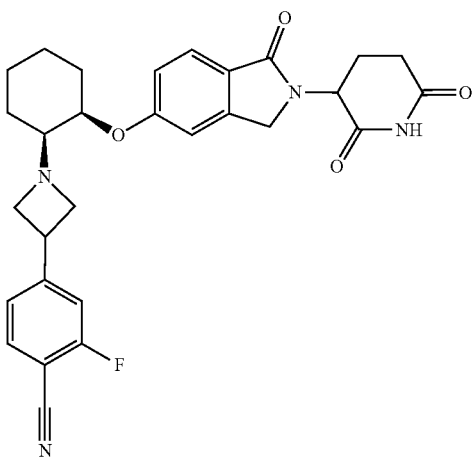 [SMILES: N#Cc1ccc(C2CN([C@H]3CCCC[C@H]3Oc3ccc4c(c3)CN(C3CCC(=O)NC3=O)C4=O)C2)cc1F] |

TABLE 1A-continued
Structure
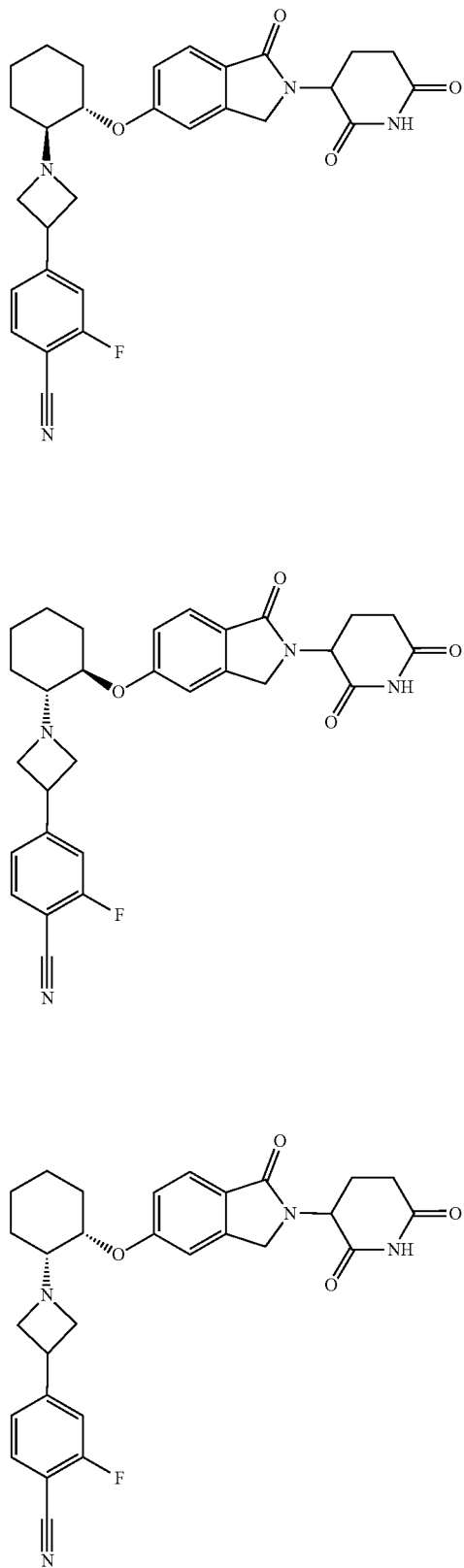
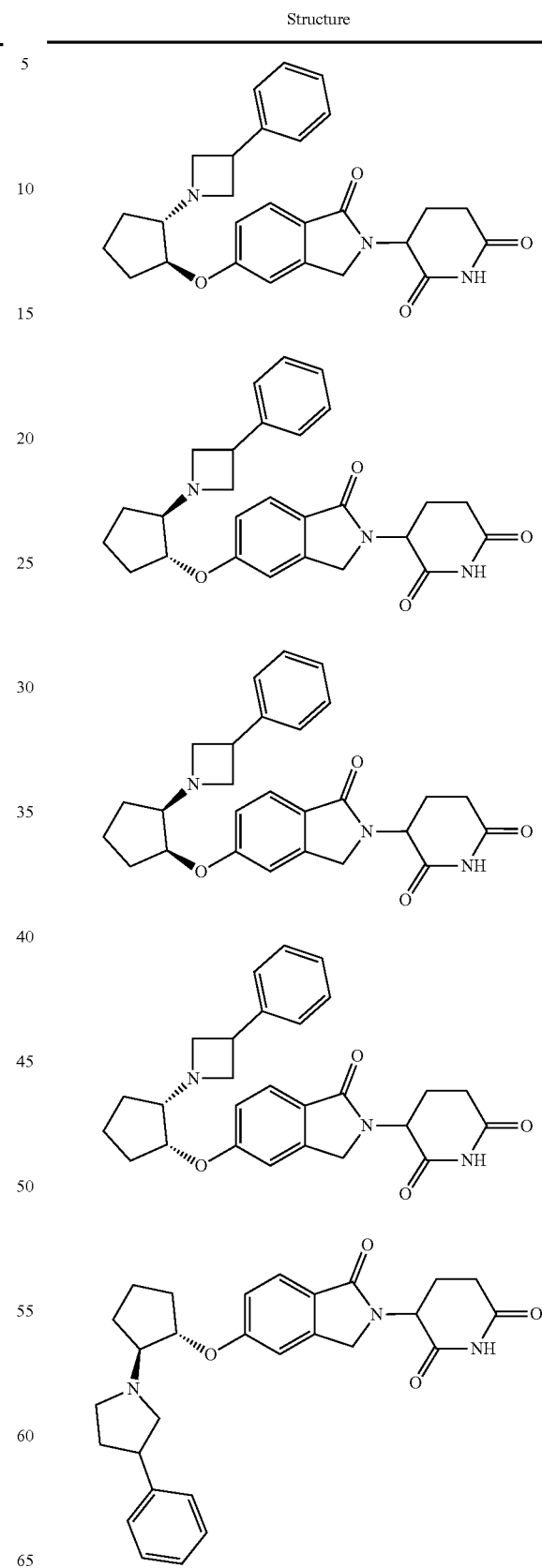

TABLE 1A-continued
Structure
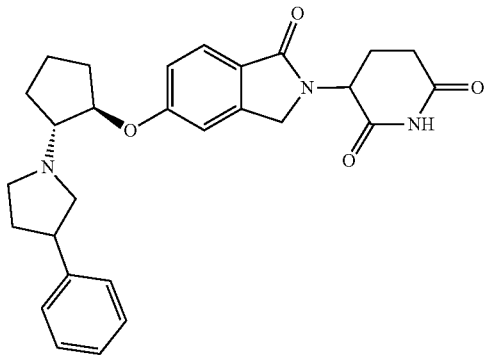 [SMILES: O=C1CCC(N2Cc3cc(O[C@@H]4CCC[C@H]4N4CCC(c5ccccc5)C4)ccc3C2=O)C(=O)N1]
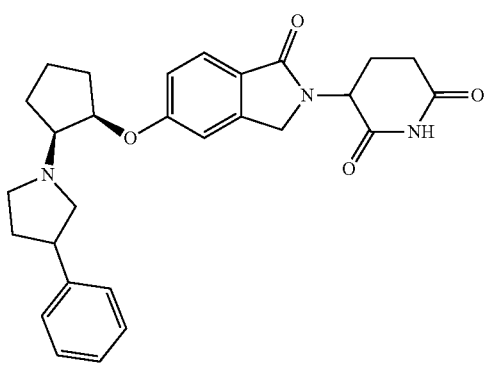 [SMILES: O=C1CCC(N2Cc3cc(O[C@@H]4CCC[C@@H]4N4CCC(c5ccccc5)C4)ccc3C2=O)C(=O)N1]
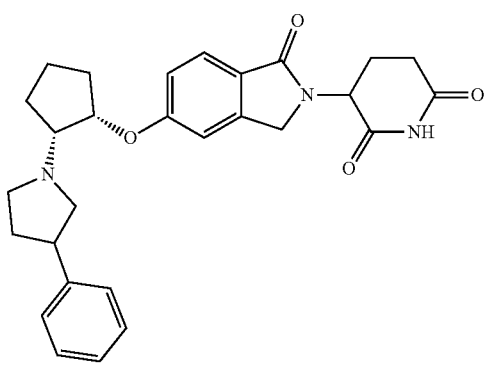 [SMILES: O=C1CCC(N2Cc3cc(O[C@H]4CCC[C@H]4N4CCC(c5ccccc5)C4)ccc3C2=O)C(=O)N1]
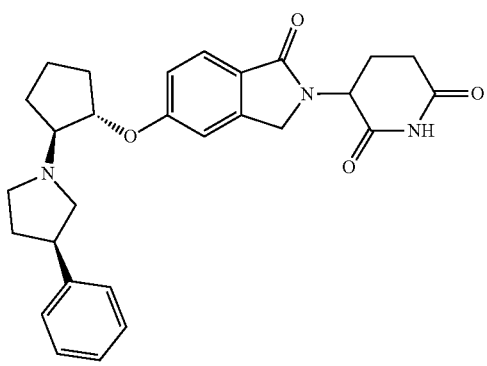 [SMILES: O=C1CCC(N2Cc3cc(O[C@H]4CCC[C@@H]4N4CC[C@H](c5ccccc5)C4)ccc3C2=O)C(=O)N1]
TABLE 1A-continued
Structure
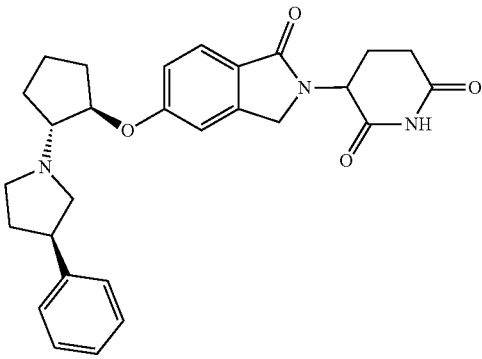 [SMILES: O=C1CCC(N2Cc3cc(O[C@@H]4CCC[C@H]4N4CC[C@H](c5ccccc5)C4)ccc3C2=O)C(=O)N1]
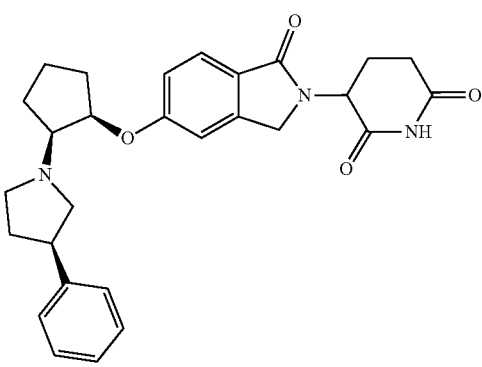 [SMILES: O=C1CCC(N2Cc3cc(O[C@@H]4CCC[C@@H]4N4CC[C@H](c5ccccc5)C4)ccc3C2=O)C(=O)N1]
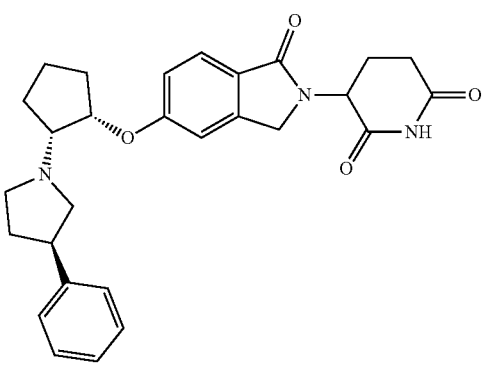 [SMILES: O=C1CCC(N2Cc3cc(O[C@H]4CCC[C@H]4N4CC[C@H](c5ccccc5)C4)ccc3C2=O)C(=O)N1]
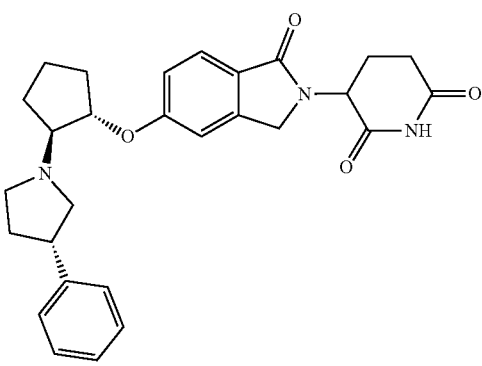 [SMILES: O=C1CCC(N2Cc3cc(O[C@H]4CCC[C@@H]4N4CC[C@@H](c5ccccc5)C4)ccc3C2=O)C(=O)N1]

199

TABLE 1A-continued

Structure

200

TABLE 1A-continued

Structure

| 201 | 202 |
|---|---|
| TABLE 1A-continued | TABLE 1A-continued |
| Structure | Structure |
| 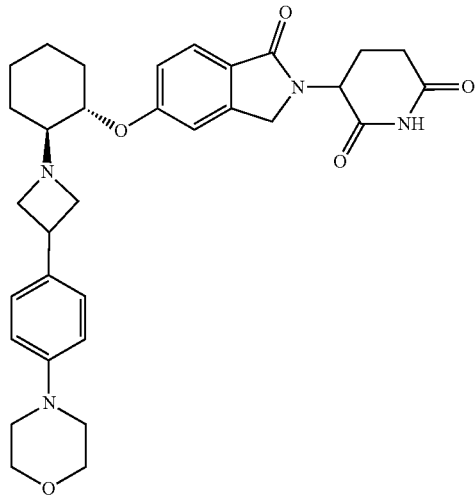 | 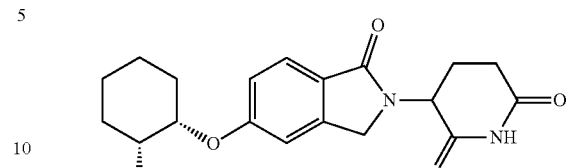 |
| 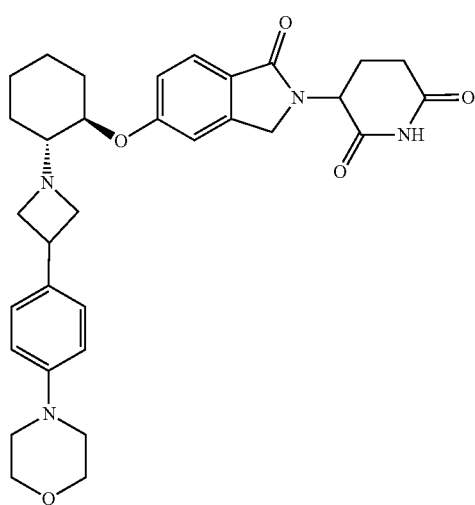 [SMILES: O=C1CCC(N2Cc3cc(O[C@@H]4CCCC[C@H]4N4CC(c5ccc(N6CCOCC6)cc5)C4)ccc3C2=O)C(=O)N1] | 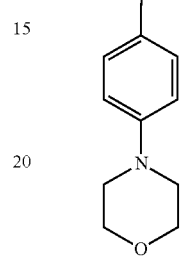 |
| 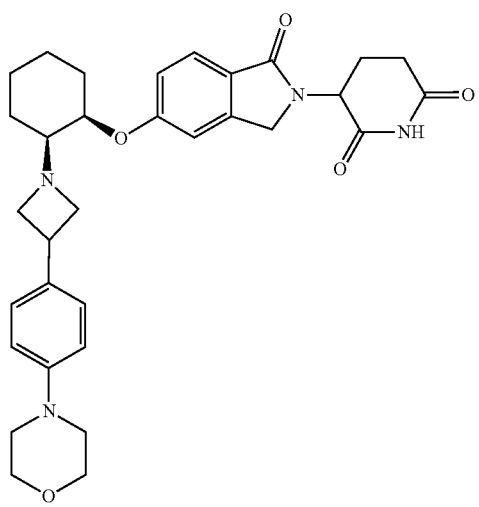 [SMILES: O=C1CCC(N2Cc3cc(O[C@@H]4CCCC[C@@H]4N4CC(c5ccc(N6CCOCC6)cc5)C4)ccc3C2=O)C(=O)N1] | 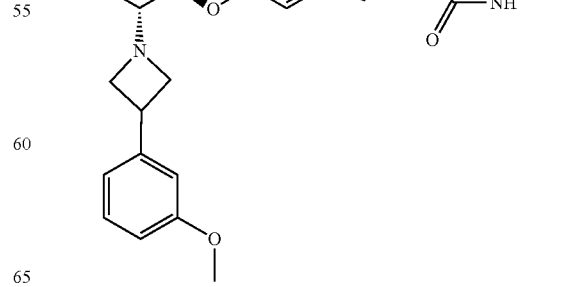 |

TABLE 1A-continued

| Structure |
|---|
| (chemical structures) |

TABLE 1A-continued
Structure
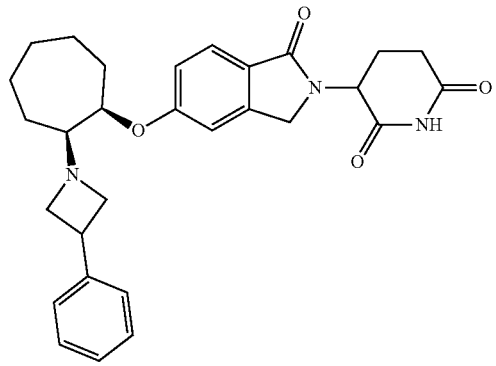 [SMILES: O=C1CCC(N2Cc3cc(O[C@@H]4CCCCC[C@@H]4N4CC(c5ccccc5)C4)ccc3C2=O)C(=O)N1]
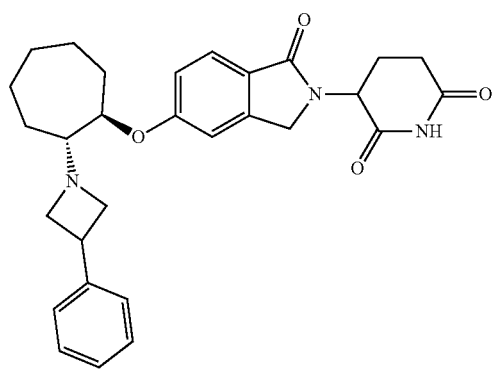 [SMILES: O=C1CCC(N2Cc3cc(O[C@@H]4CCCCC[C@H]4N4CC(c5ccccc5)C4)ccc3C2=O)C(=O)N1]
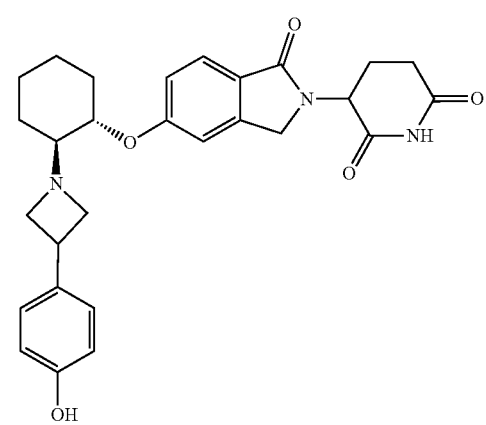 [SMILES: O=C1CCC(N2Cc3cc(O[C@H]4CCCC[C@@H]4N4CC(c5ccc(O)cc5)C4)ccc3C2=O)C(=O)N1]
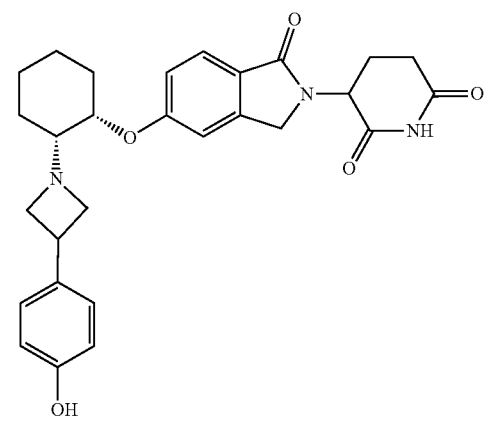 [SMILES: O=C1CCC(N2Cc3cc(O[C@H]4CCCC[C@H]4N4CC(c5ccc(O)cc5)C4)ccc3C2=O)C(=O)N1]
TABLE 1A-continued
Structure
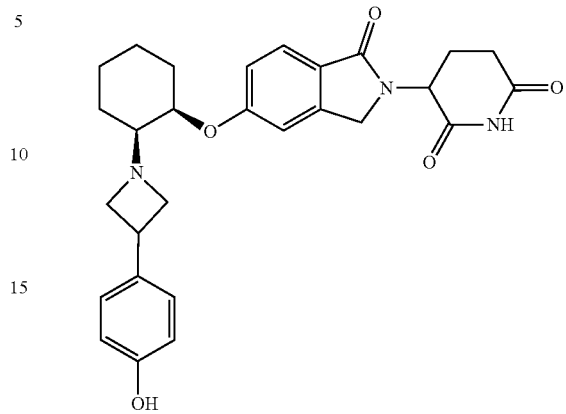
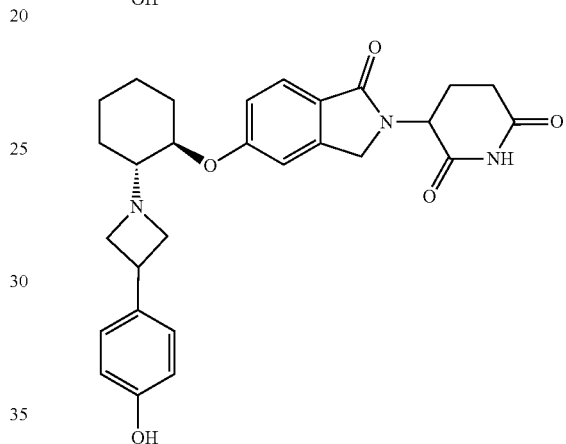
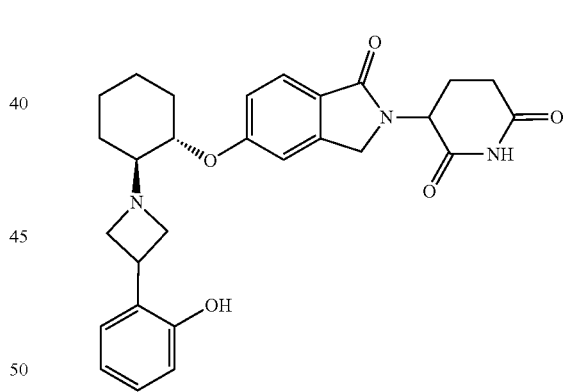
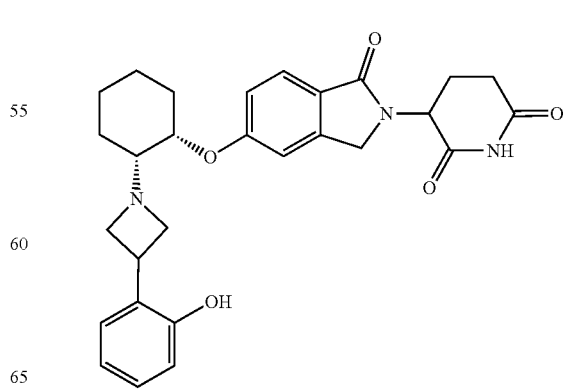

TABLE 1A-continued

| Structure |
|---|

TABLE 1A-continued

| Structure |
|---|

In some embodiments, provided herein is a compound which degrades IKZF2 selected from Table 1B, or a pharmaceutically acceptable salt, solvate, stereoisomer, and/or tautomer thereof.

TABLE 1B

| # | Structure |
|---|---|
| 1 | 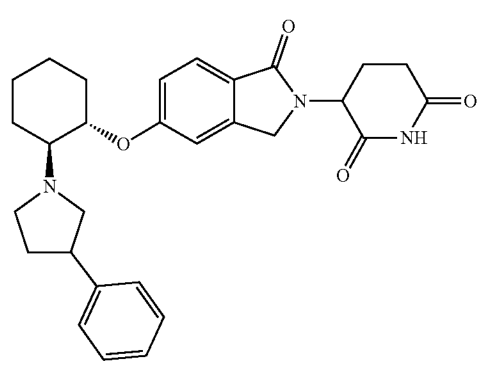 [SMILES: O=C1CCC(N2Cc3cc(O[C@H]4CCCC[C@@H]4N4CCC(c5ccccc5)C4)ccc3C2=O)C(=O)N1] |

TABLE 1B-continued

| # | Structure |
|---|---|
| 10 | 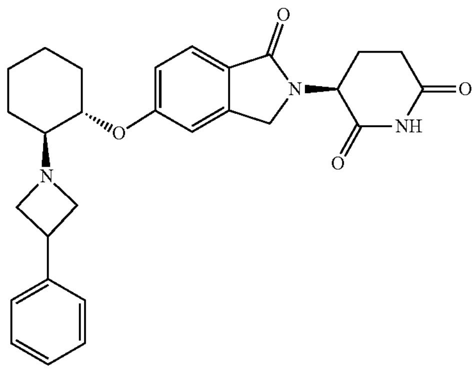 [SMILES: O=C1CC[C@H](N2Cc3cc(O[C@H]4CCCC[C@@H]4N4CC(c5ccccc5)C4)ccc3C2=O)C(=O)N1] |
| 15 | 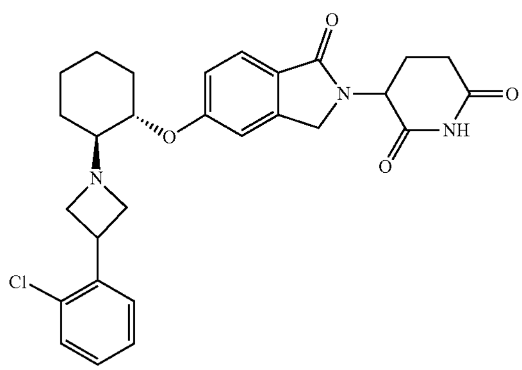 [SMILES: O=C1CCC(N2Cc3cc(O[C@H]4CCCC[C@@H]4N4CC(c5ccccc5Cl)C4)ccc3C2=O)C(=O)N1] |
| 19 | 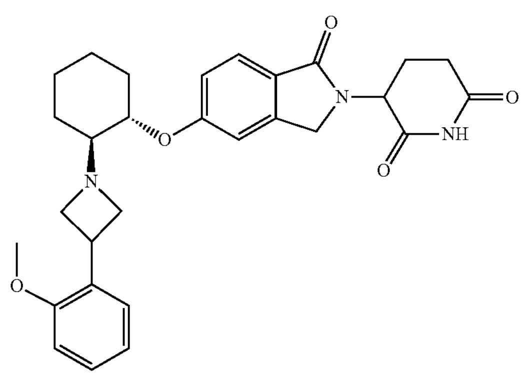 [SMILES: COc1ccccc1C1CN([C@H]2CCCC[C@@H]2Oc2ccc3c(c2)CN(C2CCC(=O)NC2=O)C3=O)C1] |
| 23 | 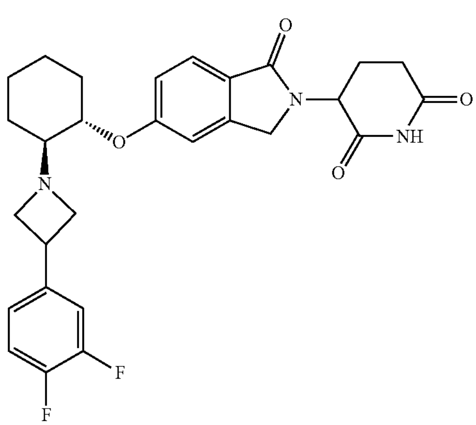 [SMILES: O=C1CCC(N2Cc3cc(O[C@H]4CCCC[C@@H]4N4CC(c5ccc(F)c(F)c5)C4)ccc3C2=O)C(=O)N1] |
| 27 | |
| 31 | |
| 35 | |
| 36 | |

TABLE 1B-continued
| # | Structure |
|---|---|
| 38 | 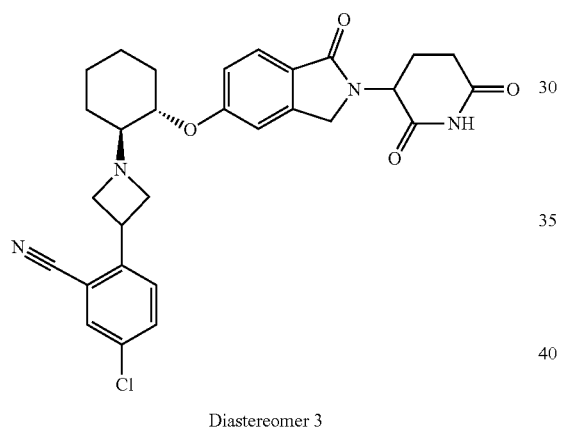
Diastereomer 2 |
| 39 | 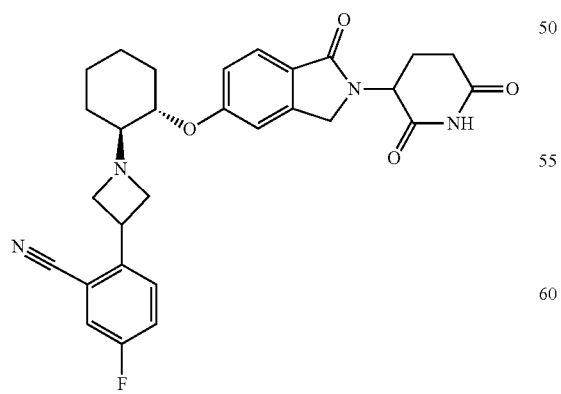
Diastereomer 3 |
| 44 | |
TABLE 1B-continued
| # | Structure |
|---|---|
| 45 | 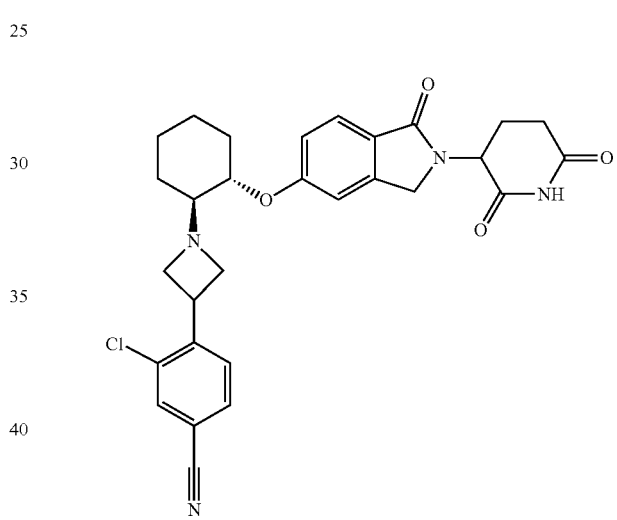
Diastereomer 3 |
| 47 | |
| 48 | 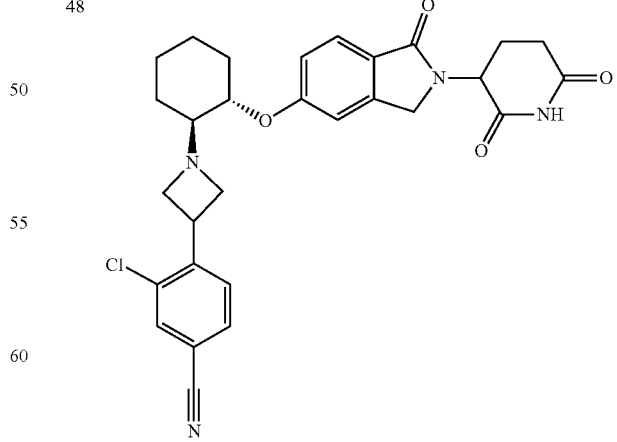
Diastereomer 2 |
(Entry 44 shown on left page: Diastereomer 2; Entry 47 shown on right page: Diastereomer 1)

TABLE 1B-continued

| # | Structure |
|---|---|
| 50 | Diastereomer 1 |
| 51 | Diastereomer 2 |
| 52 | Diastereomer 1 |
| 53 | Diastereomer 2 |
| 55 | 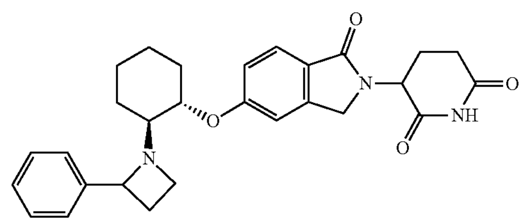 [SMILES: O=C1CCC(N2Cc3cc(O[C@H]4CCCC[C@@H]4N4CCC4c4ccccc4)ccc3C2=O)C(=O)N1] |
| 57 | 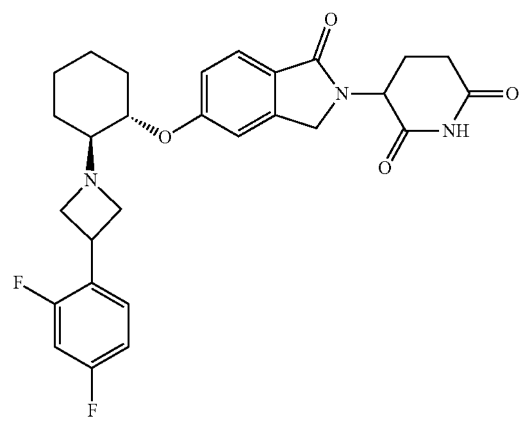 [SMILES: O=C1CCC(N2Cc3cc(O[C@H]4CCCC[C@@H]4N4CC(c5ccc(F)cc5F)C4)ccc3C2=O)C(=O)N1] |
| 58 | 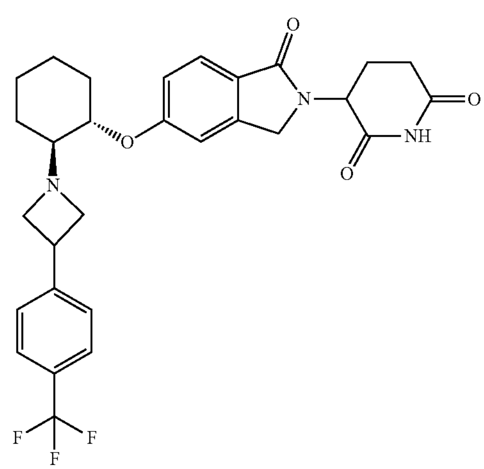 [SMILES: O=C1CCC(N2Cc3cc(O[C@H]4CCCC[C@@H]4N4CC(c5ccc(C(F)(F)F)cc5)C4)ccc3C2=O)C(=O)N1] |

TABLE 1B-continued
| # | Structure |
|---|---|
| 59 | 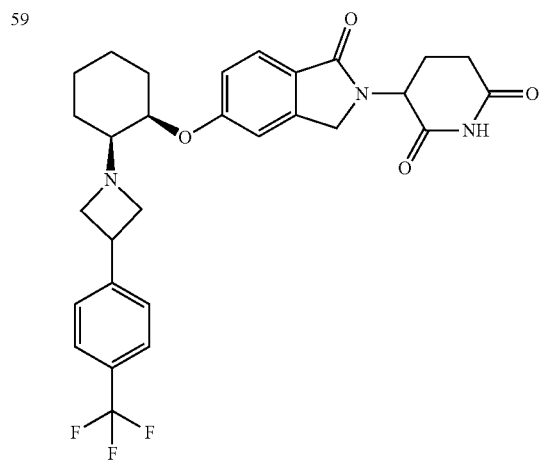 |
| 60 | 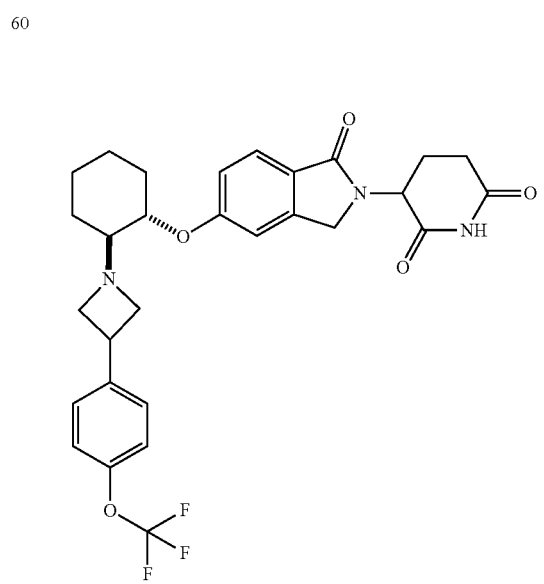 |
| 61 | 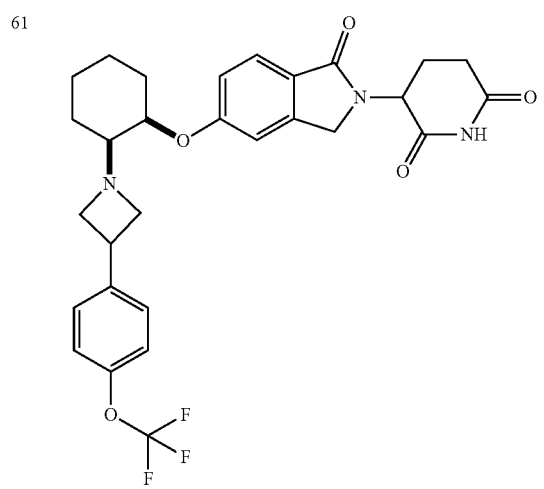 |
| 62 | 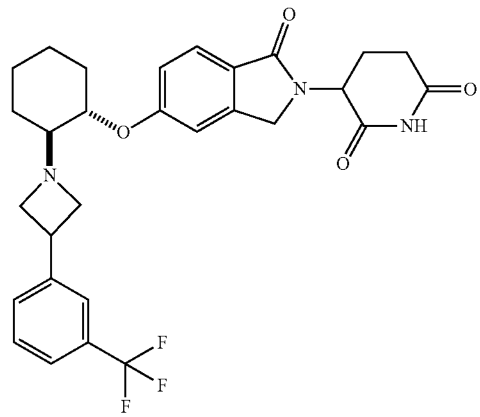 [SMILES: O=C1CCC(N2Cc3cc(O[C@H]4CCCC[C@@H]4N4CC(c5cccc(C(F)(F)F)c5)C4)ccc3C2=O)C(=O)N1] |
| 63 | 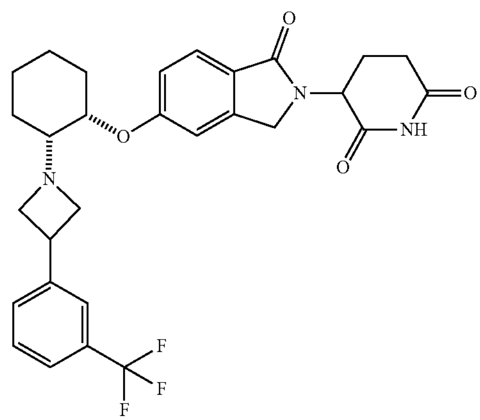 [SMILES: O=C1CCC(N2Cc3cc(O[C@H]4CCCC[C@H]4N4CC(c5cccc(C(F)(F)F)c5)C4)ccc3C2=O)C(=O)N1] |
| 64 | 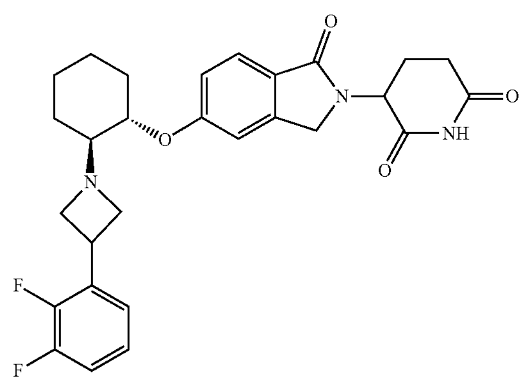 [SMILES: O=C1CCC(N2Cc3cc(O[C@H]4CCCC[C@@H]4N4CC(c5cccc(F)c5F)C4)ccc3C2=O)C(=O)N1] |
| 65 | 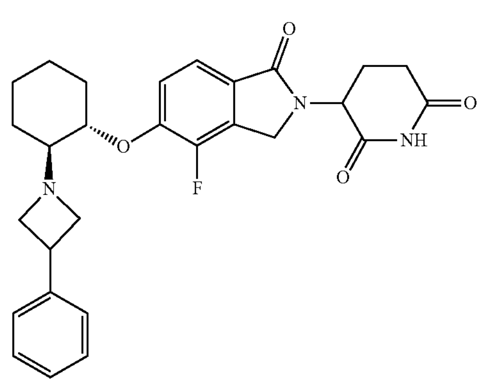 |
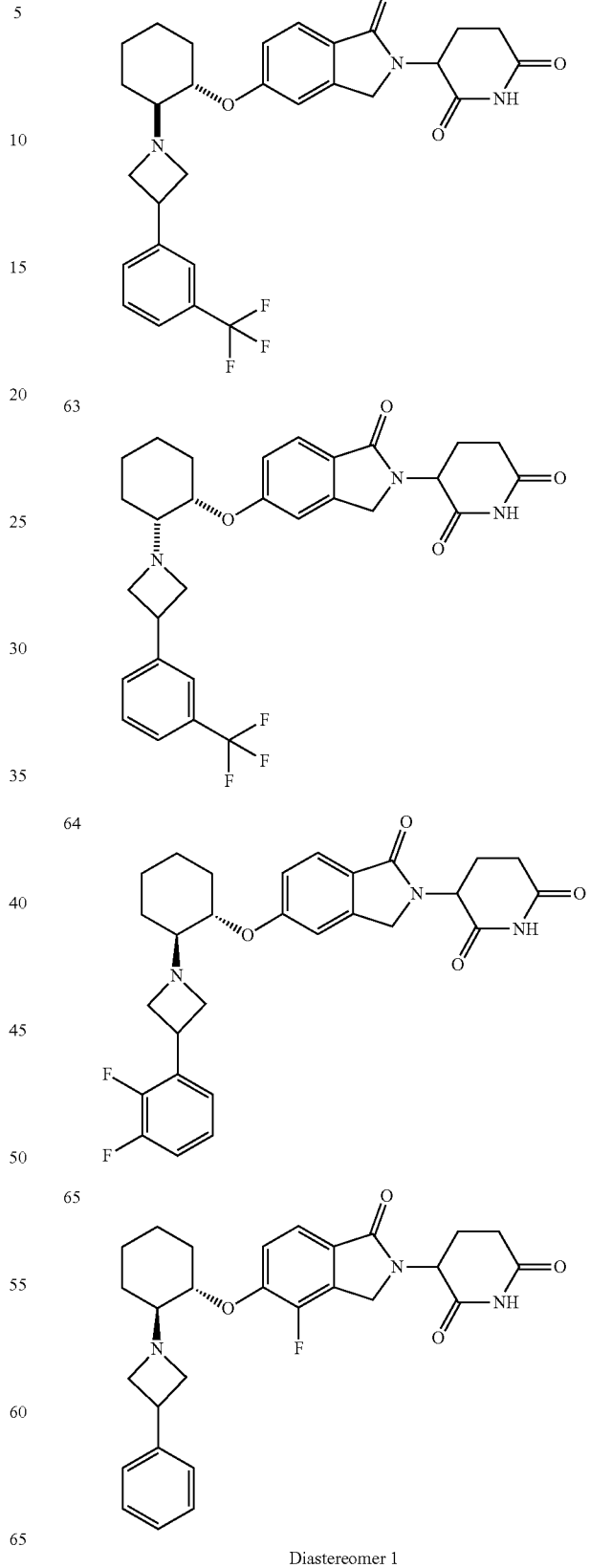
Diastereomer 1

TABLE 1B-continued
| # | Structure |
|---|-----------|
| 66 | 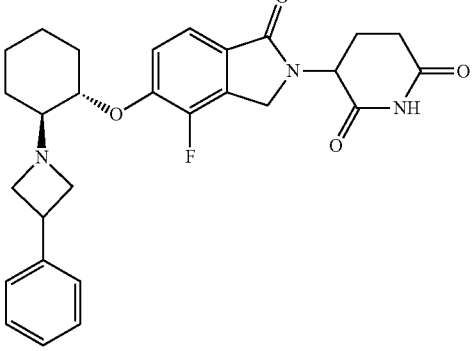 |
| 67 | Diastereomer 2<br>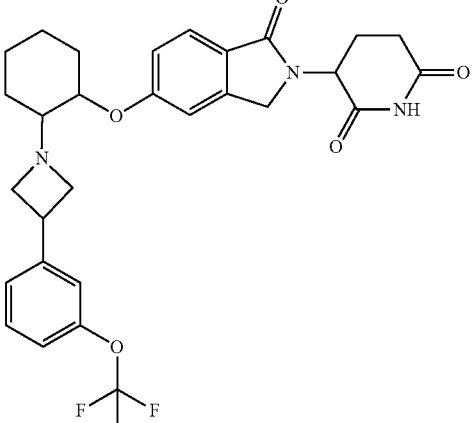 |
| 68 | 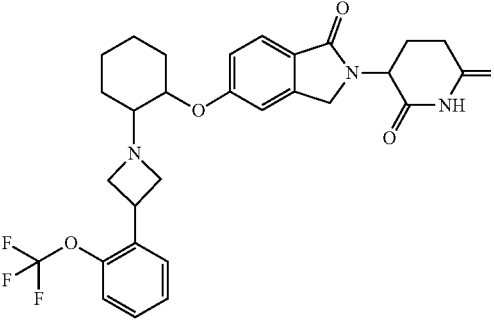 |
| 72 | 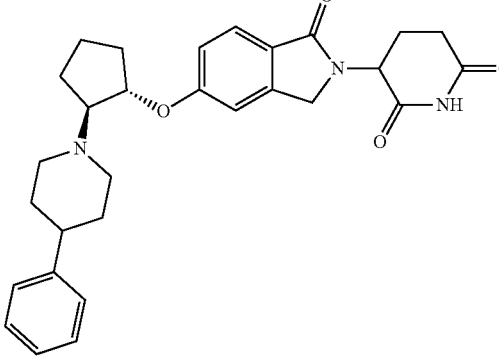 |
| 73 | 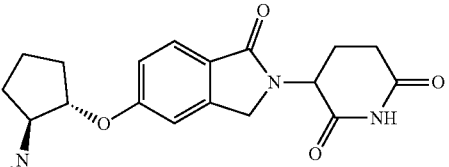 |
| 74 | 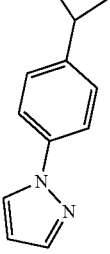 |
| 75 | 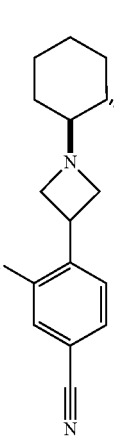 |

TABLE 1B-continued
| # | Structure |
|---|---|
| 76 | 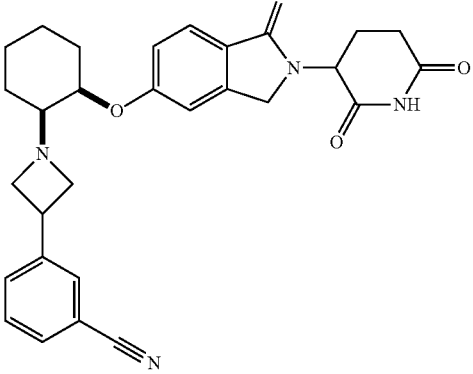 |
| 80 | 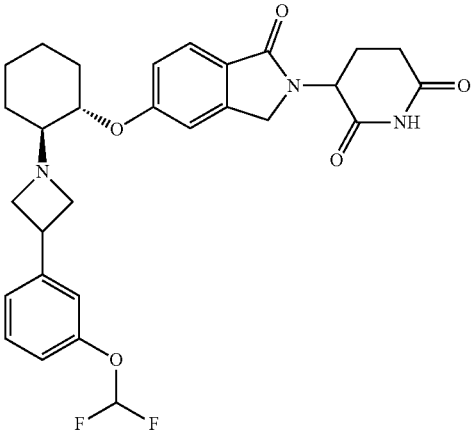 [SMILES: O=C1CCC(N2Cc3cc(O[C@H]4CCCC[C@@H]4N4CC(c5cccc(OC(F)F)c5)C4)ccc3C2=O)C(=O)N1] |
| 81 | 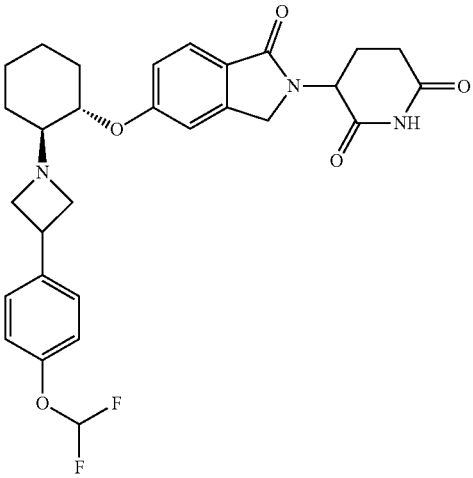 [SMILES: O=C1CCC(N2Cc3cc(O[C@H]4CCCC[C@@H]4N4CC(c5ccc(OC(F)F)cc5)C4)ccc3C2=O)C(=O)N1] |
| 83 | 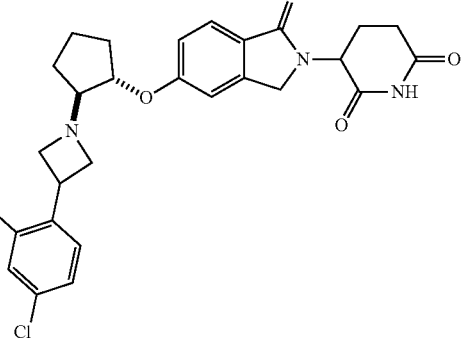 |
| 88 | 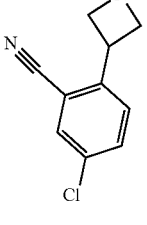 |
| 96 | 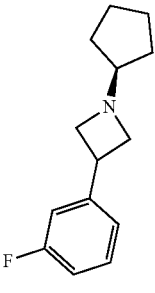 |
| 99 | 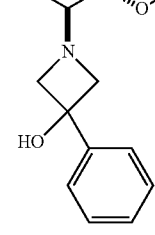 |

TABLE 1B-continued
| # | Structure |
|---|---|
| 101 | 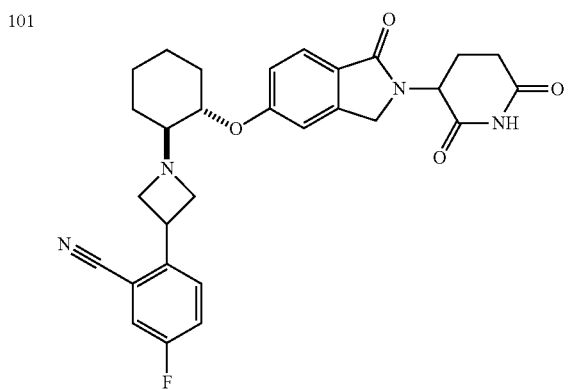 |
| 103 | 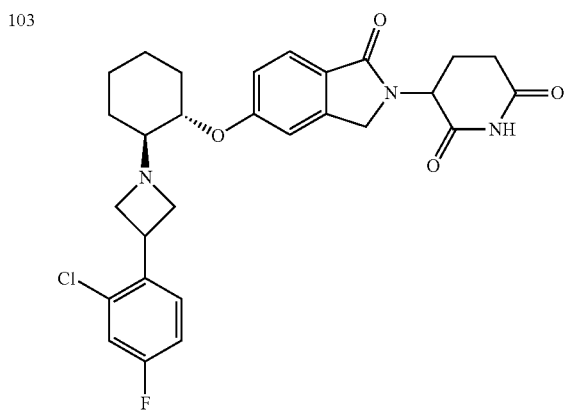 |
| 104 | 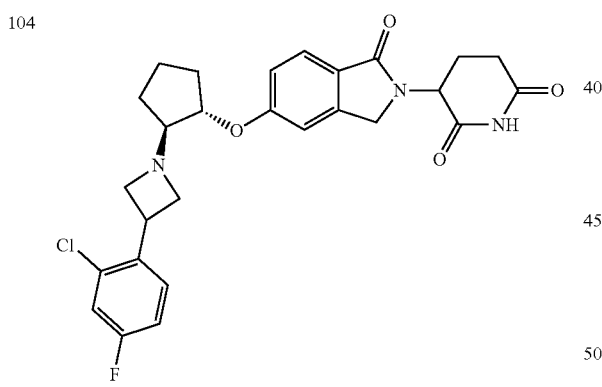 |
| 108 | 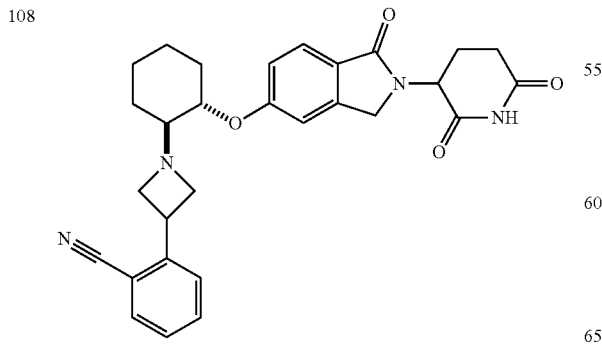 |
TABLE 1B-continued
| # | Structure |
|---|---|
| 110 | 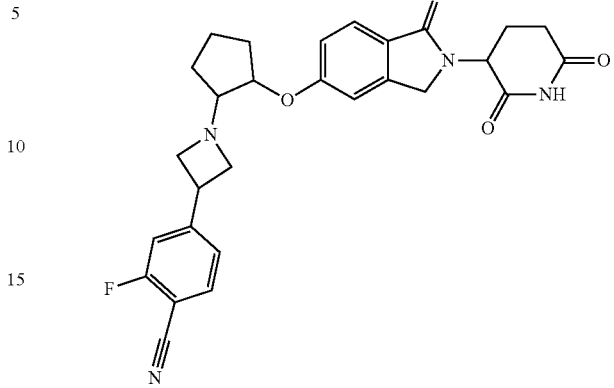 |
| 111 | 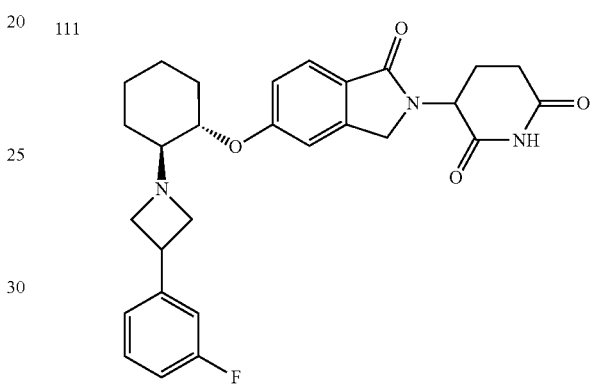 |
| 112 | 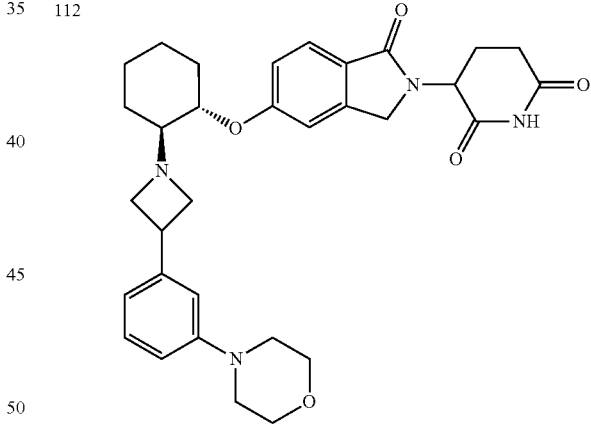 |
| 113 | 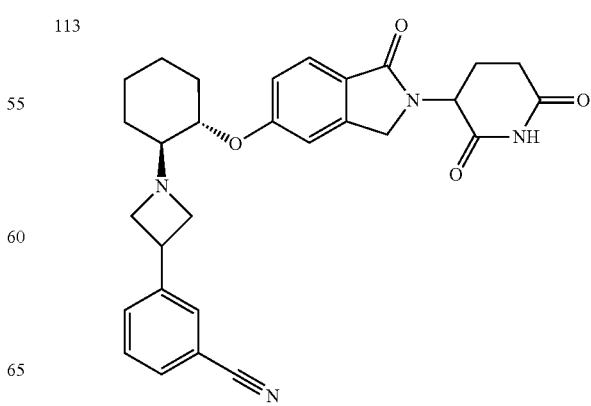 |

TABLE 1B-continued
| # | Structure |
|---|---|
| 115 | 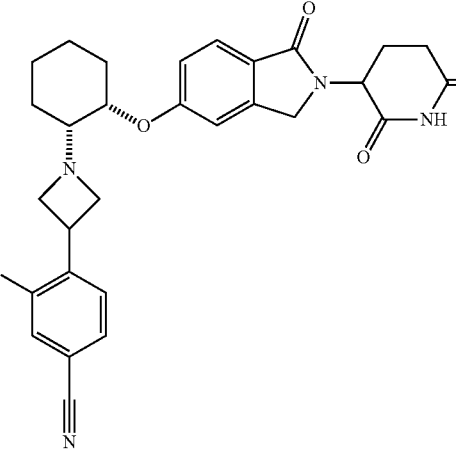 |
| 119 | 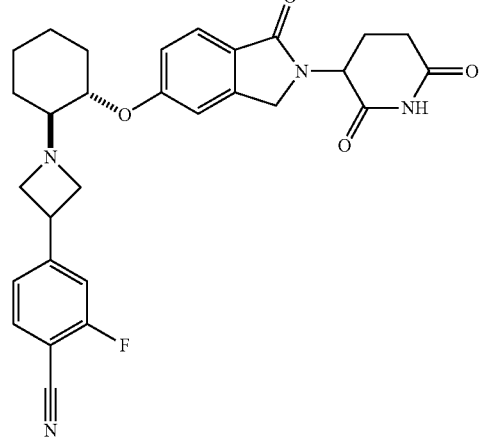 |
| 120 | 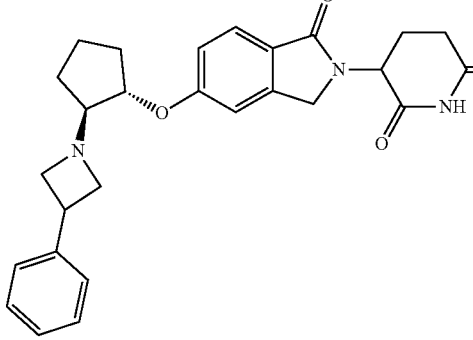 |
| 121 | 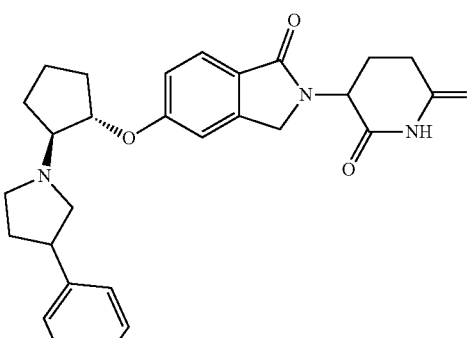 |
| 123 | 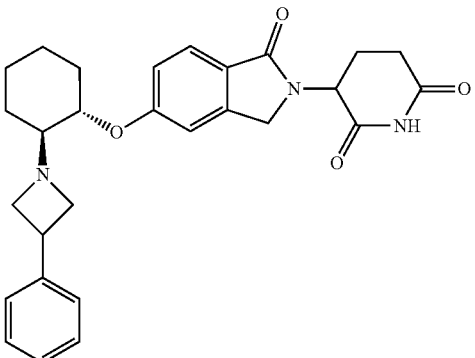 |
| 124 | 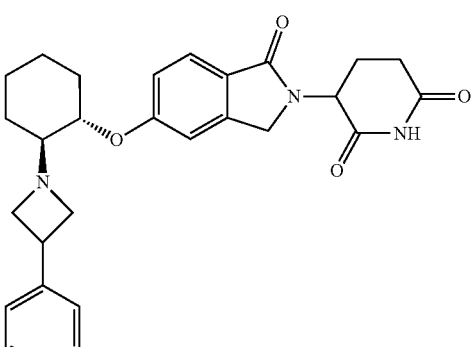 |

TABLE 1B-continued

| # | Structure |
|---|---|
| 125 | 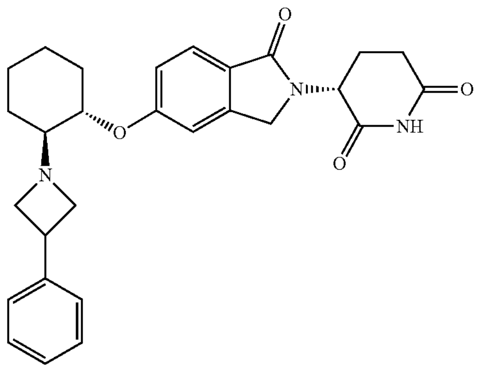 [SMILES: O=C1CC[C@@H](N2Cc3cc(O[C@H]4CCCC[C@@H]4N4CC(c5ccccc5)C4)ccc3C2=O)C(=O)N1] |
| 126 | 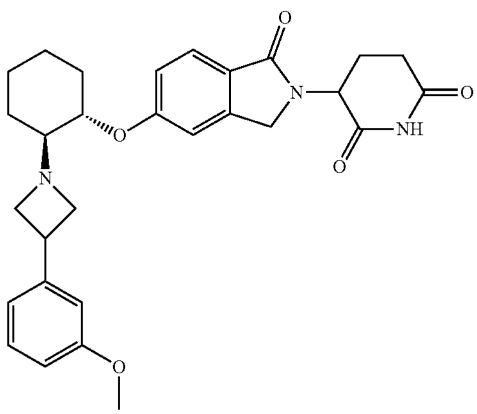 [SMILES: COc1cccc(C2CN([C@H]3CCCC[C@@H]3Oc3ccc4c(c3)CN(C3CCC(=O)NC3=O)C4=O)C2)c1] |
| 127 | 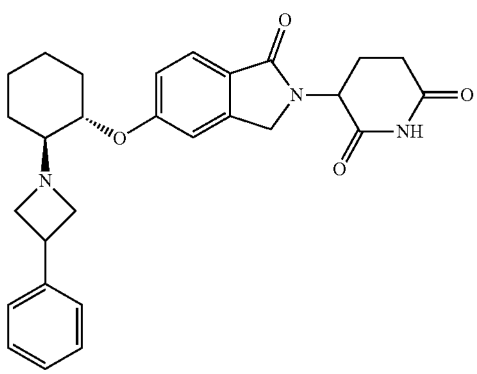 |
| 129 | 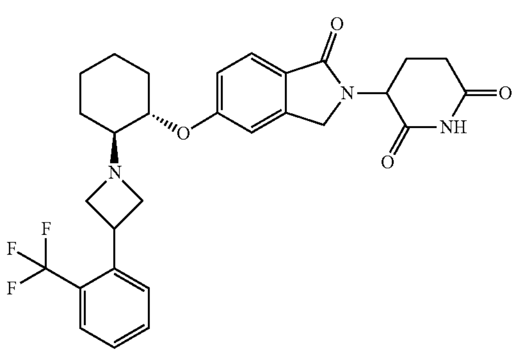 [SMILES: O=C1CCC(N2Cc3cc(O[C@H]4CCCC[C@@H]4N4CC(c5ccccc5C(F)(F)F)C4)ccc3C2=O)C(=O)N1] |
| 130 | |
| 131 | |
| 132 | |

TABLE 1B-continued

| # | Structure |
|---|---|
| 133 | *[structure image]* |
| 134 | *[structure image]* |

General Synthetic Methods

The compounds of formula I, II, III, IV, V, and VI described herein can be prepared from readily available starting materials using the following general methods and procedures. It will be appreciated that where typical process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

Additionally, as will be apparent to those skilled in the art, intermediate and final compounds obtained as enantiomeric mixtures may be separated into their separate enantiomers by liquid chromatography using a chiral stationary phase to give chiral selectivity. Suitable chiral stationary phases as well as suitable conditions for chiral separation are well known in the art. For example, numerous methods are described in F. Toda, *Enantiomeric Separation: Fundamentals and Practical Methods*, First Edition, Springer, Dordrecht, 2004, and references cited therein.

The starting materials for the following reactions are generally known compounds or can be prepared by known procedures or obvious modifications thereof. For example, many of the starting materials are available from commercial suppliers such as Sigma Aldrich (St. Louis, Missouri, USA), Bachem (Torrance, California, USA), Emka-Chemce (St. Louis, Missouri, USA). Others may be prepared by procedures, or obvious modifications thereof, described in standard reference texts such as *Fieser and Fieser's Reagents for Organic Synthesis*, Volumes 1-15 (John Wiley, and Sons, 2016), *Rodd's Chemistry of Carbon Compounds*, Volumes 1-5, and *Supplementals* (Elsevier Science Publishers, 2001), *Organic Reactions*, Volumes 1-40 (John Wiley, and Sons, 2019), *March's Advanced Organic Chemistry*, (John Wiley, and Sons, $8^{th}$ Edition, 2019), and *Larock's Comprehensive Organic Transformations* (VCH Publishers Inc., 1989).

Synthesis of Representative Compounds

The general synthesis of the compounds described herein is set forth in the reaction schemes below. In the Schemes below, substituents $R^1$, $R^2$, $R^3$, $R^4$, $R^{11}$, X, Y, Z, $Z^1$, m, n, p, q, r, s, and t are as defined throughout the specification. Q is a leaving group (including, but not limited to, Br, Cl, I, triflate, and the like).

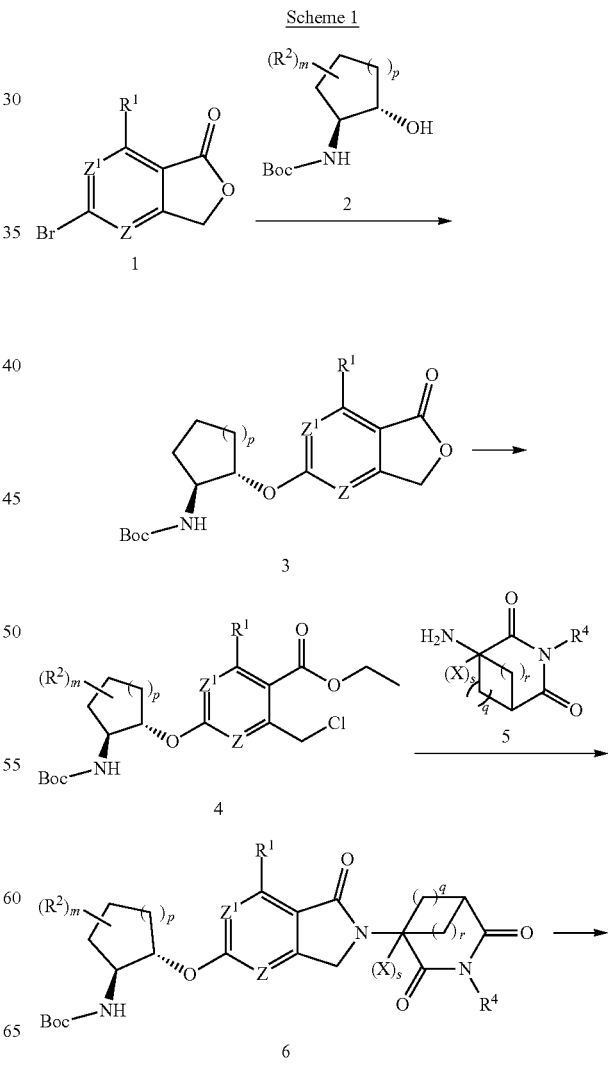

Scheme 1

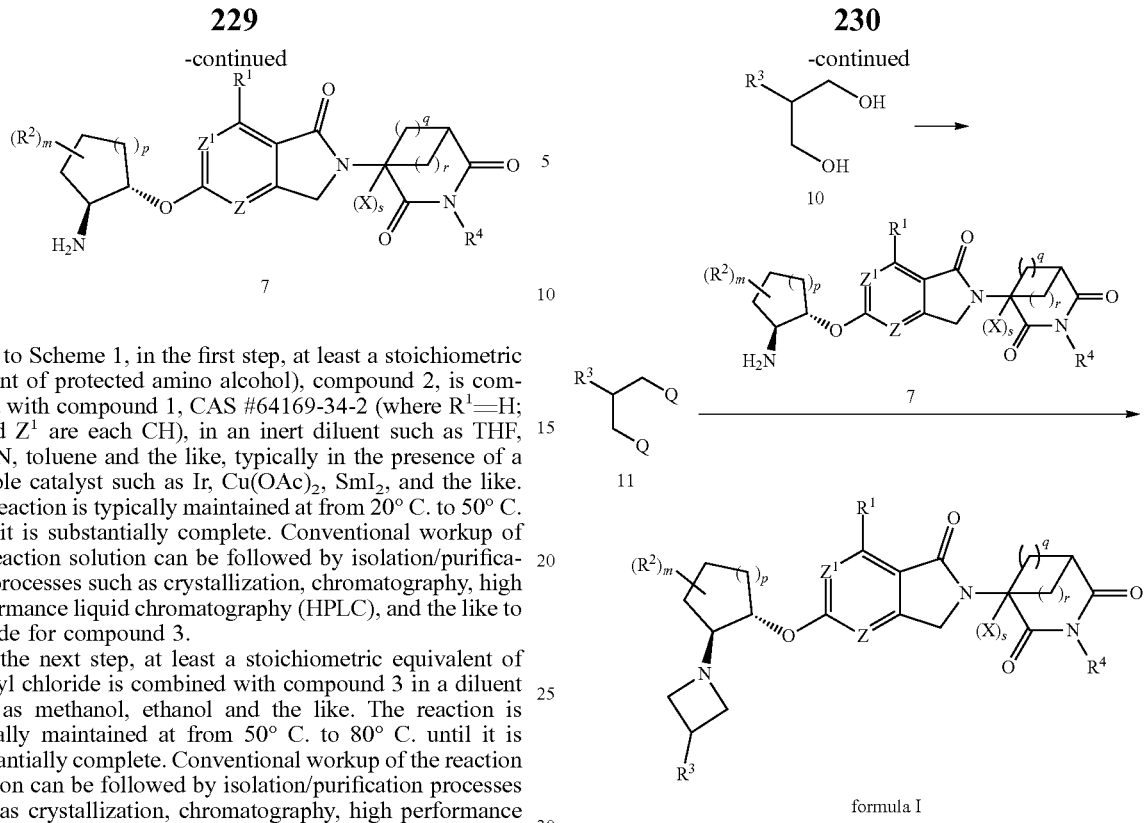

As to Scheme 1, in the first step, at least a stoichiometric amount of protected amino alcohol), compound 2, is combined with compound 1, CAS #64169-34-2 (where $R^1$=H; Z and $Z^1$ are each CH), in an inert diluent such as THF, MeCN, toluene and the like, typically in the presence of a suitable catalyst such as Ir, $Cu(OAc)_2$, $SmI_2$, and the like. The reaction is typically maintained at from 20° C. to 50° C. until it is substantially complete. Conventional workup of the reaction solution can be followed by isolation/purification processes such as crystallization, chromatography, high performance liquid chromatography (HPLC), and the like to provide for compound 3.

In the next step, at least a stoichiometric equivalent of thionyl chloride is combined with compound 3 in a diluent such as methanol, ethanol and the like. The reaction is typically maintained at from 50° C. to 80° C. until it is substantially complete. Conventional workup of the reaction solution can be followed by isolation/purification processes such as crystallization, chromatography, high performance liquid chromatography (HPLC), and the like to provide for compound 6.

In the next step, at least a stoichiometric amount of 3-aminopiperidine-2,6-dione·hydrochloride, CAS #24666-56-6 (where $R^4$=H; X=H; q=1; r=0; s=1), compound 5, is combined with compound 4 in an inert diluent such as dichloromethane, tetrachloromethane and the like in the presence of a suitable base such as triethylamine, diisopropylethylamine, pyridine and the like. The reaction is typically maintained at from 0° C. to 30° C. until it is substantially complete. Conventional workup of the reaction solution can be followed by isolation/purification processes such as crystallization, chromatography, high performance liquid chromatography (HPLC), and the like to provide for compound 6.

In the final step, the t-butoxycarbonyl (BOC) protecting group is removed by conventional conditions. The BOC group is illustrative only and other conventional amino blocking groups such as benzyl, 9-fluorenylmethoxycarbonyl (Fmoc), benzyloxycarbonyl (Cbz), p-nitrobenzyloxycarbonyl and the like could be used. Upon reaction completion, conventional workup of the reaction solution can be followed by isolation/purification processes such as crystallization, chromatography, high performance liquid chromatography (HPLC), and the like to provide for compound 7 which serves as an intermediate for the synthesis of compounds of formula I.

Scheme 2

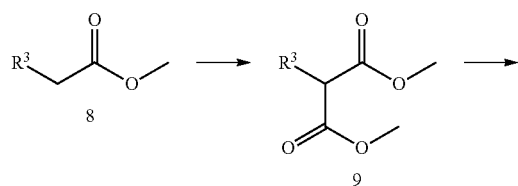

As to Scheme 2, the first step is a conventional acetylation reaction wherein at least a stoichiometric equivalent of an acetylating reagent is combined with an aryl acetate, compound 8, in an inert diluent such as THF, MeCN and the like in the presence of a suitable base such as sodium hydride, LDA, n-BuLi and the like. The reaction is typically maintained at from 0° C. to 70° C. until it is substantially complete. Conventional workup of the reaction solution can be followed by isolation/purification processes such as crystallization, chromatography, high performance liquid chromatography (HPLC), and the like to provide for compound 9.

In the next step, at least a stoichiometric amount of compound 9, in an inert diluent such as THF, MeCN, toluene and the like in the presence of a suitable reducing reagent such as lithium aluminum hydride, borane, and the like. The reaction is typically maintained at from 0° C. to 30° C. until it is substantially complete. Conventional workup of the reaction solution can be followed by isolation/purification processes such as crystallization, chromatography, high performance liquid chromatography (HPLC), and the like to provide for compound 10.

In the next step, the diol is converted to a suitable leaving group, at least a stoichiometric amount of tosyl chloride is added to compound 10, in an inert diluent such as THF, MeCN, toluene and the like in the presence of a suitable base such as triethylamine, diisopropylethylamine, pyridine and the like. The reaction is typically maintained at from 0° C. to 30° C. until it is substantially complete. The Ts group is illustrative only and other conventional leaving groups such as iodo, bromo, triflate, mesylate and the like could be used. Conventional workup of the reaction solution can be followed by isolation/purification processes such as crystallization, chromatography, high performance liquid chromatography (HPLC), and the like to provide for compound 11.

In the final step, at least a stoichiometric amount of compound 11 is added to compound 7, in an inert diluent such as THF, MeCN, toluene and the like in the presence of a suitable base such as triethylamine, diisopropylethylamine, pyridine and the like. The reaction is typically maintained at from 80° C. to 120° C. until it is substantially complete. Conventional workup of the reaction solution can be followed by isolation/purification processes such as crystallization, chromatography, high performance liquid chromatography (HPLC), and the like to provide compounds of formula I.

Scheme 3

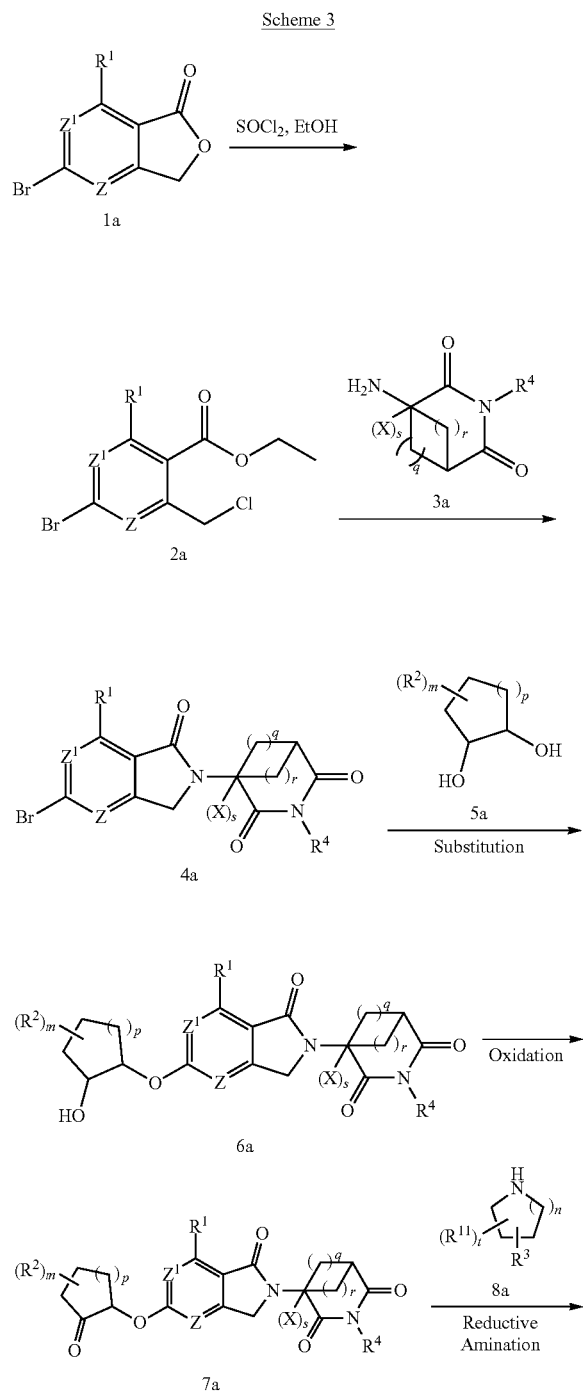

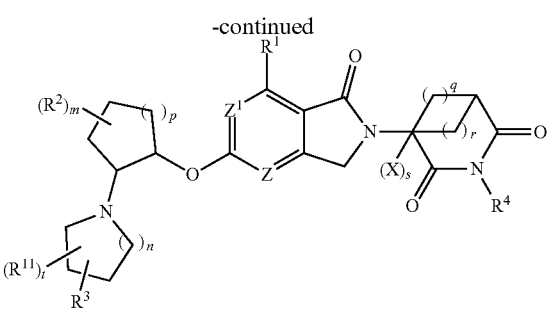

formula I

In some embodiments, compounds of formula I and sub-formulae thereof are prepared as shown in Scheme 3. In Scheme 3, the first step is a conventional esterification and chlorination reaction wherein at least a stoichiometric equivalent of thionyl chloride is combined with 5-bromoisobenzo-1(3H)-one, CAS #64169-34-2 (where $R^1$=H; Z and $Z^1$ are each CH), compound 1a in a diluent such as methanol, ethanol and the like. The reaction is typically maintained at from 50° C. to 80° C. until it is substantially complete. Conventional workup of the reaction solution can be followed by isolation/purification processes such as crystallization, chromatography, high performance liquid chromatography (HPLC), and the like to provide for compound 2a.

In the next step, at least a stoichiometric amount of 3-aminopiperidine-2,6-dione·hydrochloride, CAS #24666-56-6 (where $R^4$=H; X=H; q=1; r=0; s=1), compound 3, is combined with compound 2 in an inert diluent such as THF, DMF, MeCN, toluene and the like, typically in the presence of a suitable base such as triethylamine, diisopropylamine, DIEA, pyridine and the like. The reaction is typically maintained at from 80° C. to 100° C. until it is substantially complete. Conventional workup of the reaction solution can be followed by isolation/purification processes such as crystallization, chromatography, high performance liquid chromatography (HPLC), and the like to provide for compound 4.

In the next step, at least a stoichiometric amount of compound 5a, is combined with compound 4a in an inert diluent such as THF, MeCN, toluene and the like, typically in the presence of a suitable catalyst such as Ir, Cu(OAc)$_2$, SmI$_2$, and the like. The reaction is typically maintained at from 60° C. to 80° C. until it is substantially complete. Conventional workup of the reaction solution can be followed by isolation/purification processes such as crystallization, chromatography, high performance liquid chromatography (HPLC), and the like to provide for compound 6a.

In the next step, at least a stoichiometric amount of an oxidizing reagent is combined with compound 6a under conventional oxidation reaction conditions well known in the art including the use of Jones Reagent, mCPBA, Dess-Martin periodinane. The reaction is typically conducted in an inert solvent such as MeCN, THF, methylene chloride, toluene, and the like. The reaction is typically conducted at from about 0° C. to about 30° C. for a period of time sufficient for substantial completion of the reaction as evidenced by e.g., thin layer chromatography. Upon reaction completion, conventional workup of the reaction solution can be followed by isolation/purification processes such as crystallization, chromatography, high performance liquid chromatography (HPLC), and the like to provide for compound 7a.

In the final step, at least a stoichiometric amount of a suitable amine, compound 8a is combined with compound 7a under conventional reductive amination reaction conditions well known in the art including the use of NaCNBH$_3$, NaBH(OAc)$_3$, NaBH$_4$ and the like. The reaction is typically conducted in an inert solvent such as MeCN, MeOH, THF, and the like. The reaction is typically conducted at from about 0° C. to about 30° C. for a period of time sufficient for substantial completion of the reaction as evidenced by e.g., thin layer chromatography. Upon reaction completion, conventional workup of the reaction solution can be followed by isolation/purification processes such as crystallization, chromatography, high performance liquid chromatography (HPLC), and the like are optionally used to provide a compound of formula I.

be followed by isolation/purification processes such as crystallization, chromatography, high performance liquid chromatography (HPLC), and the like.

The intermediate boronic acid pinacol ester is added to an aqueous diluent such as acetone:H$_2$O, THF:H$_2$O, acetonitrile:H$_2$O, and the like, in the presence of a sodium perborate tetrahydrate, dihydrogen peroxide, and the like. The reaction is typically maintained at from 20° C. to 40° C. until it is substantially complete. Conventional workup of the reaction solution can be followed by isolation/purification processes such as crystallization, chromatography, high performance liquid chromatography (HPLC), and the like, to provide for compound 13, which serves as an intermediate for the synthesis of compounds of formula I.

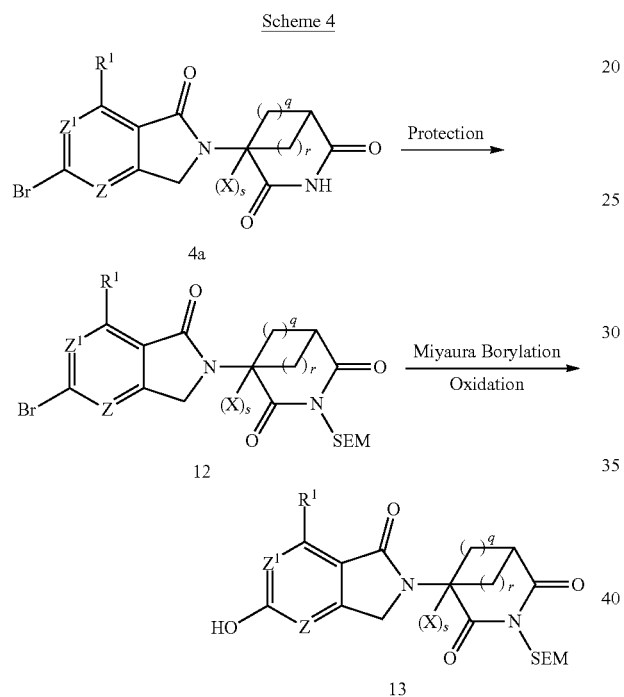

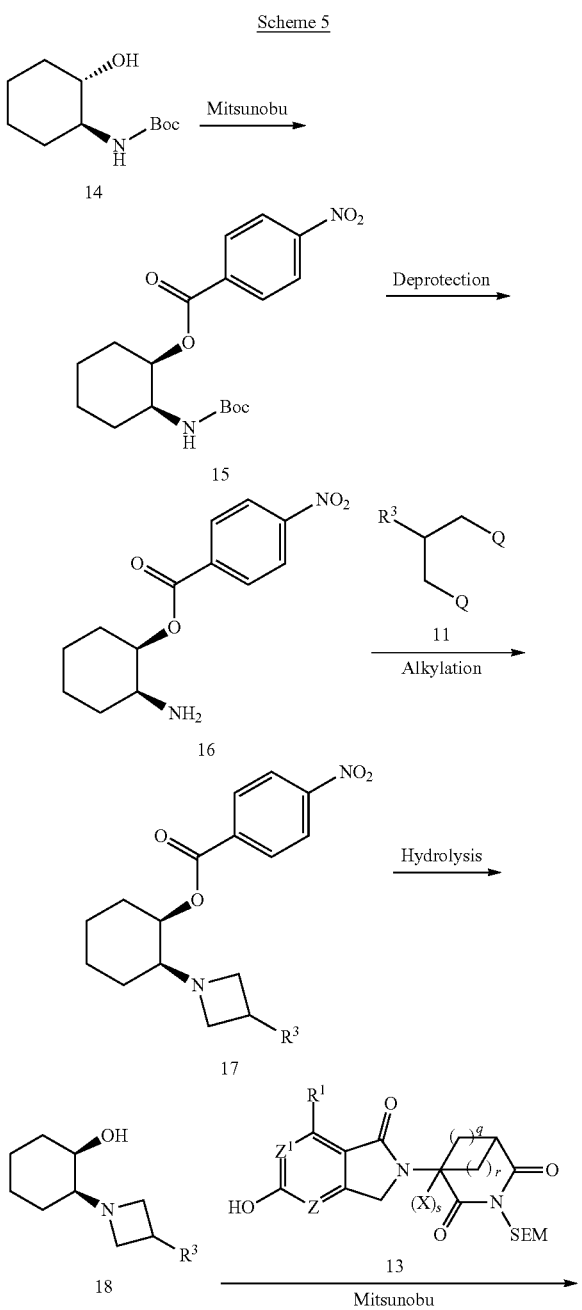

As to Scheme 4, the first step is a conventional protection reaction wherein at least a stoichiometric equivalent of 2-(trimethylsilyl)ethoxymethyl chloride is combined with compound 4a, CAS #1010100-26-1 (where R$^1$ and X=H; Z and Z$^1$ are each CH, q and s are each 1 and r is 0), in a diluent such as DMF, THF, 1,4-dioxane and the like, typically in the presence of a suitable base, such as triethylamine, DBU, DIEA, pyridine, and the like. The reaction is typically maintained at from 0° C. to 30° C. until it is substantially complete. Conventional workup of the reaction solution can be followed by isolation/purification processes such as crystallization, chromatography, high performance liquid chromatography (HPLC), and the like to provide for compound 12.

In the next step, a Miyuaura borylation reaction (*J. Org. Chem.*, 1995, 60, 7508), at least a stoichiometric amount of compound 12 and bis(pinacolato)diboron are combined, in an inert diluent such as DMSO, 1,4-dioxane, and the like, in the presence of a suitable catalyst such as PdCl$_2$(dppf)$_2$, PdCl$_2$(PPh$_3$)$_2$, and the like. The reaction is typically maintained at from 80° C. to 110° C. until it is substantially complete. Conventional workup of the reaction solution can -continued

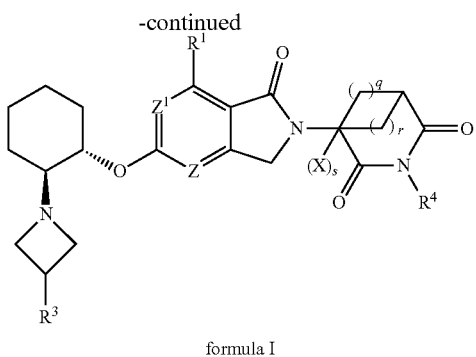

formula I

In some embodiments, compounds of formula I and sub-formulae thereof are prepared as shown in Scheme 5. In Scheme 5, the first step is a conventional Mitsunobu reaction, wherein at least a stoichiometric equivalent of 4-nitrobenzoic acid is combined with tert-butyl ((1S,2S)-2-hydroxycyclohexyl)carbamate, compound 14, CAS #145166-06-9, under conventional reaction conditions [Hughes, D. L. (2004). The Mitsunobu Reaction, Organic Reactions, (Ed.).] well known in the art, including the use diethylazodicarboxylate and triphenylphosphine. The reaction is typically conducted in an inert solvent such as acetonitrile, THF, toluene, and the like. The reaction is typically maintained at from 0° C. to 30° C. until it is substantially complete. Conventional workup of the reaction solution can be followed by isolation/purification processes such as crystallization, chromatography, high performance liquid chromatography (HPLC), and the like to provide for compound 15.

In the next step, the t-butoxycarbonyl (BOC) protecting group is removed by conventional conditions. The BOC group is illustrative only, and other conventional amino blocking groups, such as benzyl, 9-fluorenylmethoxycarbonyl (Fmoc), benzyloxycarbonyl (Cbz), p-nitrobenzyloxycarbonyl, and the like could be used. Upon reaction completion, conventional workup of the reaction solution can be followed by isolation/purification processes such as crystallization, chromatography, high performance liquid chromatography (HPLC), and the like to provide for compound 16.

In the next step, at least a stoichiometric amount of compound 11 is added to compound 16, in an inert diluent such as THF, MeCN, toluene, and the like, in the presence of a suitable base such as triethylamine, diisopropylethylamine, pyridine, and the like. The reaction is typically maintained at from 80° C. to 120° C. until it is substantially complete. Conventional workup of the reaction solution can be followed by isolation/purification processes such as crystallization, chromatography, high performance liquid chromatography (HPLC), and the like to provide for compound 17.

In the next step, the 4-nitrophenyl ester protecting group is removed under basic hydrolytic conditions to provide for compound 18. The 4-nitrophenyl ester group is illustrative only, and other conventional carboxylic acid protecting groups such as benzyl, ethyl, tert-butyl, and the like can be used. Upon reaction completion, conventional workup of the reaction solution can be followed by isolation/purification processes such as crystallization, chromatography, high performance liquid chromatography (HPLC), and the like to provide for compound 18.

In the final step, at least a stoichiometric amount of compound 18 is combined with compound 13 under conventional Mitsunobu reaction conditions well known in the art [Hughes, D. L. (2004). The Mitsunobu Reaction, Organic Reactions, (Ed.).], including the use diethylazodicarboxylate and triphenylphosphine. The reaction is typically conducted in an inert solvent such as acetonitrile, THF, toluene, and the like. The reaction is typically maintained at from 0° C. to 30° C. until it is substantially complete. Upon reaction completion, conventional workup of the reaction solution can be followed by isolation/purification processes such as crystallization, chromatography, high performance liquid chromatography (HPLC), and the like to provide a compound of formula I.

Other starting materials used herein are either well known in the art, commercially available, or can be prepared by conventional synthetic methods.

Methods

In one embodiment, the compounds of formula I, II, III, IV, V, and/or VI, and compositions described herein are useful in methods for modulating cereblon activity. The methods comprise administering to a subject an effective amount of a compound, or a pharmaceutically acceptable salt, solvate, stereoisomer, and/or tautomer thereof or a pharmaceutical composition comprising said compound, or a pharmaceutically acceptable salt, solvate, stereoisomer, and/or tautomer thereof as described herein.

In one embodiment, the compounds of formula I, II, III, IV, V and/or VI, and compositions described herein are useful in methods for treating a IKZF2 dependent disease or disorder or a disease or disorder that is mediated, at least in part by, IKZF2. The methods comprise administering to a subject suffering from a IKZF2 dependent disease or disorder an effective amount of a compound, or a pharmaceutically acceptable salt, solvate, stereoisomer, and/or tautomer thereof or a pharmaceutical composition comprising said compound, or a pharmaceutically acceptable salt, solvate, stereoisomer, and/or tautomer thereof as described herein.

In one embodiment, the compounds of formula I, II, III, IV, V, and/or VI, and compositions described herein selectively modulate IKZF (e.g. over translation termination factor GSPT1). In some embodiments, the compounds of formula I, II, III, IV, V, and/or VI, and compositions described herein selectively modulate IKZF2 over GSPT1.

In one embodiment, there is provided a compound, or a pharmaceutically acceptable salt, solvate, stereoisomer, and/or tautomer thereof or a pharmaceutical composition comprising said compound, or a pharmaceutically acceptable salt, solvate, stereoisomer, and/or tautomer thereof as described herein for use in treating an IKZF2 dependent disease or disorder.

In one embodiment, the method relates a compound, or a pharmaceutically acceptable salt, solvate, stereoisomer, and/ or tautomer thereof or a pharmaceutical composition comprising said compound, or a pharmaceutically acceptable salt, solvate, stereoisomer, and/or tautomer thereof as described herein for use in manufacture of a medicament for reducing IKZF2 protein levels where reduction of such protein levels treats or ameliorates the diseases or disorder.

In one embodiment, the methods described herein comprise use of a prodrug of the compounds described herein.

In one embodiment, the method relates to a compound, or a pharmaceutically acceptable salt, solvate, stereoisomer, and/or tautomer thereof or a pharmaceutical composition comprising said compound, or a pharmaceutically acceptable salt, solvate, stereoisomer, and/or tautomer thereof as described herein for use as described herein, wherein the concentration of compound required for cereblon target engagement dose response IC$_{50}$ is in the range of about 0.003 μM to about 0.06 μM. The cereblon target engagement dose response IC$_{50}$ is measured by the assay described in the biological example. In some embodiments, the cereblon binding concentration is from about 0.003 μM to about 0.006 μM, from about 0.005 μM to about 0.008 μM, from about 0.007 μM to about 0.01 μM, from about 0.009 μM to about 0.012 μM, from about 0.012 μM to about 0.015 μM, from about 0.015 μM to about 0.018 μM, from about 0.018 μM to about 0.021 μM, from about 0.021 μM to about 0.024 μM, from about 0.024 μM to about 0.027 μM, or from about 0.027 μM to about 0.030 μM. In some embodiments, the cereblon binding concentration is less than 0.015 μM. In some embodiments, the cereblon binding concentration is less than 0.010 μM. In some embodiments, the cereblon binding concentration is less than 0.005 μM.

In one embodiment, the method relates a compound, or a pharmaceutically acceptable salt, solvate, stereoisomer, and/or tautomer thereof or a pharmaceutical composition comprising said compound, or a pharmaceutically acceptable salt, solvate, stereoisomer, and/or tautomer thereof as described herein for use as described herein, wherein the IKZF2 degradation at 1 μM concentration of the compounds described herein is in the range of about 25%-99%. The IKZF2 degradation is measured by the assay described in the biological example. In some embodiments, the IKZF2 degradation is from about 25% to about 50%, from about 45% to about 70%, from about 65% to about 90% or from about 75% to about 99%. In some embodiments, the IKZF2 degradation is from about 25% to about 35%, from about 35% to about 45%, from about 45% to about 55%, from about 55% to about 65%, from about 65% to about 75%, from about 75% to about 85%, from about 85% to about 99%. In some embodiments, the IKZF2 degradation is more than 60%. In some embodiments, the IKZF2 degradation is more than 70%. In some embodiments, the IKZF2 degradation is more than 80%. In some embodiments, the IKZF2 degradation is more than 90%.

Non-limiting examples of IKZF2 dependent diseases or disorders include proliferative diseases or disorders which may be non-cancerous or cancerous.

Examples of non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcoidosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

In certain embodiments, the compounds or compositions described herein are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer. In certain embodiments, compounds or compositions described herein are active against solid tumors.

In certain embodiments, the compounds or compositions described herein are useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer).

In some embodiments, examples of cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, Ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilms' Tumor.

In certain embodiments, the compounds described herein are useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer) and/or any other cancer described herein.

In certain embodiments, the compounds described herein are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer. In certain embodiments, the compounds are active against solid tumors.

In certain embodiments, the compounds and compositions described herein are useful in treating IKZF2 dependent diseases or disorders such as liposarcoma, glioblastoma, bladder cancer, adrenocortical cancer, multiple myeloma, colorectal cancer, non-small cell lung cancer, Human Papilloma Virus-associated cervical, oropharyngeal, penis, anal, thyroid, or vaginal cancer or Epstein-Barr Virus-associated nasopharyngeal carcinoma, gastric cancer, rectal cancer, thyroid cancer, Hodgkin lymphoma or diffuse large B-cell lymphoma. The cancer may be selected from prostate cancer, breast carcinoma, lymphomas, leukemia, myeloma, bladder carcinoma, colon cancer, cutaneous melanoma, hepatocellular carcinoma, endometrial cancer, ovarian cancer, cervical cancer, lung cancer, renal cancer, glioblastoma multiform, glioma, thyroid cancer, parathyroid tumor, nasopharyngeal cancer, tongue cancer, pancreatic cancer, esophageal cancer, cholangiocarcinoma, gastric cancer, soft tissue sarcomas, rhabdomyosarcoma (RMS), synovial sarcoma, osteosarcoma, rhabdoid cancers, cancer for which the immune response is deficient, an immunogenic cancer, and Ewing's sarcoma. In one embodiment, the IKZF2-dependent disease or disorder is a disease or disorder is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, and gastrointestinal stromal tumor (GIST). In another embodiment, the cancer is selected from non-small cell lung cancer (NSCLC), melanoma, triple-negative breast cancer (TNBC), nasopharyngeal cancer (NPC), microsatellite stable colorectal cancer (mssCRC), thymoma, carcinoid, acute myelogenous leukemia, and gastrointestinal stromal tumor (GIST). In another embodiment, the IKZF2-dependent disease or disorder is a disease or disorder is selected from non-small cell lung cancer (NSCLC), melanoma, triple-negative breast cancer (TNBC), nasopharyngeal cancer (NPC), and microsatellite stable colorectal cancer (mssCRC).

The compounds of the disclosure can be administered in effective amounts to treat or prevent a disorder and/or prevent the development thereof in subjects.

In general, methods of using the compounds of the present application comprise administering to a subject in need thereof a therapeutically effective amount of a compound as described herein.

In certain embodiments, compounds as described herein are useful in the treatment of proliferative diseases (e.g., cancer, benign neoplasms, inflammatory disease, and autoimmune diseases). In certain embodiments, according to the methods of treatment of the present application, levels of cell proteins of interest, e.g., pathogenic and oncogenic proteins are modulated, or their growth is inhibited or the proteins are degraded by contacting said cells with an compound or composition, as described herein. In other embodiments, the compounds are useful in treating cancer.

Thus, in another aspect of the application, methods for the treatment of cancer are provided comprising administering a therapeutically effective amount of compound or composition, as described herein, to a subject in need thereof. In certain embodiments, a method for the treatment of cancer is provided comprising administering a therapeutically effective amount of a compound, or a pharmaceutical composition comprising a compound as described herein to a subject in need thereof, in such amounts and for such time as is necessary to achieve the desired result. In some embodiments, the compounds of present application are administered orally or intravenously. In certain embodiments of the present application a "therapeutically effective amount" of the compound or pharmaceutical composition is that amount effective for killing or inhibiting the growth of tumor cells. The compounds and compositions, according to the method of the present application, may be administered using any amount and any route of administration effective for killing or inhibiting the growth of tumor cells. Thus, the expression "amount effective to kill or inhibit the growth of tumor cells," as used herein, refers to a sufficient amount of agent to kill or inhibit the growth of tumor cells. The exact amount required will vary from subject to subject, depending on the species, age, and general condition of the subject, the severity of the disease, the particular anticancer agent, its mode of administration, and the like. In certain embodiments of the present application a "therapeutically effective amount" of the-compound or pharmaceutical composition described herein is that amount effective for reducing the levels of target proteins. In certain embodiments of the present application a "therapeutically effective amount" of the compound or pharmaceutical composition is that amount effective to kill or inhibit the growth of skin cells.

In certain embodiments, the method involves the administration of a therapeutically effective amount of the compound or a pharmaceutically acceptable derivative thereof to a subject (including, but not limited to a human or other mammal in need of it.

Additionally, the present application provides pharmaceutically acceptable derivatives of the compounds, and methods of treating a subject using these compounds, pharmaceutical compositions thereof, or either of these in combination with one or more additional therapeutic agents.

Another aspect of the application relates to a method of treating or lessening the severity of a disease or condition associated with a proliferation disorder in a patient, said method comprising a step of administering to said patient, a compound of Formula I or a composition comprising said compound.

It will be appreciated that the compounds and compositions, according to the method of the present application, may be administered using any amount and any route of administration effective for the treatment of cancer and/or disorders associated with cell hyperproliferation. For example, when using the compounds for the treatment of cancer, the expression "effective amount" as used herein, refers to a sufficient amount of agent to inhibit cell proliferation, or refers to a sufficient amount to reduce the effects of cancer. The exact amount required will vary from subject to subject, depending on the species, age, and general condition of the subject, the severity of the diseases, the particular anticancer agent, its mode of administration, and the like.

The present application provides methods for the treatment of a proliferative disorder in a subject in need thereof by administering to a subject in need of such treatment, a therapeutically effective amount of a compound of the present application, or a pharmaceutically acceptable salt, solvate, stereoisomer, and/or tautomer thereof. The proliferative disorder can be cancer or a precancerous condition. The present application further provides the use of a compound of the present application, or a pharmaceutically acceptable salt, salt, solvate, stereoisomer, and/or tautomer thereof, for the preparation of a medicament useful for the treatment of a proliferative disorder.

The present application also provides methods of protecting against a proliferative disorder in a subject in need thereof by administering a therapeutically effective amount of compound of the present application, or a pharmaceutically acceptable salt, salt, solvate, stereoisomer, and/or tautomer thereof, to a subject in need of such treatment. The proliferative disorder can be cancer or a precancerous condition. The present application also provides the use of compound of the present application, or a pharmaceutically acceptable salt, salt, solvate, stereoisomer, and/or tautomer thereof, for the preparation of a medicament useful for the prevention of a proliferative disorder.

As used herein, the term "proliferative disorder" refers to conditions in which unregulated or abnormal growth, or both, of cells can lead to the development of an unwanted condition or disease, which may or may not be cancerous. Exemplary proliferative disorders of the application encompass a variety of conditions wherein cell division is deregulated. Exemplary proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A proliferative disorder includes a precancer or a precancerous condition. A proliferative disorder includes cancer. Preferably, the methods provided herein are used to treat or alleviate a symptom of cancer. The term "cancer" includes solid tumors, as well as hematologic tumors and/or malignancies. A "precancer cell" or "precancerous cell" is a cell manifesting a proliferative disorder that is a precancer or a precancerous condition. A "cancer cell" or "cancerous cell" is a cell manifesting a proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

A "proliferative disorder of the hematologic system" is a proliferative disorder involving cells of the hematologic system. A proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A proliferative disorder of the hematologic system can include hyperplasia, dysplasia, and metaplasia of cells of the hematologic system. Preferably, compositions of the present application may be used to treat a cancer selected from the group consisting of a hematologic cancer of the present application or a hematologic proliferative disorder of the present application. A hematologic cancer of the present application can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "proliferative disorder of the lung" is a proliferative disorder involving cells of the lung. Proliferative disorders of the lung can include all forms of proliferative disorders affecting lung cells. Proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present application may be used to treat lung cancer or proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. Lung cancer can include "scar carcinoma", bronchioalveolar carcinoma, giant cell carcinoma, spindle cell carcinoma, and large cell neuroendocrine carcinoma. Lung cancer can include lung neoplasms having histologic and ultrastructural heterogeneity (e.g., mixed cell types).

Proliferative disorders of the lung can include all forms of proliferative disorders affecting lung cells. Proliferative disorders of the lung can include lung cancer, precancerous conditions of the lung. Proliferative disorders of the lung can include hyperplasia, metaplasia, and dysplasia of the lung. Proliferative disorders of the lung can include asbestos-induced hyperplasia, squamous metaplasia, and benign reactive mesothelial metaplasia. Proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing proliferative disorders of the lung. Prior lung diseases that may predispose individuals to development of proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "proliferative disorder of the colon" is a proliferative disorder involving cells of the colon. Preferably, the proliferative disorder of the colon is colon cancer. Preferably, compositions of the present application may be used to treat colon cancer or proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Proliferative disorders of the colon can include all forms of proliferative disorders affecting colon cells. Proliferative disorders of the colon can include colon cancer, precancerous conditions of the colon, adenomatous polyps of the colon and metachronous lesions of the colon. A proliferative disorder of the colon can include adenoma. Proliferative disorders of the colon can be characterized by hyperplasia, metaplasia, and dysplasia of the colon. Prior colon diseases that may predispose individuals to development of proliferative disorders of the colon can include prior colon cancer. Current disease that may predispose individuals to development of proliferative disorders of the colon can include Crohn's disease and ulcerative colitis. A proliferative disorder of the colon can be associated with a mutation in a gene selected from the group consisting of p53, ras, FAP and DCC. An individual can have an elevated risk of developing a proliferative disorder of the colon due to the presence of a mutation in a gene selected from the group consisting of p53, ras, FAP and DCC.

A "proliferative disorder of the pancreas" is a proliferative disorder involving cells of the pancreas. Proliferative disorders of the pancreas can include all forms of proliferative disorders affecting pancreatic cells. Proliferative disorders of the pancreas can include pancreas cancer, a precancer or precancerous condition of the pancreas, hyperplasia of the pancreas, and dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas. Pancreatic cancer can include ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma. Pancreatic cancer can also include pancreatic neoplasms having histologic and ultrastructural heterogeneity (e.g., mixed cell types).

A "proliferative disorder of the prostate" is a proliferative disorder involving cells of the prostate. Proliferative disorders of the prostate can include all forms of proliferative disorders affecting prostate cells. Proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Proliferative disorders of the prostate can include hyperplasia, metaplasia, and dysplasia of the prostate.

A "proliferative disorder of the skin" is a proliferative disorder involving cells of the skin. Proliferative disorders of the skin can include all forms of proliferative disorders affecting skin cells. Proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Proliferative disorders of the skin can include hyperplasia, metaplasia, and dysplasia of the skin.

A "proliferative disorder of the ovary" is a proliferative disorder involving cells of the ovary. Proliferative disorders of the ovary can include all forms of proliferative disorders affecting cells of the ovary. Proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Proliferative disorders of the skin can include hyperplasia, metaplasia, and dysplasia of cells of the ovary.

A "proliferative disorder of the breast" is a proliferative disorder involving cells of the breast. Proliferative disorders of the breast can include all forms of proliferative disorders affecting breast cells. Proliferative disorders of the breast can include breast cancer, a precancer or precancerous condition of the breast, benign growths or lesions of the breast, and malignant growths or lesions of the breast, and metastatic lesions in tissue and organs in the body other than the breast. Proliferative disorders of the breast can include hyperplasia, metaplasia, and dysplasia of the breast.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1 (mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "proliferative disorder". A normal cell lacks unregulated or abnormal growth, or both, that can lead to the development of an unwanted condition or disease. Preferably, a normal cell possesses normally functioning cell cycle checkpoint control mechanisms.

One skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3rd edition), Cold Spring Harbor Press, Cold Spring Harbor, N.Y. (2000); Coligan et al., Current Protocols in Immunology, John Wiley & Sons, N.Y.; Erma et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, Pa., 18th edition (1990). These texts can, of course, also be referred to in making or using an aspect of the application.

In certain embodiments, compounds of the application are useful in the treatment of proliferative diseases (e.g., cancer, benign neoplasms, inflammatory disease, and autoimmune diseases). In certain embodiments, according to the methods of treatment of the present application, levels of cell proteins of interest, e.g., pathogenic and oncogenic proteins are modulated, or their growth is inhibited by contacting said cells with an compound or composition, as described herein. In other embodiments, the compounds are useful in treating cancer.

In certain embodiments, the method involves the administration of a therapeutically effective amount of the compound or a pharmaceutically acceptable derivative thereof to a subject (including, but not limited to a human or animal) in need of it.

Additionally, the present application provides pharmaceutically acceptable derivatives of the compounds, and methods of treating a subject using these compounds, pharmaceutical compositions thereof, or either of these in combination with one or more additional therapeutic agents.

For example, other therapies or anticancer agents that may be used in combination with the compounds disclosed herein including surgery, radiotherapy, endocrine therapy, biologic response modifiers (interferons, interleukins, and tumor necrosis factor (TNF), to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabine, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of overview of cancer therapy see The Merck Manual, Twentieth Ed. 2020, the entire contents of which are hereby incorporated by reference. See also the National Cancer Institute (NCI) website (www.nci.nih.gov) and the Food and Drug Administration (FDA) website for a list of the FDA approved oncology drugs (www.fda.gov/cder/cancer/druglistframe).

In certain embodiments, the pharmaceutical compositions comprising the compounds disclosed herein further comprise one or more additional therapeutically active ingredients (e.g., chemotherapeutic and/or palliative). For purposes of the application, the term "palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

ADMINISTRATION, PHARMACEUTICAL COMPOSITIONS

Administration of the disclosed compounds and pharmaceutical compositions can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride, and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes, and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin ETGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines.

In some embodiments, a film of lipid components is hydrated with an aqueous solution of drug to a form lipid layer encapsulating the drug, as described in U.S. Pat. No. 5,262,564, which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure is directed to pharmaceutical compositions comprising a compound of Formula (I), and a pharmaceutically acceptable carrier. The pharmaceutical acceptable carrier may further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the disclosure provides a kit comprising two or more separate pharmaceutical compositions, at least one of which contains a compound of the present disclosure. In one embodiment, the kit comprises means for separately retaining said compositions, such as a container, divided bottle, or divided foil packet. An example of such a kit is a blister pack, as typically used for the packaging of tablets, capsules and the like.

The kit of the disclosure may be used for administering different dosage forms, for example, oral and parenteral, for administering the separate compositions at different dosage intervals, or for titrating the separate compositions against one another. To assist compliance, the kit of the disclosure typically comprises directions for administration.

Pharmaceutical dosage forms of a compound of this disclosure may be manufactured by any of the methods well-known in the art, such as, for example, by conventional mixing, sieving, dissolving, melting, granulating, drageemaking, tableting, suspending, extruding, spray-drying, levigating, emulsifying, (nano-/micro-) encapsulating, entrapping, or lyophilization processes. As noted above, the compositions of this disclosure can include one or more physiologically acceptable inactive ingredients that facilitate processing of active molecules into preparations for pharmaceutical use.

As noted above, the compositions are comprised of, in general, a compound of this disclosure in combination with at least one pharmaceutically acceptable excipient. Acceptable excipients are nontoxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semi-solid excipients may be selected from glycerol, propylene glycol, water, ethanol and various oils, including those of petroleum, animal, vegetable or synthetic origin, e.g., peanut oil, soybean oil, mineral oil, sesame oil, etc. In some embodiments, liquid carriers, particularly for injectable solutions, include water, saline, aqueous dextrose, and glycols.

Compressed gases may be used to disperse a compound of this disclosure in an aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The compositions of this disclosure may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of this disclosure that can be formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01-99.99 wt % of a compound of this disclosure based on the total formulation, with the balance being one or more suitable pharmaceutical excipients. In one embodiment, the compound is present at a level of about 1-80 wt %. Representative pharmaceutical formulations are described below.

FORMULATION EXAMPLES

The following are representative pharmaceutical formulations containing a compound of this disclosure.

Formulation Example 1—Tablet Formulation

The following ingredients are mixed intimately and pressed into single scored tablets.

| Ingredient | Quantity per tablet, mg |
|---|---|
| compound of this disclosure | 400 |
| Cornstarch | 50 |
| croscarmellose sodium | 25 |
| Lactose | 120 |
| magnesium stearate | 5 |

Formulation Example 2—Capsule Formulation

The following ingredients are mixed intimately and loaded into a hard-shell gelatin capsule

| Ingredient | Quantity per capsule, mg |
|---|---|
| compound of this disclosure | 200 |
| lactose, spray-dried | 148 |
| magnesium stearate | 2 |

Formulation Example 3—Suspension Formulation

The following ingredients are mixed to form a suspension for oral administration.

| Ingredient | Amount |
|---|---|
| compound of this disclosure | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| Flavoring | 0.035 mL |
| Colorings | 0.5 mg |
| distilled water | q.s. to 100 mL |

Formulation Example 4—Injectable Formulation

The following ingredients are mixed to form an injectable formulation.

| Ingredient | Amount |
|---|---|
| compound of this disclosure | 0.2 mg-20 mg |
| sodium acetate buffer solution, 0.4 M | 2.0 mL |
| HCl (1N) or NaOH (1N) | q.s. to suitable pH |
| water (distilled, sterile) | q.s. to 20 mL |

Formulation Example 5—Suppository Formulation

A suppository of total weight 2.5 g is prepared by mixing the compound of this disclosure with Witepsol® H-15 (triglycerides of saturated vegetable fatty acid; Riches-Nelson, Inc., New York), and has the following composition:

| Ingredient | Amount |
|---|---|
| Compound of this disclosure | 500 mg |
| Witepsol ® H-15 | balance |

Dosing

The dosage regimen utilizing the disclosed compound is selected in accordance with a variety of factors including type, species, age, weight, sex, and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

The following synthetic and biological examples are offered to illustrate this disclosure and are not to be construed in any way as limiting the scope of this disclosure. Unless otherwise stated, all temperatures are in degrees Celsius.

EXAMPLES

This disclosure is further understood by reference to the following examples, which are intended to be purely exemplary of this disclosure. This disclosure is not limited in scope by the exemplified embodiments, which are intended as illustrations of single aspects of this disclosure only. Any methods that are functionally equivalent are within the scope of this disclosure. Various modifications of this disclosure in addition to those described herein will become apparent to those skilled in the art from the foregoing description and accompanying figures. Such modifications fall within the scope of the appended claims.

In the specification and in the examples below, all temperatures are in degrees Celsius. In addition, the following abbreviations have the following meanings. If not defined, these abbreviations have their art recognized meaning.

| Abbreviation | Meaning |
| --- | --- |
| δ | chemical shift (ppm) |
| ACN or MeCN | acetonitrile |
| Boc | tert-butoxycarbonyl |
| BPD | bis(pinacolato)diboron |
| BRET | Bioluminescence Resonance Energy Transfer |
| Cbz | benzyloxycarbonyl |
| $CDCl_3$ | deuterated chloroform |
| DBU | 1,8-diazabicyclo[5.4.0]undec-7-ene |
| $DC_{50}$ | concentration that resulted in a 50% targeted protein degradation |
| DCM | dichloromethane |
| DEAD | diethyl azodicarboxylate |
| DHA | docosahexaenoic acid |
| DIAD | diisopropyl azodicarboxylate |
| DIEA | diisopropylethylamine |
| DMA | dimethylacetamide |
| DMAP | 4-dimethylaminopyridine |
| DMF | N,N-dimethylformamide |
| DMP | Dess-Martin periodinane |
| DMSO | dimethylsulfoxide |
| $d_6$-DMSO | deuterated dimethylsulfoxide |
| dtbbpy | 4,4'-di-tert-butyl-2,2'-dipyridyl |
| EPA | eicosapentaenoic acid |
| eq. | equivalent(s) |
| ESI | electrospray ionization |
| EtOAc | ethyl acetate |
| EtOH | ethanol |
| FBS | fetal Bovine Serum |
| FITC | fluorescein isothiocyanate |
| Fmoc | fluorenylmethyloxycarbonyl |
| g | grams |
| $^1$H NMR | proton nuclear magnetic resonance spectroscopy |
| h | hour(s) |
| HPLC | high performance liquid chromatography |
| Ir[(dF(CF$_3$)ppy)$_2$dtbbpy]PF$_6$ | [4,4'-Bis(1,1-dimethylethyl)-2,2'-bipyridine-N1,N1']bis[3,5-difluoro-2-[5-(trifluoromethyl)-2-pyridinyl-N]phenyl-C]Iridium(III) hexafluorophosphate |
| L | liter |
| LAH | lithium aluminum hydride |
| LC | liquid chromatography |
| LC-MS | liquid chromatography-mass spectrometry |
| LDA | lithium diisopropylamide |
| M | molar |
| mCPBA | meta-Chloroperoxybenzoic acid |
| MeOD | deuterated methanol |
| MeOH | methanol |
| mg | milligram |
| mmol | millimole |
| mL | milliliter |
| UL | microliter |
| umol or mmol | micromole |
| mM | micromolar |
| μm | micron |
| m/z | mass-to-charge ratio |
| MsOH | methanesulfonic acid |
| min | minute(s) |
| N | normal |
| n-BuLi | n-butyllithium |
| nm | nanometer |
| PBS | Phosphate-buffered saline |
| Pd$_2$(dba)$_3$ | tris(dibenzylideneacetone)dipalladium(0) |
| pM | picomolar |
| q.s. | amount which is sufficient |
| rt | room temperature |
| t-Bu | tert-butyl |
| TBME | tert-butyl methyl ether |
| TEA | triethylamine |
| TFA | trifluoroacetic acid |

| Abbreviation | Meaning |
|---|---|
| TfOH | trifluoromethanesulfonic acid |
| TFP | tri(2-furyl)phosphine |
| THF | tetrahydrofuran |
| TMP | 2,2,6,6-tetramethylpiperidine |
| TRITC | tetramethylrhodamine |
| TsCl | 4-toluenesulfonyl chloride |
| UV | ultraviolet |
| v/v | volume/volume ratio |
| wt % | weight percent |
| NMR abbreviations | br = broad |
| | d = doublet |
| | dd = doublet of doublets |
| | ddd = doublet of doublet of doublets |
| | dt = doublet of triplets |
| | m = multiplet |
| | q = quartet |
| | s = singlet |
| | t = triplet |

LC-MS Methods (General Method)

Method A: Experiments were performed using a Phenomenex Luna $C_{18}$ 150×30 mm×5 µm, at a flow rate of 20 mL/min, and a mass spectrometer using ESI as ionization source. The solvent A was 4.0 mL of TFA in 4 L of water, and solvent B was 4.0 mL of TFA in 4 L of acetonitrile. The gradient consisted of 10-45% solvent B over 8 minutes, LC column temperature was 40° C. UV absorbance was collected at 220 nm and 254 nm.

Method B: Experiments were performed using a Waters Xbridge $C_{18}$ 150×50 mm×10 µm, at a flow rate of 20 mL/min, and a mass spectrometer using ESI as ionization source. The solvent A was 4.0 mL of TFA in 4 L of water, and solvent B was 4.0 mL of TFA in 4 L of acetonitrile. The gradient consisted of 40-60% solvent B over 10 minutes, LC column temperature was 40° C. UV absorbance was collected at 220 nm and 254 nm.

Example A: 3-(5-(((1S,2S)-2-aminocyclohexyl) oxy)-1-oxoisoindolin-2-yl)-1-((2-(trimethylsilyl) ethoxy)methyl)piperidine-2,6-dione This intermediate was prepared according to reported literature procedure [ADCOCK, Claire et al., US2020/17461, 2020, A1].

Example 1

(S)-3-(1-oxo-5-(((1S,2S)-2-(3-phenylazetidin-1-yl) cyclohexyl)oxy)isoindolin-2-yl)piperidine-2,6-dione (Compound 10)

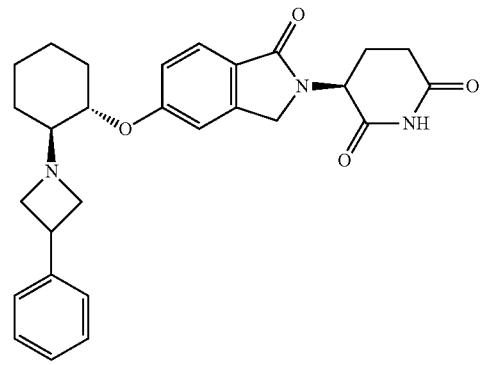 [SMILES: O=C1CC[C@H](N2Cc3cc(O[C@H]4CCCC[C@@H]4N4CC(c5ccccc5)C4)ccc3C2=O)C(=O)N1]

Step 1:

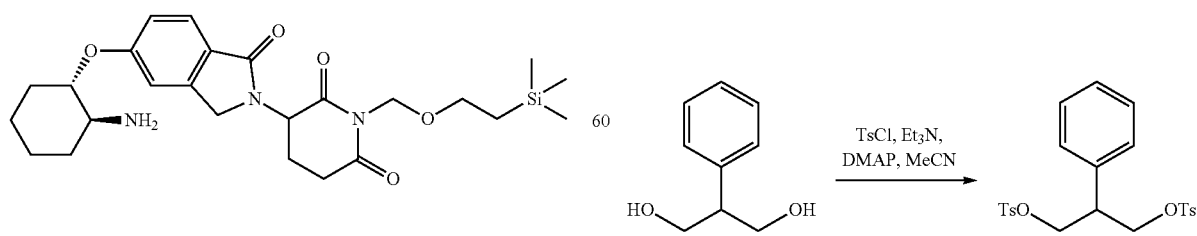

255

To a solution of 2-phenylpropane-1,3-diol (5 g, 32.85 mmol, 1 eq) in DCM (100 mL) was added TsCl (21.92 g, 114.99 mmol, 3.5 eq), DMAP (401.37 mg, 3.29 mmol, 0.1 eq) and Et$_3$N (13.30 g, 131.41 mmol, 18.29 mL, 4 eq), the mixture was stirred at 20° C. for 16 hr. The reaction mixture was concentrated under reduced pressure to give a residue. The residue was purified by silica gel column chromatography (100:1 to 50:1 Petroleum ether in Ethyl acetate) to afford 2-phenylpropane-1,3-diyl bis(4-methylbenzenesulfonate). $^1$H NMR (400 MHz, CDCl$_3$) δ 2.45 (s, 6H), 3.27 (m, 1H), 4.21 (d, J=6.02 Hz, 4H), 7.01-7.07 (m, 2H), 7.21-7.27 (m, 3H), 7.30 (d, J=8.03 Hz, 4H), 7.67 (d, J=8.53 Hz, 4H).

Step 2:

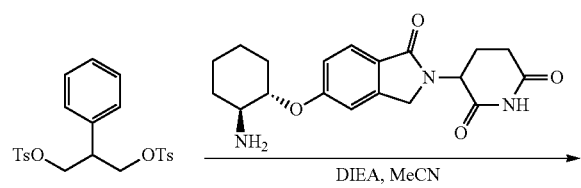

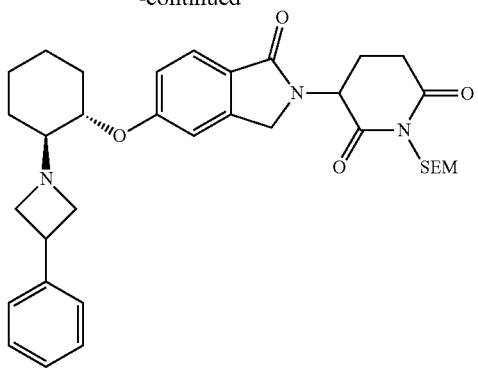

To a solution of 3-(5-(((1S,2S)-2-aminocyclohexyl)oxy)-1-oxoisoindolin-2-yl)piperidine-2,6-dione (500 mg, 1.03 mmol, 1 eq), 2-phenylpropane-1,3-diyl bis(4-methylbenzenesulfonate) (708.32 mg, 1.54 mmol, 1.5 eq), and DIEA (530.04 mg, 4.10 mmol, 714.34 μL, 4 eq) in ACN (10 mL) in a microwave tube. The sealed tube was heated at 120° C. for 16 hr. Three additional vials were set up as described above. All four reaction mixtures were combined for work up. The reaction mixture was concentrated under reduced pressure to give a residue. The residue was purified by prep-HPLC (method B) to give 3-(1-oxo-5-(((1S,2S)-2-(3-phenylazetidin-1-yl)cyclohexyl)oxy)isoindolin-2-yl)-1-((2-(trimethylsilyl)ethoxy)methyl)piperidine-2,6-dione. MS (ESI+): m/z 604.5 (M+H)$^+$.

Step 3:

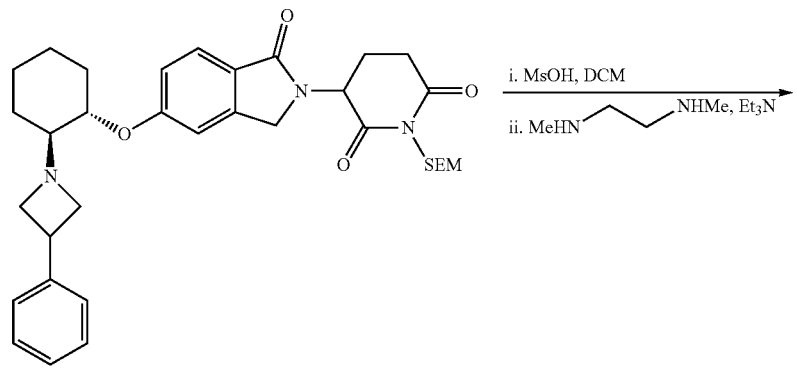

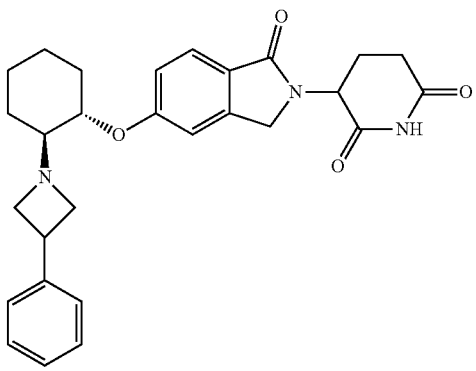

To a solution of 3-(1-oxo-5-(((1S,2S)-2-(3-phenylazetidin-1-yl)cyclohexyl)oxy)isoindolin-2-yl)-1-((2-(trimethylsilyl)ethoxy)methyl)piperidine-2,6-dione (0.7 g, 1.16 mmol, 1 eq) in DCM (50 mL) was added MsOH (445.67 mg, 4.64 mmol, 330.13 μL, 4 eq) at 20° C., after the mixture was stirred for 2 hr at 20° C., $N^1,N^2$-dimethylethane-1,2-diamine (122.63 mg, 1.39 mmol, 149.73 μL, 1.2 eq) and TEA (938.46 mg, 9.27 mmol, 1.29 mL, 8 eq) was added to the mixture. The mixture was stirred at 20° C. for 2 hours. LCMS showed the starting material was consumed completely. The reaction mixture was filtered, and the filtrate was concentrated in vacuum to give a residue. The residue was purified by prep-HPLC (method A) to give 3-(1-oxo-5-(((1S,2S)-2-(3-phenylazetidin-1-yl)cyclohexyl)oxy)isoindolin-2-yl)piperidine-2,6-dione. $^1$H NMR (400 MHz, $d_6$-DMSO) δ 1.07-1.19 (m, 1H), 1.20-1.32 (m, 1H), 1.34-1.44 (m, 2H), 1.65 (br s, 2H), 1.78-1.89 (m, 1H), 1.92-2.05 (m, 2H), 2.35-2.45 (m, 2H), 2.55-2.63 (m, 1H), 2.84-2.96 (m, 1H), 3.12 (br s, 1H), 3.26 (br d, J=7.15 Hz, 1H), 3.45-3.55 (m, 1H), 3.62 (m, 2H), 4.20-4.32 (m, 2H), 4.33-4.42 (m, 1H), 5.06 (m, 1H), 7.04 (br d, J=8.58 Hz, 1H), 7.16-7.21 (m, 2H), 7.26-7.34 (m, 4H), 7.60 (d, J=8.58 Hz, 1H), 10.97 (s, 1H).

It is contemplated that, when X is hydrogen, the stereocenter at the 3-position of the piperidine-2,6-dione may epimerize in vivo. The epimers of the stereocenter at the 3-position of the piperidine-2,6-dione product can be separated by chiral HPLC (column: (S,S)-WHELK-01, (250 mm×30 mm×10 μm); mobile phase: (0.1% IPAm in IPA).

Example 2

3-(5-((2-(3-(6-methoxypyridin-3-yl)azetidin-1-yl)cyclohexyl)oxy)-1-oxoisoindolin-2-yl)piperidine-2,6-dione (Compound 27)

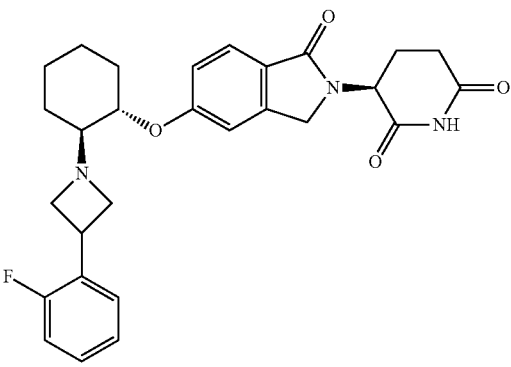 [SMILES: O=C1CC[C@H](N2Cc3cc(O[C@H]4CCCC[C@@H]4N4CC(c5ccccc5F)C4)ccc3C2=O)C(=O)N1]

Step 1:

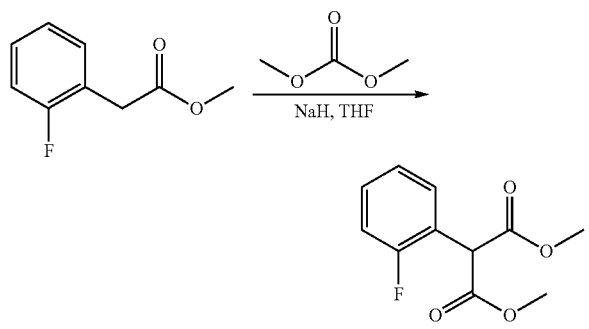

To a solution of methyl 2-(2-fluorophenyl)acetate (5 g, 28.54 mmol, 1 eq) in THF (150 mL) was added dimethyl carbonate (7.71 g, 85.62 mmol, 7.21 mL, 3 eq) at 20° C. under a $N_2$ atmosphere. NaH (2.85 g, 71.35 mmol, 60%, 2.5 eq) was added at 0° C. The mixture was stirred at 70° C. for 3 h. After cooling to 0° C., the reaction mixture was quenched with water (100 mL). The reaction mixture was partitioned between ethyl acetate (150 mL) and water (50 mL). The combined organic layers were washed with saturated brine (100 mL), dried over anhydrous $Na_2SO_4$, filtered and concentrated under reduced pressure to give a residue. The residue was purified by column chromatography (10-20% ethyl acetate in petroleum ether) to give dimethyl 2-(2-fluorophenyl)malonate. $^1$H NMR (400 MHz, $d_6$-DMSO) δ ppm 3.70 (s, 6H), 5.16 (s, 1H), 7.19-7.28 (m, 2H), 7.37-7.46 (m, 2H).

Step 2:

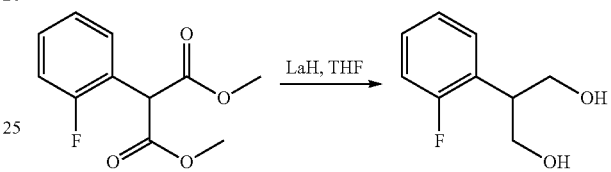

To a solution of dimethyl 2-(2-fluorophenyl)malonate (3.5 g, 15.47 mmol, 1 eq) in THF (80 mL) was added LiAlH$_4$ (1.17 g, 30.95 mmol, 2 eq) at 0° C. under a $N_2$ atmosphere. The mixture was stirred at 20° C. for 12 h. The reaction was quenched by addition of sodium sulfate decahydrate at 0° C. and filtered. The filter cake was washed with THF (3×100 mL), and the filtrate was concentrated under reduced pressure to give a residue. The residue was purified by column chromatography (25-50% ethyl acetate in petroleum ether) to give 2-(2-fluorophenyl)propane-1,3-diol. $^1$H NMR (400 MHz, $d_6$-DMSO) δ 3.35 (s, 1H), 3.55-3.78 (m, 4H), 4.62 (t, J=5.37 Hz, 2H), 7.05-7.16 (m, 2H), 7.19-7.26 (m, 1H), 7.34 (td, J=7.73, 1.86 Hz, 1H).

Step 3:

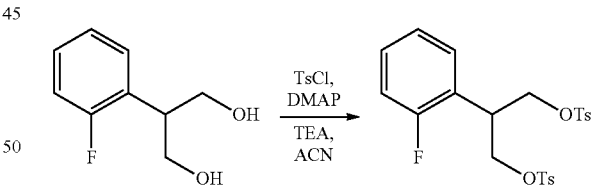

To a solution of 2-(2-fluorophenyl)propane-1,3-diol (300 mg, 1.76 mmol, 1 eq), TsCl (533.91 mg, 6.17 mmol, 3.5 eq) and DMAP (21.54 mg, 176.28 μmol, 0.1 eq) in ACN (3 mL) was added TEA (713.52 mg, 7.05 mmol, 981.46 μL, 4 eq) at 0° C. The mixture was stirred at 20° C. for 12 h. The reaction was filtered, the filter cake was washed with ACN (3×50 mL), and the filtrate was concentrated under reduced pressure to give a residue. The residue was purified by column chromatography (25-50% ethyl acetate in petroleum ether) to give 2-(2-fluorophenyl)propane-1,3-diyl bis(4-methylbenzenesulfonate). $^1$H NMR (400 MHz, $d_6$-DMSO) δ ppm 2.41 (s, 6H), 4.15-4.28 (m, 4H), 7.03-7.24 (m, 4H), 7.31 (ddd, J=15.38, 5.44, 1.69 Hz, 1H), 7.41 (d, J=8.00 Hz, 4H), 7.62 (d, J=8.38 Hz, 4H).

Step 4:

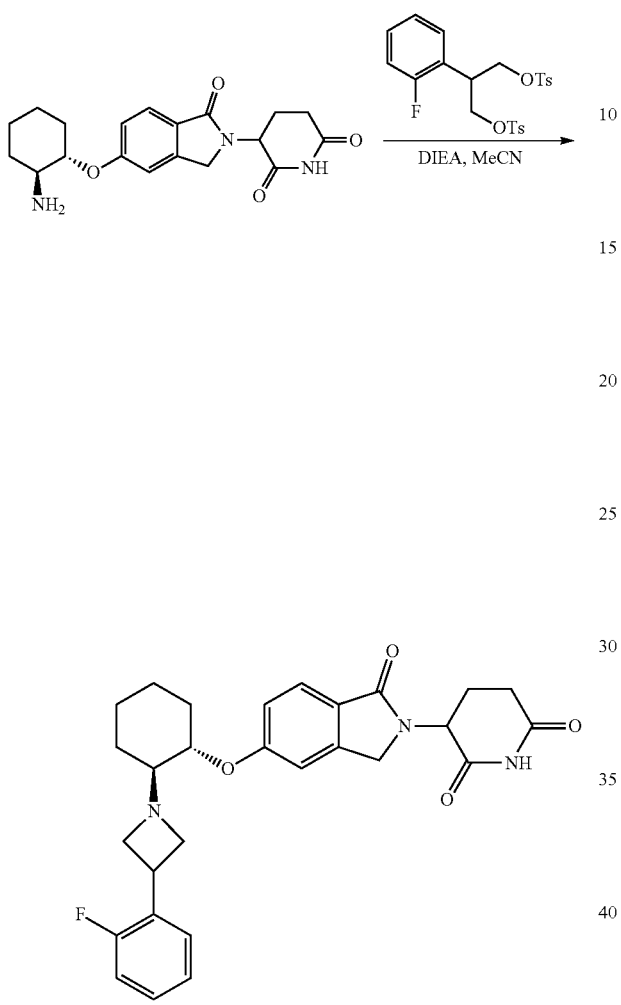

To a solution of 3-(5-(((1S,2S)-2-aminocyclohexyl)oxy)-1-oxoisoindolin-2-yl)piperidine-2,6-dione (100 mg, 279.80 μmol, 1 eq) and 2-(2-fluorophenyl)propane-1,3-diyl bis(4-methylbenzenesulfonate) (174.07 mg, 363.74 μmol, 1.3 eq) in ACN (3 mL) was added DIEA (144.65 mg, 1.12 mmol, 194.94 μL, 4 eq) at 20° C. The mixture was stirred at 120° C. for 12 h in a sealed tube. The reaction was concentrated under reduced pressure to give a residue. The residue was purified by prep-HPLC (method B) to give 3-(5-(((1S,2S)-2-(3-(2-fluorophenyl)azetidin-1-yl)cyclohexyl)oxy)-1-oxoisoindolin-2-yl)piperidine-2,6-dione. $^1$H NMR (400 MHz, d$_6$-DMSO) δ 1.17-1.51 (m, 5H), 1.69-1.82 (m, 2H), 1.98 (br dd, J=11.13, 4.75 Hz, 1H), 2.09-2.26 (m, 3H), 2.86-2.95 (m, 1H), 3.64-3.77 (m, 1H), 4.07-4.46 (m, 6H), 4.48-4.56 (m, 2H), 5.04-5.13 (m, 1H), 7.15-7.33 (m, 4H), 7.36-7.44 (m, 1H), 7.56 (br t, J=7.25 Hz, 1H), 7.67 (br d, J=7.88 Hz, 1H), 10.41-10.55 (m, 1H), 10.98 (s, 1H). MS (ESI+): m/z 492.2 (M+H)$^+$.

Example 3

Rac-4-(1-((trans)-2-((2-(2,6-dioxopiperidin-3-yl)-1-oxoisoindolin-5-yl)oxy)cyclohexyl)azetidin-3-yl)-2-fluorobenzonitrile (Compound 119) and rac-4-(1-((cis)-2-((2-(2,6-dioxopiperidin-3-yl)-1-oxoisoindolin-5-yl)oxy)cyclohexyl)azetidin-3-yl)-2-fluorobenzonitrile (Compound 122)

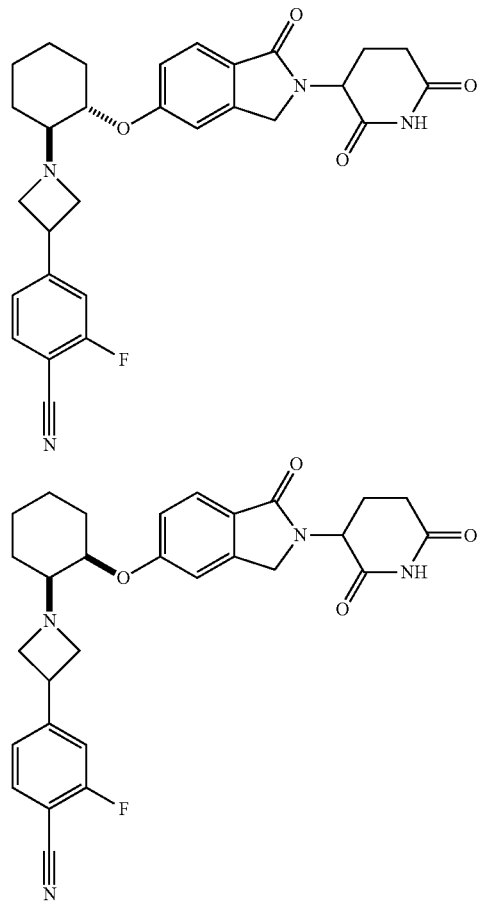

Step 1:

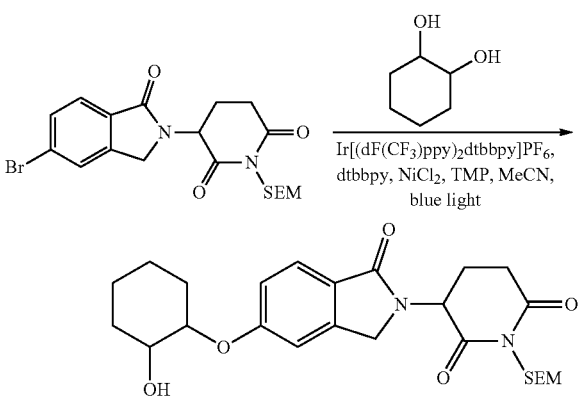

To a mixture of 3-(5-bromo-1-oxoisoindolin-2-yl)-1-((2-(trimethylsilyl)ethoxy)methyl)piperidine-2,6-dione (3.84 g, 33.08 mmol, 1.5 eq) [prepared according to literature procedure described in PCT Int. Appl. WO2020012334], cyclohexane-1,2-diol (2.55 g, 22.0 mmol, 1.0 eq), dtbbpy (295.98 mg, 1.10 mmol, 0.05 eq), Ir[(dF(CF$_3$)ppy)$_2$dtbbpy]PF$_6$ (247.44 mg, 220.56 μmol, 0.01 eq), and NiCl$_2$·glyme (242.30 mg, 1.10 mmol, 0.05 eq) in CH$_3$CN (100 mL), was added TMP (3.74 g, 26.47 mmol, 4.49 mL, 1.2 eq). The reaction mixture was stirred at 25° C. for 12 hrs. The reaction mixture was filtered and then concentrated in vacuum. The residue was purified by column chromatography (50 to 100% ethyl acetate in petroleum) to give 3-(5-((2-hydroxycyclohexyl)oxy)-1-oxoisoindolin-2-yl)-1-((2-(trimethylsilyl)ethoxy)methyl)piperidine-2,6-dione. $^1$H NMR (400 MHz, d$_6$-DMSO) δ 7.65-7.57 (m, 1H), 7.19 (s, 1H), 7.07 (dd, J=2.1, 8.4 Hz, 1H), 5.18 (dd, J=5.0, 13.4 Hz, 1H), 5.05 (q, J=9.7 Hz, 2H), 4.94 (dd, J=1.2, 4.7 Hz, 1H), 4.47 (d, J=3.6 Hz, 1H), 4.40 (dd, J=4.9, 17.1 Hz, 1H), 4.26-4.12 (m, 2H), 3.61-3.46 (m, 3H), 3.14-2.99 (m, 2H), 2.78 (br dd, J=2.1, 15.6 Hz, 1H), 2.43-2.28 (m, 1H), 2.07-2.01 (m, 2H), 1.94-1.82 (m, 1H), 1.79-1.69 (m, 1H), 1.63 (br d, J=9.6 Hz, 2H), 1.58-1.53 (m, 1H), 1.37-1.27 (m, 3H), 1.13 (br d, J=7.9 Hz, 1H), 0.90-0.78 (m, 2H), 0.02 (s, 9H).

Step 2:

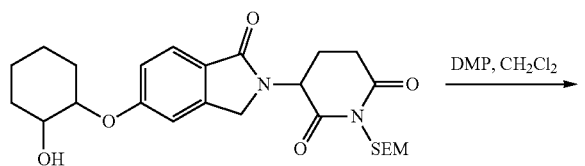

To a mixture of 3-(5-((2-hydroxycyclohexyl)oxy)-1-oxoisoindolin-2-yl)-1-((2-(trimethylsilyl)ethoxy)methyl)piperidine-2,6-dione (5 g, 10.23 mmol, 1 eq) in DCM (50 mL), was added DMP (8.68 g, 20.46 mmol, 6.34 mL, 2 eq). The mixture was stirred at 25° C. for 2 hrs. The reaction mixture was filtered and concentrated in vacuum. The residue was purified by column chromatography (50-100% Petroleum ether in Ethyl acetate) to give 3-(1-oxo-5-((2-oxocyclohexyl)oxy)isoindolin-2-yl)-1-((2-(trimethylsilyl)ethoxy)methyl)piperidine-2,6-dione. $^1$H NMR (400 MHz, d$_6$-DMSO) δ 7.59 (d, J=8.4 Hz, 1H), 7.07 (s, 1H), 7.00 (dd, J=1.2, 8.4 Hz, 1H), 5.25-5.14 (m, 2H), 5.09-4.97 (m, 2H), 4.38 (dd, J=5.0, 17.0 Hz, 1H), 4.25-4.15 (m, 1H), 3.72-3.42 (m, 2H), 3.16-3.00 (m, 1H), 2.87-2.73 (m, 1H), 2.71-2.58 (m, 1H), 2.40-2.28 (m, 3H), 2.10-1.99 (m, 2H), 1.93-1.74 (m, 3H), 1.66-1.51 (m, 1H), 0.88-0.79 (m, 2H), 0.02 (d, J=1.4 Hz, 9H).

One of skill in the art would be able to separate and isolate the individual stereoisomers of the 3-(1-oxo-5-((2-oxocyclohexyl)oxy)isoindolin-2-yl)-1-((2-(trimethylsilyl)ethoxy)methyl)piperidine-2,6-dione product reported, using techniques known in the art.

Step 3:

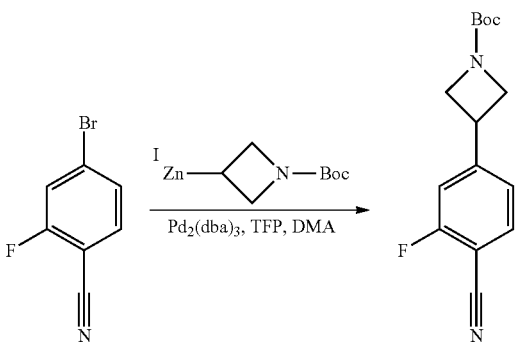

To a solution of 4-bromo-2-fluorobenzonitrile (1.59 g, 7.94 mmol, 1.00 eq) and (1-tert-butoxycarbonylazetidin-3-yl)-iodo-zinc (4.15 g, 11.91 mmol, 1.50 eq) in DMA (20 mL), was added Pd$_2$(dba)$_3$ (145.40 mg, 158.80 μmol, 0.02 eq) and TFP (184.32 mg, 794.00 μmol, 0.10 eq) under N$_2$. The reaction mixture was stirred at 25° C. for 12 h. Water (50 mL) was added, then the aqueous residue was extracted with ethyl acetate (3×50 mL), and the combined organic layers were dried with Na$_2$SO$_4$, and the solvent was evaporated under reduced pressure to give the crude product. The residue was purified by column chromatography (SiO$_2$, 0 to 50% ethyl acetate petroleum ether) to give tert-butyl 3-(4-cyano-3-fluorophenyl)azetidine-1-carboxylate. $^1$H NMR (400 MHz, d$_6$-DMSO) δ 7.90 (dd, J=7.2, 7.8 Hz, 1H), 7.56 (dd, J=1.3, 10.9 Hz, 1H), 7.40 (dd, J=1.5, 8.1 Hz, 1H), 4.24 (br t, J=8.0 Hz, 2H), 3.97-3.82 (m, 3H), 1.39 (s, 9H).

Step 4:

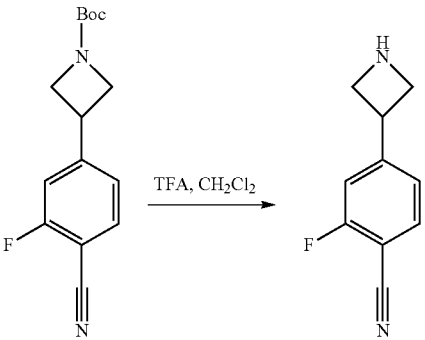 [SMILES: CC(C)(C)OC(=O)N1CC(c2ccc(C#N)c(F)c2)C1 ; N#Cc1ccc(C2CNC2)cc1F]

To a solution of tert-butyl 3-(4-cyano-3-fluorophenyl)azetidine-1-carboxylate (1.00 g, 3.62 mmol, 1.00 eq) in DCM (10 mL), was added TFA (4.62 g, 40.52 mmol, 3 mL, 11.20 eq). The reaction mixture was stirred at 25° C. for 12 h. Water (50 mL) was added, and the aqueous residue was washed with DCM (3×10 mL). The aqueous phase was lyophilized to give 4-(azetidin-3-yl)-2-fluorobenzonitrile. $^1$H NMR (400 MHz, d$_6$-DMSO) δ 8.02-7.92 (m, 1H), 7.67 (dd, J=1.3, 10.9 Hz, 1H), 7.45 (dd, J=1.4, 8.1 Hz, 1H), 4.26-4.19 (m, 2H), 4.19-4.05 (m, 3H).

Step 5:

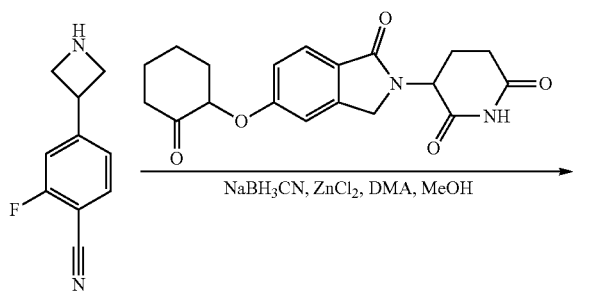

To a solution of 3-[1-oxo-5-(2-oxocyclohexoxy)isoindolin-2-yl]piperidine-2,6-dione (50 mg, 140.30 μmol, 1.00 eq) and 4-(azetidin-3-yl)-2-fluorobenzonitrile (49.44 mg, 280.60 μmol, 2.00 eq) in DMA (1 mL) and MeOH (1 mL), was added ZnCl$_2$ (76.49 mg, 561.20 μmol, 26.29 μL, 4.00 eq). The reaction mixture was stirred at 25° C. for 10 h. NaBH$_3$CN (26.45 mg, 420.90 μmol, 3.00 eq) was added. The reaction mixture was stirred at 25° C. for 2 h. The mixture was filtered, and the filtrate was concentrated to give the crude product. The residue was purified by prep-HPLC (Method A) to give rac-4-(1-((trans)-2-((2-(2,6-dioxopiperidin-3-yl)-1-oxoisoindolin-5-yl)oxy)cyclohexyl)azetidin-3-yl)-2-fluorobenzonitrile (Compound 122) and rac-4-(1-((cis)-2-((2-(2,6-dioxopiperidin-3-yl)-1-oxoisoindolin-5-yl)oxy)cyclohexyl)azetidin-3-yl)-2-fluorobenzonitrile (Compound 119).

Example 4

3-(1-oxo-5-(((1S,2S)-2-(3-phenylazetidin-1-yl)cyclohexyl)oxy)isoindolin-2-yl)piperidine-2,6-dione (Compound 127)

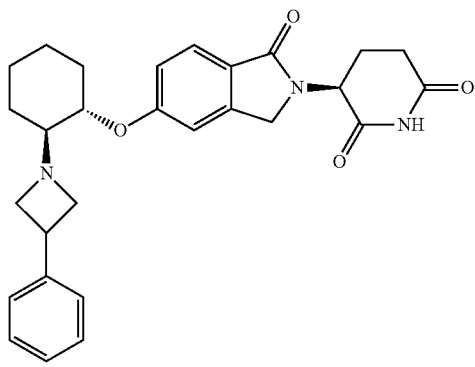 [SMILES: O=C1CC[C@H](N2Cc3cc(O[C@H]4CCCC[C@@H]4N4CC(c5ccccc5)C4)ccc3C2=O)C(=O)N1]

Step 1:

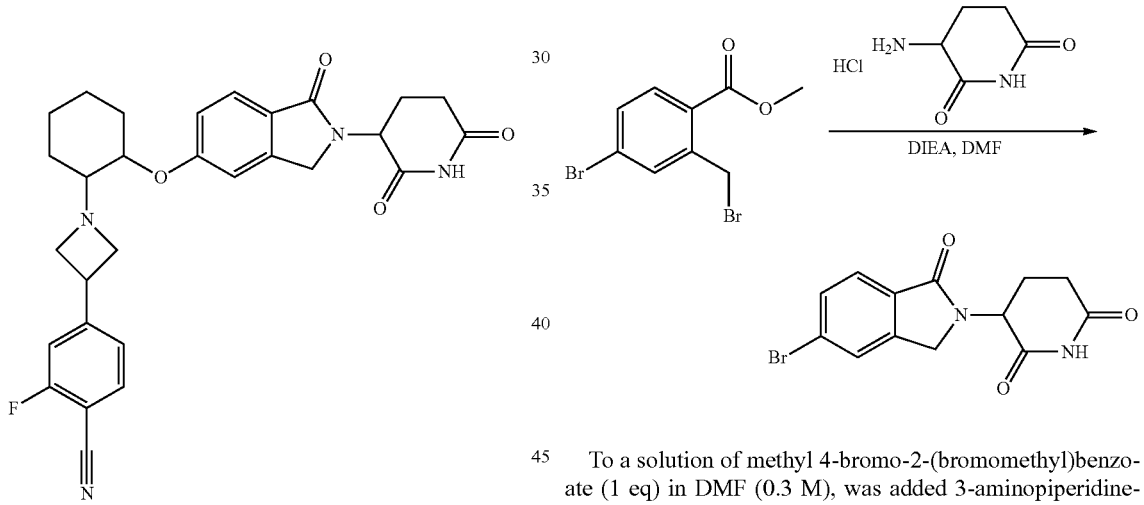

To a solution of methyl 4-bromo-2-(bromomethyl)benzoate (1 eq) in DMF (0.3 M), was added 3-aminopiperidine-2,6-dione (1.2 eq) and DIEA (4 eq) in portions at 20° C. The mixture was stirred at 120° C. for 16 hours. The reaction mixture was poured into ice-water and stirred for 20 min. The precipitated solid was filtered, and the resulting material was dried to give 3-(5-bromo-1-oxo-isoindolin-2-yl)piperidine-2,6-dione. $^1$H NMR (400 MHz, d$_6$-DMSO) δ 1.94-2.07 (m, 1H), 2.32-2.45 (m, 1H), 2.56-2.65 (m, 1H), 2.89-2.96 (m, 1H), 2.90-2.97 (m, 1H), 3.82 (s, 1H), 4.29-4.52 (m, 2H), 5.11 (dd, J=13.26, 5.13 Hz, 1H), 7.62-7.77 (m, 2H), 7.89 (s, 1H), 7.87-7.91 (m, 1H), 11.00 (s, 1H).

Step 2:

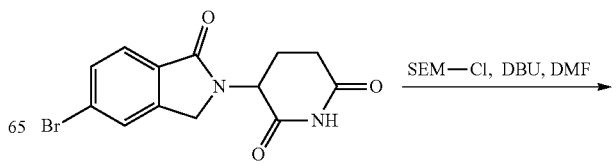

Step 4:

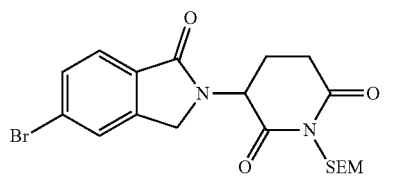

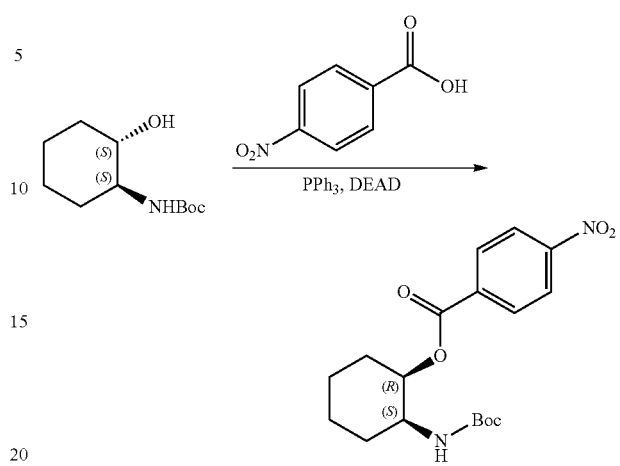

To a solution of 3-(5-bromo-1-oxo-isoindolin-2-yl)piperidine-2,6-dione (1 eq) in DMF (0.2 M), was added DBU (2 eq). 2-(chloromethoxy)ethyl-trimethyl-silane (1.6 eq) was added dropwise over 30 min at 0° C. The mixture was stirred at 20° C. for 1 hour. The reaction mixture was poured into ice-water and stirred for 20 minutes. The precipitated solid was filtered and dried to give 3-(5-bromo-1-oxo-isoindolin-2-yl)-1-(2-trimethylsilylethoxymethyl)piperidine-2,6-dione. $^1$H NMR (400 MHz, $d_6$-DMSO) δ 0.02 (s, 9H), 0.75-0.88 (m, 2H), 2.00-2.11 (m, 1H), 2.38 (qd, J=13.30, 4.50 Hz, 1H), 2.74-2.85 (m, 1H), 2.98-3.13 (m, 1H), 3.47-3.57 (m, 2H), 4.27-4.35 (m, 1H), 4.45-4.54 (m, 1H), 5.05 (q, J=9.76 Hz, 2H), 5.23 (dd, J=13.45, 5.07 Hz, 1H), 7.65-7.75 (m, 2H), 7.90 (s, 1H).

Step 3:

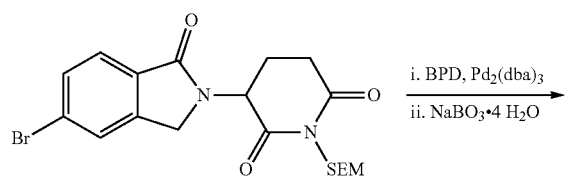

To a solution of tert-butyl ((1S,2S)-2-hydroxycyclohexyl) carbamate (1 eq), 4-nitrobenzoic acid (1.1 eq), and PPh$_3$ (1.7 eq) in THF (0.3 M), was added DEAD (1.5 eq) dropwise at 0° C. under N$_2$. The mixture was stirred at 25° C. for 12 hours under N$_2$. The reaction was poured into water, and extracted with ethyl acetate (3×). The combined organic phases were washed with saturated brine, dried over anhydrous Na$_2$SO$_4$, and concentrated in vacuum to give a residue. The residue was triturated with ethyl acetate, filtered, and the filtrate was concentrated under reduced pressure to give (1R,2S)-2-((tert-butoxycarbonyl)amino)cyclohexyl 4-nitrobenzoate, which was used directly in the next step.

Step 5:

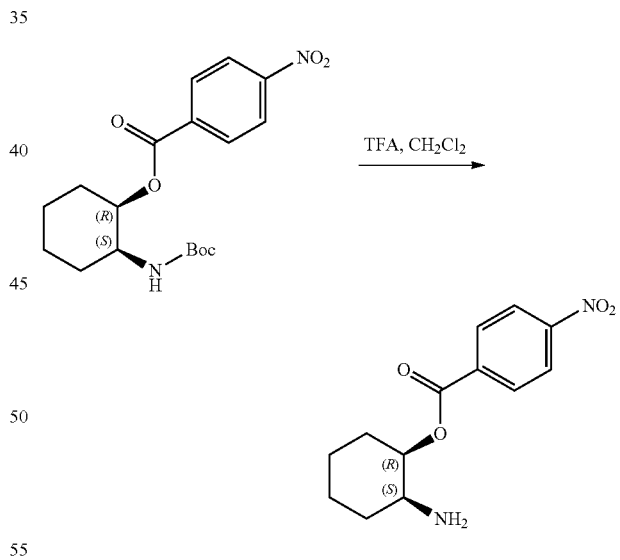

To a solution of 3-(5-bromo-1-oxo-isoindolin-2-yl)-1-(2-trimethylsilylethoxymethyl)piperidine-2,6-dione (1 eq) in dioxane (0.4 M), was added BPD (2 eq) and KOAc (5 eq). Pd$_2$(dba)$_3$ (0.03 eq) was added in portions at 20° C. under N$_2$. The mixture was stirred at 100° C. for 12 hours under N$_2$. The mixture was cooled to 20° C. THF (to make a 0.36 M solution), water (to make a 0.36 M solution), and sodium 3-oxidodioxaborirane tetrahydrate (2 eq) was added and the mixture was stirred at 25° C. for 4 hours. The reaction mixture was poured into water and extracted with ethyl acetate (3×). The combined organic phases were washed with saturated brine, dried over anhydrous Na$_2$SO$_4$, and concentrated in vacuum to give a residue. The residue was purified by silica gel chromatography (10% to 20% ethyl acetate in petroleum ether) to give 3-(5-hydroxy-1-oxo-isoindolin-2-yl)-1-(2-trimethylsilylethoxymethyl)piperidine-2,6-dione. $^1$H NMR (400 MHz, $d_6$-DMSO) δ 0.02 (s, 9H), 0.77-0.89 (m, 2H), 1.95-2.06 (m, 1H), 2.34 (qd, J=13.24, 4.32 Hz, 1H), 2.70-2.87 (m, 1H), 2.95-3.17 (m, 1H), 3.43-3.60 (m, 2H), 4.12-4.21 (m, 1H), 4.36 (d, J=16.88 Hz, 1H), 5.04 (q, J=9.67 Hz, 2H), 5.17 (dd, J=13.45, 5.07 Hz, 1H), 6.83-7.00 (m, 2H), 7.54 (d, J=8.25 Hz, 1H), 10.19 (s, 1H).

To a solution of (1R,2S)-2-((tert-butoxycarbonyl)amino) cyclohexyl 4-nitrobenzoate (1 eq) in DCM (0.3 M), was added TFA (9.23 eq) at 20° C. The reaction was stirred at 20° C. for 12 hours. The mixture was concentrated in vacuo to give a residue. The residue was triturated with ethyl acetate for 12 hours. After filtration, the mother liquor was concentrated under reduced pressure to give a residue. The residue was triturated with 1:2 v/v ethyl acetate:TBME, and the precipitated solid was collected by filtration, then triturated by CH$_2$Cl$_2$. The solid was collected by filtration and dried under reduced pressure to give [(1R,2S)-2-aminocyclohexyl] 4-nitrobenzoate·TFA. $^1$H NMR (400 MHz, d₆-DMSO) δ ppm 1.34-1.54 (m, 3H), 1.61-1.91 (m, 4H), 1.96-2.09 (m, 1H), 3.48 (br t, J=6.19 Hz, 1H), 5.25-5.38 (m, 1H), 5.75 (s, 3H), 8.29-8.40 (m, 4H).

Step 6:

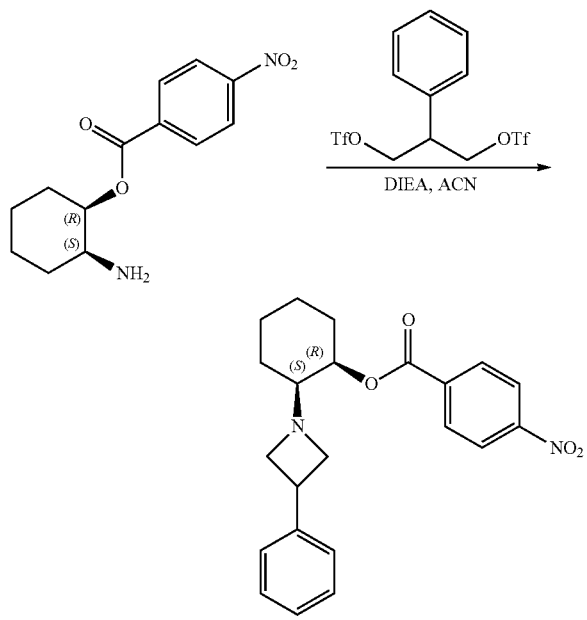

To a solution of 2-phenylpropane-1,3-diol (1 eq) in MeCN (0.35 M), was slowly added Tf₂O (2.1 eq) over 20 minutes at −20° C. DIEA (2.5 eq) was added dropwise over 20 min. The mixture was stirred for 30 minutes. A solution of [(1R,2S)-2-aminocyclohexyl] 4-nitrobenzoate·TFA (1 eq) and DIEA (3.5 eq) in MeCN (1.0 M) was added dropwise. The reaction was stirred at 70° C. for 12 hours. The mixture was concentrated under reduced pressure to give a residue. The residue was triturated with EtOAc and filtered. The filtrate was concentrated under reduced pressure to give a residue. The residue was purified by silica gel chromatography (10% to 50% ethyl acetate in petroleum ether) to give [(1R,2S)-2-(3-phenylazetidin-1-yl)cyclohexyl] 4-nitrobenzoate. ¹H NMR (400 MHz, d₆-DMSO) δ 1.29-1.38 (m, 1H), 1.47-1.65 (m, 5H), 1.66-1.77 (m, 1H), 1.92-1.98 (m, 1H), 2.46 (br d, J=7.50 Hz, 1H), 3.01-3.19 (m, 2H), 3.43-3.71 (m, 3H), 5.20-5.30 (m, 1H), 7.10-7.34 (m, 5H), 8.15-8.42 (m, 4H).

Step 7:

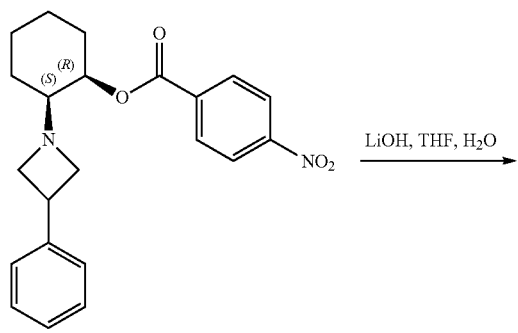

-continued

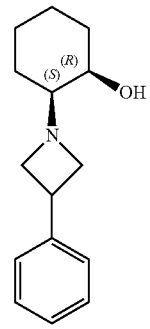

To a solution of [(1R,2S)-2-(3-phenylazetidin-1-yl)cyclohexyl] 4-nitrobenzoate (1 eq) in THF (0.35 M), was added an aqueous solution of lithium hydroxide monohydrate (2.0 M, 6.04 eq). The mixture was stirred at 20° C. for 12 hours. The organic phase was separated and the aqueous layer was extracted with THF/TBME (1 L, 1:1, v/v). The combined organic phases were concentrated under reduced pressure to give a residue. The residue was purified by silica gel chromatography (10% to 50% ethyl acetate in petroleum ether) to give (1R,2S)-2-(3-phenylazetidin-1-yl)cyclohexanol.

Step 8:

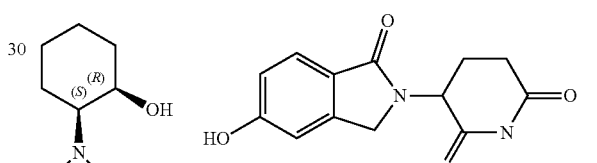

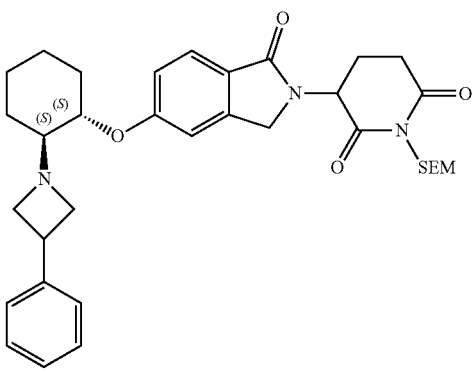

To a solution of (1R,2S)-2-(3-phenylazetidin-1-yl)cyclohexanol (1 eq), PPh₃ (1.59 eq), 3-(5-hydroxy-1-oxo-isoindolin-2-yl)-1-(2-trimethylsilylethoxymethyl)piperidine-2,6-dione (0.66 eq) in anhydrous toluene (0.2 M), was added DIAD (1.49 eq) dropwise at 0° C. The mixture was warmed to 20° C. and stirred for 12 hours. The mixture was filtered, and the filtrate was concentrated under reduced pressure to give a residue. The residue was purified by silica gel chromatography (10% to 50% ethyl acetate in petroleum ether) to give 3-(1-oxo-5-((((1S,2S)-2-(3-phenylazetidin-1yl)cyclohexyl)oxy)isoindolin-2-yl)-1-((2-(trimethylsilyl)ethoxy)methyl)piperidine-2,6-dione.

Step 9:

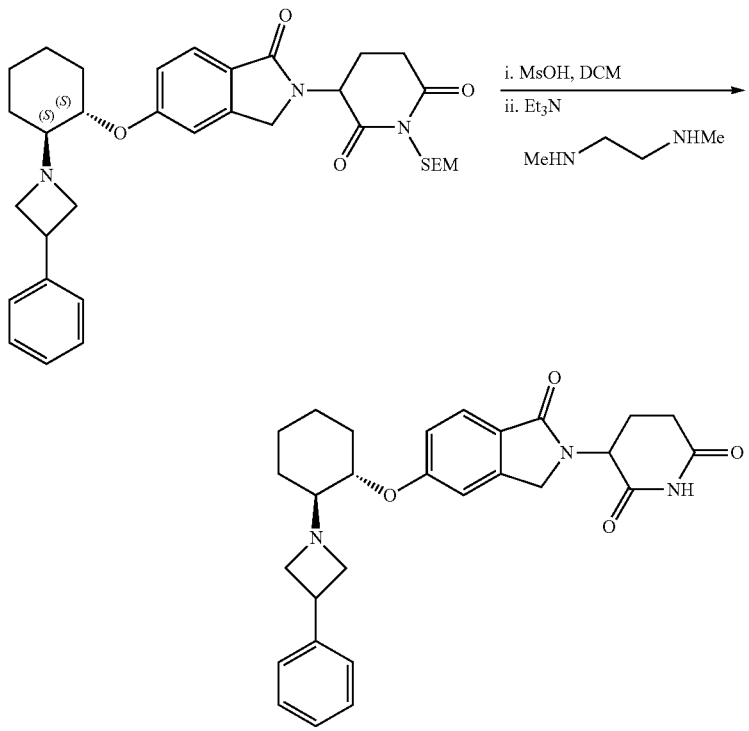

To a solution of 3-(1-oxo-5-(((1S,2S)-2-(3-phenylazetidin-1-yl)cyclohexyl)oxy)isoindolin-2-yl)-1-((2-(trimethylsilyl)ethoxy)methyl)piperidine-2,6-dione (1 eq) in DCM (0.2 M), was added MsOH (4 eq). The mixture was stirred for 2 hours at 20° C. $N^1,N^2$-dimethylethane-1,2-diamine (1.2 eq) and TEA (8 eq) was added. The mixture was stirred for 2 hours. The reaction mixture was filtered, and the filtrate concentrated in vacuo to give a residue. The residue was purified by prep-HPLC to give 3-(1-oxo-5-(((1S,2S)-2-(3-phenylazetidin-1-yl)cyclohexyl)oxy)isoindolin-2-yl)piperidine-2,6-dione. $^1$H NMR (400 MHz, d$_6$-DMSO) δ 10.96 (s, 1H), 7.60 (d, J=8.4 Hz, 1H), 7.38-7.25 (m, 4H), 7.23-7.14 (m, 2H), 7.04 (br d, J=8.4 Hz, 1H), 5.06 (dd, J=4.9, 13.3 Hz, 1H), 4.45-4.17 (m, 3H), 3.82-3.46 (m, 3H), 3.30-3.14 (m, 2H), 2.96-2.82 (m, 1H), 2.59 (br d, J=17.0 Hz, 1H), 2.48-2.27 (m, 2H), 2.09-1.92 (m, 2H), 1.92-1.80 (m, 1H), 1.66 (br s, 2H), 1.45-1.33 (m, 2H), 1.32-1.07 (m, 2H).

Additional compounds set forth in Table 2 were prepared following the procedures set forth above, with the exception that the amine was replaced in the above examples with an amine depicted in the final product.

TABLE 2

| # | Nomenclature | $^1$H NMR/MS |
|---|---|---|
| 1 | 3-(1-oxo-5-(((1S,2S)-2-(3-phenylpyrrolidin-1-yl)cyclohexyl)oxy)isoindolin-2-yl)piperidine-2,6-dione | (400 MHZ, d$_4$-MeOD) δ 1.22-1.28 (m, 1H), 1.37-1.58 (m, 3H), 1.66-1.80 (m, 1H), 1.84 (br s, 1H), 1.99 (br s, 1H), 2.06-2.25 (m, 2H), 2.36 (br s, 2H), 2.42-2.55 (m, 2H), 2.74-2.82 (m, 1H), 2.85-3.03 (m, 1H), 3.33-3.40 (m, 1H), 3.43-3.65 (m, 2H), 3.70-3.87 (m, 2H), 4.39-4.54 (m, 2H), 4.69-4.80 (m, 1H), 5.13 (br dd, J = 13.29, 5.19 Hz, 1H), 7.19-7.53 (m, 7H), 7.74-7.79 (m, 1H) |
| 10 | (S)-3-(1-oxo-5-(((1S,2S)-2-(3-phenylazetidin-1-yl)cyclohexyl)oxy)isoindolin-2-yl)piperidine-2,6-dione | (400 MHZ, d$_6$-DMSO) δ 1.07-1.19 (m, 1 H) 1.20-1.32 (m, 1 H) 1.34-1.44 (m, 2 H) 1.65 (br s, 2 H) 1.78-1.89 (m, 1 H) 1.92-2.05 (m, 2 H) 2.35-2.45 (m, 2 H) 2.55-2.63 (m, 1 H) 2.84-2.96 (m, 1 H) 3.12 (br s, 1 H) 3.26 (br d, J = 7.15 Hz, 1 H) 3.45-3.55 (m, 1 H) 3.62 (m, 2 H) 4.20-4.32 (m, 2 H) 4.33-4.42 (m, 1 H) 5.06 (m, 1 H) 7.04 (br d, J = 8.58 Hz, 1 H) 7.16-7.21 (m, 2 H) 7.26-7.34 (m, 4 H) 7.60 (d, J = 8.58 Hz, 1 H) 10.97 (s, 1 H). |
| 11 | 3-(1-oxo-5-(((1R,2R)-2-(3-phenylazetidin-1-yl)cyclohexyl)oxy)isoindolin-2-yl)piperidine-2,6-dione | (400 MHZ, d$_6$-DMSO) δ 1.07-1.19 (m, 1 H) 1.20-1.32 (m, 1 H) 1.34-1.44 (m, 2 H) 1.65 (br s, 2 H) 1.78-1.89 (m, 1 H) 1.92-2.05 (m, 2 H) 2.35-2.45 (m, 2 H) 2.55-2.63 (m, 1 H) 2.84- |

TABLE 2-continued

| # | Nomenclature | ¹H NMR/MS |
|---|---|---|
| | | 2.96 (m, 1 H) 3.12 (br s, 1 H) 3.26 (br d, J = 7.15 Hz, 1 H) 3.45-3.55 (m, 1 H) 3.62 (m, 2 H) 4.20-4.32 (m, 2 H) 4.33-4.42 (m, 1 H) 5.06 (m, 1 H) 7.04 (br d, J = 8.58 Hz, 1 H) 7.16-7.21 (m, 2 H) 7.26-7.34 (m, 4 H) 7.60 (d, J = 8.58 Hz, 1 H) 10.97 (s, 1 H) |
| 14 | (S)-3-(1-oxo-5-(((1R,2R)-2-(3-phenylazetidin-1-yl)cyclohexyl)oxy)isoindolin-2-yl)piperidine-2,6-dione | m/z (ESI⁺) 474.1 (M + H)⁺ |
| 15 | 3-(5-(((1S,2S)-2-(3-(2-chlorophenyl)azetidin-1-yl)cyclohexyl)oxy)-1-oxoisoindolin-2-yl)piperidine-2,6-dione | (400 MHZ, d₄-methanol) δ 1.31-1.57 (m, 4H), 1.81-1.98 (m, 2H), 2.14-2.57 (m, 4H), 2.74-2.99 (m, 2H), 3.62 (br s, 1H), 4.19-4.72 (m, 8H), 5.09-5.19 (m, 1H), 7.14-7.28 (m, 2H), 7.31-7.51 (m, 4H), 7.74-7.81 (m, 1H) |
| 19 | 3-(5-(((1S,2S)-2-(3-(2-methoxyphenyl)azetidin-1-yl)cyclohexyl)oxy)-1-oxoisoindolin-2-yl)piperidine-2,6-dione | (400 MHZ, d₆-DMSO) δ 1.14-1.50 (m, 4H), 1.66-1.85 (m, 2H), 1.93-2.04 (m, 1H), 2.13 (br s, 1H), 2.19 (br s, 1H), 2.31-2.46 (m, 2H), 2.53-2.70 (m, 2H), 2.85-2.98 (m, 1H), 3.57-3.72 (m, 2H), 3.73-3.85 (m, 3H), 4.02-4.14 (m, 1H), 4.19-4.57 (m, 5H), 5.08 (dd, J = 13.26, 5.00 Hz, 1H), 6.96-7.07 (m, 2H), 7.12-7.21 (m, 1H), 7.22-7.43 (m, 3H), 7.65-7.72 (m, 1H), 10.40 (br s, 1H), 10.97 (s, 1H) |
| 23 | 3-(5-(((1S,2S)-2-(3-(3,4-difluorophenyl)azetidin-1-yl)cyclohexyl)oxy)-1-oxoisoindolin-2-yl)piperidine-2,6-dione | (400 MHZ, d₄-methanol) δ 1.20-1.52 (m, 4H), 1.68-1.85 (m, 2H), 1.94-1.98 (m, 1H), 1.99-2.03 (m, 1H), 2.06-2.16 (m, 1H), 2.22 (br s, 1H), 2.31-2.47 (m, 2H), 2.56-2.70 (m, 2H), 2.85-2.97 (m, 1H), 3.77 (br d, J = 7.67 Hz, 1H), 4.22-4.56 (m, 1H), 4.22-4.56 (m, 5H), 5.08 (dd, J = 13.37, 4.82 Hz, 1H), 7.11-7.20 (m, 1H), 7.29 (br d, J = 7.23 Hz, 2H), 7.40-7.51 (m, 1H), 7.56-7.75 (m, 2H), 10.43 (br s, 1H), 10.97 (s, 1H) |
| 27 | 3-(5-(((1S,2S)-2-(3-(2-fluorophenyl)azetidin-1-yl)cyclohexyl)oxy)-1-oxoisoindolin-2-yl)piperidine-2,6-dione | (400 MHZ, d₆-DMSO) δ 1.17-1.51 (m, 5 H) 1.69-1.82 (m, 2 H) 1.98 (br dd, J = 11.13, 4.75 Hz, 1 H) 2.09-2.26 (m, 3 H) 2.86-2.95 (m, 1 H) 3.64-3.77 (m, 1 H) 4.07-4.46 (m, 6 H) 4.48-4.56 (m, 2 H) 5.04-5.13 (m, 1 H) 7.15-7.33 (m, 4 H) 7.36-7.44 (m, 1 H) 7.56 (br t, J = 7.25 Hz, 1 H) 7.67 (br d, J = 7.88 Hz, 1 H) 10.41-10.55 (m, 1 H) 10.98 (s, 1 H) |
| 3 | 3-(5-(((1S,2S)-2-(3-(4-(1H-pyrazol-1-yl)phenyl)azetidin-1-yl)cyclohexyl)oxy)-1-oxoisoindolin-2-yl)piperidine-2,6-dione | (400 MHZ, d₆-DMSO) δ 10.98 (br s, 1H), 10.56-10.19 (m, 1H), 8.92-8.42 (m, 1H), 7.95-7.46 (m, 5H), 7.36-6.93 (m, 2H), 6.64-6.47 (m, 1H), 5.11-5.02 (m, 1H), 4.63-4.17 (m, 5H), 4.12-3.96 (m, 1H), 3.83-3.70 (m, 1H), 3.01-2.81 (m, 1H), 2.69-2.53 (m, 3H), 2.46-2.11 (m, 4H), 2.03-1.91 (m, 1H), 1.87-1.68 (m, 2H), 1.56-1.13 (m, 4H) |
| 35 | 3-(1-oxo-5-(((1S,2S)-2-(3-(3-(trifluoromethoxy)phenyl)azetidin-1-yl)cyclohexyl)oxy)isoindolin-2-yl)piperidine-2,6-dione | (400 MHZ, d₆-DMSO) δ 10.96 (s, 1H), 8.19 (s, 1H), 7.60 (d, J = 8.4 Hz, 1H), 7.47-7.35 (m, 2H), 7.31 (s, 1H), 7.21-7.15 (m, 2H), 7.04 (br d, J = 8.4 Hz, 1H), 5.06 (dd, J = 5.0, 13.3 Hz, 1H), 4.41-4.20 (m, 3H), 3.68-3.55 (m, 3H), 3.15 (br t, J = 6.3 Hz, 3H), 2.97-2.84 (m, 1H), 2.59 (br d, J = 17.4 Hz, 1H), 2.37 (br d, J = 13.5 Hz, 1H), 2.06-1.93 (m, 2H), 1.83 (br d, J = 12.0 Hz, 1H), 1.65 (br s, 2H), 1.44-1.34 (m, 2H), 1.29-1.04 (m, 2H). |
| 36 | 3-(1-oxo-5-(((1S,2S)-2-(3-(2-(trifluoromethoxy)phenyl)azetidin-1-yl)cyclohexyl)oxy)isoindolin-2-yl)piperidine-2,6-dione | (400 MHZ, d₆-DMSO) δ 10.97 (s, 1H), 8.19 (s, 1H), 7.69-7.53 (m, 2H), 7.44-7.33 (m, 2H), 7.31-7.26 (m, 1H), 7.18 (s, 1H), 7.04 (br d, J = 8.3 Hz, 1H), 5.07 (dd, J = 5.0, 13.2 Hz, 1H), 4.44-4.34 (m, 1H), 4.34-4.22 (m, 2H), 3.79-3.61 (m, 3H), 2.99-2.81 (m, 1H), 2.60 (br d, J = 17.8 Hz, 1H), 2.55-2.52 (m, 3H), 2.41 (br d, J = 7.0 Hz, 2H), 2.09-1.92 (m, 2H), 1.84 (br d, J = 11.1 Hz, 1H), 1.66 (br d, J = 8.1 Hz, 2H), 1.44-1.32 (m, 2H), 1.26 (br d, J = 12.0 Hz, 1H), 1.19-1.05 (m, 1H). |
| 37 | 5-chloro-2-(1-(((1R,2S)-2-((2-(2,6-dioxopiperidin-3-yl)-1-oxoisoindolin-5-yl)oxy)cyclohexyl)azetidin-3-yl)benzonitrile Diastereomer 1 | m/z (ESI⁺) 533.1 (M + H)⁺ |

TABLE 2-continued

| # | Nomenclature | ¹H NMR/MS |
|---|---|---|
| 38 | 5-chloro-2-(1-((1S,2S)-2-((2-(2,6-dioxopiperidin-3-yl)-1-oxoisoindolin-5-yl)oxy)cyclohexyl)azetidin-3-yl)benzonitrile Diastereomer 2 | m/z (ESI⁺) 533.1 (M + H)⁺ |
| 39 | 5-chloro-2-(1-((1S,2S)-2-((2-(2,6-dioxopiperidin-3-yl)-1-oxoisoindolin-5-yl)oxy)cyclohexyl)azetidin-3-yl)benzonitrile Diastereomer 3 | m/z (ESI⁺) 533.1 (M + H)⁺ |
| 40 | 5-chloro-2-(1-((1S,2R)-2-((2-(2,6-dioxopiperidin-3-yl)-1-oxoisoindolin-5-yl)oxy)cyclohexyl)azetidin-3-yl)benzonitrile Diastereomer 4 | m/z (ESI⁺) 533.1 (M + H)⁺ |
| 41 | 3-(4-chloro-1-oxo-5-(((1S,2S)-2-(3-phenylazetidin-1-yl)cyclohexyl)oxy)isoindolin-2-yl)piperidine-2,6-dione Diastereomer 1 | m/z (ESI⁺) 508.1 (M + H)⁺ |
| 42 | 3-(4-chloro-1-oxo-5-(((1S,2S)-2-(3-phenylazetidin-1-yl)cyclohexyl)oxy)isoindolin-2-yl)piperidine-2,6-dione Diastereomer 2 | m/z (ESI⁺) 508.1 (M+H)⁺ |
| 43 | 2-(1-((1R,2R)-2-((2-(2,6-dioxopiperidin-3-yl)-1-oxoisoindolin-5-yl)oxy)cyclohexyl)azetidin-3-yl)-5-fluorobenzonitrile Diastereomer 1 | m/z (ESI⁺) 517.1 (M + H)⁺ |
| 44 | 2-(1-((1S,2S)-2-((2-(2,6-dioxopiperidin-3-yl)-1-oxoisoindolin-5-yl)oxy)cyclohexyl)azetidin-3-yl)-5-fluorobenzonitrile Diastereomer 2 | m/z (ESI⁺) 517.1 (M + H)⁺ |
| 45 | 2-(1-((1S,2S)-2-((2-(2,6-dioxopiperidin-3-yl)-1-oxoisoindolin-5-yl)oxy)cyclohexyl)azetidin-3-yl)-5-fluorobenzonitrile Diastereomer 3 | m/z (ESI⁺) 517.1 (M + H)⁺ |
| 46 | 2-(1-((1S,2R)-2-((2-(2,6-dioxopiperidin-3-yl)-1-oxoisoindolin-5-yl)oxy)cyclohexyl)azetidin-3-yl)-5-fluorobenzonitrile Diastereomer 4 | m/z (ESI⁺) 517.1 (M + H)⁺ |
| 47 | 3-chloro-4-(1-((1S,2S)-2-((2-(2,6-dioxopiperidin-3-yl)-1-oxoisoindolin-5-yl)oxy)cyclohexyl)azetidin-3-yl)benzonitrile Diastereomer 1 | m/z (ESI⁺) 533.3 (M + H)⁺ |
| 48 | 3-chloro-4-(1-((1S,2S)-2-((2-(2,6-dioxopiperidin-3-yl)-1-oxoisoindolin-5-yl)oxy)cyclohexyl)azetidin-3-yl)benzonitrile Diastereomer 2 | m/z (ESI⁺) 533.3 (M + H)⁺ |
| 49 | 3-chloro-4-(1-((1S,2R)-2-((2-(2,6-dioxopiperidin-3-yl)-1-oxoisoindolin-5-yl)oxy)cyclohexyl)azetidin-3-yl)benzonitrile Diastereomer 3 | m/z (ESI⁺) 533.3 (M + H)⁺ |
| 50 | 3-(5-(((1S,2S)-2-(3-(4-fluorophenyl)azetidin-1-yl)cyclohexyl)oxy)-1-oxoisoindolin-2-yl)piperidine-2,6-dione Diastereomer 1 | (400 MHZ, d₆-DMSO) δ 10.96 (s, 1H), 7.60 (d, J = 8.4 Hz, 1H), 7.38-7.33 (m, 2H), 7.17 (d, J = 1.6 Hz, 1H), 7.14-7.08 (m, 2H), 7.03 (dd, J = 2.2, 8.4 Hz, 1H), 5.06 (dd, J = 5.1, 13.3 Hz, 1H), 4.41-4.33 (m, 1H), 4.31-4.21 (m, 2H), 3.67-3.56 (m, 2H), 3.53-3.48 (m, 1H), 3.24-3.20 (m, 1H), 3.10 (t, J = 6.8 Hz, 1H), 2.95-2.84 (m, 1H), 2.60 (br d, J = 2.9 Hz, 2H), 2.43 (br d, J = 2.3 Hz, 1H), 2.03-1.93 (m, 1H), 1.83 (br dd, J = 2.5, 9.4 Hz, 1H), 1.65 (br d, J = 4.1 Hz, 2H), 1.43-1.35 (m, 2H), 1.23 (br s, 1H), 1.15-1.09 (m, 1H). |
| 51 | 3-(5-(((1S,2S)-2-(3-(4-fluorophenyl)azetidin-1-yl)cyclohexyl)oxy)-1-oxoisoindolin-2-yl)piperidine-2,6-dione Diastereomer 2 | (400 MHZ, d₆-DMSO) δ 11.06-10.85 (m, 1H), 7.60 (d, J = 8.5 Hz, 1H), 7.38-7.33 (m, 2H), 7.17 (d, J = 1.5 Hz, 1H), 7.14-7.08 (m, 2H), 7.03 (dd, J = 2.0, 8.5 Hz, 1H), 5.06 (dd, J = 5.0, 13.5 Hz, 1H), 4.40-4.31 (m, 1H), 4.30-4.22 (m, 2H), 3.66-3.62 (m, 1H), 3.61-3.56 (m, |

TABLE 2-continued

| # | Nomenclature | ¹H NMR/MS |
|---|---|---|
| | | 1H), 3.23-3.20 (m, 1H), 3.17 (d, J = 5.0 Hz, 1H), 3.10 (br t, J = 6.8 Hz, 1H), 2.96-2.84 (m, 2H), 2.60 (br d, J = 2.5 Hz, 1H), 2.43-2.37 (m, 1H), 1.99 (br d, J = 5.5 Hz, 1H), 1.83 (br d, J = 11.5 Hz, 1H), 1.65 (br s, 2H), 1.42-1.34 (m, 2H), 1.28-1.22 (m, 2H), 1.17-1.09 (m, 1H). |
| 52 | 3-(6-fluoro-1-oxo-5-(((1S,2S)-2-(3-phenylazetidin-1-yl)cyclohexyl)oxy)isoindolin-2-yl)piperidine-2,6-dione Diastereomer 1 | m/z (ESI⁺) 492.3 (M + H)⁺ |
| 53 | 3-(6-fluoro-1-oxo-5-(((1S,2S)-2-(3-phenylazetidin-1-yl)cyclohexyl)oxy)isoindolin-2-yl)piperidine-2,6-dione Diastereomer 2 | m/z (ESI⁺) 492.3 (M + H)⁺ |
| 54 | 3-(1-oxo-5-(((1R,2R)-2-(2-phenylazetidin-1-yl)cyclohexyl)oxy)isoindolin-2-yl)piperidine-2,6-dione | m/z (ESI⁺) 474.1 (M + H)⁺ |
| 55 | 3-(1-oxo-5-(((1S,2S)-2-(2-phenylazetidin-1-yl)cyclohexyl)oxy)isoindolin-2-yl)piperidine-2,6-dione | m/z (ESI⁺) 474.1 (M + H)⁺ |
| 56 | 3-(1-oxo-5-(((1S,2R)-2-(2-phenylazetidin-1-yl)cyclohexyl)oxy)isoindolin-2-yl)piperidine-2,6-dione | m/z (ESI⁺) 474.1 (M + H)⁺ |
| 57 | 3-(5-(((1S,2S)-2-(3-(2,4-difluorophenyl)azetidin-1-yl)cyclohexyl)oxy)-1-oxoisoindolin-2-yl)piperidine-2,6-dione | (400 MHZ, d₆-DMSO) δ 10.96 (s, 1H), 7.61 (d, J = 8.4 Hz, 1H), 7.52-7.44 (m, 1H), 7.23-6.97 (m, 4H), 5.06 (br dd, J = 4.6, 13.2 Hz, 1H), 4.43-4.33 (m, 1H), 4.32-4.21 (m, 2H), 3.64 (td, J = 3.8, 7.6 Hz, 3H), 3.27 (br s, 1H), 3.13 (br s, 1H), 2.97-2.84 (m, 1H), 2.59 (br d, J = 16.8 Hz, 2H), 2.40 (br s, 1H), 1.98 (br d, J = 5.6 Hz, 2H), 1.82 (br d, J = 11.3 Hz, 1H), 1.64 (br s, 2H), 1.37 (br s, 2H), 1.25 (br d, J = 10.7 Hz, 1H), 1.17-1.01 (m, 1H). |
| 58 | 3-(1-oxo-5-(((1S,2S)-2-(3-(4-(trifluoromethyl)phenyl)azetidin-1-yl)cyclohexyl)oxy)isoindolin-2-yl)piperidine-2,6-dione | m/z (ESI⁺) 542.1 (M + H)⁺ |
| 59 | 3-(1-oxo-5-(((1R,2S)-2-(3-(4-(trifluoromethyl)phenyl)azetidin-1-yl)cyclohexyl)oxy)isoindolin-2-yl)piperidine-2,6-dione | m/z (ESI⁺) 542.1 (M + H)⁺ |
| 60 | Rac-3-(1-oxo-5-(((trans)-2-(3-(4-(trifluoromethoxy)phenyl)azetidin-1-yl)cyclohexyl)oxy)isoindolin-2-yl)piperidine-2,6-dione | m/z (ESI⁺) 558.1 (M + H)⁺ |
| 61 | Rac-3-(1-oxo-5-((((cis)-2-(3-(4-(trifluoromethoxy)phenyl)azetidin-1-yl)cyclohexyl)oxy)isoindolin-2-yl)piperidine-2,6-dione | m/z (ESI⁺) 558.1 (M + H)⁺ |
| 62 | Rac-3-(1-oxo-5-(((trans)-2-(3-(3-(trifluoromethyl)phenyl)azetidin-1-yl)cyclohexyl)oxy)isoindolin-2-yl)piperidine-2,6-dione | (400 MHZ, d₄-methanol) 1.12-1.48 (m, 4H), 1.80 (br d, J = 9.88 Hz, 1H), 2.05 (br d, J = 13.26 Hz, 1H), 2.10-2.23 (m, 2H), 2.47 (qd, J = 13.17, 4.63 Hz, 1H), 2.68-2.80 (m, 2H), 2.83-2.95 (m, 1H), 3.46-3.54 (m, 1H), 3.64-3.73 (m, 1H), 3.81 (quin, J = 7.85 Hz, 1H), 3.93 (br s, 2H), 4.31-4.52 (m, 3H), 4.57-4.59 (m, 1H), 5.07-5.17 (m, 1H), 7.09 (dd, J = 8.50, 2.13 Hz, 1H), 7.16 (s, 1H), 7.49-7.56 (m, 2H), 7.59 (s, 2H), 7.71 (d, J = 8.38 Hz, 1H). |
| 63 | Rac-3-(1-oxo-5-((((cis)-2-(3-(3-(trifluoromethyl)phenyl)azetidin-1-yl)cyclohexyl)oxy)isoindolin-2-yl)piperidine-2,6-dione | (400 MHZ, d₄-methanol) 1.26-1.60 (m, 4H), 1.72-1.85 (m, 2H), 2.08-2.24 (m, 2H), 2.48 (qd, J = 13.03, 4.57 Hz, 1H), 2.68 (s, 1H), 2.73-2.82 (m, 1H), 2.86-3.06 (m, 1H), 3.39-3.42 (m, 1H), 3.80-3.90 (m, 2H), 4.38-4.51 (m, 2H), 4.58 (s, 3H), 4.79-4.80 (m, 1H), 5.13 (br d, J = 5.25 Hz, 1H), 7.16 (dd, J = 8.44, 1.94 Hz, 1H), 7.20 (s, 1H), 7.47-7.54 (m, 2H), 7.55-7.61 (m, 2H), 7.72 (d, J = 8.50 Hz, 1H). |
| 64 | 3-(5-(((1S,2S)-2-(3-(2,3-difluorophenyl)azetidin-1-yl)cyclohexyl)oxy)-1-oxoisoindolin-2-yl)piperidine-2,6-dione | m/z (ESI⁺) 510.1 (M + H)⁺ |

TABLE 2-continued

| # | Nomenclature | $^1$H NMR/MS |
|---|---|---|
| 65 | 3-(4-fluoro-1-oxo-5-((((1S,2S)-2-(3-phenylazetidin-1-yl)cyclohexyl)oxy)isoindolin-2-yl)piperidine-2,6-dione Diastereomer 1 | m/z (ESI$^+$) 492.1 (M + H)$^+$ |
| 66 | 3-(4-fluoro-1-oxo-5-((((1S,2S)-2-(3-phenylazetidin-1-yl)cyclohexyl)oxy)isoindolin-2-yl)piperidine-2,6-dione Diastereomer 2 | m/z (ESI$^+$) 492.1 (M + H)$^+$ |
| 67 | 3-(1-oxo-5-((2-(3-(3-(trifluoromethoxy)phenyl)azetidin-1-yl)cyclohexyl)oxy)isoindolin-2-yl)piperidine-2,6-dione | (400 MHZ, d$_6$-DMSO) δ 10.96 (s, 1H), 8.19 (s, 1H), 7.60 (d, J = 8.4 Hz, 1H), 7.47-7.35 (m, 2H), 7.31 (s, 1H), 7.21-7.15 (m, 2H), 7.04 (br d, J = 8.4 Hz, 1H), 5.06 (dd, J = 5.0, 13.3 Hz, 1H), 4.41-4.20 (m, 3H), 3.68-3.55 (m, 3H), 3.15 (br t, J = 6.3 Hz, 3H), 2.97-2.84 (m, 1H), 2.59 (br d, J = 17.4 Hz, 1H), 2.37 (br d, J = 13.5 Hz, 1H), 2.06-1.93 (m, 2H), 1.83 (br d, J = 12.0 Hz, 1H), 1.65 (br s, 2H), 1.44-1.34 (m, 2H), 1.29-1.04 (m, 2H). |
| 68 | 3-(1-oxo-5-((2-(3-(2-(trifluoromethoxy)phenyl)azetidin-1-yl)cyclohexyl)oxy)isoindolin-2-yl)piperidine-2,6-dione | (400 MHZ, d$_6$-DMSO) δ 10.97 (s, 1H), 8.19 (s, 1H), 7.69-7.53 (m, 2H), 7.44-7.33 (m, 2H), 7.31-7.26 (m, 1H), 7.18 (s, 1H), 7.04 (br d, J = 8.3 Hz, 1H), 5.07 (dd, J = 5.0, 13.2 Hz, 1H), 4.44-4.34 (m, 1H), 4.34-4.22 (m, 2H), 3.79-3.61 (m, 3H), 2.99-2.81 (m, 1H), 2.60 (br d, J = 17.8 Hz, 1H), 2.55-2.52 (m, 3H), 2.41 (br d, J = 7.0 Hz, 2H), 2.09-1.92 (m, 2H), 1.84 (br d, J = 11.1 Hz, 1H), 1.66 (br d, J = 8.1 Hz, 2H), 1.44-1.32 (m, 2H), 1.26 (br d, J = 12.0 Hz, 1H), 1.19-1.05 (m, 1H). |
| 69 | 3-(1-oxo-5-((2-(3-(2-(trifluoromethyl)phenyl)azetidin-1-yl)cyclohexyl)oxy)isoindolin-2-yl)piperidine-2,6-dione | (400 MHZ, d$_6$-DMSO) δ 10.98 (s, 1H), 10.85-10.54 (m, 1H), 7.92 (br d, J = 7.9 Hz, 1H), 7.84-7.73 (m, 2H), 7.67 (d, J = 8.3 Hz, 1H), 7.58 (br t, J = 7.6 Hz, 1H), 7.30 (br s, 1H), 7.21-7.12 (m, 1H), 5.09 (dd, J = 5.0, 13.2 Hz, 1H), 4.70-4.46 (m, 3H), 4.45-4.18 (m, 5H), 3.75 (br s, 1H), 2.99-2.82 (m, 1H), 2.53 (d, J = 1.8 Hz, 2H), 2.28-2.08 (m, 2H), 2.04-1.93 (m, 1H), 1.88-1.67 (m, 2H), 1.45 (br d, J = 12.0 Hz, 1H), 1.38-1.20 (m, 3H). |
| 70 | Rac-2-(1-((cis)-2-((2-(2,4-dioxo-3-azabicyclo[3.1.1]heptan-1-yl)-1-oxoisoindolin-5-yl)oxy)cyclopentyl)azetidin-3-yl)-5-fluorobenzonitrile | m/z (ESI$^+$) 515.1 (M + H)$^+$ |
| 71 | Rac-2-(1-((trans)-2-((2-(2,4-dioxo-3-azabicyclo[3.1.1]heptan-1-yl)-1-oxoisoindolin-5-yl)oxy)cyclopentyl)azetidin-3-yl)-5-fluorobenzonitrile | m/z (ESI$^+$) 515.1 (M + H)$^+$ |
| 72 | 3-(1-oxo-5-((((1S,2S)-2-(4-phenylpiperidin-1-yl)cyclopentyl)oxy)isoindolin-2-yl)piperidine-2,6-dione | (400 MHZ, d$_6$-DMSO) δ 10.98 (s, 1H), 10.85-10.54 (m, 1H), 7.92 (br d, J = 7.9 Hz, 1H), 7.84-7.73 (m, 2H), 7.67 (d, J = 8.3 Hz, 1H), 7.58 (br t, J = 7.6 Hz, 1H), 7.30 (br s, 1H), 7.21-7.12 (m, 1H), 5.09 (dd, J = 5.0, 13.2 Hz, 1H), 4.70-4.46 (m, 3H), 4.45-4.18 (m, 5H), 3.75 (br s, 1H), 2.99-2.82 (m, 1H), 2.53 (d, J = 1.8 Hz, 2H), 2.28-2.08 (m, 2H), 2.04-1.93 (m, 1H), 1.88-1.67 (m, 2H), 1.45 (br d, J = 12.0 Hz, 1H), 1.38-1.20 (m, 3H). |
| 73 | 3-(5-((((1S,2S)-2-(3-(4-(1H-pyrazol-1-yl)phenyl)azetidin-1-yl)cyclopentyl)oxy)-1-oxoisoindolin-2-yl)piperidine-2,6-dione | (400 MHZ, d$_6$-DMSO) δ 10.97 (s, 1H), 10.53-10.18 (m, 1H), 9.27-8.92 (m, 1H), 8.68-8.37 (m, 1H), 7.87 (t, J = 8.7 Hz, 2H), 7.82-7.73 (m, 1H), 7.72-7.49 (m, 3H), 7.29-7.04 (m, 2H), 6.63-6.52 (m, 1H), 5.82 (s, 1H), 5.57-5.53 (m, 1H), 5.13-4.84 (m, 2H), 4.63-3.82 (m, 7H), 2.98-2.85 (m, 1H), 2.66-2.56 (m, 2H), 2.41-2.38 (m, 1H), 2.27-2.11 (m, 2H), 2.03-1.93 (m, 1H), 1.88-1.56 (m, 4H). |

TABLE 2-continued

| # | Nomenclature | $^1$H NMR/MS |
|---|---|---|
| 74 | Rac-3-chloro-4-(1-((trans)-2-((2-(2,6-dioxopiperidin-3-yl)-1-oxoisoindolin-5-yl)oxy)cyclohexyl)azetidin-3-yl)benzonitrile | (400 MHZ, d$_6$-DMSO) δ 11.00-10.92 (m, 1H), 10.57-10.17 (m, 1H), 8.80-8.71 (m, 1H), 8.33-8.17 (m, 1H), 7.82-7.73 (m, 1H), 7.70-7.62 (m, 1H), 7.34-7.24 (m, 1H), 7.22-7.09 (m, 1H), 5.15-4.69 (m, 2H), 4.64-3.97 (m, 7H), 3.84-3.61 (m, 1H), 2.96-2.86 (m, 1H), 2.64-2.57 (m, 1H), 2.41-2.36 (m, 1H), 2.29-2.04 (m, 2H), 2.03-1.92 (m, 1H), 1.88-1.68 (m, 2H), 1.54-1.17 (m, 4H). |
| 75 | Rac-3-chloro-4-(1-((cis)-2-((2-(2,6-dioxopiperidin-3-yl)-1-oxoisoindolin-5-yl)oxy)cyclohexyl)azetidin-3-yl)benzonitrile | (400 MHZ, d$_6$-DMSO) δ 10.97 (s, 1H), 10.19-9.94 (m, 1H), 8.79-8.71 (m, 1H), 8.24-8.19 (m, 1H), 7.82-7.74 (m, 1H), 7.72-7.66 (m, 1H), 7.31-7.27 (m, 1H), 7.22-7.14 (m, 1H), 5.13-5.04 (m, 1H), 5.03-4.90 (m, 1H), 4.60-4.07 (m, 7H), 3.84-3.70 (m, 1H), 2.96-2.85 (m, 1H), 2.63-2.57 (m, 1H), 2.43-2.36 (m, 1H), 2.13-1.94 (m, 2H), 1.92-1.76 (m, 2H), 1.70-1.57 (m, 1H), 1.53-1.25 (m, 4H). |
| 76 | Rac-3-(1-((cis)-2-((2-(2,6-dioxopiperidin-3-yl)-1-oxoisoindolin-5-yl)oxy)cyclohexyl)azetidin-3-yl)benzonitrile | m/z (ESI$^+$) 499.1 (M + H)$^+$ |
| 77 | Rac-3-(1-((cis)-2-((2-(2,4-dioxo-3-azabicyclo[3.1.1]heptan-1-yl)-1-oxoisoindolin-5-yl)oxy)cyclohexyl)azetidin-3-yl)benzonitrile | m/z (ESI$^+$) 511.1 (M + H)$^+$ |
|  | Rac-3-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile | m/z (ESI$^+$) 511.1 (M + H)$^+$ |
| 79 | 3-(1-oxo-5-(((1S,2S)-2-(4-phenylpiperidin-1-yl)cyclohexyl)oxy)isoindolin-2-yl)piperidine-2,6-dione | (400 MHZ, d$_6$-DMSO) δ 10.99 (s, 1H), 8.97 (br t, J = 7.6 Hz, 1H), 7.73 (d, J = 8.3 Hz, 1H), 7.38 (br s, 1H), 7.35-7.30 (m, 2H), 7.29-7.15 (m, 4H), 5.15-5.05 (m, 1H), 4.90-4.79 (m, 1H), 4.51-4.23 (m, 2H), 3.73-3.51 (m, 3H), 3.23-3.13 (m, 1H), 2.99-2.73 (m, 2H), 2.61 (br d, J = 17.5 Hz, 1H), 2.45-2.35 (m, 2H), 2.29-2.09 (m, 3H), 2.03-1.81 (m, 5H), 1.77-1.59 (m, 2H), 1.51-1.28 (m, 3H). |
| 80 | 3-(5-(((1S,2S)-2-(3-(3-(difluoromethoxy)phenyl)azetidin-1-yl)cyclohexyl)oxy)-1-oxoisoindolin-2-yl)piperidine-2,6-dione | (400 MHZ, d$_6$-DMSO) δ 10.96 (s, 1H), 8.17 (s, 1H), 7.60 (d, J = 8.5 Hz, 1H), 7.42-7.39 (m, 1H), 7.38-7.31 (m, 1H), 7.24-7.16 (m, 1H), 7.13 (s, 1H), 7.07-6.97 (m, 2H), 5.06 (dd, J = 5.3, 12.8 Hz, 1H), 4.42-4.33 (m, 1H), 4.32-4.21 (m, 2H), 3.67-3.57 (m, 2H), 3.56-3.48 (m, 1H), 3.26-3.23 (m, 1H), 3.18-3.09 (m, 1H), 2.96-2.84 (m, 1H), 2.63-2.54 (m, 1H), 2.40-2.34 (m, 1H), 2.05-1.93 (m, 2H), 1.87-1.79 (m, 1H), 1.66 (br dd, J = 4.0, 5.5 Hz, 2H), 1.45-1.33 (m, 2H), 1.32-1.21 (m, 1H), 1.18-1.07 (m, 1H). |
| 1 | 3-(5-(((1S,2S)-2-(3-(4-(difluoromethoxy)phenyl)azetidin-1-yl)cyclohexyl)oxy)-1-oxoisoindolin-2-yl)piperidine-2,6-dione | m/z (ESI$^+$) 540.1 (M + H)$^+$ |
| 82 | 1-(5-(((1S,2S)-2-(3-(2-chlorophenyl)azetidin-1-yl)cyclopentyl)oxy)-1-oxoisoindolin-2-yl)-3-azabicyclo[3.1.1]heptane-2,4-dione | m/z (ESI$^+$) 506.1 (M + H)$^+$ |
| 83 | Rac-5-chloro-2-(1-((trans)-2-((2-(2,6-dioxopiperidin-3-yl)-1-oxoisoindolin-5-yl)oxy)cyclopentyl)azetidin-3-yl)benzonitrile | m/z (ESI$^+$) 519.1 (M + H)$^+$ |
| 84 | Rac-5-chloro-2-(1-((cis)-2-((2-(2,6-dioxopiperidin-3-yl)-1-oxoisoindolin-5-yl)oxy)cyclopentyl)azetidin-3-yl)benzonitrile | m/z (ESI$^+$) 519.1 (M + H)$^+$ |
| 85 | 1-(5-(((1S,2S)-2-(3-(2-chloro-4-fluorophenyl)azetidin-1-yl)cyclohexyl)oxy)-1-oxoisoindolin-2-yl)-3-azabicyclo[3.1.1]heptane-2,4-dione | m/z (ESI$^+$) 538.1 (M + H)$^+$ |
| 86 | 1-(5-(((1S,2S)-2-(3-(2-chloro-4-fluorophenyl)azetidin-1-yl)cyclopentyl)oxy)-1-oxoisoindolin-2-yl)-3-azabicyclo[3.1.1]heptane-2,4-dione | m/z (ESI$^+$) 538.1 (M + H)$^+$ |

TABLE 2-continued

| # | Nomenclature | ¹H NMR/MS |
|---|---|---|
| 87 | 1-(5-(((1S,2S)-2-(3-(3-fluorophenyl)azetidin-1-yl)cyclopentyl)oxy)-1-oxoisoindolin-2-yl)-3-azabicyclo[3.1.1]heptane-2,4-dione | m/z (ESI⁺) 492.1 (M + H)⁺ |
| 88 | 3-(5-(((1S,2S)-2-(3-(3-fluorophenyl)azetidin-1-yl)cyclopentyl)oxy)-1-oxoisoindolin-2-yl)piperidine-2,6-dione | m/z (ESI⁺) 492.1 (M + H)⁺ |
| 89 | 1-(5-(((1S,2S)-2-(3-(3-fluorophenyl)azetidin-1-yl)cyclohexyl)oxy)-1-oxoisoindolin-2-yl)-3-azabicyclo[3.1.1]heptane-2,4-dione | m/z (ESI⁺) 492.1 (M + H)⁺ |
| 90 | Rac-4-(1-((cis)-2-((2-(2,4-dioxo-3-azabicyclo[3.1.1]heptan-1-yl)-1-oxoisoindolin-5-yl)oxy)cyclohexyl)azetidin-3-yl)-3-fluorobenzonitrile | (400 MHZ, d₆-DMSO) δ 10.96 (s, 1H), 8.17 (s, 1H), 7.60 (d, J = 8.5 Hz, 1H), 7.42-7.39 (m, 1H), 7.38-7.31 (m, 1H), 7.24-7.16 (m, 2H), 7.13 (s, 1H), 7.07-6.97 (m, 2H), 5.06 (dd, J = 5.3, 12.8 Hz, 1H), 4.42-4.33 (m, 1H), 4.32-4.21 (m, 2H), 3.67-3.57 (m, 2H), 3.56-3.48 (m, 1H), 3.26-3.23 (m, 1H), 3.18-3.09 (m, 1H), 2.96-2.84 (m, 1H), 2.63-2.54 (m, 1H), 2.40-2.34 (m, 1H), 2.05-1.93 (m, 2H), 1.87-1.79 (m, 1H), 1.66 (br dd, J = 4.0, 5.5 Hz, 2H), 1.45-1.33 (m, 2H), 1.32-1.21 (m, 1H), 1.18-1.07 (m, 1H). |
| 91 | Rac-4-(1-((trans)-2-((2-(2,4-dioxo-3-azabicyclo[3.1.1]heptan-1-yl)-1-oxoisoindolin-5-yl)oxy)cyclohexyl)azetidin-3-yl)-3-fluorobenzonitrile | (400 MHZ, d₆-DMSO) δ 1.28-1.48 (m, 4 H) 1.59-1.70 (m, 1 H) 1.77-1.92 (m, 2 H) 2.06 (br d, J = 10.01 Hz, 1 H) 2.80-2.85 (m, 4 H) 3.07 (br s, 1 H) 3.70 (br t, J = 8.76 Hz, 1 H) 4.23-4.36 (m, 4 H) 4.48 (br t, J = 7.75 Hz, 2 H) 4.51-4.57 (m, 1 H) 4.92-5.06 (m, 1 H) 7.20 (m, 1 H) 7.27 (s, 1 H) 7.61-7.73 (m, 2 H) 7.83 (m, 1 H) 7.91 (m, 1 H) 10.16 (br s, 1 H) 10.94 (d, J = 2.00 Hz, 1 H). |
| 92 | Rac-4-(1-((cis)-2-((2-(2,4-dioxo-3-azabicyclo[3.1.1]heptan-1-yl)-1-oxoisoindolin-5-yloxy)cyclohexyl)azetidin-3-yl)benzonitrile | (400 MHZ, d₆-DMSO) δ 1.22-1.35 (m, 3 H) 1.39-1.50 (m, 1 H) 1.69-1.84 (m, 2 H) 2.07-2.16 (m, 1 H) 2.16-2.26 (m, 1 H) 2.82 (br s, 4 H) 3.07 (br s, 1 H) 3.70-3.81 (m, 1 H) 4.09-4.18 (m, 1 H) 4.29-4.37 (m, 4 H) 4.44-4.54 (m, 2 H) 7.17 (m, 1 H) 7.23-7.28 (m, 1 H) 7.61 (d, J = 8.50 Hz, 1 H) 7.68 (d, J = 8.00 Hz, 2 H) 7.88-7.93 (m, 2 H) 10.41-10.53 (m, 1 H) 10.93 (d, J = 2.50 Hz, 1 H). |
| 93 | Rac-4-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile | (400 MHz, d₆-DMSO) δ 1.29-1.50 (m, 4 H) 1.59-1.70 (m, 1 H) 1.78-1.93 (m, 2 H) 2.03-2.12 (m, 1 H) 2.79-2.86 (m, 4 H) 3.07 (br s, 1 H) 3.71-3.81 (m, 1 H) 4.10-4.21 (m, 1 H) 4.25-4.35 (m, 3 H) 4.37-4.48 (m, 3 H) 4.95 (br s, 1 H) 7.19 (m, 1 H) 7.26 (s, 1H)7.64(m, 3 H) 7.90 (d, J = 8.50 Hz, 2 H) 10.12 (br s, 1 H) 10.94 (d, J = 2.00 Hz, 1 H). |
| 94 | Rac-2-(1-((cis)-2-((2-(2,4-dioxo-3-azabicyclo[3.1.1]heptan-1-yl)-1-oxoisoindolin-5-yl)oxy)cyclohexyl)azetidin-3-yl)benzonitrile | m/z (ESI⁺) 511.1 (M + H)⁺ |
| 95 | Rac-2-(1-((trans)-2-((2-(2,4-dioxo-3-azabicyclo[3.1.1]heptan-1-yl)-1-oxoisoindolin-5-yl)oxy)cyclohexyl)azetidin-3-yl)benzonitrile | m/z (ESI⁺) 511.1 (M + H)⁺ |
| 96 | Rac-3-(5-(((trans)-2-(3-hydroxy-3-phenylazetidin-1-yl)cyclohexyl)oxy)-1-oxoisoindolin-2-yl)piperidine-2,6-dione | (400 MHz, d₆-DMSO) δ 1.29-1.50 (m, 4 H) 1.59-1.70 (m, 1 H) 1.78-1.93 (m, 2 H) 2.03-2.12 (m, 1 H) 2.79-2.86 (m, 4 H) 3.07 (br s, 1 H) 3.71-3.81 (m, 1 H) 4.10-4.21 (m, 1 H) 4.25-4.35 (m, 3 H) 4.37-4.48 (m, 3 H) 4.95 (br s, 1 H) 7.19 (m, 1 H) 7.26 (s, 1 H) 7.64 (m, 3 H) 7.90 (d, J = 8.50 Hz, 2 H) 10.12 (br s, 1 H) 10.94 (d, J = 2.00 Hz, 1 H). |

TABLE 2-continued

| # | Nomenclature | ¹H NMR/MS |
|---|---|---|
| 97 | Rac-3-(5-(((cis)-2-(3-hydroxy-3-phenylazetidin-1-yl)cyclohexyl)oxy)-1-oxoisoindolin-2-yl)piperidine-2,6-dione | (400 MHZ, d₆-DMSO) δ 10.98 (s, 1H), 10.66-10.47 (m, 1H), 9.89-9.71 (m, 1H), 7.74-7.66 (m, 1H), 7.59-7.51 (m, 2H), 7.48-7.33 (m, 3H), 7.31-7.25 (m, 1H), 7.22-7.14 (m, 1H), 6.72-6.62 (m, 1H), 5.09 (br dd, J = 4.2, 12.6 Hz, 1H), 4.99 (br s, 1H), 4.75-4.53 (m, 2H), 4.46-4.16 (m, 3H), 4.01-3.91 (m, 1H), 3.72 (br d, J = 7.3 Hz, 1H), 2.99-2.84 (m, 1H), 2.60 (br d, J = 16.8 Hz, 2H), 2.40 (dt, J = 4.6, 13.4 Hz, 1H), 2.15-2.03 (m, 1H), 1.98 (br dd, J = 6.9, 9.9 Hz, 1H), 1.90-1.72 (m, 2H), 1.54-1.25 (m, 4H). |
| 98 | 4-(1-(2-((2-(2,6-dioxopiperidin-3-yl)-1-oxoisoindolin-5-yl)oxy)cyclopentyl)azetidin-3-yl)benzonitrile | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 99 | Rac-5-chloro-2-(1-((trans)-2-((2-(2,6-dioxopiperidin-3-yl)-1-oxoisoindolin-5-yl)oxy)cyclohexyl)azetidin-3-yl)benzonitrile | m/z (ESI⁺) 533.1 (M + H)⁺ |
| 100 | Rac-5-chloro-2-(1-((cis)-2-((2-(2,6-dioxopiperidin-3-yl)-1-oxoisoindolin-5-yl)oxy)cyclohexyl)azetidin-3-yl)benzonitrile | m/z (ESI⁺) 533.1 (M + H)⁺ |
| 101 | Rac-2-(1-((trans)-2-((2-(2,6-dioxopiperidin-3-yl)-1-oxoisoindolin-5-yl)oxy)cyclohexyl)azetidin-3-yl)-5-fluorobenzonitrile | m/z (ESI⁺) 517.1 (M + H)⁺ |
| 102 | Rac-2-(1-((cis)-2-((2-(2,6-dioxopiperidin-3-yl)-1-oxoisoindolin-5-yl)oxy)cyclohexyl)azetidin-3-yl)-5-fluorobenzonitrile | m/z (ESI⁺) 517.1 (M + H)⁺ |
| 103 | 3-(5-((((1S,2S)-2-(3-(2-chloro-4-fluorophenyl)azetidin-1-yl)cyclohexyl)oxy)-1-oxoisoindolin-2-yl)piperidine-2,6-dione | m/z (ESI⁺) 538.1 (M + H)⁺ |
| 104 | 3-(5-((((1S,2S)-2-(3-(2-chloro-4-fluorophenyl)azetidin-1-yl)cyclopentyl)oxy)-1-oxoisoindolin-2-yl)piperidine-2,6-dione | m/z (ESI⁺) 538.1 (M + H)⁺ |
| 105 | 1-(1-oxo-5-((((1S,2S)-2-(3-phenylazetidin-1-yl)cyclopentyl)oxy)isoindolin-2-yl)-3-azabicyclo[3.1.1]heptane-2,4-dione | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 106 | 1-(1-oxo-5-((((1S,2S)-2-(3-phenylpyrrolidin-1-yl)cyclohexyl)oxy)isoindolin-2-yl)-3-azabicyclo[3.1.1]heptane-2,4-dione | m/z (ESI⁺) 500.1 (M + H)⁺ |
| 107 | 1-(1-oxo-5-((((1S,2S)-2-(3-phenylpyrrolidin-1-yl)cyclopentyl)oxy)isoindolin-2-yl)-3-azabicyclo[3.1.1]heptane-2,4-dione | m/z (ESI⁺) 500.1 (M + H)⁺ |
| 108 | Rac-2-(1-((trans)-2-((2-(2,6-dioxopiperidin-3-yl)-1-oxoisoindolin-5-yl)oxy)cyclohexyl)azetidin-3-yl)benzonitrile | m/z (ESI⁺) 499.1 (M + H)⁺ |
| 109 | Rac-2-(1-((cis)-2-((2-(2,6-dioxopiperidin-3-yl)-1-oxoisoindolin-5-yl)oxy)cyclohexyl)azetidin-3-yl)benzonitrile | m/z (ESI⁺) 499.1 (M + H)⁺ |

TABLE 2-continued

| # | Nomenclature | ¹H NMR/MS |
|---|---|---|
| 110 | 4-(1-(2-((2-(2,6-dioxopiperidin-3-yl)-1-oxoisoindolin-5-yl)oxy)cyclopentyl)azetidin-3-yl)-2-fluorobenzonitrile | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 111 | 3-(5-(((1S,2S)-2-(3-(3-fluorophenyl)azetidin-1-yl)cyclohexyl)oxy)-1-oxoisoindolin-2-yl)piperidine-2,6-dione | m/z (ESI⁺) 492.2 (M + H)⁺ |
| 112 | 3-(5-(((1S,2S)-2-(3-(3-morpholinophenyl)azetidin-1-yl)cyclohexyl)oxy)-1-oxoisoindolin-2-yl)piperidine-2,6-dione | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 113 | 3-(1-(((1S,2S)-2-((2-(2,6-dioxopiperidin-3-yl)-1-oxoisoindolin-5-yl)oxy)cyclohexyl)azetidin-3-yl)benzonitrile | m/z (ESI⁺) 499.1 (M + H)⁺ |
| 114 | 1-(1-oxo-5-(((1S,2S)-2-(3-phenylazetidin-1-yl)cyclohexyl)oxy)isoindolin-2-yl)-3-azabicyclo[3.1.1]heptane-2,4-dione | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 115 | Rac-4-(1-((cis)-2-((2-(2,6-dioxopiperidin-3-yl)-1-oxoisoindolin-5-yl)oxy)cyclohexyl)azetidin-3-yl)-3-fluorobenzonitrile | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 116 | Rac-4-(1-((trans)-2-((2-(2,6-dioxopiperidin-3-yl)-1-oxoisoindolin-5-yl)oxy)cyclohexyl)azetidin-3-yl)-3-fluorobenzonitrile | (400 MHZ, d₆-DMSO) δ 11.00 (s, 1H), 10.21-9.91 (m, 1H), 7.96-7.88 (m, 1H), 7.87-7.78 (m, 1H), 7.76-7.66 (m, 2H), 7.31 (s, 1H), 7.21 (br d, J = 8.5 Hz, 1H), 5.21-5.04 (m, 1H), 4.97 (br s, 1H), 4.61-4.43 (m, 3H), 4.40 (br d, J = 6.8 Hz, 1H), 4.37-4.19 (m, 3H), 3.71 (br t, J = 9.4 Hz, 1H), 3.01-2.85 (m, 1H), 2.13-1.95 (m, 3H), 1.92-1.75 (m, 2H), 1.73-1.58 (m, 1H), 1.53-1.21 (m, 5H). |
| 117 | 4-(1-(2-((2-(2,6-dioxopiperidin-3-yl)-1-oxoisoindolin-5-yl)oxy)cyclohexyl)azetidin-3-yl)benzonitrile | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 118 | 3-(1-oxo-5-((2-(3-phenylazetidin-1-yl)cyclohexyl)oxy)isoindolin-2-yl)piperidine-2,6-dione | m/z (ESI⁺) 474.1 (M + H)⁺ |
| 119 | Rac-4-(1-((trans)-2-((2-(2,6-dioxopiperidin-3-yl)-1-oxoisoindolin-5-yl)oxy)cyclohexyl)azetidin-3-yl)-2-fluorobenzonitrile | (400 MHZ, CDCl₃) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 120 | 3-(1-oxo-5-(((1S,2S)-2-(3-phenylazetidin-1-yl)cyclopentyl)oxy)isoindolin-2-yl)piperidine-2,6-dione | m/z (ESI⁺) 460.1 (M + H)⁺ |

TABLE 2-continued

| # | Nomenclature | $^1$H NMR/MS |
|---|---|---|
| 121 | 3-(1-oxo-5-(((1S,2S)-2-(3-phenylpyrrolidin-1-yl)cyclopentyl)oxy)isoindolin-2-yl)piperidine-2,6-dione | (400 MHZ, CDCl$_3$) δ 11.00 (s, 1H), 10.20-9.88 (m, 1H), 7.98-7.85 (m, 2H), 7.71 (d, J = 8.3 Hz, 1H), 7.68-7.62 (m, 2H), 7.30 (s, 1H), 7.20 (br d, J = 7.9 Hz, 1H), 5.18-5.03 (m, 1H), 4.97 (br s, 1H), 4.54-4.37 (m, 4H), 4.36-4.23 (m, 2H), 4.20-4.07 (m, 1H), 3.88-3.71 (m, 1H), 3.02-2.86 (m, 1H), 2.18-1.94 (m, 3H), 1.93-1.78 (m, 2H), 1.73-1.59 (m, 1H), 1.55-1.31 (m, 4H). |
| 122 | Rac-4-(1-((cis)-2-((2-(2,6-dioxopiperidin-3-yl)-1-oxoisoindolin-5-yl)oxy)cyclohexyl)azetidin-3-yl)-2-fluorobenzonitrile | (400 MHZ, d$_6$-DMSO) δ 10.97 (s, 1H), 10.14-9.91 (m, 1H), 7.99 (t, J = 7.5 Hz, 1H), 7.77-7.65 (m, 2H), 7.53-7.42 (m, 1H), 7.28 (s, 1H), 7.22-7.14 (m, 1H), 5.12-5.04 (m, 1H), 4.98-4.89 (m, 1H), 4.57-4.01 (m, 7H), 3.85-3.70 (m, 1H), 2.98-2.85 (m, 1H), 2.63-2.57 (m, 1H), 2.41-2.36 (m, 1H), 2.13-1.94 (m, 2H), 1.93-1.75 (m, 2H), 1.71-1.56 (m, 1H), 1.51-1.23 (m, 4H). |
| 123 | 3-(5-(((1S,2S)-2-(3-(4-fluorophenyl)azetidin-1-yl)cyclohexyl)oxy)-1-oxoisoindolin-2-yl)piperidine-2,6-dione | (400 MHZ, d$_6$-DMSO) δ 11.06-10.85 (m, 1H), 7.60 (d, J = 8.5 Hz, 1H), 7.38-7.33 (m, 2H), 7.17 (d, J = 1.5 Hz, 1H), 7.14-7.08 (m, 2H), 7.03 (dd, J = 2.0, 8.5 Hz, 1H), 5.06 (dd, J = 5.0, 13.5 Hz, 1H), 4.40-4.31 (m, 1H), 4.30-4.22 (m, 2H), 3.66-3.62 (m, 1H), 3.61-3.56 (m, 1H), 3.23-3.20 (m, 1H), 3.17 (d, J = 5.0 Hz, 1H), 3.10 (br t, J = 6.8 Hz, 1H), 2.96-2.84 (m, 2H), 2.60 (br d, J = 2.5 Hz, 1H), 2.43-2.37 (m, 1H), 1.99 (br d, J = 5.5 Hz, 1H), 1.83 (br d, J = 11.5 Hz, 1H), 1.65 (br s, 2H), 1.42-1.34 (m, 2H), 1.28-1.22 (m, 2H), 1.17-1.09 (m, 1H). |
| 124 | 3-(5-(((1S,2S)-2-(3-(4-morpholinophenyl)azetidin-1-yl)cyclohexyl)oxy)-1-oxoisoindolin-2-yl)piperidine-2,6-dione | (400 MHZ, d$_6$-DMSO) δ 1.15-1.49 (m, 4 H) 1.69-1.84 (m, 2 H) 1.93-2.02 (m, 1 H) 2.09-2.27 (m, 2 H) 2.36-2.45 (m, 1 H) 2.60 (br d, J = 16.69 Hz, 2 H) 2.86-2.95 (m, 1 H) 3.04-3.12 (m, 4 H) 3.69-3.75 (m, 5 H) 3.83-3.94 (m, 1 H) 4.22-4.43 (m, 5 H) 4.46-4.56 (m, 1 H) 5.08 (m, 1 H) 6.95 (d, J = 9.06 Hz, 2 H) 7.12-7.19 (m, 1 H) 7.25-7.30 (m, 1 H) 7.33 (d, J = 8.11 Hz, 1 H) 7.66 (m, 1 H) 10.05-10.43 (m, 1 H) 10.97 (s, 1 H). |
| 125 | (R)-3-(1-oxo-5-(((1S,2S)-2-(3-phenylazetidin-1-yl)cyclohexyl)oxy)isoindolin-2-yl)piperidine-2,6-dione | m/z (ESI$^+$) 474.1 (M + H)$^+$ |
| 126 | 3-(5-(((1S,2S)-2-(3-(3-methoxyphenyl)azetidin-1-yl)cyclohexyl)oxy)-1-oxoisoindolin-2-yl)piperidine-2,6-dione | (400 MHZ, d$_6$-DMSO) δ 1.13-1.50 (m, 4H), 1.67-1.86 (m, 2H), 1.94-2.03 (m, 1H), 2.08-2.28 (m, 2H), 2.31-2.47 (m, 2H), 2.52-2.70 (m, 2H), 2.85-2.97 (m, 1H), 3.79 (s, 3H), 3.91-4.05 (m, 1H), 4.23-4.46 (m, 5H), 4.54 (br d, J = 9.01 Hz, 1H), 5.08 (br dd, J = 13.32, 4.94 Hz, 1H), 6.85-6.93 (m, 1H), 6.99-7.07 (m, 2H), 7.14-7.20 (m, 1H), 7.25-7.35 (m, 2H), 7.66 (dd, J = 8.44, 1.56 Hz, 1H), 10.63 (br s, 1H), 10.96 (s, 1H), 10.91-11.00 (m, 1H). |
| 127 | 3-(1-oxo-5-(((1S,2S)-2-(3-phenylazetidin-1-yl)cyclohexyl)oxy)isoindolin-2-yl)piperidine-2,6-dione | (400 MHZ, d$_6$-DMSO) δ 10.96 (s, 1H), 7.60 (d, J = 8.4 Hz, 1H), 7.38-7.25 (m, 4H), 7.23-7.14 (m, 2H), 7.04 (br d, J = 8.4 Hz, 1H), 5.06 (dd, J = 4.9, 13.3 Hz, 1H), 4.45-4.17 (m, 3H), 3.82-3.46 (m, 3H), 3.30-3.04 (m, 2H), 2.96-2.82 (m, 1H), 2.59 (br d, J = 17.0 Hz, 1H), 2.48-2.27 (m, 2H), 2.09-1.92 (m, 2H), 1.92-1.80 (m, 1H), 1.66 (br s, 2H), 1.45-1.33 (m, 2H), 1.32-1.21 (m, 1H), 1.20-1.07 (m, 1H). |
| 128 | 3-(1-oxo-5-(((1S,2R)-2-(3-phenylazetidin-1-yl)cyclohexyl)oxy)isoindolin-2-yl)piperidine-2,6-dione | (400 MHZ, d$_6$-DMSO) δ 10.98 (s, 1H), 10.03 (br dd, J = 3.2, 4.3 Hz, 1H), 7.78-7.62 (m, 1H), 7.48-7.25 (m, 6H), 7.20 (dd, J = 1.7, 8.2 Hz, 1H), 5.09 (br dd, J = 4.9, 12.9 Hz, 1H), 4.98 (br s, 1H), 4.47-4.21 (m, 5H), 4.15-3.90 (m, 1H), 3.78 (br d, J = 10.3 Hz, 1H), 3.01-2.80 (m, 1H), 2.60 (br d, J = 17.8 Hz, 2H), 2.39 (br dd, J = 4.3, 12.9 Hz, 1H), 2.15-1.63 (m, 3H), 1.73-1.58 (m, 1H), 1.66-1.57 (m, 1H), 1.53-1.24 (m, 4H). |
| 129 | 3-(1-oxo-5-(((1S,2S)-2-(3-(2-(trifluoromethyl)phenyl)azetidin-1-yl)cyclohexyl)oxy)isoindolin-2-yl)piperidine-2,6-dione | (400 MHZ, d$_6$-DMSO) δ 10.98 (s, 1H), 10.85-10.54 (m, 1H), 7.92 (br d, J = 7.9 Hz, 1H), 7.84-7.73 (m, 2H), 7.67 (d, J = 8.3 Hz, 1H), 7.58 (br t, J = 7.6 Hz, 1H), 7.30 (br s, 1H), 7.21-7.12 (m, 1H), 5.09 (dd, J = 5.0, 13.2 Hz, 1H), |

TABLE 2-continued

| # | Nomenclature | $^1$H NMR/MS |
|---|---|---|
| | | 4.70-4.46 (m, 3H), 4.45-4.18 (m, 5H), 3.75 (br s, 1H), 2.99-2.82 (m, 1H), 2.53 (d, J = 1.8 Hz, 2H), 2.28-2.08 (m, 2H), 2.04-1.93 (m, 1H), 1.88-1.67 (m, 2H), 1.45 (br d, J = 12.0 Hz, 1H), 1.38-1.20 (m, 3H). |
| 130 | 3-(1-oxo-5-(((1S,2S)-2-(3-phenylazetidin-1-yl)cyclohexyl)oxy)isoindolin-2-yl)piperidine-2,6-dione 2-hydroxypropane-1,2,3-tricarboxylate | m/z (ESI+) 474.1 (M + H)+ |
| 131 | 3-(1-oxo-5-(((1S,2S)-2-(3-phenylazetidin-1-yl)cycloheptyl)oxy)isoindolin-2-yl)piperidine-2,6-dione | m/z (ESI$^+$) 488.1 (M + H)$^+$ |
| 132 | 3-(5-(((1S,2S)-2-(3-(4-hydroxyphenyl)azetidin-1-yl)cyclohexyl)oxy)-1-oxoisoindolin-2-yl)piperidine-2,6-dione | m/z (ESI$^+$) 490.3 (M + H)$^+$ |
| 133 | 3-(5-(((1S,2S)-2-(3-(2-hydroxyphenyl)azetidin-1-yl)cyclohexyl)oxy)-1-oxoisoindolin-2-yl)piperidine-2,6-dione | m/z (ESI$^+$) 490.2 (M + H)$^+$ |
| 134 | 3-(5-(((1S,2S)-2-(3-(3-hydroxyphenyl)azetidin-1-yl)cyclohexyl)oxy)-1-oxoisoindolin-2-yl)piperidine-2,6-dione | m/z (ESI$^+$) 490.2 (M + H)$^+$ |

BIOLOGICAL EXAMPLES

Cereblon (CRBN) Target Engagement

HEK293T cells were harvested ca. 75% confluent with trypsin and plated (500,000 cells/well) in a 6-well tissue culture plate in 2 mL of Dulbecco's Modified Eagle Medium (DMEM)+10% Fetal Bovine Serum (FBS) and incubated overnight at 37° C.

The NanoLuc-CRBN fusion vector (Nluc-CRBN; Promega) contains the coding region of human E3 ligase component cereblon (CRBN) fused to the C-terminus of the NanoLuc luciferase coding region. A mixture of 10 ng Nluc-CRBN and 990 ng DDB1 Expression Vector (Promega) was added to 125 µL Opti-Minimum Essential Medium (Opti-MEM™; Thermo Fisher) along with 2 µL P3000 reagent (Thermo Fisher) in a 1.5 mL epppendorf tube. This solution was added to Lipofectamine 3000 transfection reagent (5 µL; Thermo Fisher) in Opti-MEM (125 µL), mixed well, and incubated for 15 minutes at room temperature. The transfection mixture was added dropwise to cells and incubated overnight at 37° C., 5% $CO_2$. Following transfection, cells were washed once with PBS, and trypsin (250 µL) was added and incubated 30-45 sec to dislodge cells. Complete media (2 mL) was added to resuspend cells to form a single cell suspension. Cells were centrifuged at 320×g for 5 min at room temperature, the supernatant was removed, and the cell pellet resuspended in Opti-MEM (3 mL; wash step repeated ×2). After final resuspension in 5 mL Opti-MEM, cells were counted and resuspended at 200,000 cells/mL in Opti-MEM.

Cereblon target engagement was monitored by Bioluminescence Resonance Energy Transfer (BRET) in transfected HEK-293T cells using the NanoBRET TE Intracellular E3 Ligase Assay (Promega). Briefly, 384-well plates (white opaque plates, Corning 3574, low binding surface) were seeded with transfected HEK-293T cells (38 µL/well). 2 µL of 10 µM CRBN tracer (diluted 1:5 in Tracer Dilution Buffer) was added to each well. Plates were centrifuged at 320×g for 1 min at room temperature. Test compounds were added in a 11-point dilution series (typically 10 µM to 100 µM) using a TECAN D300e Digital Dispenser. Plates were shaken for 2 minutes on a microplate shaker to mix compounds. Plates were centrifuged at 320×g for 1 min at room temperature, and subsequently incubated for 2 hours at 37° C.

After incubation, plates were allowed to cool to room temperature for 15 minutes. 20 µL of 3× Complete NanoBRET™ Nano-Glo® Substrate plus Inhibitor Solution (Promega, 1:166 Substrate and 1:500 dilution of Extracellular NanoLuc® Inhibitor diluted in Opti-MEM) were added to each well. Plates were incubated with shaking at room temperature for 3 minutes covered with foil. Plates were read on a CLARIOstar microplate reader (BMG LabTech), measuring at 450 nm (donor emission) and 610 nm (acceptor emission). The $IC_{50}$ values were determined by regression to best fit four-parameter logistic curves using GraphPad Prism.

IKZF2 Degradation Assay

Generation of Stable Cell Lines

Polycistronic plasmids were constructed for the mammalian expression of fluorescent reporter fusions of human transcription factors IKZF1 (Ikaros), IKZF2 (Helios), and IKZF3 (Aiolos). The respective protein sequences had their C-terminal end joined to a GGGGS linker repeated three times followed by mNeonGreen, P2A sequence, and mScarlet. The DNA sequences of the open reading frames are as follows:

```
IKZF1-mNeonGreen-P2A-mScarlet coding sequence (SEQ ID NO: 1):
ATGGATGCTGATGAGGGTCAAGACATGTCCCAAGTTTCAGGGAAGGAAAGC

CCCCCTGTAAGCGATACTCCAGATGAGGGCGATGAGCCCATGCCGATCCCCG

AGGACCTCTCCACCACCTCGGGAGGACAGCAAAGCTCCAAGAGTGACAGAG
```

-continued

```
TCGTGGCCAGTAATGTTAAAGTAGAGACTCAGAGTGATGAAGAGAATGGGC
GTGCCTGTGAAATGAATGGGGAAGAATGTGCGGAGGATTTACGAATGCTTG
ATGCCTCGGGAGAGAAAATGAATGGCTCCCACAGGGACCAAGGCAGCTCGG
CTTTGTCGGGAGTTGGAGGCATTCGACTTCCTAACGGAAAACTAAAGTGTGA
TATCTGTGGGATCATTTGCATCGGGCCCAATGTGCTCATGGTTCACAAAGA
AGCCACACTGGAGAACGGCCCTTCCAGTGCAATCAGTGCGGGCCTCATTCA
CCCAGAAGGGCAACCTGCTCCGGCACATCAAGCTGCATTCCGGGGAGAAGC
CCTTCAAATGCCACCTCTGCAACTACGCCTGCCGCCGGAGGGACGCCCTCAC
TGGCCACCTGAGGACGCACTCCGTTGGTAAACCTCACAAATGTGGATATTGT
GGCCGAAGCTATAAACAGCGAAGCTCTTTAGAGGAACATAAAGAGCGCTGC
CACAACTACTTGGAAAGCATGGGCCTTCCGGGCACACTGTACCCAGTCATTA
AAGAAGAAACTAATCACAGTGAAATGGCAGAAGACCTGTGCAAGATAGGAT
CAGAGAGATCTCTCGTGCTGGACAGACTAGCAAGTAACGTCGCCAAACGTA
AGAGCTCTATGCCTCAGAAATTTCTTGGGGACAAGGGCCTGTCCGACACGCC
CTACGACAGCAGCGCCAGCTACGAGAAGGAGAACGAAATGATGAAGTCCCA
CGTGATGGACCAAGCCATCAACAACGCCATCAACTACCTGGGGGCCGAGTCC
CTGCGCCCGCTGGTGCAGACGCCCCCGGGCGGTTCCGAGGTGGTCCCGGTCA
TCAGCCCGATGTACCAGCTGCACAAGCCGCTCGCGGAGGGCACCCCGCGCTC
CAACCACTCGGCCCAGGACAGCGCCGTGGAGAACCTGCTGCTGCTCTCCAAG
GCCAAGTTGGTGCCCTCGGAGCGCGAGGCGTCCCCGAGCAACAGCTGCCAA
GACTCCACGGACACCGAGAGCAACAACGAGGAGCAGCGCAGCGGTCTCATC
TACCTGACCAACCACATCGCCCCGCACGCGCGCAACGGGCTGTCGCTCAAGG
AGGAGCACCGCGCCTACGACCTGCTGCGCGCCGCCTCCGAGAACTCGCAGG
ACGCGCTCCGCGTGGTCAGCACCAGCGGGGAGCAGATGAAGGTGTACAAGT
GCGAACACTGCCGGGTGCTCTTCCTGGATCACGTCATGTACACCATCCACAT
GGGCTGCCACGGCTTCCGTGATCCTTTTGAGTGCAACATGTGCGGCTACCAC
AGCCAGGACCGGTACGAGTTCTCGTCGCACATAACGCGAGGGGAGCACCGC
TTCCACATGAGCGGTGGAGGCGGTTCAGGTGGCGGAGGAAGCGGGGGAGGT
GGAAGTATGGTGTCTAAAGGAGAAGAAGATAATATGGCTTCTCTGCCTGCTA
CACACGAACTGCATATTTTCGGATCTATTAATGGCGTGGATTTCGATATGGTG
GGACAGGGAACAGGAAACCCTAACGATGGATACGAAGAACTGAATCTGAAG
TCTACCAAAGGAGATCTGCAATTCTCTCCTTGGATCCTGGTCCCTCACATTGG
ATATGGATTCCATCAATATCTGCCTTACCCTGACGGAATGTCTCCTTTCCAAG
CTGCTATGGTCGATGGCTCTGGATATCAGGTCCACAGAACAATGCAATTTGA
AGATGGCGCCTCTCTGACAGTGAATTACAGATATACATACGAAGGCTCTCAT
ATTAAAGGCGAAGCCCAAGTGAAAGGCACAGGCTTTCCTGCCGACGGCCCT
GTGATGACCAACTCTCTGACCGCTGCCGATTGGTGCAGATCTAAGAAGACCT
ACCCTAATGATAAAACCATTATCTCTACCTTCAAATGGTCTTACACAACAGG
CAATGGCAAGAGATACAGATCTACCGCCAGAACCACCTATACCTTTGCTAAG
CCTATGGCTGCCAATTACCTGAAAAATCAGCCTATGTATGTGTTCAGAAAAA
CCGAACTGAAACACTCTAAAACCGAACTGAATTTCAAAGAATGGCAAAAGG
```

```
CTTTCACAGATGTGATGGGAATGGATGAACTGTACAAGGGAAGCGGAGCTA

CAAATTTTAGTCTTCTTAAACAAGCCGGTGACGTGGAGGAAAATCCCGGCCC

AATGGTGAGCAAGGGCGAGGCCGTGATCAAGGAGTTCATGCGCTTCAAGGT

GCACATGGAGGGCAGCATGAACGGCCACGAGTTCGAGATCGAGGGCGAGGG

CGAGGGCCGCCCCTACGAGGGCACCCAGACCGCCAAGCTGAAGGTGACCAA

GGGCGGCCCCCTGCCCTTCTCTTGGGACATCCTGAGCCCCCAGTTCATGTACG

GCAGCCGCGCCTTCACCAAGCACCCCGCCGACATCCCCGACTACTACAAGCA

GAGCTTCCCCGAGGGCTTCAAGTGGGAGCGCGTGATGAACTTCGAGGACGG

CGGCGCCGTGACCGTGACCCAGGACACCAGCCTGGAGGACGGCACCCTGAT

CTACAAGGTGAAGCTGCGCGGCACCAACTTCCCCCCCGACGGCCCCGTGATG

CAGAAGAAGACCATGGGCTGGGAGGCCAGCACCGAGCGCCTGTACCCCGAG

GACGGCGTGCTGAAGGGCGACATCAAGATGGGCCTGCGCCTGAAGGACGGC

GGCAGATACCTGGCCGACTTCAAGACCACCTACAAGGCCAAGAAGCCCGTG

CAGATGCCCGGCGCCTACAACGTGGACCGCAAGCTGGACATCACCAGCCAC

AACGAGGACTACACCGTGGTGGAGCAGTACGAGCGCAGCGAGGGCCGCCAC

AGCACCGGCGGCATGGACGAGCTGTACAAGTGA

IKZF2-mNeonGreen-P2A-mScarlet coding sequence (SEQ ID NO: 2):
ATGGAAACAGAGGCTATTGATGGCTATATAACGTGTGACAATGAGCTTTCAC

CCGAAAGGGAGCACTCCAATATGGCAATTGACCTCACCTCAAGCACACCCAA

TGGACAGCATGCCTCACCAAGTCACATGACAAGCACAAATTCAGTAAAGCTA

GAAATGCAGAGTGATGAAGAGTGTGACAGGAAACCCCTGAGCCGTGAAGAT

GAGATCAGGGGCCATGATGAGGGTAGCAGCCTAGAAGAACCCCTAATTGAG

AGCAGCGAGGTGGCTGACAACAGGAAAGTCCAGGAGCTTCAAGGCGAGGGA

GGAATCCGGCTTCCGAATGGTAAACTGAAATGTGACGTCTGTGGCATGGTTT

GCATTGGGCCCAATGTGCTTATGGTACATAAAAGGAGTCACACTGGTGAACG

CCCCTTCCACTGTAACCAGTGTGGAGCTTCTTTTACTCAGAAGGGCAACCTTC

TGAGACACATAAAGTTACACTCTGGAGAGAAGCCGTTCAAATGTCCTTTCTG

TAGCTACGCCTGTAGAAGAAGGGACGCCCTCACAGGACACCTCAGGACCCA

TTCTGTGGGTAAACCTCACAAGTGCAACTACTGTGGACGAAGCTACAAGCAG

CGCAGTTCACTGGAGGAGCACAAGGAACGCTGCCACAACTATCTCCAGAAT

GTCAGCATGGAGGCTGCTGGGCAGGTCATGAGTCACCATGTACCTCCTATGG

AAGATTGTAAGGAACAAGAGCCTATTATGGACAACAATATTTCTCTGGTGCC

TTTTGAGAGACCTGCTGTCATAGAGAAGCTCACGGGGAATATGGGAAAACGT

AAAAGCTCCACTCCACAAAAGTTTGTGGGGGAAAAGCTCATGCGATTCAGCT

ACCCAGATATTCACTTTGATATGAACTTAACATATGAGAAGGAGGCTGAGCT

GATGCAGTCTCATATGATGGACCAAGCCATCAACAATGCAATCACCTACCTT

GGAGCTGAGGCCCTTCACCCTCTGATGCAGCACCCGCCAAGCACAATCGCTG

AAGTGGCCCCAGTTATAAGCTCAGCTTATTCTCAGGTCTATCATCCAAATAG

GATAGAAAGACCCATTAGCAGGGAAACTGCTGATAGTCATGAAAACAACAT

GGATGGCCCCATCTCTCTCATCAGACCAAAGAGTCGACCCCAGGAAAGAGA

GGCCTCTCCCAGCAATAGCTGCCTGGATTCCACTGACTCAGAAAGCAGCCAT
```

-continued

```
GATGACCACCAGTCCTACCAAGGACACCCTGCCTTAAATCCCAAGAGGAAAC

AAAGCCCAGCTTACATGAAGGAGGATGTCAAAGCTTTGGATACTACCAAGG

CTCCTAAGGGCTCTCTGAAGGACATCTACAAGGTCTTCAATGGAGAAGGAGA

ACAGATTAGGGCCTTCAAGTGTGAGCACTGCCGAGTCCTTTTCCTAGACCAT

GTCATGTACACCATTCACATGGGTTGCCATGGCTACCGGGACCCACTGGAAT

GCAACATCTGTGGCTACAGAAGCCAGGACCGTTATGAGTTTTCATCACACAT

TGTTCGAGGGGAGCACACATTCCACCTCGACGGTGGAGGCGGTTCAGGTGGC

GGAGGAAGCGGGGGAGGTGGAAGTATGGTGTCTAAAGGAGAAGAAGATAA

TATGGCTTCTCTGCCTGCTACACACGAACTGCATATTTTCGGATCTATTAATG

GCGTGGATTTCGATATGGTGGGACAGGGAACAGGAAACCCTAACGATGGAT

ACGAAGAACTGAATCTGAAGTCTACCAAAGGAGATCTGCAATTCTCTCCTTG

GATCCTGGTCCCTCACATTGGATATGGATTCCATCAATATCTGCCTTACCCTG

ACGGAATGTCTCCTTTCCAAGCTGCTATGGTCGATGGCTCTGGATATCAGGTC

CACAGAACAATGCAATTTGAAGATGGCGCCTCTCTGACAGTGAATTACAGAT

ATACATACGAAGGCTCTCATATTAAAGGCGAAGCCCAAGTGAAAGGCACAG

GCTTTCCTGCCGACGGCCCTGTGATGACCAACTCTCTGACCGCTGCCGATTGG

TGCAGATCTAAGAAGACCTACCCTAATGATAAAACCATTATCTCTACCTTCA

AATGGTCTTACACAACAGGCAATGGCAAGAGATACAGATCTACCGCCAGAA

CCACCTATACCTTTGCTAAGCCTATGGCTGCCAATTACCTGAAAAATCAGCCT

ATGTATGTGTTCAGAAAAACCGAACTGAAACACTCTAAAACCGAACTGAATT

TCAAAGAATGGCAAAAGGCTTTCACAGATGTGATGGGAATGGATGAACTGT

ACAAGGGAAGCGGAGCTACAAATTTTAGTCTTCTTAAACAAGCCGGTGACGT

GGAGGAAAATCCCGGCCCAATGGTGAGCAAGGGCGAGGCCGTGATCAAGGA

GTTCATGCGCTTCAAGGTGCACATGGAGGGCAGCATGAACGGCCACGAGTTC

GAGATCGAGGGCGAGGGCGAGGGCCGCCCCTACGAGGGCACCCAGACCGCC

AAGCTGAAGGTGACCAAGGGCGGCCCCCTGCCCTTCTCTTGGGACATCCTGA

GCCCCCAGTTCATGTACGGCAGCCGCGCCTTCACCAAGCACCCCGCCGACAT

CCCCGACTACTACAAGCAGAGCTTCCCCGAGGGCTTCAAGTGGGAGCGCGTG

ATGAACTTCGAGGACGGCGGCGCCGTGACCGTGACCCAGGACACCAGCCTG

GAGGACGGCACCCTGATCTACAAGGTGAAGCTGCGCGGCACCAACTTCCCCC

CCGACGGCCCCGTGATGCAGAAGAAGACCATGGGCTGGGAGGCCAGCACCG

AGCGCCTGTACCCCGAGGACGGCGTGCTGAAGGGCGACATCAAGATGGCCC

TGCGCCTGAAGGACGGCGGCAGATACCTGGCCGACTTCAAGACCACCTACA

AGGCCAAGAAGCCCGTGCAGATGCCCGGCGCCTACAACGTGGACCGCAAGC

TGGACATCACCAGCCACAACGAGGACTACACCGTGGTGGAGCAGTACGAGC

GCAGCGAGGGCCGCCACAGCACCGGCGGCATGGACGAGCTGTACAAGTGA

IKZF3-mNeonGreen-P2A-mScarlet coding sequence (SEQ ID NO: 3):
ATGGAAGATATACAAACAAATGCGGAACTGAAAAGCACTCAGGAGCAGTCT

GTGCCCGCAGAAAGTGCAGCGGTTTTGAATGACTACAGTTTAACCAAATCTC

ATGAAATGGAAAATGTGGACAGTGGAGAAGGCCCAGCCAATGAAGATGAAG

ACATAGGAGATGATTCAATGAAAGTGAAAGATGAATACAGTGAAAGAGATG
```

-continued

AGAATGTTTTAAAGTCAGAACCCATGGGAAATGCAGAAGAGCCTGAAATCC

CTTACAGCTATTCAAGAGAATATAATGAATATGAAAACATTAAGTIGGAGAG

ACATGTTGTCTCATTCGATAGTAGCAGGCCAACCAGTGGAAAGATGAACTGC

GATGTGTGTGGATTATCCTGCATCAGCTTCAATGTCTTAATGGTTCATAAGCG

AAGCCATACTGGTGAACGCCCATTCCAGTGTAATCAGTGTGGGGCATCTTTT

ACTCAGAAAGGTAACCTCCTCCGCCACATTAAACTGCACACAGGGGAAAAA

CCTTTTAAGTGTCACCTCTGCAACTATGCATGCCAAAGAAGAGATGCGCTCA

CGGGGCATCTTAGGACACATTCTGTGGAGAAACCCTACAAATGTGAGTTTTG

TGGAAGGAGTTACAAGCAGAGAAGTTCCCTTGAGGAGCACAAGGAGCGCTG

CCGTACATTTCTTCAGAGCACTGACCCAGGGGACACTGCAAGTGCGGAGGCA

AGACACATCAAAGCAGAGATGGGAAGTGAAAGAGCTCTCGTACTGGACAGA

TTAGCAAGCAATGTGGCAAAACGAAAAAGCTCAATGCCTCAGAAATTCATTG

GTGAGAAGCGCCACTGCTTTGATGTCAACTATAATTCAAGTTACATGTATGA

GAAAGAGAGTGAGCTCATACAGACCCGCATGATGGACCAAGCCATCAATAA

CGCCATCAGCTATCTTGGCGCCGAAGCCCTGCGCCCCTTGGTCCAGACACCG

CCTGCTCCCACCTCGGAGATGGTTCCAGTTATCAGCAGCATGTATCCCATAG

CCCTCACCCGGGCTGAGATGTCAAACGGTGCCCCTCAAGAGCTGGAAAAGA

AAAGCATCCACCTTCCAGAGAAGAGCGTGCCTTCTGAGAGAGGCCTCTCTCC

CAACAATAGTGGCCACGACTCCACGGACACTGACAGCAACCATGAAGAACG

CCAGAATCACATCTATCAGCAAAATCACATGGTCCTGTCTCGGGCCCGCAAT

GGGATGCCACTTCTGAAGGAGGTTCCCCGCTCTTACGAACTCCTCAAGCCCC

CGCCCATCTGCCCAAGAGACTCCGTCAAAGTGATCAACAAGGAAGGGGAGG

TGATGGATGTGTATCGGTGTGACCACTGCCGCGTCCTCTTCCTGGACTATGTG

ATGTTCACGATTCACATGGGCTGCCACGGCTTCCGTGACCCTTTCGAGTGTAA

CATGTGTGGATATCGAAGCCATGATCGGTATGAGTTCTCGTCTCACATAGCC

AGAGGAGAACACAGAGCCCTGCTGAAGCTCGACGGTGGAGGCGGTTCAGGT

GGCGGAGGAAGCGGGGGAGGTGGAAGTATGGTGTCTAAAGGAGAAGAAGA

TAATATGGCTTCTCTGCCTGCTACACACGAACTGCATATTTTCGGATCTATTA

ATGGCGTGGATTTCGATATGGTGGACAGGGAACAGGAAACCCTAACGATG

GATACGAAGAACTGAATCTGAAGTCTACCAAAGGAGATCTGCAATTCTCTCC

TTGGATCCTGGTCCCTCACATTGGATATGGATTCCATCAATATCTGCCTTACC

CTGACGGAATGTCTCCTTTCCAAGCTGCTATGGTCGATGGCTCTGGATATCAG

GTCCACAGAACAATGCAATTTGAAGATGGCGCCTCTCTGACAGTGAATTACA

GATATACATACGAAGGCTCTCATATTAAAGGCGAAGCCCAAGTGAAAGGCA

CAGGCTTTCCTGCCGACGGCCCTGTGATGACCAACTCTCTGACCGCTGCCGA

TTGGTGCAGATCTAAGAAGACCTACCCTAATGATAAAACCATTATCTCTACC

TTCAAATGGTCTTACACAACAGGCAATGGCAAGAGATACAGATCTACCGCCA

GAACCACCTATACCTTTGCTAAGCCTATGGCTGCCAATTACCTGAAAAATCA

GCCTATGTATGTGTTCAGAAAAACCGAACTGAAACACTCTAAAACCGAACTG

AATTTCAAAGAATGGCAAAAGGCTTTCACAGATGTGATGGGAATGGATGAA

```
-continued
CTGTACAAGGGAAGCGGAGCTACAAATTTTAGTCTTCTTAAACAAGCCGGTG

ACGTGGAGGAAAATCCCGGCCCAATGGTGAGCAAGGGCGAGGCCGTGATCA

AGGAGTTCATGCGCTTCAAGGTGCACATGGAGGGCAGCATGAACGGCCACG

AGTTCGAGATCGAGGGCGAGGGCGAGGGCCGCCCCTACGAGGGCACCCAGA

CCGCCAAGCTGAAGGTGACCAAGGGCGGCCCCCTGCCCTTCTCTTGGGACAT

CCTGAGCCCCCAGTTCATGTACGGCAGCCGCGCCTTCACCAAGCACCCCGCC

GACATCCCCGACTACTACAAGCAGAGCTTCCCCGAGGGCTTCAAGTGGGAGC

GCGTGATGAACTTCGAGGACGGCGGCGCCGTGACCGTGACCCAGGACACCA

GCCTGGAGGACGGCACCCTGATCTACAAGGTGAAGCTGCGCGGCACCAACTT

CCCCCCCGACGGCCCCGTGATGCAGAAGAAGACCATGGGCTGGGAGGCCAG

CACCGAGCGCCTGTACCCCGAGGACGGCGTGCTGAAGGGCGACATCAAGAT

GGCCCTGCGCCTGAAGGACGGCGGCAGATACCTGGCCGACTTCAAGACCAC

CTACAAGGCCAAGAAGCCCGTGCAGATGCCCGGCGCCTACAACGTGGACCG

CAAGCTGGACATCACCAGCCACAACGAGGACTACACCGTGGTGGAGCAGTA

CGAGCGCAGCGAGGGCCGCCACAGCACCGGCGGCATGGACGAGCTGTACAA

GTGA
```

IKZF1, IKZF2, and IKZF3 constructs were cloned into the UCOE Hygromycin expression vectors (Millipore Sigma). Reporter constructs were transfected using cationic lipid reagents into adherent HEK 293T cells and stable integrants were selected by treatment with 200 μg/mL hygromycin B. Clonal populations were obtained from the population of stable integrants either by limiting dilution or fluorescence activated cell sorting.

The clonal stable cell lines were maintained under constant 200 μg/mL hygromycin B selection while being passaged for use in the degradation assays. Flow analysis on a BD Accuri C6 showed the HEK 293T CMV-IKZF1 Clone 7 cell line to have an average Fluorescein isothiocyanate mean fluorescence intensity (FITC MFI) of 230,000 and phycoerythrin mean fluorescence intensity (PE MFI) of 33,000. HEK 293T EF1a-IKZF2 Clone 9 had an average FITC MFI of 150,000 and PE MFI of 26,000. HEK 293T EF1a-IKZF3 Clone 9 had an average FITC MFI of 400,000 and PE MFI of 60,000. The fluorescence intensity of the IKZF1/2/3-mNeonGreen (FITC channel) and mScarlet (PE channel) reporters were routinely analyzed by flow cytometry to confirm consistent expression levels between experiments.

IKZF1/2/3 Reporter Degradation Assay

The IKZF1/IKZF2/IKZF3 degradation assays were carried out by harvesting the HEK 293T reporter cell lines and resuspending the cells in media formulated for reduced background fluorescence (FluoroBrite; Thermo Fisher). The respective cell lines were seeded at a density of 4000 cells/well into black-walled 384-well optical grade assay tissue culture plates. The cells were incubated overnight at 37° C. to allow for attachment to the assay plate. Dilutions of the compounds were prepared in DMSO from 10 mM compound stocks. The assay plates were treated with appropriate concentrations of the compounds by dispensing the DMSO dilutions in quadruplicate wells with an upper limit of 0.5% final DMSO.

After 24 hour incubation with the compounds, the assay plates were imaged on an ImageXpress Pico microscopy system (cells maintained at 37° C. during imaging) to obtain the fluorescent readouts. The assay plates were imaged in the FITC and Tetramethylrhodamine (TRITC) channels to obtain the mNeonGreen fluorescence intensity (reporter degradation data) and mScarlet fluorescence intensity (for cell segmentation). 293T-IKZF1 and 293T-IKZF3 reporter cell lines were imaged with exposures of 500 milliseconds (ms) for both FITC and TRITC channels, while the 293T-IKZF2 reporter cell line was imaged with exposures of 1000 ms for FITC and 1250 ms for TRITC. The resulting data was analyzed with Cell Reporter Xpress software using the 2-channel cell scoring analysis with a "percent positive" readout. The TRITC channel was selected for the "nuclei" segmentation with a threshold of 20 while the FITC channel was selected for the "Marker 1" segmentation and a threshold of 100 for the IKZF1 and IKZF3 reporter lines. The IKZF2 reporter line had a threshold of 120 set for the FITC channel, and 20 for TRITC. The minimum segmentation width was set to 6 micrometers and the maximum segmentation width was set to 15 micrometers for all cell lines. The $DC_{50}$ calculations were determined by regression to best fit four-parameter logistic curves using GraphPad Prism.

Table 3 shows results from the assays described above.

TABLE 3

| # | IKZF1 $DC_{50}$ (μM) | IKZF2 $DC_{50}$ (μM) | IKZF3 $DC_{50}$ (μM) | IKZF2 % Degradation @ 1 μM |
|---|---|---|---|---|
| 1 | >30.0 | 0.024 | >30.0 | 79.9 |
| 10 | >30.0 | 0.006 | >30.0 | 78.7 |
| 11 | >30.0 | >30.0 | >30.0 | — |
| 13 | >30.0 | >30.0 | >30.0 | — |
| 14 | >30.0 | 0.292 | >30.0 | 33.5 |
| 15 | >30.0 | 0.004 | >30.0 | 78.9 |
| 19 | >30.0 | 0.004 | >30.0 | 84.5 |
| 23 | >30.0 | 0.005 | >30.0 | 79.2 |
| 27 | >30.0 | 0.005 | >30.0 | 82.1 |
| 31 | >30.0 | 0.0005 | >30.0 | 83.3 |

Table 4 shows further results from the assays described above.

TABLE 4

| # | CRBN Binding EC$_{50}$ (μM) | IKZF2 % Degradation @ 1 μM |
|---|---|---|
| 35 | 0.017 | 84.6 |
| 36 | 0.031 | 82.3 |
| 37 | 0.025 | <15 |
| 38 | 0.052 | 84.9 |
| 39 | 0.008 | 84.6 |
| 40 | 0.011 | <15 |
| 41 | 0.061 | <15 |
| 42 | 0.043 | <15 |
| 43 | 0.042 | <15 |
| 44 | 0.065 | 85.6 |
| 45 | 0.022 | 88 |
| 46 | 0.022 | <15 |
| 47 | 0.005 | 86.7 |
| 48 | 0.045 | 78.9 |
| 49 | 0.011 | <15 |
| 50 | 0.004 | 73.6 |
| 51 | 0.018 | 74.2 |
| 52 | 0.011 | 90.5 |
| 53 | 0.029 | 86.9 |
| 54 | 0.089 | <15 |
| 55 | 0.158 | 38.1 |
| 56 | 0.239 | <15 |
| 57 | 0.006 | 85.8 |
| 58 | 0.071 | 85.8 |
| 59 | 0.011 | 32.7 |
| 60 | 0.015 | 84.9 |
| 61 | 0.014 | 36.3 |
| 62 | 0.046 | 87.5 |
| 63 | 0.015 | 44.9 |
| 64 | 0.011 | 76.3 |
| 65 | 0.052 | 75.1 |
| 66 | 0.024 | 74.8 |
| 67 | 0.017 | 37.8 |
| 68 | 0.026 | 42.5 |
| 69 | 0.025 | <15 |
| 70 | >10.0 | — |
| 71 | 0.037 | <15 |
| 72 | 0.007 | 38.2 |
| 73 | 0.005 | 63.6 |
| 74 | 0.02 | 63 |
| 75 | 0.012 | 36.8 |
| 76 | 0.022 | 73.7 |
| 77 | >10.0 | — |
| 78 | >10.0 | — |
| 79 | 0.012 | <15 |
| 80 | 0.008 | 76.7 |
| 81 | 0.009 | 77.6 |
| 82 | 0.921 | — |
| 83 | 0.036 | 48.8 |
| 84 | 0.014 | <15 |
| 85 | >10.0 | — |
| 86 | >10.0 | — |
| 87 | >10.0 | — |
| 88 | 0.0302 | 71.4 |
| 89 | 6.81 | — |
| 90 | >10.0 | — |
| 91 | >10.0 | — |
| 92 | >10.0 | — |
| 93 | >10.0 | — |
| 94 | >10.0 | — |
| 95 | >10.0 | — |
| 96 | 0.042 | 78.9 |
| 97 | 0.031 | <15 |
| 98 | 0.032 | <15 |
| 99 | 0.044 | 80.2 |
| 100 | 0.025 | <15 |
| 101 | 0.033 | 79.2 |
| 102 | 0.024 | — |
| 103 | 0.015 | 73.4 |
| 104 | 0.018 | 71.2 |
| 105 | >10.0 | — |
| 106 | >10.0 | — |
| 107 | >10.0 | — |
| 108 | 0.058 | 71.3 |
| 109 | 0.037 | <15 |
| 110 | 0.019 | 48.8 |
| 111 | 0.006 | 76.5 |
| 112 | 0.025 | 72.6 |
| 113 | 0.013 | 73.7 |
| 115 | 0.012 | 63.6 |
| 116 | 0.024 | <15 |
| 117 | 0.031 | <15 |
| 118 | 0.036 | <15 |
| 119 | 0.008 | 63.8 |
| 120 | 0.011 | 78.8 |
| 121 | 0.006 | 75.9 |
| 122 | 0.02 | <15 |
| 123 | 0.011 | 74.4 |
| 124 | 0.002 | 70.2 |
| 125 | 0.006 | 83.2 |
| 126 | 0.005 | 84.3 |
| 127 | 0.004 | 77.9 |
| 128 | 0.018 | <15 |
| 129 | 0.017 | 83.8 |
| 130 | 0.004 | 84.8 |
| 131 | 0.011 | 92.3 |
| 132 | 0.011 | 77.2 |
| 133 | 0.014 | 56.4 |
| 134 | 0.012 | 75 |

GSPT1 Degradation Assay

Generation of Stable Cell Lines

HEK293_hGSPT1_HiBiT-tagged cells were generated using CRISPR-Cas12a technology. Briefly, ~400,000 HEK293 cells were transiently co-transfected with precomplexed ribonuclear proteins (RNPs) consisting of 80 pmol of crRNA (IDT), 62 pmol of Cas12a protein (IDT), 3 μg of ssODN donor (IDT; AltR™ modifications), 78 pmol of electroporation enhancer (IDT), and 200 ng of pMaxGFP (Lonza). The transfection was performed via nucleofection (Lonza, 4D-Nucleofector X-unit) using solution P3 and program CM-130 in a (20 μL) cuvette. Five days post-nucleofection, cells were single-cell-sorted for GFP+ (transfected) cells by FACs in 96-well plates and clonally selected. Clones were screened and verified for the desired modification via targeted deep sequencing using gene-specific primers with partial Illumina adapter overhangs as previously described. In brief, clonal cell pellets were harvested, lysed, and used to generate gene-specific amplicons with partial Illumina adapters in PCR #1. Amplicons were indexed in PCR #2 and pooled with other targeted amplicons for other loci to create sequence diversity. Additionally, 10% PhiX sequencing control V3 (Illumina) was added to the pooled amplicon library prior to running the sample on a Miseq Sequencer System (Illumina) to generate paired 2×250 bp reads. Samples were demultiplexed using the index sequences, fastq files were generated, and NGS analysis was performed using CRIS.py. Final clones were authenticated using the PowerPlex fusion system (Promega) and tested negative for mycoplasma by the MycoAlert™Plus mycoplasma detection kit (Lonza).

Editing construct sequences and screening primers are outlined below (sequence from 5' to 3'). hGSPT1Cas12acrRNA, CAGE635.GSPT1.g1: TTTCTCTGGAACCAGTTTCAGAACT (SEQ ID NO: 4); CAGE635.g1.anti.ssODN: ttcctcacagtattgtgcagggtcat-caagaaaatgcttaGCTAATCTTCTTGAACAGCCGC CAGCCGCTCACgtcCttctctgaaccagtttcagaactttccaat-tgcaatggtcttacctagaaatgaaattttaa (HiBiT tag and silent blocking modifications to prevent Cas12a recutting after integration are in upper case) (SEQ ID NO: 5); CAGE635.hGSPT1.DS.F:

GGTTTGGCAGTAAAGCTAGTTAAT; (SEQ ID NO: 6)
CAGE635.hGSPT1.DS.R: GTGAAGTAGGCTTCTGCAGTC (SEQ ID NO: 7).

GSPT1 Reporter Degradation Assay

The GSPT1 degradation assay was carried out by harvesting the HEK 293T reporter cell lines and resuspending the cells in media formulated for reduced background fluorescence (FluoroBrite; Thermo Fisher). The respective cell lines were seeded at a density of 8,000 cells/well into white-opaque 384-well optical grade assay tissue culture plates (Greiner 781080-20). The cells were incubated overnight at 37° C. to allow for attachment to the assay plate. Dilutions of the compounds were prepared in DMSO from 10 mM compound stocks. Test compounds were added in a 10-point dilution series (typically 10 μM to 100 pM) using a TECAN D300e Digital Dispenser with an upper limit of 0.5% final DMSO. Plates were centrifuged at 320×g for 2 minutes at room temperature, and subsequently incubated at 37° C.

After 24 hour incubation with the compounds, the plates were allowed to cool to room temperature for 10 minutes. 30 μL of HiBiT lytic buffer+1:50 HiBiT substrate Solution were added to each well. Plates were centrifuged at 320×g for 2 minutes at room temperature and then incubated with shaking at room temperature for 10 minutes covered with foil. Plates were read on a CLARIOstar microplate reader (BMG LabTech), measuring at 450 nm (donor emission) and 610 nm or 630 nm (acceptor emission). The $DC_{50}$ values were determined by regression to best fit four-parameter logistic curves using GraphPad Prism.

Table 5 shows results from the assays described above for certain compounds described herein demonstrating selectivity.

TABLE 5

| # | GSPT1 Degradation $DC_{50}$ (μM) | GSPT1 % Degradation @ 1 μM (%) |
|---|---|---|
| 1 | >30.0 | — |
| 10 | >30.0 | — |
| 23 | >30.0 | — |
| 35 | >30.0 | — |
| 36 | >30.0 | — |
| 50 | >30.0 | — |
| 52 | >30.0 | — |

TABLE 5-continued

| # | GSPT1 Degradation $DC_{50}$ (μM) | GSPT1 % Degradation @ 1 μM (%) |
|---|---|---|
| 64 | >30.0 | — |
| 65 | >30.0 | — |
| 66 | >30.0 | — |
| 100 | >30.0 | — |
| 111 | >30.0 | — |
| 124 | >30.0 | — |
| 125 | >30.0 | — |
| 127 | >30.0 | — |
| 129 | >30.0 | — |
| 130 | >30.0 | — |
| 131 | >30.0 | — |
| 132 | >30.0 | — |
| 133 | >30.0 | — |
| 134 | >30.0 | — |

It is contemplated that certain compounds of formula I described herein selectively modulate IKZF proteins over GSPT1 when compared to compounds having an oxygen-linked phenyl described in the art. Further, it is contemplated that certain compounds of formula I described herein selectively modulate IKZF2 over GSPT1.

This data is further corroborated by immunoblot analysis as described below.

Immunoblot Analysis (KG-1 Cells)

Cells were seeded in 6-well plates (5×10^5 cells per well). After overnight incubation, the cells were treated with indicated concentrations for 24 hr. The harvested cells were spinned down, washed with PBS, and lysed with RIPA Lysis buffer and Extraction Buffer (Thermo Scientific Cat 89900) per the manufacturer's instructions. Protein quantitation was performed using the Pierce Rapid Gold BCA Protein Assay Kit (Cat A53225) using the Microplate Procedure per the manufacturer's instructions. Cell lysates were analyzed with the WES/Jess Simple Western System according to the manufacturer's instructions. The primary antibodies used were anti-IKZF2 (Abcam, ab129434, 1:25), anti-GSPT1 (Abcam, ab49878).

Compounds of the disclosure tested in the assay described above induced significant degradation of IKZF2 in KG-1 cells after 24 h of treatment, with no detectable activity against GSPT1. Results were consistent with the degradation data in the IKZF2 GFP reporter and GSPT1 HiBiT-tagged cells.

What is claimed is:

1. A compound selected from:

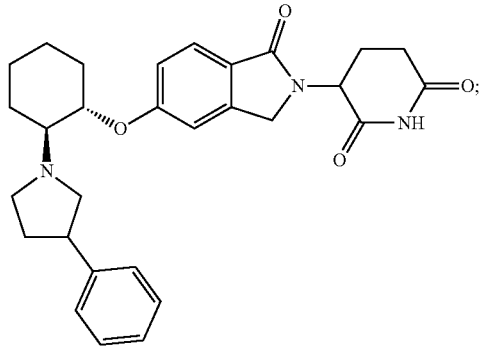

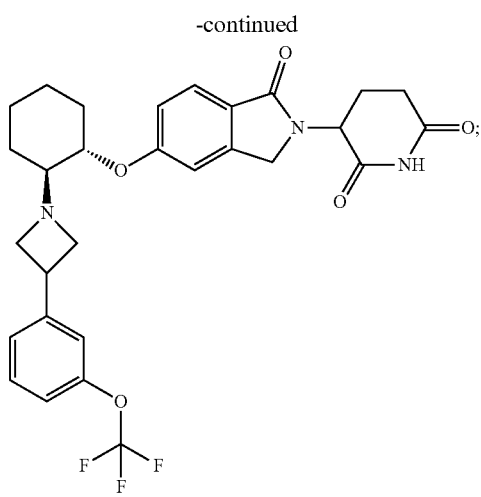

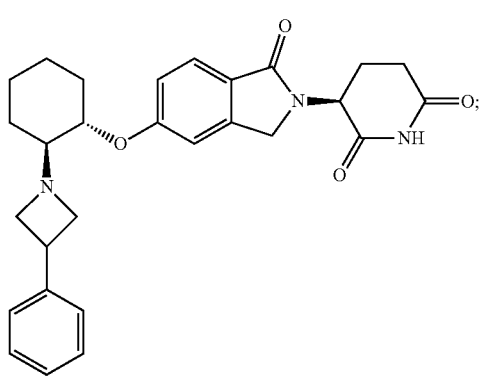

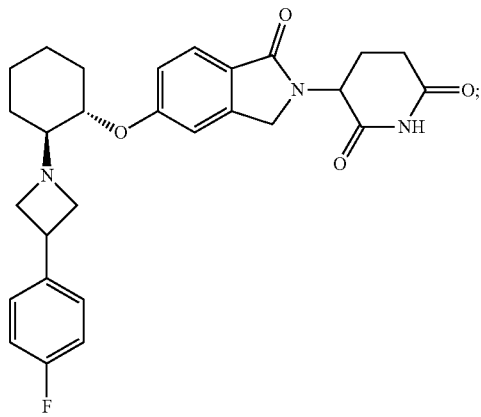

-continued

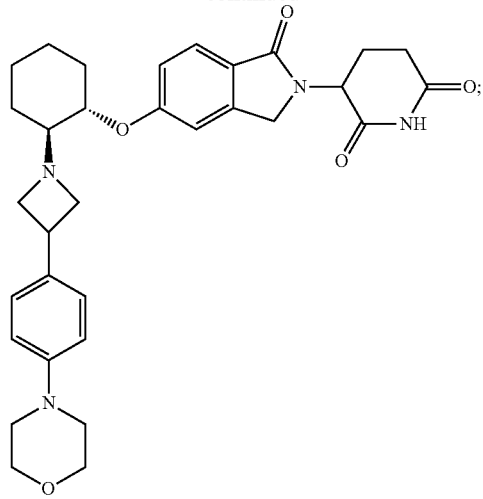

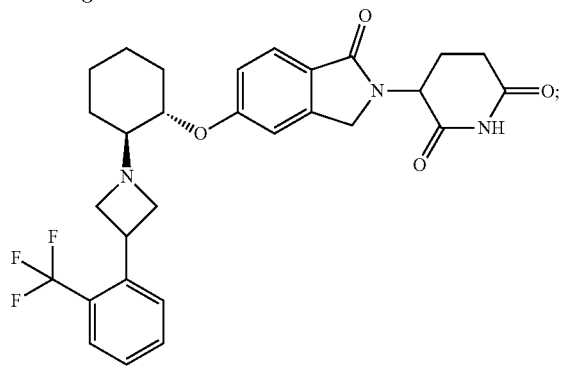

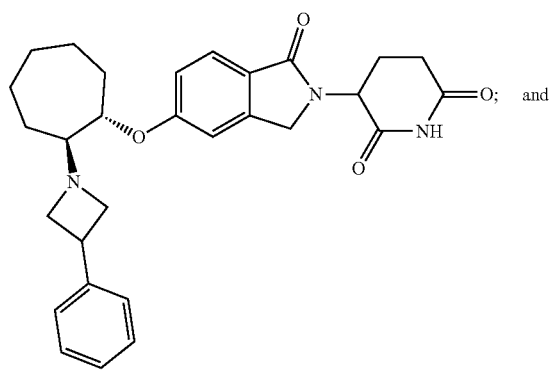

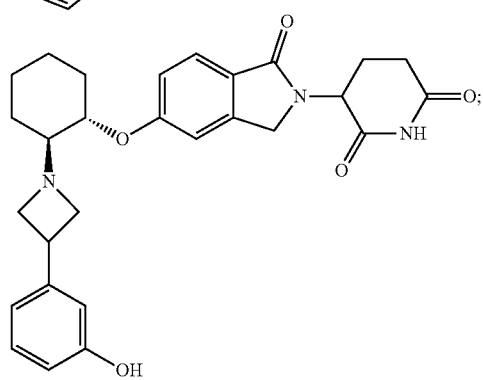

or a pharmaceutically acceptable salt, solvate, stereoisomer, or tautomer thereof.

2. The compound of claim 1, wherein the compound is:

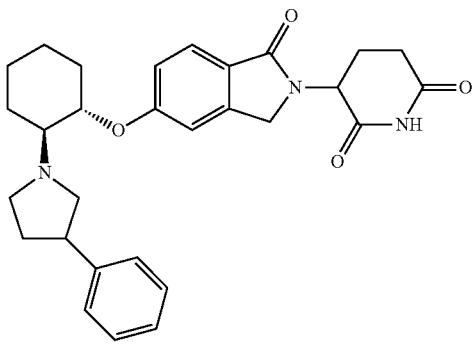 [SMILES: O=C1CCC(N2Cc3cc(O[C@H]4CCCC[C@@H]4N4CCC(c5ccccc5)C4)ccc3C2=O)C(=O)N1]

or a pharmaceutically acceptable salt, solvate, stereoisomer, or tautomer thereof.

3. The compound of claim 1, wherein the compound is:

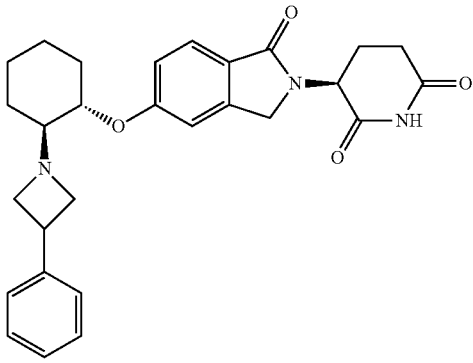 [SMILES: O=C1CC[C@H](N2Cc3cc(O[C@H]4CCCC[C@@H]4N4CC(c5ccccc5)C4)ccc3C2=O)C(=O)N1]

or a pharmaceutically acceptable salt, solvate, stereoisomer, or tautomer thereof.

4. The compound of claim 1, wherein the compound is:

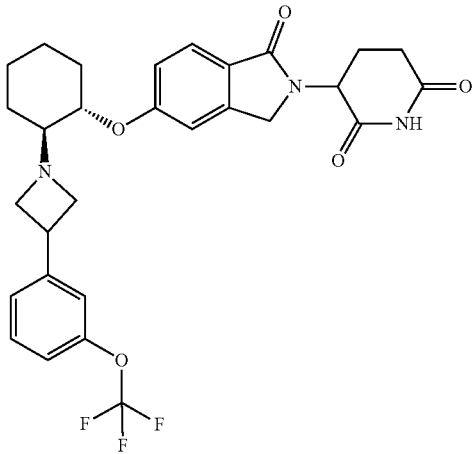 [SMILES: O=C1CCC(N2Cc3cc(O[C@H]4CCCC[C@@H]4N4CC(c5cccc(OC(F)(F)F)c5)C4)ccc3C2=O)C(=O)N1]

or a pharmaceutically acceptable salt, solvate, stereoisomer, or tautomer thereof.

5. The compound of claim 1, wherein the compound is:

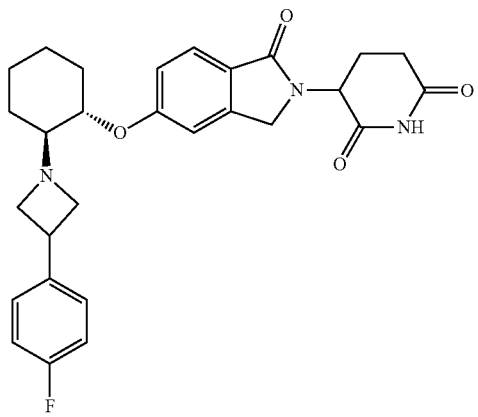 [SMILES: O=C1CCC(N2Cc3cc(O[C@H]4CCCC[C@@H]4N4CC(c5ccc(F)cc5)C4)ccc3C2=O)C(=O)N1]

or a pharmaceutically acceptable salt, solvate, stereoisomer, or tautomer thereof.

6. The compound of claim 1, wherein the compound is:

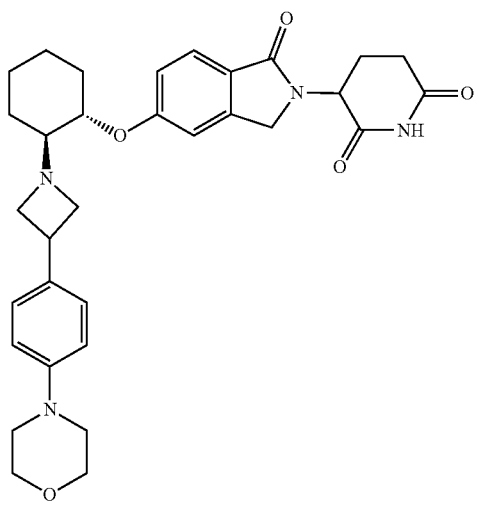 [SMILES: O=C1CCC(N2Cc3cc(O[C@H]4CCCC[C@@H]4N4CC(c5ccc(N6CCOCC6)cc5)C4)ccc3C2=O)C(=O)N1]

or a pharmaceutically acceptable salt, solvate, stereoisomer, or tautomer thereof.

7. The compound of claim 1, wherein the compound is:

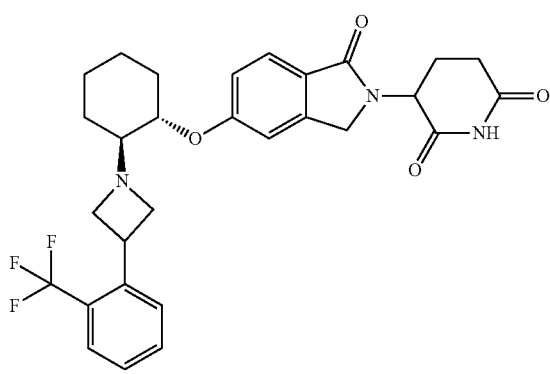 [SMILES: O=C1CCC(N2Cc3cc(O[C@H]4CCCC[C@@H]4N4CC(c5ccccc5C(F)(F)F)C4)ccc3C2=O)C(=O)N1]

or a pharmaceutically acceptable salt, solvate, stereoisomer, or tautomer thereof.

8. The compound of claim 1, wherein the compound is:

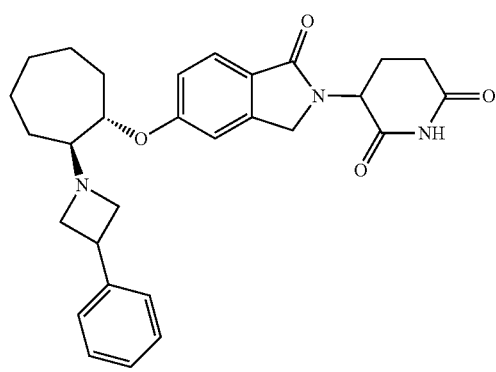 [SMILES: O=C1CCC(N2Cc3cc(O[C@H]4CCCCC[C@@H]4N4CC(c5ccccc5)C4)ccc3C2=O)C(=O)N1]

or a pharmaceutically acceptable salt, solvate, stereoisomer, or tautomer thereof.

9. The compound of claim 1, wherein the compound is:

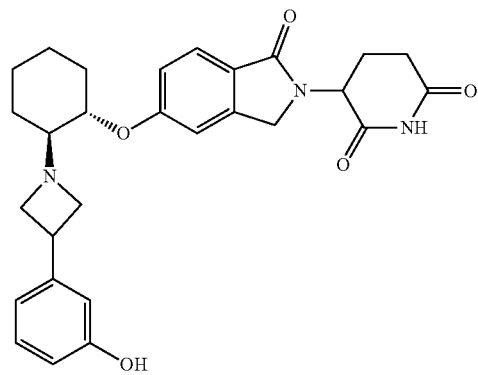 [SMILES: O=C1CCC(N2Cc3cc(O[C@H]4CCCC[C@@H]4N4CC(c5cccc(O)c5)C4)ccc3C2=O)C(=O)N1]

or a pharmaceutically acceptable salt, solvate, stereoisomer, or tautomer thereof.

10. A pharmaceutical composition comprising a pharmaceutically acceptable excipient and a compound selected from:

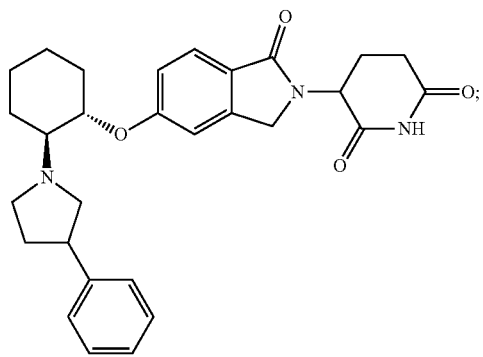 [SMILES: O=C1CCC(N2Cc3cc(O[C@H]4CCCC[C@@H]4N4CCC(c5ccccc5)C4)ccc3C2=O)C(=O)N1]

315
-continued
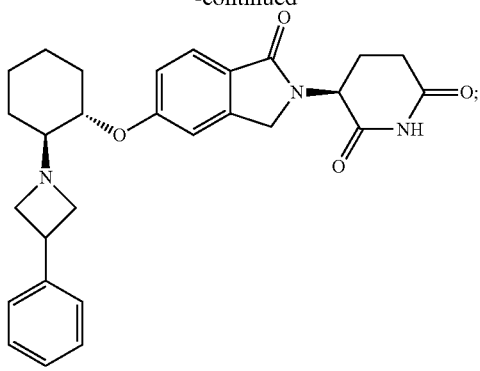
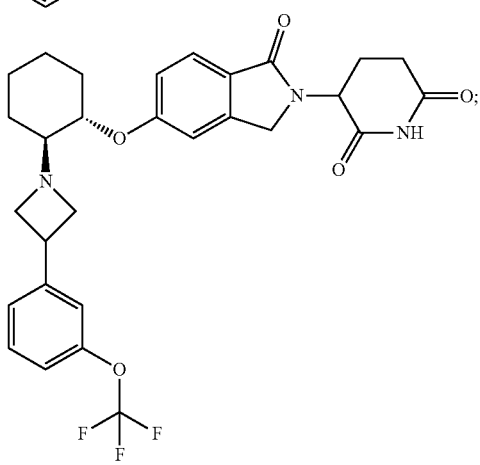
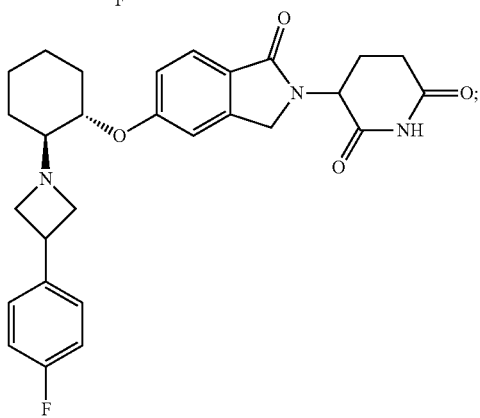
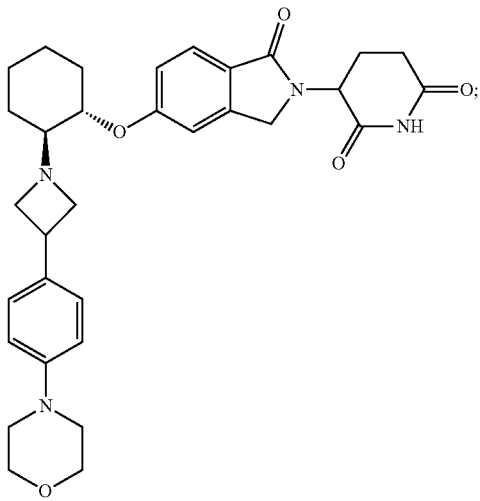
316
-continued
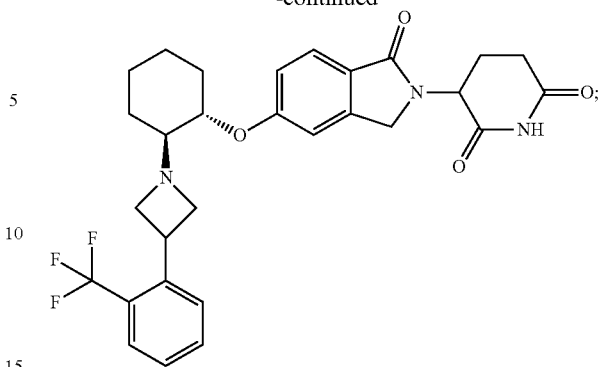
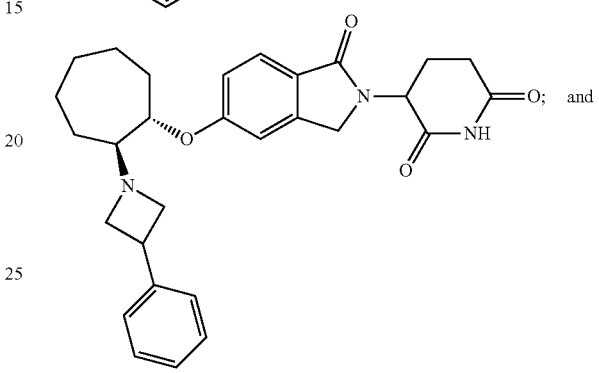
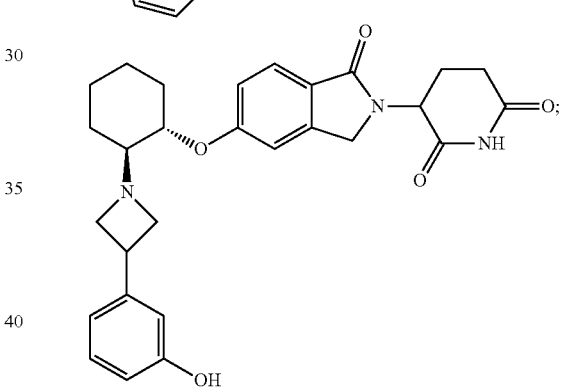
or a pharmaceutically acceptable salt, solvate, stereoisomer, or tautomer thereof.
11. The pharmaceutical composition of claim 10, wherein the compound is:
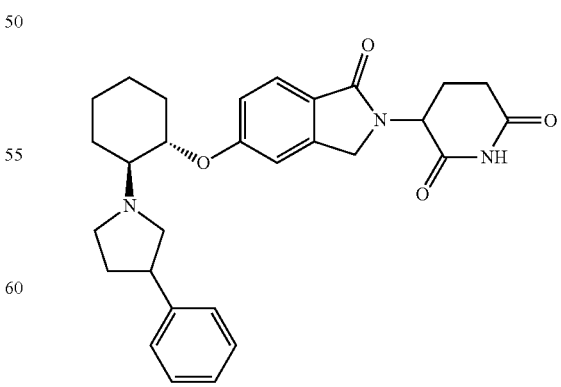
or a pharmaceutically acceptable salt, solvate, stereoisomer, or tautomer thereof.

12. The pharmaceutical composition of claim 10, wherein the compound is:

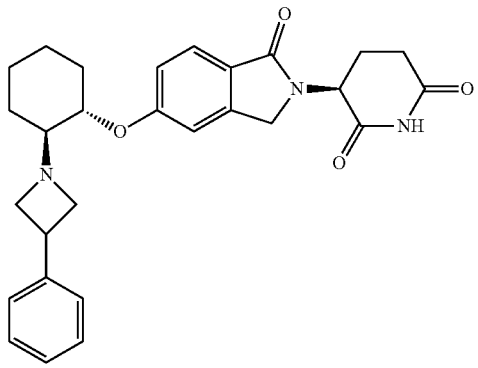 [SMILES: O=C1CC[C@H](N2Cc3cc(O[C@H]4CCCC[C@@H]4N4CC(c5ccccc5)C4)ccc3C2=O)C(=O)N1]

or a pharmaceutically acceptable salt, solvate, stereoisomer, or tautomer thereof.

13. The pharmaceutical composition of claim 10, wherein the compound is:

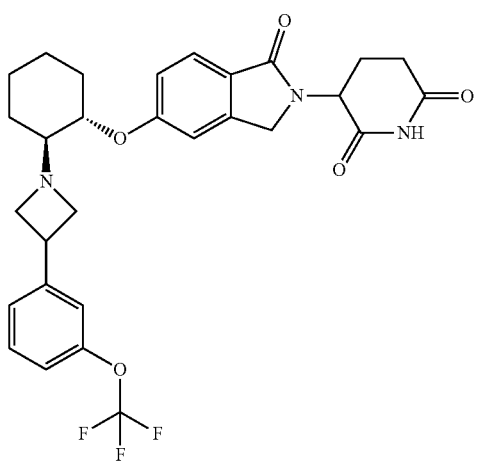 [SMILES: O=C1CCC(N2Cc3cc(O[C@H]4CCCC[C@@H]4N4CC(c5cccc(OC(F)(F)F)c5)C4)ccc3C2=O)C(=O)N1]

or a pharmaceutically acceptable salt, solvate, stereoisomer, or tautomer thereof.

14. The pharmaceutical composition of claim 10, wherein the compound is:

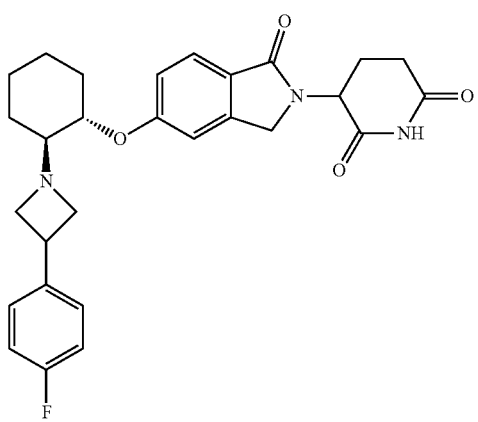 [SMILES: O=C1CCC(N2Cc3cc(O[C@H]4CCCC[C@@H]4N4CC(c5ccc(F)cc5)C4)ccc3C2=O)C(=O)N1]

or a pharmaceutically acceptable salt, solvate, stereoisomer, or tautomer thereof.

15. The pharmaceutical composition of claim 10, wherein the compound is:

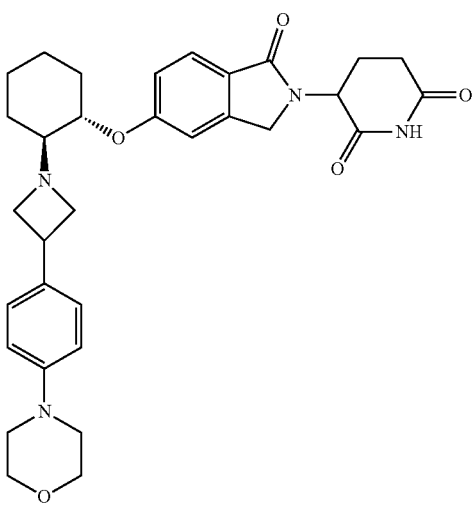 [SMILES: O=C1CCC(N2Cc3cc(O[C@H]4CCCC[C@@H]4N4CC(c5ccc(N6CCOCC6)cc5)C4)ccc3C2=O)C(=O)N1]

or a pharmaceutically acceptable salt, solvate, stereoisomer, or tautomer thereof.

16. The pharmaceutical composition of claim 10, wherein the compound is:

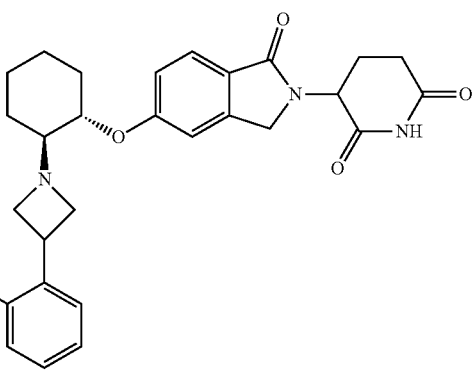

or a pharmaceutically acceptable salt, solvate, stereoisomer, or tautomer thereof.

17. The pharmaceutical composition of claim 10, wherein the compound is:

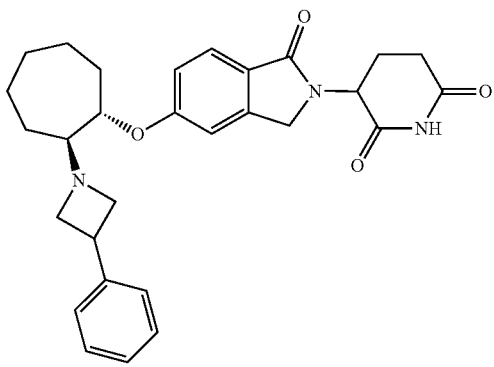 [SMILES: O=C1CCC(N2Cc3cc(O[C@H]4CCCCC[C@@H]4N4CC(c5ccccc5)C4)ccc3C2=O)C(=O)N1]

or a pharmaceutically acceptable salt, solvate, stereoisomer, or tautomer thereof.

18. The pharmaceutical composition of claim 10, wherein the compound is:

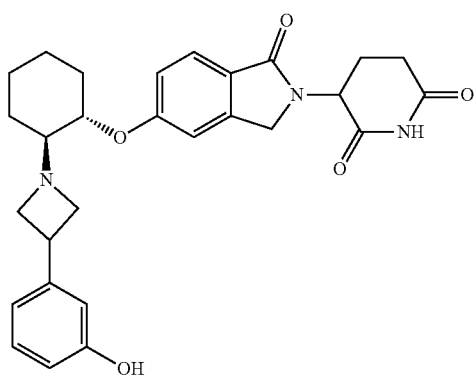 [SMILES: O=C1CCC(N2Cc3cc(O[C@H]4CCCC[C@@H]4N4CC(c5cccc(O)c5)C4)ccc3C2=O)C(=O)N1]

or a pharmaceutically acceptable salt, solvate, stereoisomer, or tautomer thereof.

19. A method for modulating cereblon activity, which method comprises contacting cereblon with an effective amount of a compound of claim 1, or a pharmaceutically acceptable salt, solvate, stereoisomer, or tautomer thereof, under conditions wherein cereblon is modulated.

20. A method for modulating cereblon activity, which method comprises contacting cereblon with an effective amount of a pharmaceutical composition of claim 10, under conditions wherein cereblon is modulated.

21. A method to degrade IKZF2 in a subject, which method comprises administering to said subject an effective amount of a compound of claim 1, or a pharmaceutically acceptable salt, solvate, stereoisomer, or tautomer thereof.

22. A method to degrade IKZF2 in a subject, which method comprises administering to said subject an effective amount of a pharmaceutical composition of claim 10.

23. A method to treat cancer in a subject in need thereof, which method comprises selecting a subject whose cancer is mediated by IKZF2 and administering to said subject an effective amount of a compound of claim 1, or a pharmaceutically acceptable salt, solvate, stereoisomer, or tautomer thereof.

24. A method to treat cancer in a subject in need thereof, which method comprises selecting a subject whose cancer is mediated by IKZF2 and administering to said subject an effective amount of a pharmaceutical composition of claim 10.

25. A compound, which is:

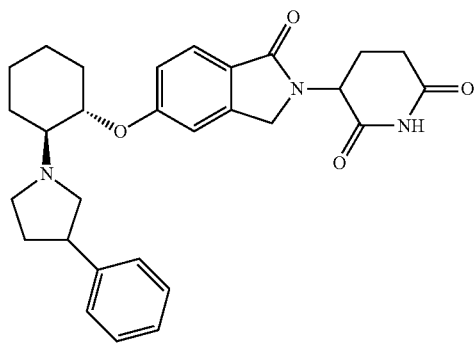 [SMILES: O=C1CCC(N2Cc3cc(O[C@H]4CCCC[C@@H]4N4CCC(c5ccccc5)C4)ccc3C2=O)C(=O)N1]

or a pharmaceutically acceptable salt thereof.

26. A compound which is:

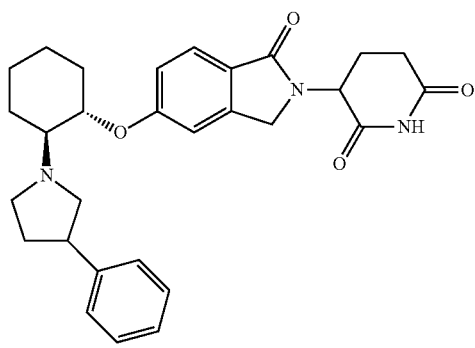 [SMILES: O=C1CCC(N2Cc3cc(O[C@H]4CCCC[C@@H]4N4CCC(c5ccccc5)C4)ccc3C2=O)C(=O)N1]

27. A compound, which is:

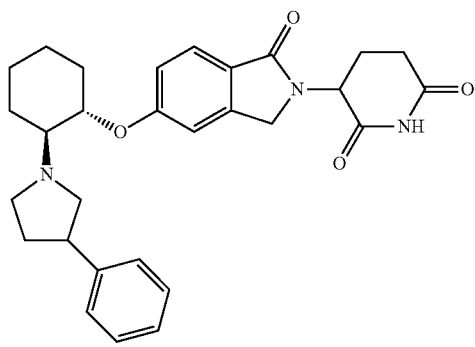 [SMILES: O=C1CCC(N2Cc3cc(O[C@H]4CCCC[C@@H]4N4CCC(c5ccccc5)C4)ccc3C2=O)C(=O)N1]

or a pharmaceutically acceptable salt thereof.

28. A compound which is:
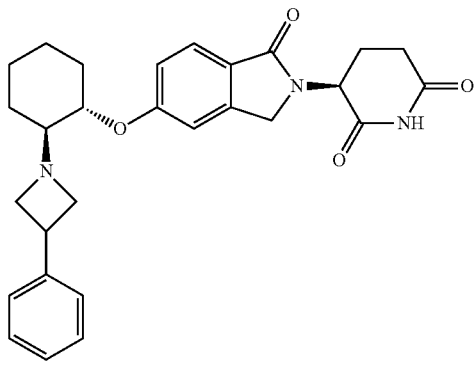 [SMILES: O=C1CC[C@H](N2Cc3cc(O[C@H]4CCCC[C@@H]4N4CC(c5ccccc5)C4)ccc3C2=O)C(=O)N1]
29. A compound, which is:
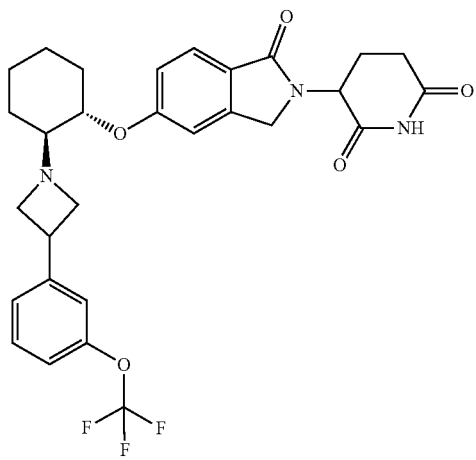 [SMILES: O=C1CCC(N2Cc3cc(O[C@H]4CCCC[C@@H]4N4CC(c5cccc(OC(F)(F)F)c5)C4)ccc3C2=O)C(=O)N1]
or a pharmaceutically acceptable salt thereof.
30. A compound which is:
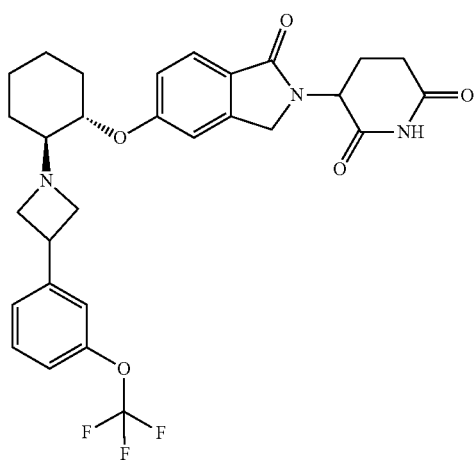 [SMILES: O=C1CCC(N2Cc3cc(O[C@H]4CCCC[C@@H]4N4CC(c5cccc(OC(F)(F)F)c5)C4)ccc3C2=O)C(=O)N1]
31. A compound, which is:
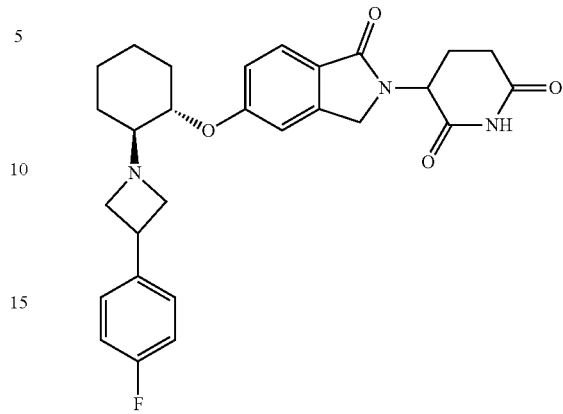
or a pharmaceutically acceptable salt thereof.
32. A compound which is:
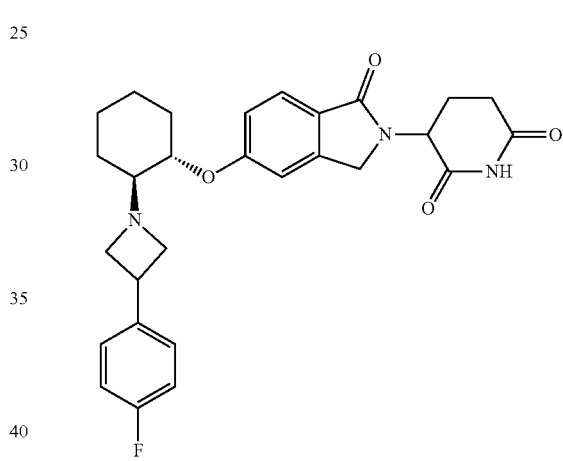
33. A compound, which is:
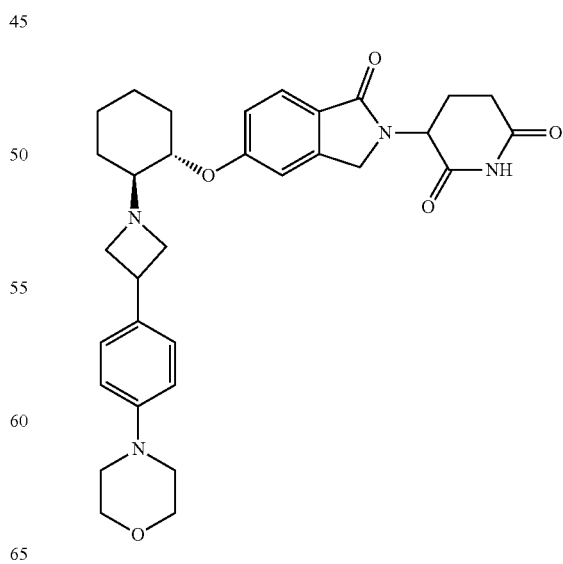
or a pharmaceutically acceptable salt thereof.

34. A compound which is:
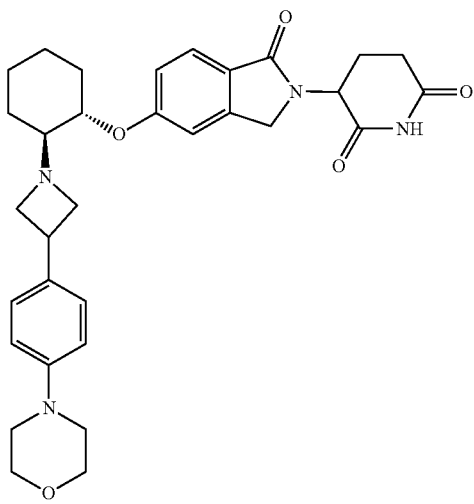 [SMILES: O=C1CCC(N2Cc3cc(O[C@H]4CCCC[C@@H]4N4CC(c5ccc(N6CCOCC6)cc5)C4)ccc3C2=O)C(=O)N1]
35. A compound, which is:
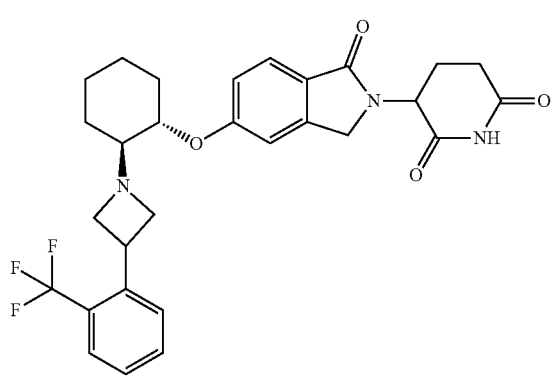 [SMILES: O=C1CCC(N2Cc3cc(O[C@H]4CCCC[C@@H]4N4CC(c5ccccc5C(F)(F)F)C4)ccc3C2=O)C(=O)N1]
or a pharmaceutically acceptable salt thereof.
36. A compound which is:
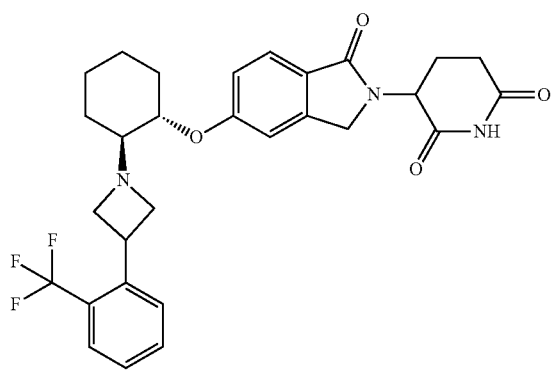 [SMILES: O=C1CCC(N2Cc3cc(O[C@H]4CCCC[C@@H]4N4CC(c5ccccc5C(F)(F)F)C4)ccc3C2=O)C(=O)N1]
37. A compound, which is:
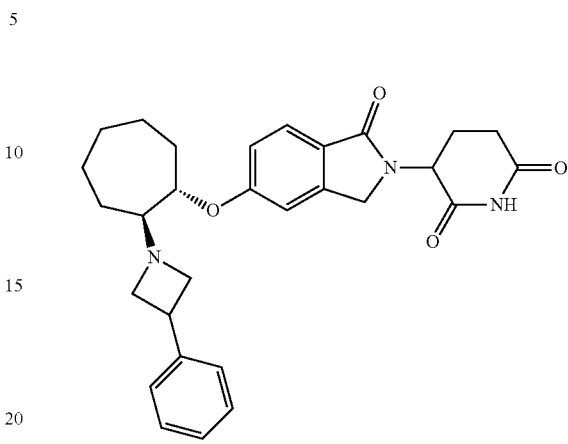
or a pharmaceutically acceptable salt thereof.
38. A compound which is:
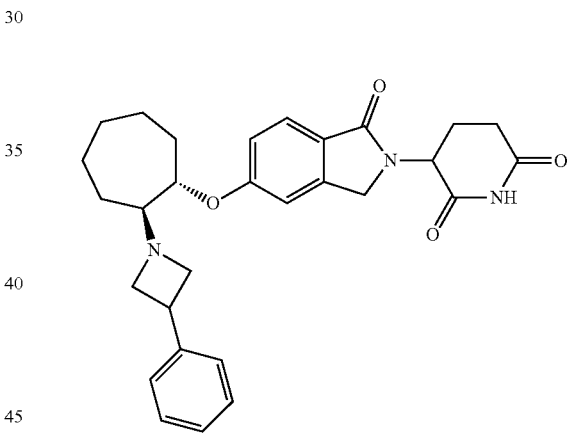
39. A compound, which is:
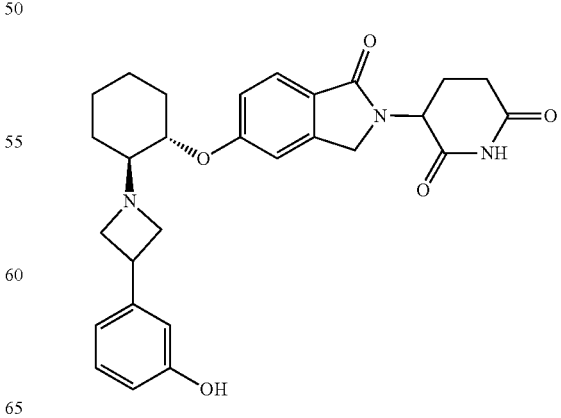
or a pharmaceutically acceptable salt thereof.

40. A compound which is:
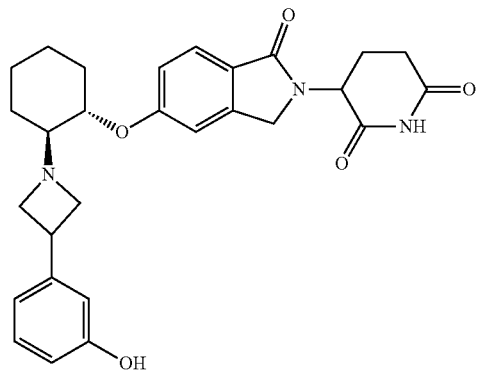 [SMILES: O=C1CCC(N2Cc3cc(O[C@H]4CCCC[C@@H]4N4CC(c5cccc(O)c5)C4)ccc3C2=O)C(=O)N1]

UNITED STATES PATENT AND TRADEMARK OFFICE
CERTIFICATE OF CORRECTION

PATENT NO. : 11,878,968 B2
APPLICATION NO. : 18/052462
DATED : January 23, 2024
INVENTOR(S) : Pengyu Yang et al.

Page 1 of 1

It is certified that error appears in the above-identified patent and that said Letters Patent is hereby corrected as shown below:

In the Claims

In Claim 27, Column 320, Lines 52-65, please replace

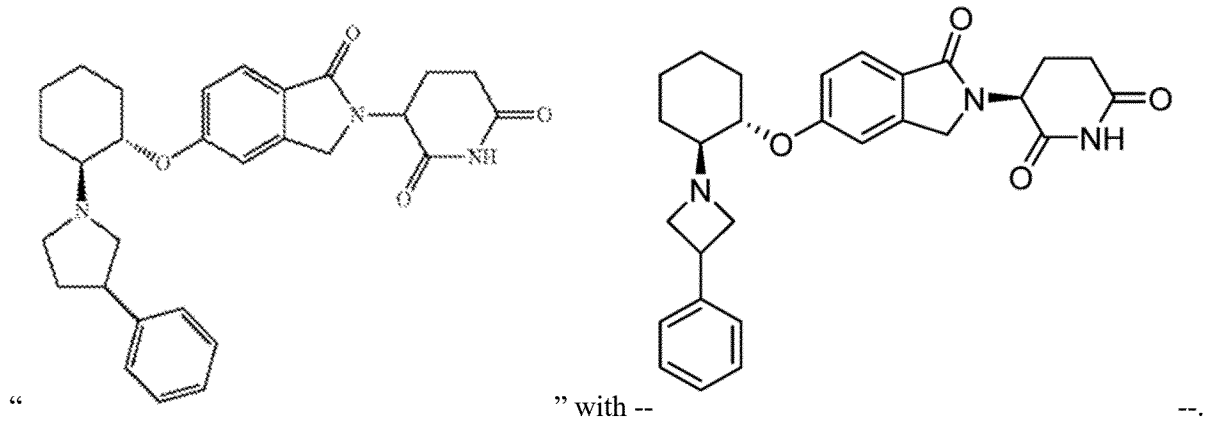

" with -- --.

Signed and Sealed this
Fourteenth Day of May, 2024

Katherine Kelly Vidal
Director of the United States Patent and Trademark Office